(12) United States Patent
Yoshinaga et al.

(10) Patent No.: US 11,110,038 B2
(45) Date of Patent: *Sep. 7, 2021

(54) DENTAL POLYMERIZABLE MONOMERS, COMPOSITIONS, ADHESIVE DENTAL MATERIALS AND KITS

(71) Applicants: Mitsui Chemicals, Inc., Tokyo (JP); Sun Medical Co., Ltd., Moriyama (JP)

(72) Inventors: Kazuhiko Yoshinaga, Ichihara (JP); Yoshimitsu Tanabe, Ichihara (JP); Shinsuke Kinoshita, Ichihara (JP); Takenori Mitamura, Ichihara (JP); Hiroki Murai, Ichihara (JP); Takeshi Yokoyama, Moriyama (JP); Yoshihisa Kamimoto, Moriyama (JP); Tatsuya Ori, Moriyama (JP); Hirohisa Shimizu, Moriyama (JP); Masami Arata, Moriyama (JP); Masuji Tsuchikawa, Moriyama (JP); Sayaka Miyamori, Moriyama (JP); Yoshiaki Katsura, Moriyama (JP)

(73) Assignees: MITSUI CHEMICALS, INC., Tokyo (JP); SUN MEDICAL CO., LTD., Moriyama (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/588,283

(22) Filed: Sep. 30, 2019

(65) Prior Publication Data
US 2020/0030194 A1 Jan. 30, 2020

Related U.S. Application Data

(63) Continuation of application No. 15/561,339, filed as application No. PCT/JP2016/060633 on Mar. 31, 2016, now Pat. No. 10,470,980.

(30) Foreign Application Priority Data

| Mar. 31, 2015 | (JP) | 2015-071482 |
| Mar. 31, 2015 | (JP) | 2015-071483 |
| Mar. 31, 2015 | (JP) | 2015-071484 |
| Mar. 31, 2015 | (JP) | 2015-073578 |
| Mar. 31, 2015 | (JP) | 2015-073579 |

(51) Int. Cl.
| A61K 6/00 | (2020.01) |
| A61K 6/30 | (2020.01) |
| A61K 6/62 | (2020.01) |
| A61K 6/887 | (2020.01) |
| C07C 271/20 | (2006.01) |

(52) U.S. Cl.
CPC .......... *A61K 6/30* (2020.01); *A61K 6/00* (2013.01); *A61K 6/62* (2020.01); *A61K 6/887* (2020.01); *C07C 271/20* (2013.01); *C07C 2602/42* (2017.05)

(58) Field of Classification Search
None
See application file for complete search history.

(56) References Cited

U.S. PATENT DOCUMENTS

| 5,530,038 | A | 6/1996 | Yamamoto et al. |
| 5,587,406 | A | 12/1996 | Yamamoto et al. |
| 5,834,532 | A | 11/1998 | Yamamoto et al. |
| 5,849,270 | A | 12/1998 | Podszun et al. |
| 6,071,983 | A | 6/2000 | Yamamoto et al. |
| 6,136,881 | A | 10/2000 | Sekiguchi et al. |
| 6,288,138 | B1 | 9/2001 | Yamamoto et al. |
| 7,329,692 | B2 * | 2/2008 | Kalgutkar ............ C07C 313/02 522/25 |

(Continued)

FOREIGN PATENT DOCUMENTS

| CN | 1723244 A | 1/2006 |
| CN | 101808981 A | 8/2010 |

(Continued)

OTHER PUBLICATIONS

Margerum, J.D., et al., "Photopolymerization Mechanisms. II. Rates of Ionic Dark Addition of Benzenesulfinate Ions to Acrylic Monomers", The Journal of Physical Chemistry, vol. 77, No. (23), pp. 2720-2725, 1973.

(Continued)

*Primary Examiner* — Tae H Yoon
(74) *Attorney, Agent, or Firm* — Buchanan Ingersoll & Rooney PC

(57) ABSTRACT

A dental adhesive curable composition containing a polymerizable monomer including a polymerizable monomer represented by formula (1') and defined amounts of an acidic group-containing polymerizable monomer, a polymerization initiator containing a peroxide and a photopolymerization initiator, and a reductant containing a sulfinic acid compound and/or a salt thereof, and a filler:

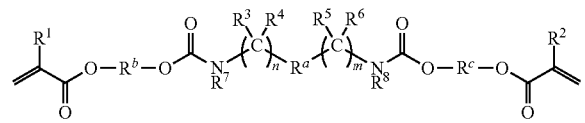

(1')

wherein the R groups, n and m are defined. A dental adhesive curable kit and a mobile tooth fixing material are also provided.

4 Claims, No Drawings

(56) References Cited

U.S. PATENT DOCUMENTS

| | | | |
|---|---|---|---|
| 8,183,306 B2* | 5/2012 | Kohro | A61K 6/891 |
| | | | 523/116 |
| 8,426,490 B2 | 4/2013 | Bissinger et al. | |
| 8,664,294 B2 | 3/2014 | Jia et al. | |
| 9,125,802 B2 | 9/2015 | Sugiura et al. | |
| 9,447,224 B2 | 9/2016 | Izumi et al. | |
| 10,130,563 B2 | 11/2018 | Yoshinaga et al. | |
| 10,130,564 B2 | 11/2018 | Yoshinaga et al. | |
| 10,470,980 B2* | 11/2019 | Yoshinaga | A61K 6/30 |
| 2002/0082315 A1 | 6/2002 | Moszner et al. | |
| 2005/0215660 A1 | 9/2005 | Tomikawa et al. | |
| 2006/0052470 A1 | 3/2006 | Grech et al. | |
| 2009/0010865 A1 | 1/2009 | Kim et al. | |
| 2010/0197824 A1 | 8/2010 | Bissinger et al. | |
| 2010/0292359 A1 | 11/2010 | Ori et al. | |
| 2011/0230617 A1 | 9/2011 | Haremza et al. | |
| 2012/0129973 A1 | 5/2012 | Sun | |
| 2012/0228567 A1 | 9/2012 | Izumi et al. | |
| 2012/0296003 A1 | 11/2012 | Naruse et al. | |
| 2013/0274426 A1 | 10/2013 | Sugiura et al. | |
| 2013/0299736 A1 | 11/2013 | Haremza et al. | |
| 2014/0056951 A1 | 2/2014 | Losick et al. | |
| 2015/0196462 A1 | 7/2015 | Sun | |
| 2017/0174621 A1 | 6/2017 | Yoshinaga et al. | |
| 2017/0181932 A1 | 6/2017 | Yoshinaga et al. | |
| 2018/0110683 A1 | 4/2018 | Yoshinaga et al. | |

FOREIGN PATENT DOCUMENTS

| | | | |
|---|---|---|---|
| CN | 102216400 A | | 10/2011 |
| CN | 102574980 A | | 7/2012 |
| GB | 1443715 A | | 7/1976 |
| JP | 362027403 A | * | 2/1987 |
| JP | S62-25115 A | | 2/1987 |
| JP | 63162769 A | | 7/1988 |
| JP | H06157451 A | | 6/1994 |
| JP | H0797306 A | | 4/1995 |
| JP | H07291819 A | | 11/1995 |
| JP | H09157126 A | | 6/1997 |
| JP | H09216924 A | | 8/1997 |
| JP | H1179925 A | | 3/1999 |
| JP | H11240815 A | | 9/1999 |
| JP | H11315059 A | | 11/1999 |
| JP | 2000-63480 A | | 2/2000 |
| JP | 2000204069 A | | 7/2000 |
| JP | 3370538 B2 | | 1/2003 |
| JP | 4162738 B2 | | 10/2008 |
| JP | 2011207806 A | | 10/2011 |
| JP | 2012006880 A | | 1/2012 |
| JP | 2012046468 A | | 3/2012 |
| JP | 5191486 B2 | | 2/2013 |
| JP | 2013100255 A | | 5/2013 |
| JP | 2013544823 A | | 12/2013 |
| WO | 2008140103 A1 | | 11/2008 |
| WO | 2012086189 A1 | | 6/2012 |
| WO | 2012/151554 A1 | | 11/2012 |
| WO | 2012157566 A1 | | 11/2012 |
| WO | 2015152221 A1 | | 10/2015 |

OTHER PUBLICATIONS

International Preliminary Report on Patentability (PCT/IB/33) dated Oct. 3, 2017 for International Application No. PCT/JP2016/060633.
International Search Report (PCT/ISA/210) dated Jun. 7, 2016, by the Japanese Patent Office as the International Searching Authority for International Application No. PCT/JP2016/060633.
Written Opinion (PCT/ISA/237) dated Jun. 7, 2016, by the Japanese Patent Office as the International Searching Authority for International Application No. PCT/JP2016/060633.
Watanabe, T., "Effect of filler particle size on the cure depth of light-cured composite resins", J.Fukuoka Dent. Coll. vol. 19 No. (1), pp. 11-24, 1992.
He et al., "Synthesis and characterization of new dimethacrylate monomer and its application in dental resin", Journal of Biomaterials Science, Polymer Edition, 2013, vol. 24, No. 4, pp. 417-430.
Wang, et al., "Developments in matrix of dental composite resin", International Journal of Stomatology, 2007, vol. 34, No. 6, pp. 443-445.
Decision to Grant dated Apr. 25, 2021, issued by the State Intellectual Property Office in the People's Republic of China in corresponding Chinese Patent Application No. 201680015373.3. (4 pages).

* cited by examiner

DENTAL POLYMERIZABLE MONOMERS, COMPOSITIONS, ADHESIVE DENTAL MATERIALS AND KITS

CROSS-REFERENCE TO RELATED APPLICATIONS

This application is a continuation of U.S. application Ser. No. 15/561,339, filed Sep. 25, 2017, now U.S. Pat. No. 10,470,980, which is a U.S. national stage application of PCT/JP2016/060633, filed Mar. 31, 2016, which claims priority to Japanese Patent Application Nos. 2015-073578, filed Mar. 31, 2015, 2015-073579, filed Mar. 31, 2015, 2015-071482, filed Mar. 31, 2015, 2015-071483, filed Mar. 31, 2015, and 2015-071484, filed Mar. 31, 2015, the contents of all of which are hereby incorporated by reference.

TECHNICAL FIELD

The present invention relates to dental polymerizable monomers, dental compositions, dental adhesive compositions, dental adhesive curable compositions, mobile tooth fixing materials and dental curable kits.

BACKGROUND ART

Composite resins that are a typical example of dental compositions usually contain a polymerizable monomer composition and additives such as a filler, a polymerization initiator, a polymerization inhibitor, a dye, and etc. In a composite resin including such components, a filler usually has the largest weight fraction followed by a polymerizable monomer composition and these two components represent a major proportion of the weight of the composite resin. The polymerizable monomer composition serves as a binder for the filler. The properties of monomers, and the properties of cured products of the compositions are significantly influential on the properties and performance of the composite resin containing the monomer composition, and cured products thereof.

From the points of view of aspects such as the biological safety of monomers and the mechanical strength and wear resistance of cured products, the polymerizable monomer compositions frequently include radically polymerizable polyfunctional methacrylates. Typically, the polyfunctional methacrylate compositions are based on 2,2-bis[4-(3-methacryloyloxy-2-hydroxypropoxy)phenyl]propane (hereinafter, written as Bis-GMA) or 2,2,4-trimethylhexamethylenebis(2-carbamoyloxyethyl) dimethacrylate (hereinafter, written as UDMA), and contain triethylene glycol dimethacrylate (hereinafter, written as TEGDMA) to control the viscosity.

In the dental clinical practice, the use of composite resins in the restoration of tooth defects has a long history and is still expanding. However, the mechanical properties of cured composite resins are still insufficient. In particular, the poor strength obstructs the application of the resins to sites subjected to a high stress, for example, the use as molar tooth crowning materials.

In recent years, clinical experts strongly demand the expansion of the use of composite resins to such high-stress sites. Therefore, the development of composite resins having higher mechanical properties is an urgent necessity. As mentioned above, the properties of cured products of polymerizable monomer compositions used for composite resins significantly affect the properties of cured products of the composite resins containing the compositions.

Techniques have been reported in which Bis-GMA and UDMA that are widely used as main components of polymerizable monomer compositions are replaced by other monomers so as to enhance the mechanical strength of cured products of composite resins (Patent Literature 1 and Patent Literature 2).

Further, techniques aiming to improve main component monomers have been reported. For example, main component monomers are improved so as to enhance the refractive index of cured products of polymerizable monomer compositions (Patent Literature 3), and main component monomers are improved so as to enhance the degree of polymerization shrinkage between before and after the curing of polymerizable monomer compositions (Patent Literature 4).

Dental adhesive compositions, which are a typical example of dental materials, usually contain a polymerizable monomer containing no acidic groups, a polymerizable monomer containing an acidic group, a polymerization initiator, a polymerization inhibitor and other functional additives. The performance of dental adhesive compositions that is of greatest interest is to bond a prosthesis and a filling material to tooth structure. To enhance this performance, many studies report improved polymerizable monomers with an acidic group which are components considered to have a direct impact on adhesion (for example, Patent Literature 5).

A typical dental adhesive composition contains a polymerizable monomer containing no acidic groups in an amount that is equal to or greater than that of a polymerizable monomer containing an acidic group. This fact is rarely focused on in conventional techniques.

From points of view such as the biological safety of monomers and the mechanical strength and wear resistance of cured products, radically polymerizable polyfunctional (meth)acrylate compounds are frequently used as the acidic group-free polymerizable monomers. Typical examples of such polyfunctional (meth)acrylate compounds include 2,2-bis[4-(3-methacryloyloxy-2-hydroxypropoxy)phenyl]propane (hereinafter, written as Bis-GMA), 2,2,4-trimethylhexamethylenebis(2-carbamoyloxyethyl) dimethacrylate (hereinafter, written as UDMA) and triethylene glycol dimethacrylate (hereinafter, written as TEGDMA).

Dental adhesive compositions have found a wide use in dental clinical practice. A typical example is various dental adhesive materials such as adhesive cements for bonding a prosthesis to tooth structure, bonding materials, coating materials, orthodontic adhesives and mobile tooth fixing materials. Of these materials, adhesive cements are required to attain an enhancement in bond strength but have not reached a satisfactory level of this important performance. Further, such materials are known to be poor in storage stability. Dental adhesive compositions are recently being applied to new applications, for example, the fixation of mobile teeth (Patent Literature 6).

A tooth that has lost its function due to caries, an accident or the like is restored by, for example, fixing a coronal restoration material made of a metal or a ceramic such as porcelain, called an inlay or a crown, to the tooth. Such a coronal restoration material is fixed to the tooth with an adhesive called a dental cement. Of dental cements, adhesive resin cements that are frequently used are compositions which include a (meth)acrylate polymerizable monomer as a polymerizable monomer, and an inorganic or organic filler and a chemical polymerization initiator, and are cured by radical polymerization.

Some of the properties to be possessed by the above dental compositions are curability which ensures a sufficient exhibition of the performance of the composition, and excellent stability (storage stability) which allows the performance to be exhibited over a long period. Further, adhesive materials are required to have adhesion to ensure that the dental restoration material will not come off from the tooth structure after the treatment. An approach to attaining this requirement is to add an acidic group-containing polymerizable monomer as a polymerizable monomer so as to impart adhesion with respect to teeth and various coronal restorations.

To satisfy the performances described above, compositions incorporated with various polymerization initiators have been developed. Resin cements currently available in the market are divided into chemically polymerizable resins which use a redox initiator including a peroxide and a reductant such as an amine compound, and dual-cure resins which combine a redox system with a photopolymerization initiator. A chemically polymerizable resin is usually stored as separate parts composed of a peroxide-containing composition and a reductant-containing composition, and the two compositions are mixed with each other immediately before use. If the compositions contain an acidic component for ensuring adhesion with respect to tooth structure and dental restoration materials, as is the case in dental cements, dental adhesives and the like, the acidic component inhibits radical polymerization to cause a decrease in polymerization efficiency, and polymerizability is low because of the susceptibility to oxygen.

Studies report that the polymerizability of a composition containing an acidic component is improved by adding a chemical polymerization initiator which easily initiates polymerization and curing even under acidic conditions (Patent Literature 7, Patent Literature 8 and Patent Literature 9). Patent Literature 7, Patent Literature 8 and Patent Literature 9 present polymerization catalyst systems which exhibit a high polymerization curing performance even under acidic and wet conditions by virtue of containing, as reductants, a combination of an N-phenylglycine (NPG) compound that is an amine compound, and a sulfinic acid compound.

In Patent Literature 7 and Patent Literature 8, the materials are stored as a powder and a liquid, and the reductants need to be held by a specific jig or the like and be stored separately from the polymerizable monomers. That is, the manner in which the materials are stored is limited. Patent Literature 9 proposes a dental adhesive kit which allows reductants, in particular, an NPG compound that is an amine compound to be stored in a composition by the selective addition of a polymerizable monomer which is not gelled even in the presence of the NPG compound. The composition proposed in Patent Literature 9, however, is designed to withstand long storage in a cold and dark place (about 4° C.) and is still to be improved in terms of storage stability at higher temperatures such as room temperature (about 25° C.).

Patent Literature 10 describes the utility, in a photopolymerizable liquid adhesive composition, of a methacrylate compound with a specific structure represented by the general formula (1) described later wherein the structure represented by the general formula (2c) described later includes RB in the general formula (3c) described later.

Patent Literature 2 describes the use, in a high-strength dental composition, of a methacrylate compound with a specific structure represented by the general formula (1) described later wherein the structure represented by the general formula (2c) described later includes RC in the general formula (3c) described later.

Further, Patent Literature 11 describes the utility, in a dental filling material, of a methacrylate compound with a specific structure represented by the general formula (1) described later wherein the structure represented by the general formula (2c) described later includes any of RD and RE in the general formula (3c) described later.

However, no studies exist which report that a methacrylate compound with a specific structure represented by the general formula (1) wherein the structure represented by the general formula (2c) includes any of the alicyclic structures RB and RC and the aromatic ring structures RD and RE in the general formula (3c) is effective for enhancing properties, in particular, storage stability of a dental adhesive curable composition.

Sufficient curability of a curable composition that contains an acidic component which imparts adhesion to the composition is largely attributed to reductants such as an amine compound and a sulfinic acid compound. It is therefore necessary to ensure that the amine compound and the sulfinic acid compound exist stably in the adhesive curable composition so that the composition will attain storage stability.

A known approach to controlling the deactivation of an amine compound is to remove acidic components in the paste and to disperse the compound as particles in the composition. On the other hand, a sulfinic acid compound is known to be deactivated mainly by undergoing addition reaction with a double bond moiety of a polymerizable monomer (commonly known as "Michael addition reaction"). Non Patent Literature 1 mentions that the reaction rate of Michael addition reaction varies significantly depending on the types of (meth)acrylates, indicating that the selection of an appropriate type of a polymerizable monomer is an effective approach to controlling the deactivation of a sulfinic acid compound.

Another example of the use of dental adhesive compositions is mobile tooth fixing materials.

Gingival retraction associated with age or a progress of periodontal disease makes it difficult to support the teeth sufficiently, resulting in loosening and exfoliation of the teeth. Such loose teeth are called mobile teeth. Mobile teeth are treated by fixing the mobile teeth to healthy teeth to restrain the loose teeth and eliminating the cause of the gingival recession while the loose teeth are being fixed. An example material used to fix a mobile tooth to a healthy tooth is a mobile tooth fixing material. The mobile tooth fixing material is required to be resistant to breakage or exfoliation when it is distorted by an action such as mastication of food or brushing or cleaning of teeth during the fixing period. To meet this material need, the mobile tooth fixing material is required to have excellent flexibility so that a cured product of the material will follow a distortion and is also required to have excellent strength and toughness so that the cured product will not be destroyed or deformed. Further, good adhesion is also required because the fixation to a healthy tooth involves bonding to tooth structure and this bonding needs to persist for several months depending on the length of the fixing period.

One of the mobile tooth fixing materials currently used is Super-Bond (manufactured by Sun Medical Co., Ltd.). This product has been used widely as a mobile tooth fixing material because of its excellent adhesion to tooth structure and appropriate strength, flexibility and toughness against external stress. Super-Bond is a chemically polymerizable product composed of three components: liquid, powder and catalyst V, and thus the use thereof involves complicated handling and a waiting time for curing. Mobile tooth fixing materials having flexibility have been reported (Patent Literature 12 and Patent Literature 13), but it cannot be said that they have sufficient performances in view of the fact that they have a poor balance among flexural strength, flexibility and toughness and are more prone to breakage or exfoliation than Super-Bond.

From the foregoing, requirements for mobile tooth fixing materials are that cured products thereof exhibit excellent strength, flexibility and toughness and have good adhesion with respect to tooth structure, and that the material is a one-part composition so that it can be used with simple handling. Further, photopolymerization curability makes it possible for the user to cure the material at the desired time, realizing a marked enhancement in handleability.

In general, from points of view such as the biological safety of monomers and the mechanical strength and wear resistance of cured products, a polymerizable monomer composition used in a dental adhesive composition frequently includes a radically polymerizable polyfunctional methacrylate. Typically, the polyfunctional methacrylate compositions are based on 2,2-bis[4-(3-methacryloyloxy-2-hydroxypropoxy)phenyl]propane (hereinafter, written as Bis-GMA) or 2,2,4-trimethylhexamethylenebis(2-carbamoyloxyethyl) dimethacrylate (hereinafter, written as UDMA). Attempts have been reported in which the mechanical strength of cured products of such a dental composition is enhanced by using monomers alternative to Bis-GMA and UDMA (Patent Literature 14 and Patent Literature 2). However, an enhancement in mechanical strength tends to be accompanied by decreases in flexibility and toughness, and consequently the balance among flexural strength, flexibility and toughness is unsatisfactory.

Patent Literature 15 discloses a photopolymerizable orthodontic resin composition. This resin composition is suited for the fabrication of splints or bite plates used in the dental treatment for troubles such as jaw movement dysfunction (temporomandibular arthrosis), bruxism and occlusal abnormality.

A cured product of this resin composition contains a crosslinked polyurethane powder in order to attain appropriate elasticity, but has no adhesion with respect to tooth structure and thus cannot be used as a mobile tooth fixing material which requires adhesion with tooth structure.

As described above, there has been a demand for a composition which has excellent strength, flexibility and toughness, exhibits good adhesion with respect to tooth structure, and is a one-part formulation so that it can be used with simple handling.

Dental curable compositions are used as dental adhesives, coating materials, filling or sealing materials and the like in dental clinical practice.

Dental curable compositions are used to fill chips or cavities in teeth or to fill caries, or are used as adhesives to fix a metallic or ceramic coronal restoration material called an inlay or a crown to a tooth. Such a composition generally includes a polymerizable monomer, a radical polymerization initiator and a filling material such as a filler. When adhesion with respect to adherends is required, the composition frequently contains an acidic component. Such dental curable compositions are required to have adhesion to prevent the exfoliation of fillings, and to have sealability to prevent the entry of contaminants from the bond interface. However, an acidic component present in the dental curable composition generally serves as a factor inhibiting radical polymerization. Further, water and oxygen which are abundant in the mouth are generally inhibitory to radical polymerization. Dental curable compositions are required to exhibit the performances described hereinabove in the presence of these polymerization inhibitory factors. Compositions incorporated with various polymerization initiators have been developed to attain such performances.

Patent Literature 7 and Patent Literature 8 show that radical polymerization is allowed to take place without problem even under wet and acidic conditions by the use of an aromatic amine compound having a nonaromatic carbonyl group, and an organic sulfinic acid compound. Further, Patent Literature 3 presents that the use of an alkali metal or an alkaline earth metal makes it possible to attain enhanced storage stability while an aromatic amine compound having a nonaromatic carbonyl group, and an organic sulfinic acid compound are present in a paste.

Although Patent Literature 16 proposes a technique which enhances storage stability in a paste state, the technique of Patent Literature 16 assumes that the paste is stored under refrigeration. Radical polymerizability persists even during room-temperature storage as long as the storage is about 2 years long, but the polymerization rate is decreased significantly. It can be said that a need for further improvement is arising in light of the recent dental market environment which more often requires that dental curable compositions have thermal stability and can be stored at room temperature.

From literature such as Non Patent Literature 1, it is known that a dental curable composition containing an organic sulfinic acid compound is generally degraded to a significant extent during room-temperature storage by the nucleophilic addition of the organic sulfinic acid compound to (meth)acrylate frequently used in dental curable compositions. Non Patent Literature 4 reports that an organic sulfinic acid compound having an electron withdrawing group has a low rate of nucleophilic addition reaction but the polymerization promoting effect of the organic sulfinic acid compound is low at the same time. It is easily inferred that a dental curable composition containing such a compound is likely to suffer a curing failure and eventually a bonding failure when applied to a wet environment such as at an interface with tooth structure.

Regarding dental curable compositions containing an organic sulfinic acid compound and a polymerizable monomer, none of the literatures describes the stability of bond strength over a long period at room temperature or the stability of bond strength in an accelerated test at a higher temperature that ensures the stability of bond strength at room temperature.

CITATION LIST

Patent Literature

Patent Literature 1: JP-A-2000-204069
Patent Literature 2: JP-A-2013-544823
Patent Literature 3: JP-A-H11-315059
Patent Literature 4: WO 2012-157566
Patent Literature 5: JP-A-2012-6880
Patent Literature 6: JP-A-2013-100255
Patent Literature 7: JP-A-H7-97306
Patent Literature 8: JP-A-H7-291819
Patent Literature 9: Japanese Patent No. 5191486
Patent Literature 10: Japanese Patent No. 3370538
Patent Literature 11: Japanese Patent No. 3182738
Patent Literature 12: JP-A-2012-46468
Patent Literature 13: JP-A-2011-207806
Patent Literature 14: JP-A-2000-204069
Patent Literature 15: Japanese Patent No. 4162738
Patent Literature 16: WO 2008/140103

Non Patent Literature

Non Patent Literature 1: Margerum, J. D.; Brault, R. G.; Lackner, A. M.; Miller, L. J., The Journal of Physical Chemistry, 1973, 77(23), 2720

SUMMARY OF INVENTION

Technical Problem

The present invention is aimed at providing polymerizable monomers useful for dental materials, compositions, adhesive dental materials, kits, etc. Objects of the first to the fifth aspects of the present invention are as described below.

As described hereinabove, known dental compositions require a further improvement in mechanical strength. In light of the problems discussed above, the first aspect of the present invention is directed to enhancing mechanical properties of cured products obtained by curing a dental composition. Specifically, an object is to provide a dental polymerizable monomer and a dental polymerizable monomer composition which each give a cured product that has properties satisfying high elastic modulus and high strength. Another object is to provide a dental polymerizable monomer and a dental polymerizable monomer composition which each give a dental composition that has a low polymerization shrinkage factor before and after curing. A further object is to provide a dental composition which contains any of the above-described dental polymerizable monomers and dental polymerizable monomer compositions, and a cured product thereof.

As described hereinabove, known dental adhesive compositions require a further enhancement in adhesion and a further improvement in storage stability. In light of the problems discussed above, the second aspect of the present invention has an object of providing a specific polymerizable monomer that is used in a dental adhesive composition and imparts particularly high bonding performance and excellent storage stability to the dental adhesive composition, and a dental adhesive composition containing such a monomer.

An object of the third aspect of the present invention is to develop a dental adhesive curable composition which has a small delay in curing time after being long stored at room temperature and exhibits excellent bonding performance.

In the fixation of mobile teeth, objects are not only to prevent the breakage or exfoliation of cured products but also to realize easy handling. After careful studies on damages caused to cured products during the treatment, it has been found that a cured product used as a mobile tooth fixing material requires excellent flexibility to follow a distortion and also requires excellent strength and toughness to resist breakage or deformation. An object of the fourth aspect of the present invention is to provide a mobile tooth fixing material which exhibits good adhesion with respect to tooth structure while ensuring strength, flexibility and toughness of cured products and which includes a composition to realize simplified handling during use.

The fifth aspect of the present invention is made in light of the problems in the art discussed hereinabove, and has an object of providing a dental curable composition which exhibits high adhesion with tooth structure and has excellent storage stability, and a dental cement including such a composition.

Solution to Problem

The present inventors carried out extensive studies in order to solve the problems in the art discussed hereinabove, and have consequently completed dental monomers of the present invention.

The present invention provides a dental polymerizable monomer described in [1] below.

[1] A dental polymerizable monomer (A) including a urethane (meth)acrylate represented by the following general formula (1):

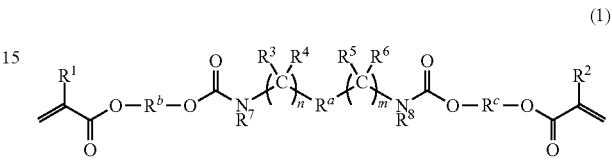

(1)

(In the general formula (1), $R^a$ is a divalent $C_{6-9}$ aromatic hydrocarbon group or a divalent $C_{6-9}$ optionally bridged cyclic hydrocarbon group, $R^1$ and $R^2$ are each a hydrogen atom or a $C_{1-3}$ alkyl group, $R^3$, $R^4$, $R^5$ and $R^6$ are each a hydrogen atom or a hydrocarbon group, $R^7$ and $R^8$ are each a hydrogen atom or a methyl group, m and n are each independently 0 to 4, and $R^b$ and $R^c$ are each independently a $C_{2-6}$ linear alkylene or $C_{2-6}$ linear oxyalkylene group optionally substituted with a $C_{1-3}$ alkyl group or a (meth)acryloyloxymethylene group in place of a hydrogen atom.)

The present inventor has found that a dental polymerizable monomer composition which contains a urethane methacrylate having a structure with appropriate rigidity and a structure with appropriate flexibility gives a cured product which exhibits properties satisfying high elastic modulus and high strength. Further, the present inventor has found that the dental polymerizable monomer composition shows a low polymerization shrinkage factor when it is cured. After extensive studies, the present inventor completed the first aspect of the present invention.

The first aspect of the present invention provides dental polymerizable monomers, dental polymerizable monomer compositions, dental compositions and cured products of the dental compositions described in [2] to [4] and [10] to [15] below.

[2] A dental polymerizable monomer (Aa) described in [1], wherein in the general formula (1), $R^1$ and $R^2$ are each a methyl group, $R^a$ is a divalent $C_{6-9}$ bridged cyclic hydrocarbon group, and m and n are each 1.

[3] The dental polymerizable monomer (Aa) described in [2], wherein in the general formula (1), the moiety of the general formula (3a) below that is interposed between the two carbamoyl groups is a bridged cyclic hydrocarbon group represented by the general formula (2a) below.

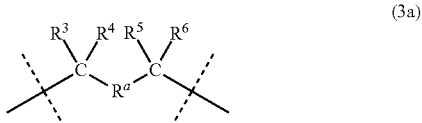

(3a)

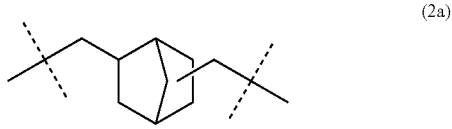

(2a)

[4] The dental polymerizable monomer (Aa) described in [2] or [3], wherein in the general formula (1), $R^7$ and $R^8$ are each a hydrogen atom, and $R^b$ and $R^c$ are each independently a $C_{2-6}$ linear alkylene or $C_{2-6}$ linear oxyalkylene group optionally substituted with a $C_{1-3}$ alkyl group in place of a hydrogen atom.

[10] A dental polymerizable monomer composition (Ba) including the polymerizable monomer (A) described in [1], the polymerizable monomer (A) including a urethane methacrylate of the general formula (1) in which:

$R^1$ and $R^2$ are each a methyl group; $R^3$, $R^4$, $R^5$ and $R^6$ are each a hydrogen atom; and $R^a$ is a divalent $C_{6-9}$ bridged cyclic hydrocarbon group, and m and n are each independently 0 or 1;

$R^a$ is a divalent $C_{6-9}$ aromatic hydrocarbon group, and m and n are each 0; or $R^a$ is a divalent $C_{6-9}$ unbridged cyclic hydrocarbon group, and one of m and n is 0 and the other is 1.

[11] The dental polymerizable monomer composition (Ba) described in [10], further including a (meth)acrylate monomer (Ca) having a viscosity at 25° C. of 1 to 5,000 mPa·s.

[12] The dental polymerizable monomer composition (Ba) described in [10] or [11], wherein the viscosity at 25° C. is 1 to 100,000 mPa·s.

[13] A dental composition (a) including the dental polymerizable monomer composition (Ba) described in any one of [10] to [12].

[14] The dental composition (a) described in [13], further including a filler.

[15] A cured product of the dental composition (a) described in [13] or [14].

The present inventor has found that a dental adhesive composition which contains a urethane (meth)acrylate having a structure with appropriate hydrophobicity, a structure with appropriate rigidity and a structure with appropriate flexibility exhibits a high bonding performance and attains excellent storage stability. After extensive studies, the present inventor completed the second aspect of the present invention.

The second aspect of the present invention provides polymerizable monomers for dental adhesive compositions, and dental adhesive compositions described in [5] to [9] and [16] to [22] below.

[5] A polymerizable monomer (Ab) for dental adhesive compositions described in [1], the polymerizable monomer (Ab) being of the general formula (1) in which:

$R^1$ and $R^2$ are each a hydrogen atom or a methyl group; and $R^a$ is a divalent $C_{6-9}$ aromatic hydrocarbon group or a divalent $C_{6-9}$ bridged cyclic hydrocarbon group, and m is 1; or $R^a$ is a divalent $C_{6-9}$ unbridged cyclic hydrocarbon group, and m and n are each 1.

[6] The polymerizable monomer (Ab) for dental adhesive compositions described in [5], wherein n is 1.

[7] The polymerizable monomer (Ab) for dental adhesive compositions described in [5] or [6], wherein $R^a$ is a divalent $C_{6-9}$ aromatic hydrocarbon group, and $R^3$, $R^4$, $R^5$ and $R^6$ are each a hydrogen atom;

$R^a$ is a divalent $C_{6-9}$ bridged cyclic hydrocarbon group, and $R^3$, $R^4$, $R^5$ and $R^6$ are each a hydrogen atom;

$R^a$ is a divalent $C_{6-9}$ unbridged cyclic hydrocarbon group, and $R^3$, $R^4$, $R^5$ and $R^6$ are each a hydrogen atom; or $R^a$ is a divalent $C_{6-9}$ aromatic hydrocarbon group, and $R^3$, $R^4$, $R^5$ and $R^6$ are each a methyl group.

[8] The polymerizable monomer (Ab) for dental adhesive compositions described in [7], wherein the moiety of the general formula (2″b) below including $R^a$ in the general formula (1) is a structure represented by any of the general formulas (3b), (4b), (5b), (6b) and (7b) below.

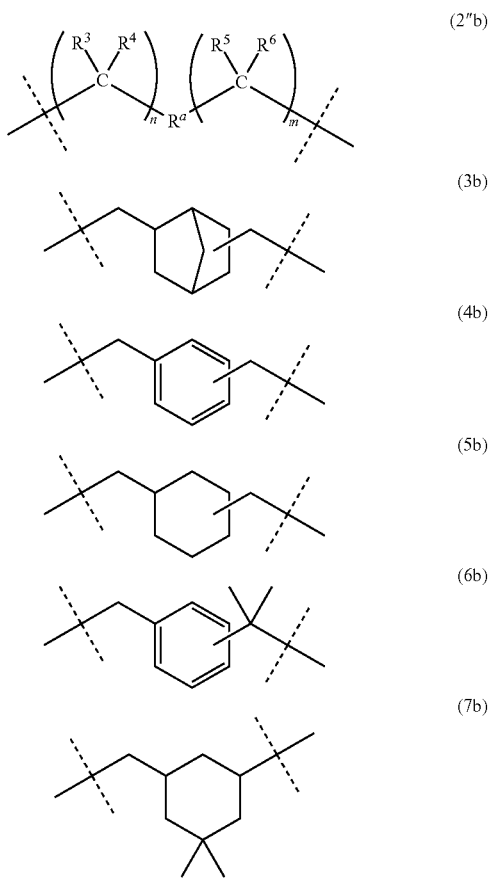

[9] The polymerizable monomer (Ab) for dental adhesive compositions described in any one of [5] to [8], wherein in the general formula (1), $R^7$ and $R^8$ are each a hydrogen atom, and $R^b$ and $R^c$ are each independently a $C_{2-6}$ linear alkylene or $C_{2-6}$ linear oxyalkylene group optionally substituted with a $C_{1-3}$ alkyl group in place of a hydrogen atom.

[16] A dental adhesive composition (b) including the polymerizable monomer (A) of the general formula (1) described in [1].

[17] The dental adhesive composition (b) described in [16], wherein the polymerizable monomer (A) is of the general formula (1) in which m and n are each independently 0 or 1.

[18] The dental adhesive composition (b) including a polymerizable monomer (A) described in [17], the polymerizable monomer (A) including a urethane acrylate of the general formula (1) in which:

$R^1$ and $R^2$ are each a hydrogen atom; and $R^a$ is a divalent $C_{6-9}$ aromatic hydrocarbon group or a divalent $C_{6-9}$ bridged cyclic hydrocarbon group, and m and n are each independently 0 or 1; or $R^a$ is a divalent $C_{6-9}$ unbridged cyclic hydrocarbon group, and m and n are each 1.

[19] The dental adhesive composition (b) described in any one of [16] to [18], further including a (meth)acrylate monomer (Bb) containing an acidic group and a (meth) acryloyl group in the molecule.

[20] The dental adhesive composition (b) described in any one of [16] to [19], further including a (meth)acrylate monomer (Cb) having a viscosity at 25° C. of 1 to 5,000 mPa·s.

[21] The dental adhesive composition (b) described in any one of [16] to [20], further including at least one selected from a polymerization initiator (Db), a polymerization inhibitor (Eb) and a filler (Fb).

[22] The dental adhesive composition (b) described in any one of [16] to [21], wherein the viscosity at 25° C. is 1 to 100,000 mPa·s.

As a result of extensive studies directed to solving the problems discussed hereinabove, the present inventors have found that a dental adhesive curable composition (c) including a polymerizable monomer (A) that is a compound with a specific structure described below, an acidic group-containing polymerizable monomer (Bc), a polymerization initiator (Cc) and a reductant (Dc) can solve the aforementioned problems and attain the aforementioned objects, and has a small change in curing time after being long stored at room temperature and exhibits excellent adhesion. Based on the finding, the third aspect of the present invention has been completed.

That is, the third aspect of the present invention comprehends the items described in [23] to [40] below.

[23] A dental adhesive curable composition (c) including the polymerizable monomer (A) of the general formula (1) described in [1], an acidic group-containing polymerizable monomer (Bc), a polymerization initiator (Cc) and a reductant (Dc).

[24] A dental adhesive curable kit (αc) for preparing a dental adhesive curable composition (c) described in [23], the dental adhesive curable kit (αc) including at least a first composition and a second composition, at least one of the first composition and the second composition including a polymerizable monomer (A), the first composition including a reductant (Dc), the second composition including an acidic group-containing polymerizable monomer (Bc) and a polymerization initiator (Cc).

[25] The dental adhesive curable kit (αc) described in [24], wherein at least one of the first composition and the second composition further includes an additional polymerizable monomer (Ec) other than the polymerizable monomers (A) and (Bc).

[26] The dental adhesive curable composition (c) described in [23], wherein the polymerization initiator (Cc) includes a peroxide (Cc1).

[27] The dental adhesive curable composition (c) described in [26], wherein the peroxide (Cc1) is a diacyl peroxide (Cc11).

[28] The dental adhesive curable composition (c) described in any one of [23], [26] and [27], wherein the polymerization initiator (s) (Cc) includes a photopolymerization initiator (Cc2).

[29] The dental adhesive curable composition (c) described in [28], wherein the photopolymerization initiator (Cc2) is an α-ketocarbonyl compound (Cc21).

[30] The dental adhesive curable composition (c) described in any one of [23] and [26] to [29], wherein the reductants (Dc) include an amine compound (Dc1) and/or a salt thereof, and a sulfinic acid compound (Dc2) and/or a salt thereof.

[31] The dental adhesive curable composition (c) described in [30], wherein the amine compound (Dc1) and/or the salt thereof is an aromatic substituted glycine compound (Dc11) or a salt thereof.

[32] The dental adhesive curable composition (c) described in [30], wherein the amine compound (Dc1) and/or the salt thereof is an aromatic tertiary amine (Dc12).

[33] The dental adhesive curable composition (c) described in any one of [23] and [26] to [32], further including a filler (Fc).

[34] The dental adhesive curable composition (c) described in [33], wherein the filler (Fc) is an inorganic glass filler (Fc1) and/or a fine particulate silica filler (Fc2).

[35] The dental adhesive curable composition (c) described in any one of [23] and [26] to [34], wherein the polymerizable monomer (A) is of the general formula (1) in which m and n are each 1.

[36] The dental adhesive curable composition (c) described in any one of [23] and [26] to [34], wherein the polymerizable monomer (A) is of the general formula (1) in which one of m and n is 0 and the other is 1.

[37] The dental adhesive curable composition (c) described in any one of [23] and [26] to [36], wherein $R^3$, $R^4$, $R^5$ and $R^6$ in the general formula (1) are each a hydrogen atom.

[38] The dental adhesive curable composition (c) described in any one of [23] and [26] to [37], wherein $R^a$ in the general formula (1) is a divalent $C_{6-9}$ optionally bridged cyclic hydrocarbon group.

[39] The dental adhesive curable composition (c) described in any one of [23] and [26] to [37], wherein $R^a$ in the general formula (1) is a divalent $C_{6-9}$ aromatic hydrocarbon group.

[40] A dental adhesive resin cement including the dental adhesive curable composition (c) described in any one of [23] and [26] to [39].

As a result of extensive studies directed to solving the problems discussed hereinabove, the present inventor has succeeded in attaining good adhesion with respect to tooth structure while satisfying strength, flexibility and toughness of cured products and has also succeeded in simplifying handling during use, by using a urethane (meth)acrylate having a specific rigid skeleton. Based on the finding, the fourth aspect of the present invention has been completed.

That is, the fourth aspect of the present invention comprehends the items described in [41] to [50] below.

[41] A mobile tooth fixing material (βd) including a dental adhesive composition (d), the dental adhesive composition (d) including the polymerizable monomer (A) described in [1], a polymerizable monomer (Bd) having at least one acidic group in the molecule, and a photopolymerization initiator (Cd), the polymerizable monomer (A) being of the general formula (1) in which $R^a$ is a divalent $C_{6-9}$ aromatic hydrocarbon group or a divalent $C_{6-9}$ optionally bridged cyclic hydrocarbon group, $R^1$ and $R^2$ are each a hydrogen atom or a methyl group, and $R^7$ and $R^8$ are each a hydrogen atom.

[42] The mobile tooth fixing material (βd) including the dental adhesive composition (d) described in [41], which includes a flexible filler (Dd) in an amount of 0.5 to 70 parts by weight per 100 parts by weight of the dental adhesive composition (d).

[43] The mobile tooth fixing material (βd) including the dental adhesive composition (d) described in [42], wherein the filler (Dd) includes a filler including a crosslinked polymer.

[44] The mobile tooth fixing material (βd) including the dental adhesive composition (d) described in [42] or [43], wherein the filler (s) (Dd) includes a filler including a polyurethane.

[45] The mobile tooth fixing material (βd) including the dental adhesive composition (d) described in any one of [41] to [44], wherein the acidic group in the polymerizable monomer (Bd) having at least one acidic group in the molecule is at least one group selected from a carboxyl group, a phosphoric group and a sulfonic group.

[46] The mobile tooth fixing material (βd) including the dental adhesive composition (d) described in any one of [41] to [45], wherein the polymerizable monomer (A) is of the general formula (1) in which at least one of n and m is 1.

[47] The mobile tooth fixing material (βd) including the dental adhesive composition (d) described in any one of [41] to [46], wherein the polymerizable monomer (A) is of the general formula (1) in which the moiety represented by the general formula (2'd) below is a group represented by any of the general formulas (3d) to (7d) below.

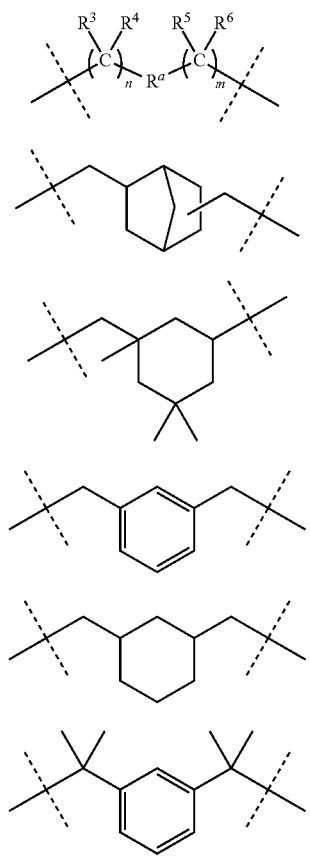

[48] The mobile tooth fixing material (βd) including the dental adhesive composition (d) described in [47], wherein the polymerizable monomer (A) is such that the moiety represented by the general formula (2'd) is a group represented by any of the general formulas (3d) to (5d).

[49] The mobile tooth fixing material (βd) including the dental adhesive composition (d) described in [48], wherein the polymerizable monomer (A) is such that the moiety represented by the general formula (2'd) is a group represented by the general formula (3d).

[50] The mobile tooth fixing material (βd) including the dental adhesive composition (d) described in any one of [41] to [49], which is a one-part composition.

The present inventors extensively studied dental curable compositions usable as dental cements focusing on the adhesion to teeth and the thermal stability of a first composition including an organic sulfinic acid compound. As a result, surprisingly, the present inventors have found that high adhesion to teeth and the thermal stability of a first composition including an organic sulfinic acid compound can be satisfied at the same time by using, as a polymerization accelerator, a system which combines an organic sulfinic acid compound having an electron withdrawing group and an aromatic amine compound having a nonaromatic carbonyl group. Based on the finding, the fifth aspect of the present invention has been completed.

That is, the fifth aspect of the present invention comprehends the items described in [51] to [61] below.

[51] A dental curable kit (αe) including at least a first composition and a second composition as components for forming a dental curable composition (e),
the first composition and the second composition each including a polymerizable monomer (αe),
the first composition including an aromatic amine compound (be) having a nonaromatic carbonyl group and an organic sulfinic acid compound (ce) having an electron withdrawing group,
the second composition including a polymerization initiator (de),
a mixture of the first composition and the second composition having a change in curing time of not more than 3 minutes before and after storage of the first composition at 75° C. for 24 hours.

[52] The dental curable kit (αe) described in [51], wherein the polymerizable monomer (αe) present in the first composition is an acidic group-free polymerizable monomer (αe-1).

[53] The dental curable kit (αe) described in [51] or [52], wherein the polymerizable monomer (αe) present in the second composition includes an acidic group-containing polymerizable monomer (αe-2).

[54] The dental curable kit (αe) described in any one of [51] to [53], wherein the polymerization initiator (de) is a peroxide (de-1).

[55] The dental curable kit (αe) described in any one of [51] to [54], wherein the first composition further includes an aromatic tertiary amine (ee).

[56] The dental curable kit (αe) described in any one of [51] to [55], wherein at least one of the first composition and the second composition further includes a filler (fe).

[57] The dental curable kit (αe) described in any one of [51] to [56], wherein the aromatic amine compound (be) having a nonaromatic carbonyl group is a compound represented by the following formula (5e).

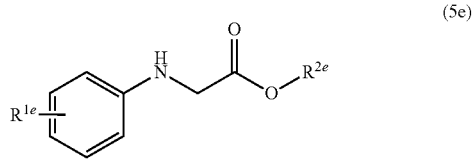

(In the formula (5e), $R^{1e}$ is a hydrogen atom or an alkyl group optionally having a functional group, and $R^{2e}$ is a hydrogen atom or a metal atom.)

[58] The dental curable kit (αe) described in any one of [51] to [57], wherein in the organic sulfinic acid compound (ce) having an electron withdrawing group, the Hammett substituent constant σp of the electron withdrawing group is 0.01 to 2.00.

[59] The dental curable kit (αe) described in any one of [51] to [58], wherein the amount of the organic sulfinic acid compound (ce) having an electron withdrawing group is 0.001 to 20 parts by weight per 100 parts by weight of the total of the polymerizable monomers (a) present in the dental curable kit (αe) as components for forming a dental curable composition (e).

[60] The dental curable kit (αe) described in any one of [51] to [59], wherein the weight ratio (ce)/(be) of the organic sulfinic acid compound (ce) having an electron withdrawing group to the aromatic amine compound (be) having a nonaromatic carbonyl group is 1/2 to 50/1.

[61] A dental cement including a dental curable composition (e) prepared from the dental curable kit (αe) described in any one of [51] to [60].

Advantageous Effects of Invention

Polymerizable monomers (A) obtained in the present invention are useful as dental materials.

A dental composition which contains a dental polymerizable monomer according to the first aspect of the present invention gives a cured product which has properties satisfying high elastic modulus and high strength. Thus, the dental composition obtained in the first aspect is suited for composite resin applications, for example, filling composite resins, coronal restoration composite resins, CAD/CAM block materials, artificial tooth materials and the like.

A dental adhesive composition which contains a polymerizable monomer for dental adhesive compositions according to the second aspect of the present invention has a high bonding performance and exhibits excellent storage stability. Thus, the dental adhesive composition obtained in the second aspect is suited as adhesive cements, bonding materials, mobile tooth fixing materials and the like.

A dental adhesive curable composition according to the third aspect of the present invention exhibits a sufficient curing performance even after long stored under room temperature storage conditions, and attains an excellent bonding performance while involving a simple bonding operation.

The fourth aspect of the present invention can provide a mobile tooth fixing material which satisfies strength, flexibility and toughness of cured products, attains good adhesion with respect to tooth structure, and is usable with easy handling.

A dental curable composition according to the fifth aspect of the present invention is advantageous in that it has high adhesion with respect to tooth structure and has excellent storage stability. Thus, the dental curable composition of the fifth aspect is best suited as a dental cement.

DESCRIPTION OF EMBODIMENTS

The present invention will be described in detail hereinbelow. In the present specification, the term "(meth)acrylic" means acrylic or methacrylic. For example, "(meth)acrylic acid" indicates methacrylic acid or acrylic acid. Similarly, the term "(meth)acryloyl" indicates "acryloyl" or "methacryloyl", and the term "(meth)acrylate" means "acrylate" or "methacrylate".

A dental polymerizable monomer (A) in the present invention is a urethane methacrylate which may be represented by the following general formula (1).

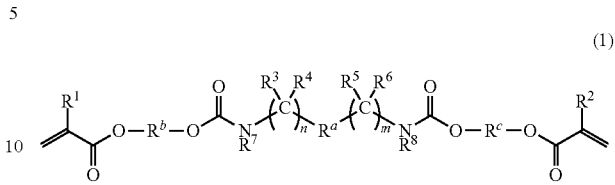

(1)

In the general formula (1), $R^a$ is a divalent aromatic hydrocarbon group or a divalent optionally bridged cyclic hydrocarbon group, $R^1$ and $R^2$ are each a hydrogen atom or a $C_{1-3}$ alkyl group, $R^3$, $R^4$, $R^5$ and $R^6$ are each a hydrogen atom or a hydrocarbon group, $R^7$ and $R^8$ are each a hydrogen atom or a methyl group, m and n are each independently 0 to 4, and $R^b$ and $R^c$ are each independently a $C_{2-6}$ linear alkylene or $C_{2-6}$ linear oxyalkylene group optionally substituted with a $C_{1-3}$ alkyl group or a (meth)acryloyloxymethylene group in place of a hydrogen atom.

The number of carbon atoms in the divalent aromatic hydrocarbon group or the divalent optionally bridged cyclic hydrocarbon group present in $R^a$ in the general formula (1) is not limited, but is preferably 6 to 9.

Hereinbelow, aspects of the present invention will be described in greater detail.

[Dental Polymerizable Monomers (Aa)]

The first aspect of the present invention relates to a dental polymerizable monomer (Aa) represented by the general formula (1) in which $R^1$ and $R^2$ are each a methyl group, $R^a$ is a divalent $C_{6-9}$ bridged cyclic hydrocarbon group, and m and n are each 1. Such monomers will be described in detail below.

From points of view such as industrial productivity, $R^7$ and $R^8$ of the dental polymerizable monomer (Aa) are, in a preferred embodiment, each a hydrogen atom.

From points of view such as hydrophobicity, it is preferable that one of $R^7$ and $R^8$ be a methyl group, and it is more preferable that both be methyl groups.

In a preferred embodiment, the dental polymerizable monomer (Aa) is a urethane methacrylate which may be represented by the general formula (1) in which $R^7$ and $R^8$ are hydrogen atoms, namely, the general formula (1a) below.

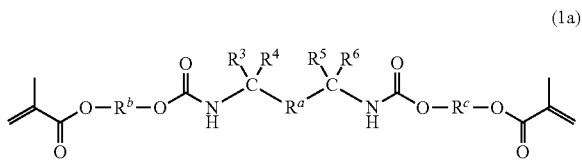

(1a)

The definitions of $R^a$, $R^3$, $R^4$, $R^5$, $R^6$, $R^b$ and $R^c$ in the general formula (1a) are the same as in the general formula (1).

When used as a dental polymerizable monomer (Aa), the divalent bridged cyclic hydrocarbon group present in $R^a$ in the general formulas (1) and (1a) has 6 to 9 carbon atoms to ensure appropriate rigidity, and preferably has 6 to 7 carbon atoms. Specific examples of the bridged cyclic hydrocarbon groups include bicyclo[2.2.1]heptylene group. In this case, in the general formulas (1) and (1a), the hydrocarbon ring in $R^a$ may be bonded to the two carbon atoms adjacent to $R^a$ at any positions without limitation. To attain the advantageous effects of the first aspect of the present invention, it is preferable that such two bonds be not present on the same carbon atom in the hydrocarbon ring, and it is more preferable that such two bonds be not on carbon atoms adjacent to each other. Such regioisomers may be used singly, or two or more may be used in combination.

When used as a dental polymerizable monomer (Aa), $R^3$, $R^4$, $R^5$ and $R^6$ in the general formula (1) and the general formula (1a) are each a hydrogen atom or a hydrocarbon group. To ensure appropriate rigidity, $R^3$, $R^4$, $R^5$ and $R^6$ are preferably each a methyl group or a hydrogen atom, and more preferably each a hydrogen atom.

When used as a dental polymerizable monomer (Aa), the moiety of the general formula (3a) below that is interposed between the two carbamoyl groups in the general formula (1) and the general formula (1a) is, in a preferred embodiment, represented by the following general formula (2a).

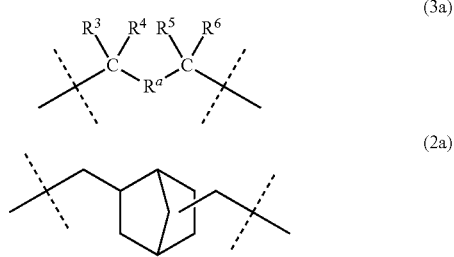

When used as a dental polymerizable monomer (Aa), to ensure that the dental polymerizable monomer (Aa) has appropriate flexibility, $R^b$ and $R^c$ in the general formulas (1) and (1a) are each independently a $C_{2-6}$ linear alkylene or $C_{2-6}$ linear oxyalkylene group optionally substituted with a $C_{1-3}$ alkyl group or a (meth)acryloyloxymethylene group in place of a hydrogen atom. Preferably, $R^b$ and $R^c$ are each a $C_{2-6}$ linear alkylene or $C_{2-6}$ linear oxyalkylene group optionally substituted with a $C_{1-3}$ alkyl group in place of a hydrogen atom.

Of the compounds represented by the general formula (1), a dental polymerizable monomer (Aa) constituting a preferred embodiment is one in which $R^7$ and $R^8$ are each a hydrogen atom, and $R^b$ and $R^c$ are each independently a $C_{2-6}$ linear alkylene or $C_{2-6}$ linear oxyalkylene group optionally substituted with a $C_{1-3}$ alkyl group in place of a hydrogen atom.

In a preferred embodiment, $R^b$ and $R^c$ in the general formulas (1) and (1a) are each a $C_{2-4}$ linear alkylene group or a $C_{2-4}$ linear oxyalkylene group in each of which any hydrogen atom may be substituted by a $C_{1-3}$ alkyl group.

Examples of the linear alkylene groups include —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—. Of these, preferred linear alkylene groups are, for example, —$CH_2CH_2$—, —$CH_2CH_2CH_2$— and —$CH_2CH_2CH_2CH_2$—. Examples of the linear oxyalkylene groups include —$CH_2CH_2OCH_2CH_2$— and —$CH_2CH_2OCH_2CH_2OCH_2CH_2$—. Of these, a preferred linear oxyalkylene group is, for example, —$CH_2CH_2OCH_2CH_2$—. To ensure that the dental polymerizable monomer (Aa) will exhibit appropriate flexibility, the linear alkylene groups or the linear oxyalkylene groups each usually have 2 to 6 carbon atoms, preferably 2 to 4 carbon atoms, and more preferably 2 carbon atoms.

The above linear alkylene groups or linear oxyalkylene groups may be substituted with an alkyl group or a (meth)acryloyloxymethylene group described below in place of a hydrogen atom. The number of such substituents is preferably 0 to 4, more preferably 0 to 2, and still more preferably 0 to 1 per one linear alkylene group or linear oxyalkylene group. In a preferred embodiment, the number of substituents is 0, that is, the linear alkylene group or the linear oxyalkylene group has no substituents, in which case the viscosity of the monomer is advantageously reduced.

Examples of the alkyl groups which may substitute for hydrogen atoms in the linear alkylene groups or the linear oxyalkylene groups include $CH_3$—, $CH_3CH_2$—, $CH_3CH_2CH_2$— and $(CH_3)_2CH$—. To ensure that the dental polymerizable monomer (Aa) will exhibit appropriate flexibility, the alkyl groups preferably have 1 to 3 carbon atoms, more preferably 1 to 2 carbon atoms, and still more preferably 1 carbon atom.

Examples of the (meth)acryloyloxymethylene groups which may substitute for hydrogen atoms in the linear alkylene group or the linear oxyalkylene group include methacryloyloxymethylene group and acryloyloxymethylene group.

Of the dental polymerizable monomers (Aa) that are urethane methacrylates, those urethane methacrylates represented by the following chemical formulas are preferable.

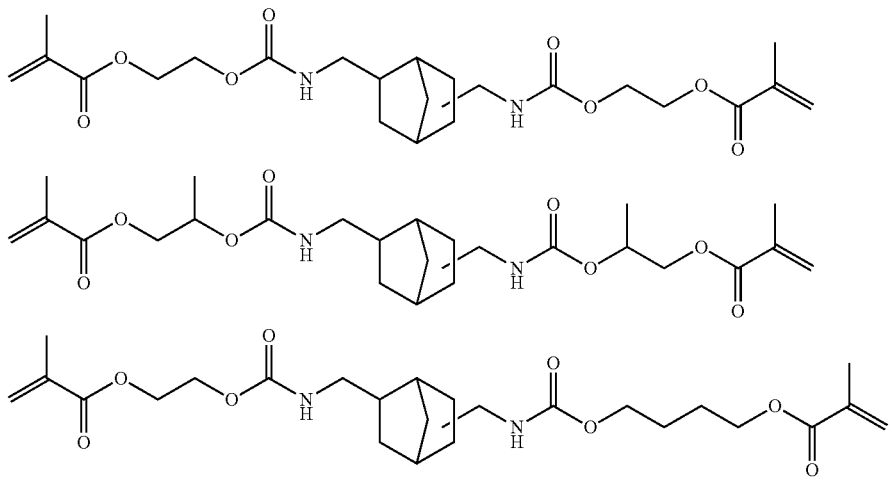

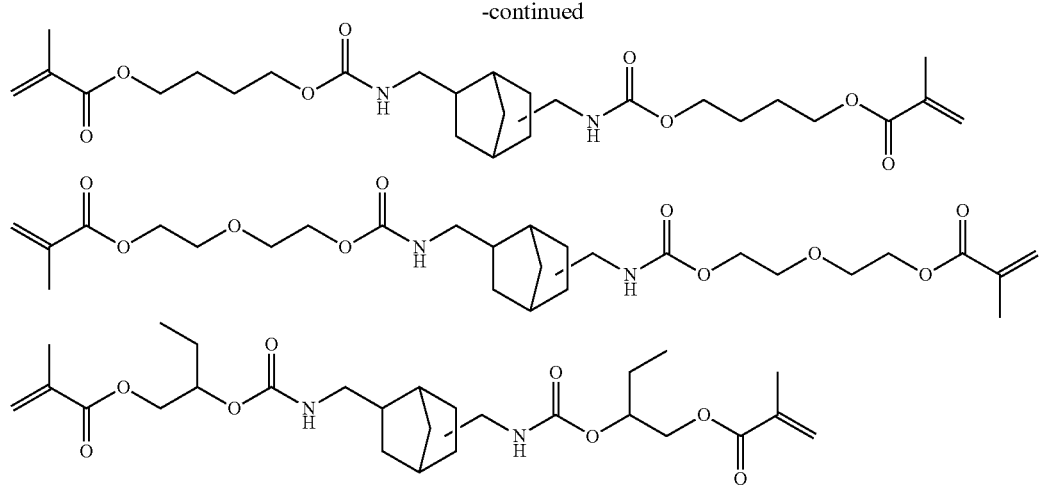

The urethane methacrylates may be used singly, or two or more may be used in combination.

The dental polymerizable monomer (A), and the dental polymerizable monomer (Aa) (in particular, one in which $R^7$ and $R^8$ are hydrogen atoms) representing a preferred embodiment thereof, may be obtained by, for example, reacting a diisocyanate (a1a) with appropriate rigidity represented by the general formula (4a) below with a hydroxymethacrylate (a2a) with appropriate flexibility represented by the general formula (5a) below.

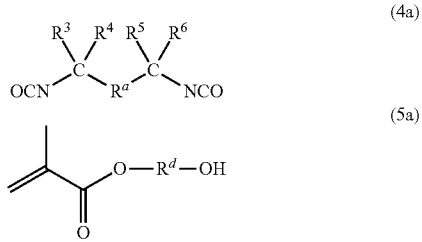

In the general formula (4a), $R^a$ is defined the same as $R^a$ in the general formula (1), namely, a divalent aromatic hydrocarbon group or a divalent optionally bridged cyclic hydrocarbon group. In the case of a dental polymerizable monomer (Aa), $R^a$ is a divalent $C_{6-9}$ bridged cyclic hydrocarbon group. Details (for example, preferred embodiments) of $R^a$ in the general formula (4a) are the same as the detailed description of $R^a$ in the general formula (1) representing a dental polymerizable monomer (Aa). $R^3$, $R^4$, $R^5$ and $R^6$ in the general formula (4a) are each a hydrogen atom or a hydrocarbon group. Details (for example, preferred embodiments) of $R^3$, $R^4$, $R^5$ and $R^6$ in the general formula (4a) are the same as the detailed description of $R^3$, $R^4$, $R^5$ and $R^6$ in the general formula (1) representing a dental polymerizable monomer (Aa). A specific preferred diisocyanate (a1a) is a compound represented by the following general formula (6a).

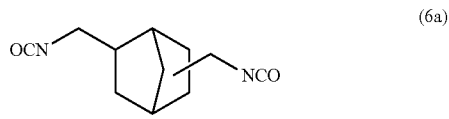

The diisocyanates (a1a) may be used singly, or two or more may be used in combination.

In the general formula (5a) above, $R^d$ is a $C_{2-6}$ linear alkylene group or a $C_{2-6}$ linear oxyalkylene group which each independently is optionally substituted with a $C_{1-3}$ alkyl group or a (meth)acryloyloxymethylene group in place of a hydrogen atom. Details (for example, preferred embodiments) of $R^d$ in the general formula (5a) are the same as the detailed description of $R^b$ and $R^c$ in the general formula (1) representing a dental polymerizable monomer (Aa).

The hydroxymethacrylates (a2a) may be used singly, or two or more may be used in combination.

In the reaction, the diisocyanate (a1a) and the hydroxymethacrylate (a2a) may be used in any quantitative ratio without limitation. Usually, they are used in such amounts that the proportion of the isocyanate groups in the diisocyanate (a1a) is equal to that of the hydroxyl groups in the hydroxymethacrylate (a2a), namely, the ratio is 1:1. If the proportion of the isocyanate groups in the diisocyanate (a1a) is above this ratio, isocyanate groups will remain after the reaction. If the proportion of the hydroxyl groups in the hydroxymethacrylate (a2a) is above this ratio, hydroxyl groups will remain after the reaction. Depending on the purpose of use, the compounds are sometimes reacted in such a ratio that one of the raw materials will remain in a slight amount.

As described hereinabove, the dental polymerizable monomers (A) and (Aa) can be obtained, for example, by reacting the diisocyanate (a1a) with the hydroxymethacrylate (a2a). The reaction may be performed by a known method or a method in accordance with a known method.

For example, the dental polymerizable monomers (A) and (Aa) may be obtained by mixing the diisocyanate (a1a) with the hydroxymethacrylate (a2a). During this process, the isocyanate groups in the diisocyanate (a1a) react with the hydroxyl groups in the hydroxymethacrylate (a2a) to form the carbamoyl groups. This reaction is sometimes called the urethane-forming reaction.

The reaction may be performed in the presence or absence of a catalyst. To enhance the reaction rate, a catalyst is preferably added. Known catalysts capable of accelerating the urethane-forming reaction may be used as the catalysts.

Examples of the urethane-forming catalysts include organotin compounds such as dibutyltin dilaurate, dibutyltin dioctoate and tin octanoate; organic compounds of metals other than tin such as copper naphthenate, cobalt naphthenate, zinc naphthenate, acetylacetonatozirconium, acetylacetonatoiron and acetylacetonatogermanium; amine compounds and salts thereof such as triethylamine, 1,4-diazabicyclo[2.2.2]octane, 2,6,7-trimethyl-1-diazabicyclo[2.2.2]octane, 1,8-diazabicyclo[5.4.0]undecene, N,N-dimethylcyclohexylamine, pyridine, N-methylmorpholine, N,N,N',N'-tetramethylethylenediamine, N,N,N',N'-tetramethyl-1,3-butanediamine, N,N,N',N'-pentamethyldiethylenetriamine, N,N,N',N'-tetra(3-dimethylaminopropyl)-methanediamine, N,N'-dimethylpiperazine and 1,2-dimethylimidazole; and trialkylphosphine compounds such as tri-n-butylphosphine, tri-n-hexylphosphine, tricyclohexylphosphine and tri-n-octylphosphine.

Of these, dibutyltin dilaurate and tin octanoate are preferable because such a compound facilitates the reaction at a low dose and shows high selectivity with respect to the diisocyanate compound. When the urethane-forming catalyst is used, the amount in which the catalyst is added is preferably 0.001 to 0.5 wt %, more preferably 0.002 to 0.3 wt %, and still more preferably 0.005 to 0.2 wt % relative to 100 wt % of the total weight of the diisocyanate (a1a) and the hydroxymethacrylate (a2a). If the amount is below the lower limit, the effect of the catalyst is so decreased that the reaction may take a significantly long time. If the amount is above the upper limit, the catalytic effect is so increased that a large amount of reaction heat is generated to make it difficult to control the temperature at times. The whole amount of the catalyst may be added at the start of the reaction, or the catalyst may be added to the reaction system successively or in portions as required. Such successive or portionwise addition of the catalyst prevents the generation of a large amount of reaction heat at an initial stage of the reaction, thus making it easier to control the reaction temperature.

The reaction temperature is not particularly limited, but is preferably 0 to 120° C., more preferably 20 to 100° C., and still more preferably 40 to 90° C. At a reaction temperature below the lower limit, the reaction rate is markedly decreased and the reaction requires a very long time to complete or does not complete at times. On the other hand, the reaction at a temperature above the upper limit may involve side reactions generating impurities. Such impurities may cause the coloration of the methacrylate compound produced.

To ensure stable production at the aforementioned preferred range of temperatures, it is preferable that the reaction temperature be controlled. The urethane-forming reaction is usually exothermic. In the case where the reaction generates a large amount of heat and the temperature of the reaction product may be elevated above the preferred range of the reaction temperature, cooling is sometimes performed. When the reaction has substantially completed and the temperature of the reaction product may be decreased below the preferred range of the reaction temperature, heating is sometimes performed.

The dental polymerizable monomers (A) and (Aa) have polymerization activity. Therefore, undesired polymerization can take place during their production when the monomers are subjected to high temperatures. To prevent such undesired polymerization, a known polymerization inhibitor may be added before the start of the reaction or during the reaction. The polymerization inhibitor is not particularly limited as long as it can suppress the reaction of (meth)acrylate groups during the production of dental polymerizable monomers (A) and (Aa). Examples include dibutylhydroxytoluene (BHT), hydroquinone (HQ), hydroquinone monomethyl ether (MEHQ) and phenothiazine (PTZ). Of these polymerization inhibitors, BHT is particularly preferable because the consumption of the inhibitor by the reaction with isocyanate groups is small as compared to other phenolic polymerization inhibitors and also because the coloration encountered with amine polymerization inhibitors is small. The amount of the polymerization inhibitor added is not particularly limited, but is preferably 0.001 to 0.5 wt %, more preferably 0.002 to 0.3 wt %, and still more preferably 0.005 to 0.3 wt % relative to the total weight of the diisocyanate (a1a) and the hydroxymethacrylate (a2a) taken as 100 wt %. If the amount is below the lower limit, the polymerization inhibitor may fail to perform as expected. If the amount is above the upper limit, a dental composition containing such a polymerizable monomer (A) or (Aa) may exhibit a markedly low curing rate and may have a limited practical applicability. A polymerization inhibitor may be already present as a stabilizer in the diisocyanate (a1a) or the hydroxymethacrylate (a2a) used as a raw material for the dental polymerizable monomer (A) or (Aa).

The urethane-forming reaction may involve a solvent. The solvent is not particularly limited as long as the solvent does not have practical reactivity with respect to the diisocyanate (a1a) and the hydroxymethacrylate (a2a), does not inhibit the reaction, and can dissolve the raw materials and the product. The reaction may be performed in the absence of solvents. The diisocyanate (a1a) is usually a low viscous liquid and is miscible with the hydroxymethacrylate (a2a) to allow the reaction to take place without solvents.

The diisocyanate (a1a) and the hydroxymethacrylate (a2a) may be mixed with each other by any method without limitation. For example, a controlled amount of the hydroxymethacrylate (a2a) may be admixed with the diisocyanate (a1a) placed in a reaction vessel; a controlled amount of the diisocyanate (a1a) may be admixed with the hydroxymethacrylate (a2a) placed in a reaction vessel; or controlled amounts of the diisocyanate (a1a) and the hydroxymethacrylate (a2a) may be added to a reaction vessel at the same time and mixed with each other. By these mixing methods, the amount of heat generated by the urethane-forming reaction can be controlled in an appropriate range and thus the temperature control during the reaction is facilitated. Alternatively, the urethane-forming reaction may be performed in such a manner that the whole amounts of the diisocyanate (a1a) and the hydroxymethacrylate (a2a) are added to a reaction vessel and thereafter the temperature is increased. During the reaction, the reaction temperature may be sharply increased due to the generation of reaction heat and a temperature control by cooling may be appropriately required at times.

Oxygen is effective as a polymerization inhibitor for compounds containing a (meth)acryloyl group. Thus, oxygen is sometimes introduced into the reactor to prevent undesired polymerization of (meth)acryloyl groups during the reaction. For example, oxygen may be introduced into the reactor in such a form as dried air, oxygen gas or a mixed gas of oxygen with an inert gas such as nitrogen, and is preferably introduced into the reactor as dried air or a mixed gas of oxygen with an inert gas such as nitrogen. For example, dried air may be obtained by removing water using a known drying method such as the use of a condensing air dryer or the like. A mixed gas of oxygen and an inert gas such as nitrogen may be obtained by mixing oxygen gas or the above dried air containing oxygen with a prescribed proportion of nitrogen. Here, nitrogen is preferably one that has been dehydrated by a known drying method. The method for introduction is not particularly limited. For example, the gas may be introduced in the form of bubbles from the bottom of the reaction vessel continuously or intermittently. Alternatively, the gas may be introduced continuously or intermittently to the space at the top of the reaction vessel. The rate of the introduction of dried air may be determined appropriately in accordance with factors such as the size of the reaction vessel. When, for example, the volume of the reaction vessel is 1 L, the introduction rate is usually 1 to 500 ml/min, and preferably 1 to 300 ml/min. If the rate is below 1 ml/min, oxygen cannot be introduced in a sufficient amount and may fail to serve as a polymerization inhibitor. If the rate is above 500 ml/min, the volatilization of the diisocyanate during the reaction is increased and the properties of the dental polymerizable monomers (A) and (Aa) after curing may be deteriorated.

If water is present as an impurity in the system during the urethane-forming reaction, the diisocyanate (a1a) and water can react with each other to form impurities having a higher molecular weight than the target product. The increase in the amount of such impurities disadvantageously causes the increase in the viscosity of the product. Thus, it is preferable that as little water as possible be present in the reaction system during the urethane-forming reaction.

From the above viewpoint, the amount of water present in the hydroxymethacrylate (a2a) is preferably as small as possible. Specifically, the amount of water is preferably not more than 0.5 wt %, more preferably not more than 0.3 wt %, and still more preferably not more than 0.1 wt % relative to the hydroxymethacrylate (a2a). In the case where the hydroxymethacrylate (a2a) contains more water than described above, it is preferable that the hydroxymethacrylate be dehydrated by a known method before used as a raw material for a urethane methacrylate that is a dental polymerizable monomer (A) or a dental polymerizable monomer (Aa) representing a preferred embodiment of the monomer. The reaction vessel in which the urethane-forming reaction will be performed is preferably dried by a known method to remove water therefrom.

Of the dental polymerizable monomers (A) and the dental polymerizable monomers (Aa) representing a preferred embodiment of the monomers, one in which $R^7$ and $R^8$ are methyl groups may be produced, for example, as described below. A dental polymerizable monomer (A) or (Aa) in which $R^7$ and $R^8$ are hydrogen atoms may be synthesized by the aforementioned method and may be thereafter reacted with a methylating agent (for example, methyl iodide) in the presence of a base (for example, sodium hydride) to form a dental polymerizable monomer (A) or (Aa) in which $R^7$ and $R^8$ are methyl groups.

[Dental Polymerizable Monomer Compositions (Ba)]

A dental polymerizable monomer composition (Ba) representing an embodiment of the first aspect of the present invention contains the dental polymerizable monomer (Aa) described hereinabove. Preferably, the dental polymerizable monomer composition (Ba) contains 1 to 99 wt % of the dental polymerizable monomer (Aa).

The dental polymerizable monomer composition (Ba) may contain, instead of the dental polymerizable monomer (Aa), a dental polymerizable monomer (A) represented by the general formula (1) in which $R^1$ and $R^2$ are each a methyl group, $R^3$, $R^4$, $R^5$ and $R^6$ are each a hydrogen atom, and $R^a$ is a divalent $C_{6-9}$ bridged cyclic hydrocarbon group, and m and n are each independently 0 or 1, or $R^a$ is a divalent $C_{6-9}$ aromatic hydrocarbon group, and m and n are each 0, or $R^a$ is a divalent $C_{6-9}$ unbridged cyclic hydrocarbon group, and one of m and n is 0 and the other is 1 (hereinafter, this dental polymerizable monomer will be also written as the dental polymerizable monomer (Aa')).

In this case, the dental polymerizable monomer composition (Ba) preferably contains 1 to 99 wt % of the dental polymerizable monomer (Aa').

Of the dental polymerizable monomers (Aa'), to attain higher rigidity, a more preferred dental polymerizable monomer (Aa') is one in which $R^a$ is a divalent $C_{6-9}$ bridged cyclic hydrocarbon group, and m and n are each independently 0 or 1, or $R^a$ is a divalent $C_{6-9}$ unbridged cyclic hydrocarbon group, and one of m and n is 0 and the other is 1; and a still more preferred dental polymerizable monomer (Aa') is one in which $R^a$ is a divalent $C_{6-9}$ bridged cyclic hydrocarbon group, and m and n are each 1, or $R^a$ is a divalent $C_{6-9}$ unbridged cyclic hydrocarbon group, and one of m and n is 0 and the other is 1.

Specific examples of the bridged cyclic hydrocarbon groups include bicyclo[2.2.1]heptylene group. Specific examples of the unbridged cyclic hydrocarbon groups include cyclohexylene group and 3,5,5-trimethylcyclohexylene group. To attain appropriate rigidity, $R^a$ in a preferred embodiment is a bridged cyclic hydrocarbon group. To attain appropriate hydrophobicity, $R^a$ in a preferred embodiment is an unbridged cyclic hydrocarbon group, in particular, a 3,5,5-trimethylcyclohexylene group.

Here, the hydrophobicity of compounds may be evaluated based on the 1-octanol/water partition coefficient measured in accordance with JIS 7260-107 or JIS 7260-117. The larger the partition coefficient, the higher the hydrophobicity. The hydrophobic tendency may be calculated by evaluating an index of expected equilibrium water content using a computational scientific technique. The lower the expected equilibrium water content, the higher the hydrophobicity.

When $R^a$ in the general formula (1) or (1a) is a cyclic hydrocarbon group, the hydrocarbon ring present in the cyclic hydrocarbon group may be bonded to the two carbon atoms adjacent to $R^a$ at any positions without limitation. To attain the advantageous effects of the first aspect of the present invention, it is preferable that such two bonds be not present on the same carbon atom in the hydrocarbon ring, and it is more preferable that such two bonds be not on carbon atoms adjacent to each other. Such regioisomers may be used singly, or two or more may be used in combination.

Details regarding the divalent $C_{6-9}$ bridged cyclic hydrocarbon groups (such as a preferred number of carbon atoms in the cyclic hydrocarbon group, and specific examples) are the same as the detailed description of the cyclic hydrocarbon groups represented by $R^a$ in the dental polymerizable monomer (Aa).

To ensure appropriate hydrophobicity and appropriate rigidity, the number of carbon atoms in the divalent unbridged cyclic hydrocarbon group is 6 to 9, and preferably 6 to 7. Specific examples of the unbridged cyclic hydrocarbon groups include cyclohexyl group and 3,5,5-trimethyl-cyclohexylene group.

To ensure appropriate hydrophobicity and appropriate rigidity, the number of carbon atoms in the divalent aromatic hydrocarbon group is 6 to 9, and preferably 6 to 7. Specific examples of such divalent aromatic hydrocarbon groups include phenylene group. In the general formula (1), the aromatic ring present in the aromatic hydrocarbon group may be bonded to the two carbon atoms adjacent to $R^a$ at any positions of ortho positions, meta positions and para positions. To attain the advantageous effects of the present invention, it is preferable that such two bonds be present on the meta positions or the para positions, and it is more preferable that such two bonds be on the meta positions. Such regioisomers may be used singly, or two or more may be used in combination.

Details (such as definitions and preferred embodiments) of $R^b$, $R^c$, $R^7$ and $R^8$ in the dental polymerizable monomer (Aa') are the same as the detailed description of $R^b$, $R^c$, $R^7$ and $R^8$ in the dental polymerizable monomer (Aa). The dental polymerizable monomer (Aa') may be produced by the same method as the dental polymerizable monomers (A) and (Aa).

The dental polymerizable monomer composition (Ba) is substantially a mixture of compounds having a polymerizable group, namely, a mixture of monomers. The polymerizable groups are not particularly limited as long as the polymerization reaction is accelerated by a known polymerization initiator to afford a cured product. Typical examples include (meth)acryloyl groups, aryl groups and epoxy groups, with (meth)acryloyl groups being preferable.

The viscosity of the dental polymerizable monomer composition (Ba) at 25° C. is preferably 1 to 100,000 mPa·s, more preferably 5 to 50,000 mPa·s, and still more preferably 10 to 20,000 mPa·s. If the viscosity is above this range, the polymerizable monomer composition (Ba) may exhibit poor miscibility when it is mixed together with additional components described later.

The dental polymerizable monomer composition (Ba) may contain the polymerization inhibitor described hereinabove in order to prevent undesired polymerization thereof and to attain enhanced storage stability.

[(Meth)Acrylate Monomers (Ca)]

The dental polymerizable monomer composition (Ba) may contain a (meth)acrylate monomer (Ca) other than the dental polymerizable monomers (Aa) and (Aa'). The incorporation of a (meth)acrylate monomer (Ca) to the dental polymerizable monomer composition (Ba) may serve to control, for example, the viscosity and mechanical strength of the dental polymerizable monomer composition. (Meth)acrylate monomers described below may be selected in accordance with the purpose and may be added in an appropriate amount so that the purpose will be fulfilled.

The number of the polymerizable groups present in the (meth)acrylate monomer (Ca) may be 1, or may be 2 or greater. The number of the polymerizable groups is preferably 2 to 10. The number of the polymerizable groups is more preferably 2 to 6. The number of the polymerizable groups is still more preferably 2 to 4. The (meth)acrylate monomer (Ca) may be composed of one kind of compound, or may be composed of a mixture of two or more kinds of compounds.

The molecular weight of the (meth)acrylate monomer (Ca) is preferably 80 to 2000, and more preferably 150 to 1000. If the molecular weight is below this range, the compound has a low boiling point. Thus, the above lower limit is advantageous from the point of view of handling properties in the preparation of a dental composition. If the molecular weight is higher than the above range, the compound tends to exhibit a high viscosity. Thus, the above upper limit is advantageous from the point of view of handling properties in the preparation of a dental composition.

Examples of the (meth)acrylate monomers (Ca) having one polymerizable group include those polymerizable compounds represented by the general formula (7a) below.

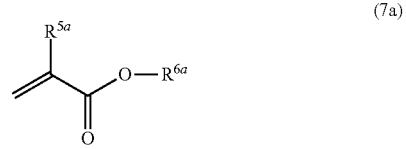

(7a)

In the general formula (7a), $R^{5a}$ is a hydrogen atom or a methyl group, and $R^{6a}$ is a $C_{1-20}$ monovalent organic group which may contain oxygen or nitrogen.

Examples of the monovalent organic groups include hydrocarbon groups such as $C_{1-20}$ acyclic hydrocarbon groups, for example, alkyl groups, alkenyl groups and alkynyl groups, and $C_{1-20}$ cyclic hydrocarbon groups, for example, cycloalkyl groups, cycloalkenyl groups, cycloalkynyl groups and aryl groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, alkoxyalkyl groups, alkoxyalkylene glycol groups and tetrahydrofurfuryl groups. The $C_{1-20}$ cyclic hydrocarbon groups may have acyclic hydrocarbon moieties. Further, the acyclic hydrocarbon moieties present in these groups may be linear or branched.

In the case where the $C_{1-20}$ hydrocarbon groups or the $C_{1-20}$ oxygen-containing hydrocarbon groups contain linear alkylene moieties, at least one of the methylene groups in such moieties may be substituted by an ester bond, an amide bond, a carbonate bond, a urethane bond (a carbamoyl group) or a urea bond (but the methylene groups are not substituted contiguously).

Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl-containing compounds represented by the general formula (7a) include methyl methacrylate, ethyl methacrylate, propyl methacrylate, butyl methacrylate, hexyl methacrylate, cyclohexyl methacrylate, ethoxydiethylene glycol methacrylate, methoxytriethylene glycol methacrylate, phenoxyethyl methacrylate, 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate and 1,4-cyclohexanedimethanol monomethacrylate.

Examples of the acryloyl-containing compounds represented by the general formula (7a) include methyl acrylate, ethyl acrylate, propyl acrylate, butyl acrylate, hexyl acrylate, cyclohexyl acrylate, ethoxydiethylene glycol acrylate, methoxytriethylene glycol acrylate, phenoxyethyl acrylate, 2-hydroxyethyl acrylate, 2-hydroxypropyl acrylate, 2-hydroxybutyl acrylate, 2-hydroxy-3-phenoxypropyl acrylate, 4-hydroxybutyl acrylate and 1,4-cyclohexanedimethanol monoacrylate.

Examples of the (meth)acrylate monomers (Ca) having two or more polymerizable groups include those polymerizable compounds represented by the general formula (8a) below.

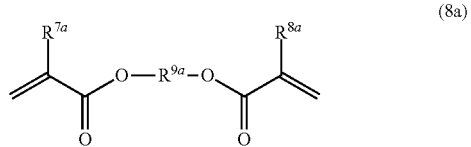

In the general formula (8a), $R^{7a}$ and $R^{8a}$ each represent a hydrogen atom or a methyl group and may be the same as or different from each other; and $R^{9a}$ represents a $C_{1-40}$ divalent organic group which may contain oxygen or nitrogen. The dental polymerizable monomers (Aa) are not categorized as the compounds represented by the general formula (8a).

Examples of the divalent organic groups include hydrocarbon groups, for example, $C_{1-40}$ acyclic hydrocarbon groups such as alkylene groups, alkenylene groups and alkynylene groups, and $C_{1-40}$ cyclic hydrocarbon groups such as cycloalkylene groups, cycloalkenylene groups, cycloalkynylene groups and arylene groups; and $C_{1-40}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-40}$ cyclic hydrocarbon groups may have acyclic hydrocarbon moieties. Further, the acyclic hydrocarbon moieties present in these groups may be linear or branched.

In the case where the $C_{1-40}$ hydrocarbon groups or the $C_{1-40}$ oxygen-containing hydrocarbon groups contain linear alkylene moieties, at least one of the methylene groups in such moieties may be substituted by an ester bond, an amide bond, a carbonate bond, a urethane bond (a carbamoyl group) or a urea bond (but the methylene groups are not substituted contiguously).

Further, hydrogen atoms present in the organic groups such as the $C_{1-40}$ hydrocarbon groups and the $C_{1-40}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

Among the polymerizable compounds represented by the general formula (8a), some preferred polymerizable compounds are those polymerizable compounds in which $R^{9a}$ is a linear alkylene group having 2 to 20 carbon atoms, desirably 4 to 12 carbon atoms.

Examples of the compounds which correspond to the above preferred polymerizable compounds and have methacryloyl groups include 1,4-butanediol dimethacrylate, 1,6-hexanediol dimethacrylate, 1,8-octanediol dimethacrylate, 1,9-nonanediol dimethacrylate and 1,10-decanediol dimethacrylate.

Examples of the compounds which correspond to the above preferred polymerizable compounds and have acryloyl groups include 1,4-butanediol diacrylate, 1,6-hexanediol diacrylate, 1,8-octanediol diacrylate, 1,9-nonanediol diacrylate and 1,10-decanediol diacrylate.

Among the polymerizable compounds represented by the general formula (8a), other preferred polymerizable compounds are those polymerizable compounds in which $R^{9a}$ is a linear oxyalkylene group having 2 to 20 carbon atoms, desirably 4 to 12 carbon atoms.

Examples of the compounds which correspond to the above preferred polymerizable compounds and have methacryloyl groups include ethylene glycol dimethacrylate, diethylene glycol dimethacrylate, triethylene glycol dimethacrylate, tetraethylene glycol dimethacrylate, polyethylene glycol dimethacrylate, tripropylene glycol dimethacrylate, tetrapropylene glycol dimethacrylate and polypropylene glycol dimethacrylate.

Examples of the compounds which correspond to the above preferred polymerizable compounds and have acryloyl groups include ethylene glycol diacrylate, diethylene glycol diacrylate, triethylene glycol diacrylate, tetraethylene glycol diacrylate, polyethylene glycol diacrylate, tripropylene glycol diacrylate, tetrapropylene glycol diacrylate and polypropylene glycol diacrylate.

Among the polymerizable compounds represented by the general formula (8a), other preferred polymerizable compounds are carbamoyl group-containing polymerizable compounds represented by the general formula (9a) below. The dental polymerizable monomers (Aa) are not categorized as the compounds represented by the general formula (9a).

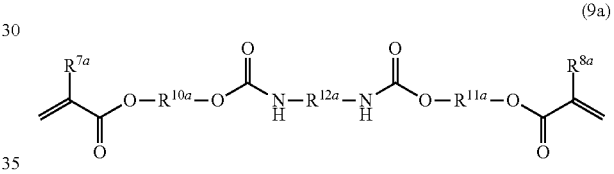

In the general formula (9a), $R^{7a}$ and $R^{8a}$ each represent a hydrogen atom or a methyl group and may be the same as or different from each other; and $R^{10a}$ and $R^{11}a$ each represent a $C_{1-12}$ divalent organic group which may contain oxygen, and may be the same as or different from each other.

Examples of the divalent organic groups include hydrocarbon groups, for example, $C_{1-12}$ acyclic hydrocarbon groups such as alkylene groups, and $C_{2-12}$ cyclic hydrocarbon groups such as cycloalkylene groups and arylene groups; and $C_{1-12}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. Further, the acyclic hydrocarbon moieties present in these groups may be linear or branched.

Further, hydrogen atoms present in the organic groups such as the $C_{1-12}$ hydrocarbon groups and the $C_{1-12}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

In the general formula (9a), $R^{12a}$ represents a $C_{1-20}$ divalent organic group which may contain oxygen. Examples of the divalent organic groups include $C_{1-20}$ acyclic hydrocarbon groups such as alkylene groups, and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. Further, the acyclic hydrocarbon moieties present in these groups may be linear or branched.

Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl group-containing compounds represented by the general formula (9a) include urethane methacrylates formed by the reaction between a hydroxymethacrylate such as 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate or 1,4-cyclohexanedimethanol monomethacrylate, and a diisocyanate such as 2,4- or 2,6-toluene diisocyanate, 4,4'-, 2,4'- or 2,2'-diphenylmethane-diisocyanate, 1,6-hexamethylene diisocyanate, or 2,2,4- or 2,4,4-trimethyl-1,6-hexamethylene-diisocyanate. Examples of such urethane methacrylates include 2,2,4-trimethylhexamethylene bis(2-carbamoyloxyethyl) dimethacrylate (UDMA).

Examples of the acryloyl group-containing compounds represented by the general formula (9a) include urethane acrylates formed by the reaction between a hydroxyacrylate such as 2-hydroxyethyl acrylate, 2-hydroxypropyl acrylate, 2-hydroxybutyl acrylate, 2-hydroxy-3-phenoxypropyl acrylate, 4-hydroxybutyl acrylate or 1,4-cyclohexanedimethanol monoacrylate, and a diisocyanate such as 2,4- or 2,6-toluene diisocyanate, 4,4'-, 2,4'- or 2,2'-diphenylmethane-diisocyanate, 1,6-hexamethylene diisocyanate, or 2,2,4- or 2,4,4-trimethyl-1,6-hexamethylene-diisocyanate. Examples of such urethane acrylates include 2,2,4-trimethylhexamethylene bis(2-carbamoyloxyethyl) diacrylate).

Among the polymerizable compounds represented by the general formula (8a), other preferred compounds are those polymerizable compounds represented by the general formula (10a) below.

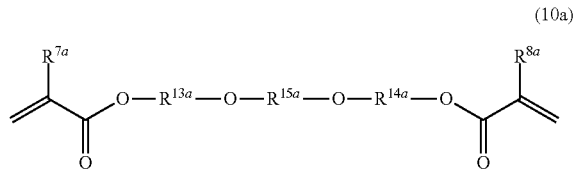
(10a)

In the general formula (10a), $R^{7a}$ and $R^{8a}$ each represent a hydrogen atom or a methyl group and may be the same as or different from each other; and $R^{13a}$ and $R^{14a}$ each represent a $C_{1-12}$ divalent organic group which may contain oxygen, and may be the same as or different from each other.

Examples of the divalent organic groups include hydrocarbon groups, for example, $C_{1-12}$ acyclic hydrocarbon groups such as alkylene groups, and $C_{2-12}$ cyclic hydrocarbon groups such as cycloalkylene groups and arylene groups; and $C_{1-12}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{2-12}$ cyclic hydrocarbon groups may have acyclic hydrocarbon moieties. Further, the acyclic hydrocarbon moieties present in these groups may be linear or branched.

Further, hydrogen atoms present in the organic groups such as the $C_{1-12}$ hydrocarbon groups and the $C_{1-12}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

In the general formula (10a), $R^{15a}$ represents a $C_{1-20}$ divalent organic group which may contain oxygen.

Examples of the divalent organic groups include $C_{1-20}$ hydrocarbon groups such as alkylene groups, cycloalkylene groups and arylene groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-20}$ cyclic hydrocarbon groups may have acyclic hydrocarbon moieties. The acyclic hydrocarbon moieties contained in these groups may be linear or branched.

Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl group-containing compounds represented by the general formula (10a) include 2,2-bis[4-(3-methacryloyloxy-2-hydroxypropoxy)phenyl] propane (Bis-GMA), ethylene oxide-modified bisphenol A dimethacrylate and propylene oxide-modified bisphenol A dimethacrylate.

Examples of the acryloyl group-containing compounds represented by the general formula (10a) include 2,2-bis[4-(3-acryloyloxy-2-hydroxypropoxy)phenyl]propane, ethylene oxide-modified bisphenol A diacrylate and propylene oxide-modified bisphenol A diacrylate.

[Dental Compositions (a)]

A dental composition (a) representing an embodiment of the first aspect of the present invention contains the dental polymerizable monomer (Aa) or (Aa') described hereinabove. Preferably, the dental composition (a) contains 1 to 99 wt % of the dental polymerizable monomer (Aa) or (Aa'). The dental composition (a) is sometimes produced by first producing a dental polymerizable monomer composition (Ba) as described hereinabove, and thereafter adding optional components described later to the monomer composition (Ba). Alternatively, the composition may be produced by adding, to the dental polymerizable monomer (Aa) or (Aa'), constituent components for the dental polymerizable monomer composition (Ba) other than the polymerizable monomers (Aa) and (Aa'), and optional components described later. The dental composition (a) may be a blend of the dental polymerizable monomer composition (Ba) and a polymerization initiator described later.

By virtue of the incorporation of the dental polymerizable monomer (Aa) or (Aa') to the dental composition (a), namely, by virtue of the incorporation of the dental polymerizable monomer composition (Ba) to the dental composition (a), the dental composition gives a cured product which has properties satisfying high elastic modulus and high strength.

The detailed reasons why the dental composition (a) attains such characteristics are not clear. The molecule of the dental polymerizable monomer (Aa) or (Aa') has a $C_{6-9}$ divalent optionally bridged cyclic hydrocarbon group or a $C_{6-9}$ divalent aromatic hydrocarbon group. In this case, it is assumed that the exhibition of the above characteristics is attributed to the presence of such a $C_{6-9}$ divalent optionally bridged cyclic hydrocarbon group or a $C_{6-9}$ divalent aromatic hydrocarbon group, and $C_{2-6}$ linear alkylene groups or $C_{2-6}$ linear oxyalkylene groups. The $C_{6-9}$ divalent optionally bridged cyclic hydrocarbon group or the $C_{6-9}$ divalent aromatic hydrocarbon group in the molecule imparts appropriate rigidity to the molecule, and the $C_{2-6}$ linear alkylene groups or the $C_{2-6}$ linear oxyalkylene groups in the same molecule impart appropriate flexibility. Consequently, they enhance the elastic modulus and strength of a cured product obtained by curing a composition containing the dental polymerizable monomer (Aa) or (Aa'). Another possible reason is that the dental polymerizable monomer (Aa) or (Aa') is a methacrylate compound having a methacryloyl group as a polymerizable group. In general, cured products of methacrylate compounds have higher values of elastic modulus and strength than the elastic modulus and strength of cured products of acrylate compounds having a similar structure. This fact probably contributes to the enhancements in the elastic modulus and strength of a cured product of the dental polymerizable monomer (Aa) or (Aa'). It is probably for the reasons described above that a cured product of the dental polymerizable monomer (Aa) or (Aa') attains enhanced elastic modulus and strength as compared to cured products of conventional dental polymerizable monomers. It is therefore probable that a cured product of the dental composition (a) comes to have properties satisfying high elastic modulus and high strength because of its containing a considerable amount of a cured product of the dental polymerizable monomer (Aa) or (Aa') having such high mechanical properties.

The polymerizable monomer (Aa) or (Aa') is preferably used in the range of 1 to 99 wt % relative to 100 wt % of the total of the dental composition (a). When, for example, the dental composition (a) does not contain a filler (for example, when the dental composition (a) is used as a filler-free filling material), the content of the polymerizable monomer (Aa) or (Aa') is preferably in the range of 50 to 99 wt %, and more preferably 60 to 95 wt % relative to 100 wt % of the total of the dental composition (a). When the dental adhesive composition (a) contains a filler (for example, when the dental composition (a) is used as a composite resin), the content of the polymerizable monomer (Aa) or (Aa') is preferably in the range of 1 to 50 wt %, and more preferably 2 to 40 wt % relative to 100 wt % of the total of the dental adhesive composition (a). If the content is below the lower limit of the range, the strength, flexibility and toughness of cured products are sometimes decreased. If the content exceeds the upper limit, the composition sometimes exhibits excessively high viscosity and consistency.

The (meth)acrylate monomer (Ca) may be added to the dental polymerizable monomer composition (Ba) or may not be used. When the (meth)acrylate monomer (Ca) is added, one, or two or more kinds of (meth)acrylate monomers (Ca) may be used. When the (meth)acrylate monomer (Ca) is added to the dental polymerizable monomer composition (Ba), at least one specific low-viscosity (meth)acrylate monomer is preferably added as the (meth)acrylate monomer (Ca). The viscosity of the low-viscosity (meth)acrylate monomer at 25° C. is preferably 1 to 5,000 mPa·s, more preferably 1 to 3,000 mPa·s, and still more preferably 1 to 1,000 mPa·s. The viscosity is a value measured with a cone-plate viscometer at 25° C. The addition of such a low-viscosity (meth)acrylate monomer makes it possible to effectively reduce the viscosity of the dental polymerizable monomer composition (Ba).

Preferred low-viscosity (meth)acrylate monomers are, among the polymerizable compounds represented by the general formulas (7a) to (10a) above, those polymerizable compounds of the general formula (8a) in which $R^{9a}$ in the general formula (8a) is a $C_{2-20}$ linear alkylene group or a $C_{2-20}$ linear oxyalkylene group. Specific examples include 1,4-butanediol dimethacrylate, 1,6-hexanediol dimethacrylate, 1,8-octanediol dimethacrylate, 1,9-nanonediol dimethacrylate, 1,10-decanediol dimethacrylate, 1,4-butanediol diacrylate, 1,6-hexanediol diacrylate, 1,8-octanediol diacrylate, 1,9-nonanediol diacrylate, 1,10-decanediol diacrylate, ethylene glycol dimethacrylate, diethylene glycol dimethacrylate, triethylene glycol dimethacrylate, tetraethylene glycol dimethacrylate, polyethylene glycol dimethacrylate, tripropylene glycol dimethacrylate, tetrapropylene glycol dimethacrylate, polypropylene glycol dimethacrylate, ethylene glycol diacrylate, diethylene glycol diacrylate, triethylene glycol diacrylate, tetraethylene glycol diacrylate, polyethylene glycol diacrylate, tripropylene glycol diacrylate, tetrapropylene glycol diacrylate and polypropylene glycol diacrylate. These low-viscosity (meth)acrylate monomers have a flexible main chain structure such as an alkylene group or an oxyalkylene group. Thus, the toughness of cured products of the dental composition (a) is effectively enhanced by combining the dental polymerizable monomer (Aa) which includes a urethane methacrylate with a structure exhibiting appropriate rigidity, together with, as the (meth)acrylate monomer (Ca), at least one low-viscosity (meth)acrylate monomer with a flexible main chain structure described above.

The dental composition (a) may optionally contain components described below, in addition to the aforementioned dental polymerizable monomer (Aa) or (Aa'), dental polymerizable monomer composition (Ba) and (meth)acrylate monomer (Ca).

The dental composition (a) may contain a polymerization initiator (Da). The polymerization initiator (Da) may be any of general polymerization initiators used in the dental field, and is usually selected in consideration of the polymerizability of the polymerizable monomers and the polymerization conditions. By selecting the type of a polymerization initiator, room-temperature polymerizability, thermal polymerizability or photopolymerizability may be imparted to the dental composition (a).

In the case of self curing, for example, a redox polymerization initiator that is a combination of an oxidant and a reductant is preferable. When using a redox polymerization initiator, an oxidant and a reductant which are separately packaged need to be mixed with each other immediately before use.

The oxidants are not particularly limited. Examples include organic peroxides such as diacyl peroxides, peroxy esters, dialkyl peroxides, peroxyketals, ketone peroxides and hydroperoxides. Examples of the organic peroxides include such diacyl peroxides as benzoyl peroxide, 2,4-dichlorobenzoyl peroxide and m-toluoyl peroxide; such peroxy esters as t-butyl peroxybenzoate, bis-t-butyl peroxyisophthalate, 2,5-dimethyl-2,5-bis(benzoylperoxy)hexane, t-butyl peroxy-2-ethylhexanoate and t-butyl peroxyisopropyl carbonate; such dialkyl peroxides as dicumyl peroxide, di-t-butyl peroxide and lauroyl peroxide; such peroxyketals as 1,1-bis(t-butylperoxy)-3,3,5-trimethylcyclohexane; such ketone peroxides as methyl ethyl ketone peroxide; and such hydroperoxides as t-butyl hydroperoxide.

The reductants are not particularly limited, but tertiary amines are usually used. Examples of the tertiary amines include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-i-propylaniline, N,N-bis(2-hydroxyethyl)-4-t-butylaniline, N,N-di(2-hydroxyethyl)-3,5-di-i-propylaniline, N,N-bis(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N,N-bis(methacryloyloxyethyl)-N-methylamine, N,N-bis(methacryloyloxyethyl)-N-ethylamine, N,N-bis(2-hydroxyethyl)-N-methacryloyloxyethylamine, N,N-bis(methacryloyloxyethyl)-N-(2-hydroxyethyl)amine and tris(methacryloyloxyethyl)amine.

Besides these organic peroxide/amine systems, other redox polymerization initiators such as cumene hydroperoxide/thiourea systems, ascorbic acid/$Cu^{2+}$ salt systems and organic peroxide/amine/sulfinic acid (or sulfinate salt) systems may be used. Further, other polymerization initiators such as tributyl borane and organic sulfinic acids are also suitably used.

In the case of thermal polymerization with heating, it is preferable to use peroxides or azo compounds.

The peroxides are not particularly limited, and examples include benzoyl peroxide, t-butyl hydroperoxide and cumene hydroperoxide. The azo compounds are not particularly limited, and examples include azobisisobutyronitrile.

In the case of photopolymerization with the application of visible lights, suitable initiators are redox initiators such as α-diketones/tertiary amines, α-diketones/aldehydes and α-diketones/mercaptans.

Examples of the photopolymerization initiators, although not particularly limited to, include α-diketones/reductants, ketals/reductants and thioxanthones/reductants. Examples of the α-diketones include camphorquinone, benzil and 2,3-pentanedione. Examples of the ketals include benzyl dimethyl ketal and benzyl diethyl ketal. Examples of the thioxanthones include 2-chlorothioxanthone and 2,4-diethylthioxanthone. Examples of the reductants include tertiary amines such as Michler's ketone, 2-(dimethylamino)ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine and dimethylaminophenanthrol; aldehydes such as citronellal, lauryl aldehyde, phthalic dialdehyde, dimethylaminobenzaldehyde and terephthalaldehyde; and thiol group-containing compounds such as 2-mercaptobenzoxazole, decanethiol, 3-mercaptopropyltrimethoxysilane, 4-mercaptoacetophenone, thiosalicylic acid and thiobenzoic acid. Organic peroxides may be added to these redox systems. That is, α-diketone/organic peroxide/reductant systems may be suitably used.

In the case of photopolymerization with the application of UV lights, some suitable initiators are benzoin alkyl ethers and benzyl dimethyl ketal. Further, such photopolymerization initiators as (bis)acylphosphine oxides are also suitably used.

Of the (bis)acylphosphine oxides, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide and benzoyldi-(2,6-dimethylphenyl) phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide and (2,5,6-trimethylbenzoyl)-2,4,4-trimethylpentylphosphine oxide. These (bis)acylphosphine oxide photopolymerization initiators may be used singly or in combination with various reductants such as amines, aldehydes, mercaptans and sulfinate salts. These reductants may be suitably used also in combination with the visible light photopolymerization initiators described hereinabove.

The polymerization initiators may be used singly, or two or more may be used in appropriate combination.

The dental composition (a) may contain a polymerization inhibitor (Ea). The polymerization inhibitor (Ea) may be any of known compounds which can suppress the undesired polymerization reaction of the polymerizable groups present in the dental polymerizable monomer (Aa), the dental polymerizable monomer composition (Ba) and the dental composition (a). Examples include dibutylhydroxytoluene (BHT), hydroquinone (HQ), hydroquinone monomethyl ether (MEHQ) and phenothiazine (PTZ).

As already mentioned, the polymerization inhibitor (Ea) is sometimes added during the production of the dental polymerizable monomer (Aa). Similarly, the polymerization inhibitor is sometimes added during the production of a (meth)acrylate monomer containing an acidic group and a (meth)acryloyl group in the molecule, and the production of the low-viscosity (meth)acrylate monomer (Ca). Further, the polymerization inhibitor (Ea) is sometimes already present in raw materials for the production of these (meth)acrylate monomers. Further, as will be described later, the polymerization inhibitor may be added during the production of the dental composition (a). A single, or two or more kinds of the polymerization inhibitors may be used appropriately.

The dental composition (a) may further contain a filler (Fa). The filler may be any of general fillers used in the dental field. The fillers are usually broadly categorized into organic fillers and inorganic fillers.

Examples of the organic fillers include fine powders of polymers such as polymethyl methacrylate, polyethyl methacrylate, methyl methacrylate-ethyl methacrylate copolymer, crosslinked polymethyl methacrylate, crosslinked polyethyl methacrylate, ethylene-vinyl acetate copolymer and styrene-butadiene copolymer.

The dental composition (a) may contain a flexible filler (Fa') as the organic filler. The incorporation of a flexible filler (Fa') into the dental composition (a) makes it possible to enhance the strength, flexibility and toughness of cured products of the composition. When, in particular, the dental composition (a) is used as a mobile tooth fixing material, the addition of a flexible filler constitutes a preferred embodiment. Details of the flexible filler (Fa') (such as index of flexibility, embodiments of crosslinked polymers, combinations with other compounds, specific compounds, preferred amount of ethylenic double bonds, preferred particle size, and preferred content) are the same as the detailed description of a flexible filler (Dd) described later in the fourth aspect of the present invention.

In the first aspect of the invention, one of the most preferred embodiments is represented by a dental composition (a) which contains the polymerizable monomer (Aa) or (Aa') and a flexible filler (Dd) used in the fourth aspect of the invention that will be described later.

Examples of the inorganic fillers include fine powders of inorganic substances such as various glasses (based on silicon dioxide and optionally containing oxides of, for example, heavy metals, boron and aluminum), various ceramics, diatomaceous earth, kaolin, clay minerals (such as montmorillonite), activated clay, synthetic zeolite, mica, calcium fluoride, ytterbium fluoride, calcium phosphate, barium sulfate, zirconium dioxide, titanium dioxide and hydroxyapatite. Specific examples of the inorganic fillers include barium borosilicate glasses (such as Kimble Raysorb T3000, Schott 8235, Schott GM27884 and Schott GM39923), strontium boroaluminosilicate glasses (such as Raysorb T4000, Schott G018-093 and Schott GM32087), lanthanum glasses (such as Schott GM31684), fluoroaluminosilicate glasses (such as Schott G018-091 and Schott G018-117), and boroaluminosilicate glasses containing zirconium and/or cesium (such as Schott G018-307, G018-308 and G018-310).

In an embodiment, an organic inorganic composite filler may be used which is obtained by adding a polymerizable monomer beforehand to the inorganic filler to give a paste, which is then cured by polymerization and crushed.

In a preferred embodiment of the dental composition, the composition contains a microfiller having a particle diameter of 0.1 μm or less. Such a composition is suited as a dental composite resin. Preferred examples of the materials for such micron size fillers include silica (for example, product name: AEROSIL), alumina, zirconia and titania. The addition of such a micron size inorganic filler is advantageous in order for a cured product of the composite resin to achieve a high polish and smoothness by being polished.

These fillers may have been surface treated with agents such as silane coupling agents in accordance with purposes. Examples of such surface treating agents include known silane coupling agents, for example, organosilicon compounds such as γ-methacryloxyalkyltrimethoxysilanes (the number of carbon atoms between the methacryloxy group and the silicon atom: 3 to 12), γ-methacryloxyalkyltriethoxysilanes (the number of carbon atoms between the methacryloxy group and the silicon atom: 3 to 12), vinyltrimethoxysilane, vinylethoxysilane and vinyltriacetoxysilane. The surface treating agent is usually used with a concentration in the range of 0.1 to 20 wt %, and preferably 1 to 10 wt % with respect to 100 wt % of the filler.

The fillers may be used singly, or two or more may be used in combination appropriately.

To impart a bonding performance to the dental composition (a), a (meth)acrylate monomer (11a), other than the (meth)acrylate monomer (Ca), containing an acidic group and a (meth)acryloyl group in the molecule may be added to the dental composition (a) (but the (meth)acrylate monomers (Ca) do not belong to the (meth)acrylate monomers (11a)).

The structure of the (meth)acrylate monomer (11a) is not limited as long as the compound includes an acidic group and a (meth)acryloyl group in the molecule. Here, the acidic groups comprehend those groups which can function as acidic groups under practical conditions, for example, those groups which are readily hydrolyzed into acidic groups under practical conditions, for example, acid anhydride groups obtained from acid groups such as carboxyl groups.

Examples of the acidic groups include phosphoric acid residues, pyrophosphoric acid residues, thiophosphoric acid residues, carboxylic acid residues, sulfonic acid residues and acid anhydride residues of these acids. The number of acidic groups in the molecule is not limited but is usually 1 to 10.

The number of (meth)acryloyl groups in the molecule is not limited but is usually 1 to 10.

Examples of the polymerizable compounds having a methacryloyl group and a phosphate residue include 2-methacryloyloxyethyl dihydrogen phosphate, 9-methacryloyloxynonyl dihydrogen phosphate, 10-methacryloyloxydecyl dihydrogen phosphate, 11-methacryloyloxyundecyl dihydrogen phosphate, 20-methacryloyloxyeicosyl dihydrogen phosphate, 1,3-dimethacryloyloxypropyl-2-dihydrogen phosphate, 2-methacryloyloxyethyl phenyl phosphoric acid, 2-methacryloyloxyethyl 2'-bromoethyl phosphoric acid, methacryloyloxyethyl phenyl phosphonate, and acid chlorides of these compounds.

Examples of the polymerizable compounds having an acryloyl group and a phosphate residue include 2-acryloyloxyethyl dihydrogen phosphate, 9-acryloyloxynonyl dihydrogen phosphate, 10-acryloyloxydecyl dihydrogen phosphate, 11-acryloyloxyundecyl dihydrogen phosphate, 20-acryloyloxyeicosyl dihydrogen phosphate, 1,3-diacryloyloxypropyl-2-dihydrogen phosphate, 2-acryloyloxyethyl phenyl phosphoric acid, 2-acryloyloxyethyl 2'-bromoethyl phosphoric acid, acryloyloxyethyl phenyl phosphonate, and acid chlorides of these compounds.

Examples of the polymerizable compounds having a methacryloyl group and a pyrophosphate residue include di(2-methacryloyloxyethyl) pyrophosphate, and acid chlorides thereof.

Examples of the polymerizable compounds having an acryloyl group and a pyrophosphate residue include di(2-acryloyloxyethyl) pyrophosphate, and acid chlorides thereof.

Examples of the polymerizable compounds having a methacryloyl group and a thiophosphate residue include 2-methacryloyloxyethyl dihydrogen dithiophosphate, 10-methacryloyloxydecyl dihydrogen thiophosphate, and acid chlorides of these compounds.

Examples of the polymerizable compounds having an acryloyl group and a thiophosphate residue include 2-acryloyloxyethyl dihydrogen dithiophosphate, 10-acryloyloxydecyl dihydrogen thiophosphate, and acid chlorides of these compounds.

Examples of the polymerizable compounds having a methacryloyl group and a carboxylate residue include 4-methacryloyloxyethoxycarbonylphthalic acid (also called 4-methacryloyloxyethyltrimellitic acid), 5-methacryloylaminopentylcarboxylic acid, 11-methacryloyloxy-1,1-undecanedicarboxylic acid, and acid chlorides and acid anhydrides of these compounds.

Examples of the polymerizable compounds having an acryloyl group and a carboxylate residue include 4-acryloyloxyethoxycarbonylphthalic acid, 5-acryloylaminopentylcarboxylic acid, 11-acryloyloxy-1,1-undecanedicarboxylic acid, and acid chlorides and acid anhydrides of these compounds.

Examples of the polymerizable compounds having a methacryloyl group and a sulfonate residue include 2-sulfoethyl methacrylate and 2-methacrylamide-2-methylpropanesulfonic acid.

Examples of the polymerizable compounds having an acryloyl group and a sulfonate residue include 2-sulfoethyl acrylate and 2-acrylamido-2-methylpropanesulfonic acid.

The (meth)acrylate monomers (11a) containing an acidic group and a (meth)acryloyl group in the molecule may be appropriately used singly, or two or more may be used in combination.

The (meth)acrylate monomer (11a) is preferably used in the range of 0.5 to 50 wt %, and more preferably 1 to 30 wt % relative to 100 wt % of the total of the dental adhesive composition (a). If the content is below the lower limit of this range, the viscosity tends to be increased at times. If the content exceeds the upper limit, cured products tend to have a lowered strength and to be discolored at times.

The dental composition (a) may be produced by mixing prescribed amounts of the dental polymerizable monomer (Aa) and other optional components. The production method is not limited and may be conventional. For example, prescribed amounts of the components may be kneaded sufficiently with use of a known kneading apparatus, and the kneadate may be subjected to treatments such as deaeration under reduced pressure as required. The proportions of the components are not particularly limited, and the components may be added in effective amounts in accordance with the use application of the dental composition (a).

The dental composition (a) may be used in any applications without limitation. Typical examples of cured products of the dental composition (a) include dental restorative materials, dental prosthetic materials, dental temporary repairing materials, denture base resins, denture base liners, impression materials, luting materials (resin cements, resin-modified glass ionomer cements), dental fissure sealants, CAD/CAM resin blocks, temporary crowns and adhesive materials.

[Polymerizable Monomers (Ab) for Dental Adhesive Compositions]

The second aspect of the present invention relates to a polymerizable monomer (Ab) for dental adhesive compositions represented by the general formula (1) in which $R^1$ and $R^2$ are each a hydrogen atom or a methyl group, and m is 1. That is, the second aspect relates to a urethane (meth)acrylate which may be represented by the following general formula (1'b) and which exhibits excellent bonding performance. Such urethane (meth)acrylates will be described in detail below. The polymerizable monomer (Ab) for dental adhesive compositions does not contain acidic groups described later. The polymerizable monomer (Ab) does not contain hydroxyl groups.

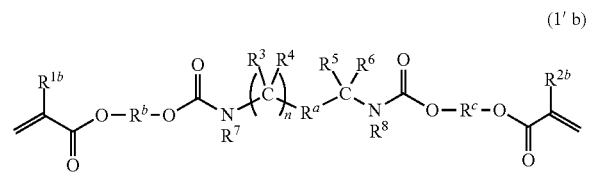

(1' b)

In the general formula (1'b), the definitions of $R^a$, $R^3$, $R^4$, $R^5$, $R^6$, $R^7$, $R^8$, $R^b$, $R^c$ and n are the same as in the general formula (1), and $R^{1b}$ and $R^{2b}$ are each a hydrogen atom or a methyl group. When one of $R^{1b}$ and $R^{2b}$ is a hydrogen atom, the general formula (1'b) represents an acrylate monomer. The monomer of the general formula (1'b) being an acrylate monomer constitutes a preferred embodiment because a dental composition containing the general formula (1'b) gives cured products having higher toughness. In particular, it is preferable that $R^{1b}$ and $R^{2b}$ be both hydrogen atoms. When one of $R^{1b}$ and $R^{2b}$ is a methyl group, the general formula (1'b) represents a methacrylate monomer. The monomer of the general formula (1'b) being a methacrylate monomer constitutes a preferred embodiment because a dental composition containing the general formula (1'b) gives cured products having higher elastic modulus. In particular, it is preferable that $R^{1b}$ and $R^{2b}$ be both methyl groups.

In the general formula (1'b), n is preferably 0 or 1. When n is 0, one of the carbon atoms in $R^a$ is bonded to nitrogen in the carbamoyl group. To attain appropriate rigidity, n is preferably 1.

From points of view such as industrial productivity, $R^7$ and $R^8$ of the polymerizable monomer (Ab) are, in a preferred embodiment, each a hydrogen atom.

From points of view such as appropriate hydrophobicity, it is preferable that one of $R^7$ and $R^8$ be a methyl group, and it is more preferable that both be methyl groups.

In a preferred embodiment, the polymerizable monomer (Ab) is a urethane (meth)acrylate represented by the general formula (1'b) in which $R^7$ and $R^8$ are hydrogen atoms and n is 0 or 1, that is, a urethane (meth)acrylate represented by the following general formula (1b).

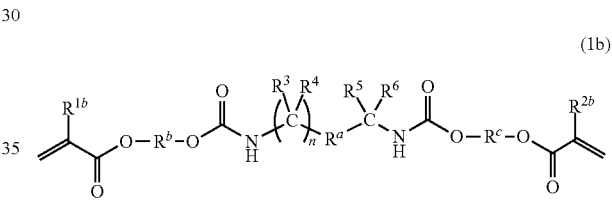

(1b)

The definitions of $R^a$, $R^3$, $R^4$, $R^5$, $R^6$, $R^{1b}$, $R^{2b}$, $R^b$ and $R^c$ in the general formula (1b) are the same as in the general formula (1'b), and nb is 0 or 1.

The number of carbon atoms in the divalent aromatic hydrocarbon group or the divalent optionally bridged cyclic hydrocarbon group present in $R^a$ in the general formula (1'b) or (1b) is not limited but, to attain appropriate hydrophobicity and appropriate rigidity, is 6 to 9, and preferably 6 to 7.

In a preferred embodiment, the polymerizable monomer (Ab) for dental adhesive compositions is represented by the general formula (1) in which $R^1$ and $R^2$ are each a hydrogen atom or a methyl group, and $R^a$ is a divalent $C_{6-9}$ aromatic hydrocarbon group or a divalent $C_{6-9}$ bridged cyclic hydrocarbon group, and m is 1, or $R^a$ is a divalent $C_{6-9}$ unbridged cyclic hydrocarbon group, and m and n are each 1.

That is, of the polymerizable monomers represented by the general formula (1'b), a preferred embodiment is constituted by a polymerizable monomer in which:

$R^a$ is a divalent $C_{6-9}$ aromatic hydrocarbon group or a divalent $C_{6-9}$ bridged cyclic hydrocarbon group, or $R^a$ is a divalent $C_{6-9}$ unbridged cyclic hydrocarbon group, and n is 1.

In a preferred embodiment, the divalent group present in $R^a$ is an aromatic hydrocarbon group. Specific examples of such aromatic hydrocarbon groups include phenylene group. In the general formula (1'b) or (1b), the aromatic ring present in the aromatic hydrocarbon group may be bonded to the two carbon atoms adjacent to $R^a$ at any positions of ortho positions, meta positions and para positions. To attain the advantageous effects of the present invention, it is preferable that such two bonds be present on the meta positions or the para positions, and it is more preferable that such two bonds be on the meta positions. Such regioisomers may be used singly, or two or more may be used in combination.

In a preferred embodiment, the divalent group present in $R^a$ is an optionally bridged cyclic hydrocarbon group. Specifically, the optionally bridged cyclic hydrocarbon group is a cyclic hydrocarbon group having a bridged structure, or a cyclic hydrocarbon group having no bridged structures.

Specific examples of the bridged cyclic hydrocarbon groups include bicyclo[2.2.1]heptylene group. Specific examples of the unbridged cyclic hydrocarbon groups include cyclohexylene group and 3,5,5-trimethylcyclohexylene group. In the general formula (1'b) or (1b), the hydrocarbon ring present in the optionally bridged cyclic hydrocarbon group may be bonded to the two carbon atoms adjacent to $R^a$ at any positions without limitation. To attain the advantageous effects of the second aspect of the present invention, it is preferable that such two bonds be not present on the same carbon atom in the hydrocarbon ring, and it is more preferable that such two bonds be not on carbon atoms adjacent to each other. Such regioisomers may be used singly, or two or more may be used in combination.

To attain appropriate rigidity, the divalent group present in $R^a$ is preferably an aromatic hydrocarbon group or a bridged cyclic hydrocarbon group, and particularly preferably a bridged cyclic hydrocarbon group.

To attain appropriate hydrophobicity, the divalent group present in $R^a$ is preferably an unbridged cyclic hydrocarbon group.

$R^{1b}$ and $R^{2b}$ in the general formula (1'b) or (1b) may be each a hydrogen atom or a methyl group. From the point of view of hydrophobicity, it is preferable that one of $R^{1b}$ and $R^{2b}$ be a methyl group, and it is more preferable that both be methyl groups. From the point of view of polymerization reactivity, it is preferable that one of $R^{1b}$ and $R^{2b}$ be a hydrogen atom, and it is more preferable that both be hydrogen atoms.

$R^3$, $R^4$, $R^5$ and $R^6$ in the general formula (1'b) or (1b) are each a hydrogen atom or a hydrocarbon group. To attain appropriate rigidity, $R^3$, $R^4$, $R^5$ and $R^6$ are preferably each a hydrogen atom or a methyl group. To attain appropriate rigidity, $R^3$, $R^4$, $R^5$ and $R^6$ are, in a more preferred embodiment, each a hydrogen atom. To attain appropriate hydrophobicity, $R^3$, $R^4$, $R^5$ and $R^6$ are, in a more preferred embodiment, each a methyl group.

To attain appropriate rigidity, a polymerizable monomer (Ab) for dental adhesive compositions which constitutes a preferred embodiment is one represented by the general formula (1) in which $R^1$ and $R^2$ are each a hydrogen atom or a methyl group, and $R^a$ is a divalent $C_{6-9}$ aromatic hydrocarbon group and $R^3$, $R^4$, $R^5$ and $R^6$ are each a hydrogen atom, or $R^a$ is a divalent $C_{6-9}$ bridged cyclic hydrocarbon group and $R^3$, $R^4$, $R^5$ and $R^6$ are each a hydrogen atom.

To attain appropriate hydrophobicity, a preferred embodiment is constituted by a polymerizable monomer in which $R^1$ and $R^2$ are each a hydrogen atom or a methyl group, and $R^a$ is a divalent $C_{6-9}$ unbridged cyclic hydrocarbon group and $R^3$, $R^4$, $R^5$ and $R^6$ are each a hydrogen atom, or $R^a$ is a divalent $C_{6-9}$ aromatic hydrocarbon group and $R^3$, $R^4$, $R^5$ and $R^6$ are each a methyl group.

In order to attain, for example, appropriate rigidity, the moiety of the general formulas (2'b) and (2b) below that is interposed between the two carbamoyl groups in the general formulas (1'b) and (1b) may be, in a preferred embodiment, any of the structures represented by the following general formulas (3b) to (7b). Of these structures, those structures represented by the general formulas (3b) to (6b) are preferable, those structures represented by the general formulas (3b) to (5b) are more preferable, those structures represented by the general formulas (3b) and (4b) are still more preferable, and the structure represented by the general formula (3b) is particularly preferable.

In order to attain, for example, appropriate hydrophobicity, the moiety may be, in another preferred embodiment, any of the structures represented by the following general formulas (5b) to (7b). Of these structures, the structure represented by the general formula (5b) is more preferable.

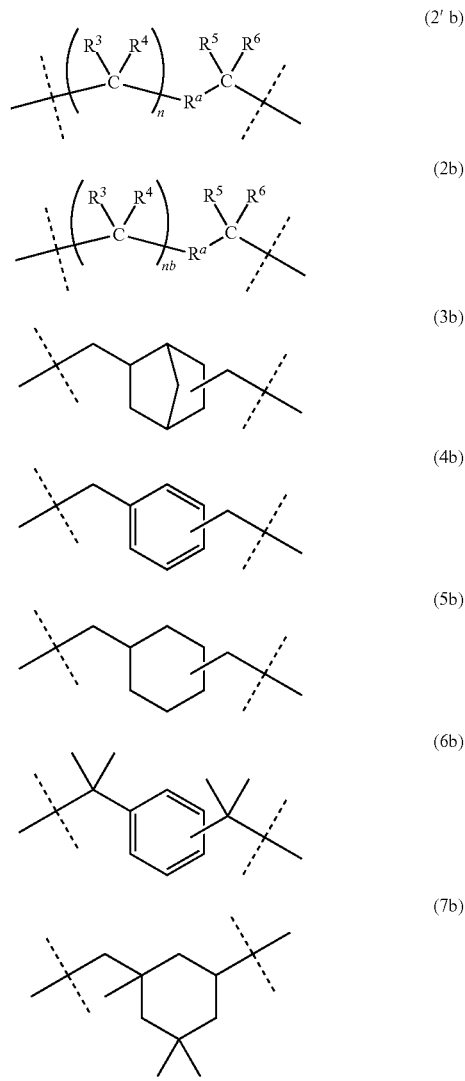

The general formulas (4b) to (6b) usually represent mixtures including regioisomers. In particular, regioisomers represented by the following general formulas (8b) to (10b) are preferable.

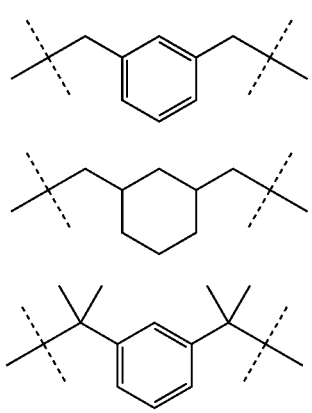

(8b)

(9b)

(10b)

To ensure that the polymerizable monomer (Ab) for dental adhesive compositions has appropriate flexibility, $R^b$ and $R^c$ in the general formulas (1'b) and (1b) are each independently a $C_{2-6}$ linear alkylene or $C_{2-6}$ linear oxyalkylene group optionally substituted with a $C_{1-3}$ alkyl group or a (meth)acryloyloxymethylene group in place of a hydrogen atom. Preferably, $R^b$ and $R^c$ are each a $C_{2-6}$ linear alkylene or $C_{2-6}$ linear oxyalkylene group optionally substituted with a $C_{1-3}$ alkyl group in place of a hydrogen atom.

Of the compounds represented by the general formula (1), a polymerizable monomer (Ab) in a preferred embodiment is one in which $R^7$ and $R^8$ are each a hydrogen atom, and $R^b$ and $R^c$ are each independently a $C_{2-6}$ linear alkylene or $C_{2-6}$ linear oxyalkylene group optionally substituted with a $C_{1-3}$ alkyl group in place of a hydrogen atom.

In a more preferred embodiment, $R^b$ and $R^c$ in the general formulas (1'b) and (1b) are each a $C_{2-4}$ linear alkylene or $C_{2-4}$ linear oxyalkylene group optionally substituted with a $C_{1-3}$ alkyl group in place of a hydrogen atom.

Examples of the linear alkylene groups include —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$—. Of these, preferred linear alkylene groups are, for example, —CH$_2$CH$_2$—, —CH$_2$CH$_2$CH$_2$— and —CH$_2$CH$_2$CH$_2$CH$_2$—. Examples of the linear oxyalkylene groups include —CH$_2$CH$_2$OCH$_2$CH$_2$— and —CH$_2$CH$_2$OCH$_2$CH$_2$OCH$_2$CH$_2$—. Of these, a preferred linear oxyalkylene group is, for example, —CH$_2$CH$_2$OCH$_2$CH$_2$—. To ensure that the polymerizable monomer (Ab) for the dental adhesive composition will exhibit appropriate flexibility, the linear alkylene groups or the linear oxyalkylene groups each usually have 2 to 6 carbon atoms, preferably 2 to 4 carbon atoms, and more preferably 2 carbon atoms.

The above linear alkylene groups or linear oxyalkylene groups may be substituted with an alkyl group or a (meth)acryloyloxymethylene group described below in place of a hydrogen atom. The number of such substituents is preferably 0 to 4, more preferably 0 to 2, and still more preferably 0 to 1 per one linear alkylene group or linear oxyalkylene group. In a preferred embodiment, the number of substituents is 0, that is, the linear alkylene group or the linear oxyalkylene group has no substituents, in which case the viscosity of the monomer is advantageously reduced.

Examples of the alkyl groups which may substitute for hydrogen atoms in the linear alkylene groups or the linear oxyalkylene groups include CH$_3$—, CH$_3$CH$_2$—, CH$_3$CH$_2$CH$_2$— and (CH$_3$)$_2$CH—. To ensure that the polymerizable monomer (Ab) which is a urethane (meth)acrylate will exhibit appropriate flexibility, the alkyl groups preferably have 1 to 3 carbon atoms, more preferably 1 to 2 carbon atoms, and still more preferably 1 carbon atom.

The (meth)acryloyloxymethylene group which may substitute for a hydrogen atom in the linear alkylene group or the linear oxyalkylene group may be any of methacryloyloxymethylene group and acryloyloxymethylene group. From the point of view of hydrophobicity, methacryloyloxymethylene group is preferable.

Of the polymerizable monomers (Ab) for dental adhesive compositions which are urethane (meth)acrylates, those urethane (meth)acrylates represented by the following formulas are preferable.

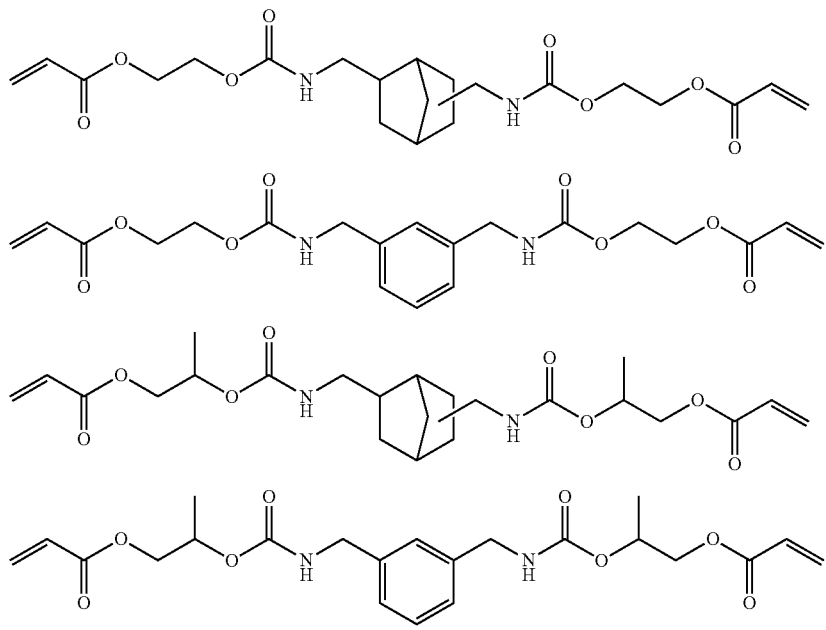

-continued
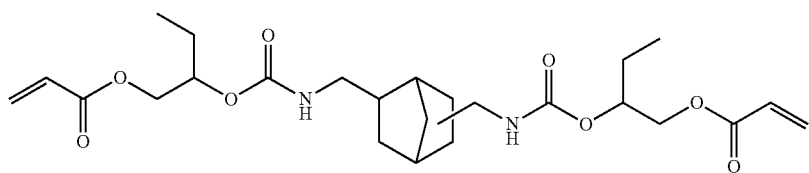
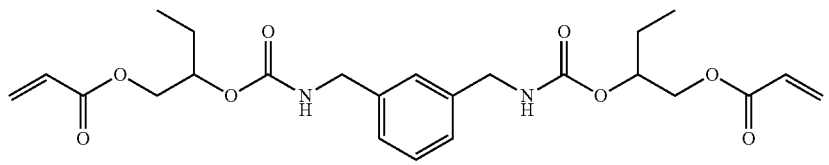
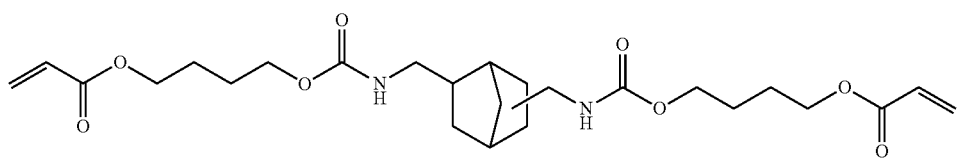
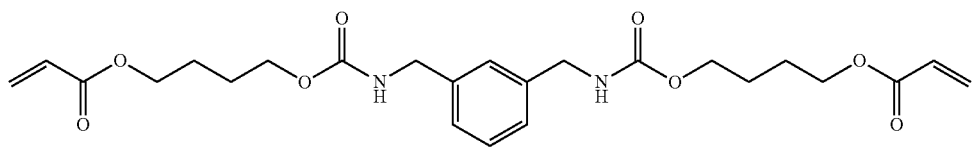
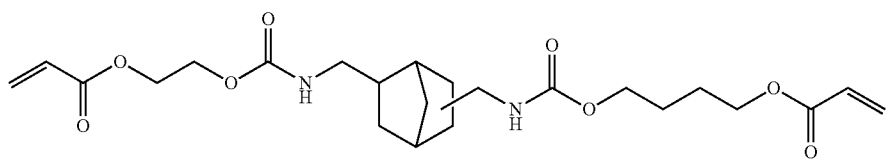
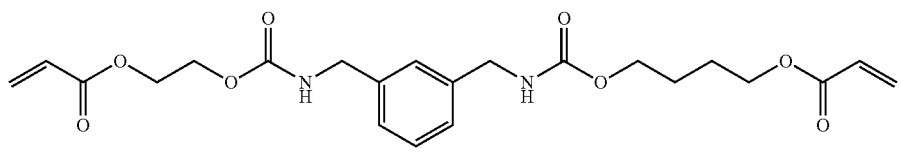
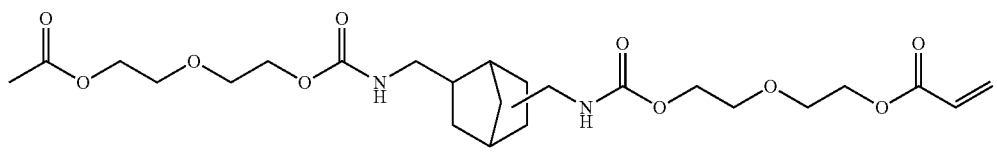
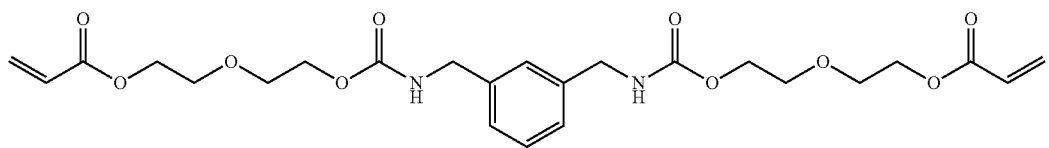
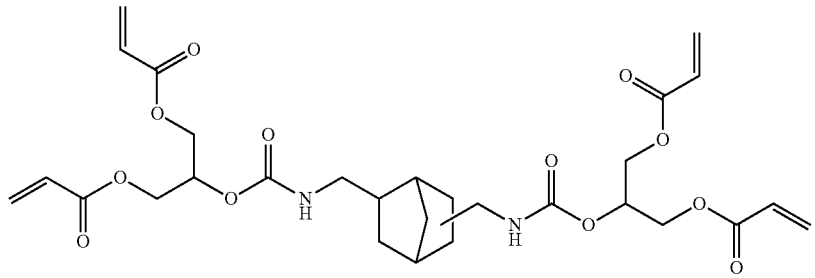

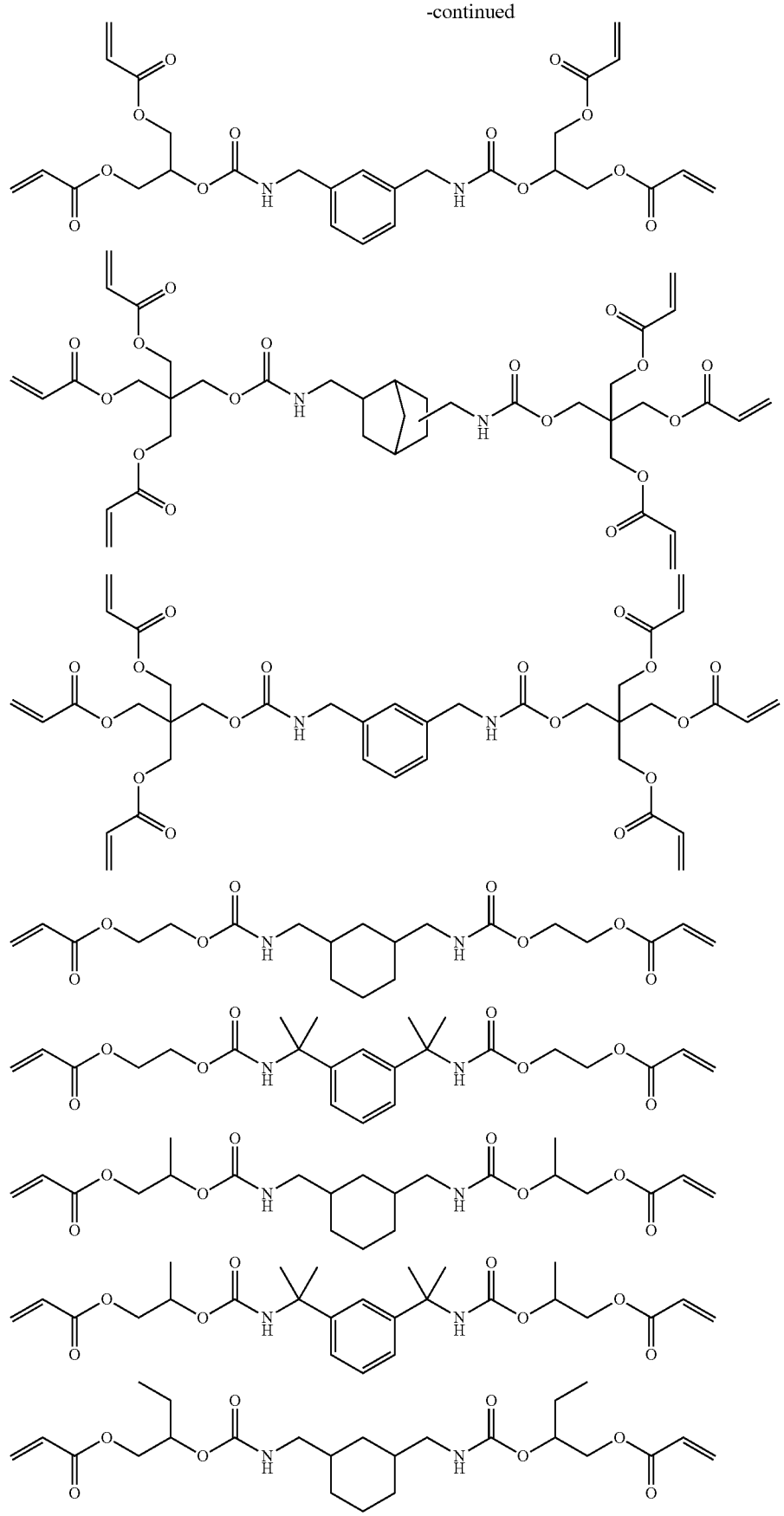

-continued
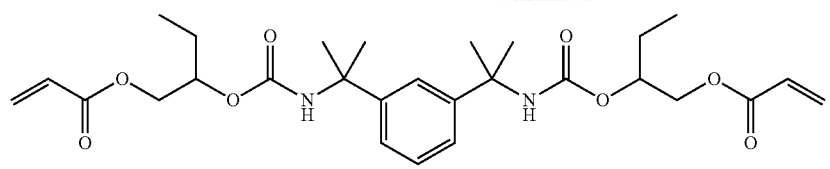
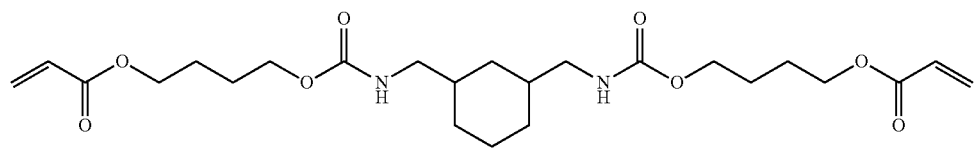
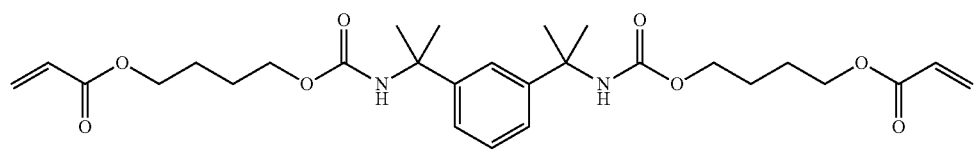
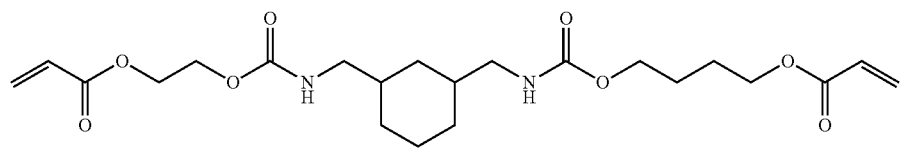
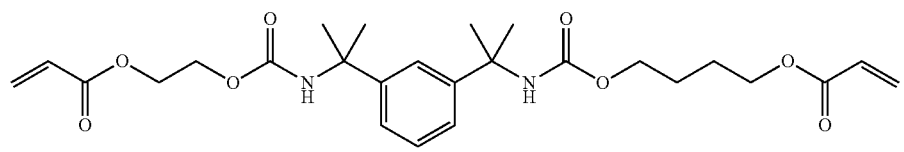
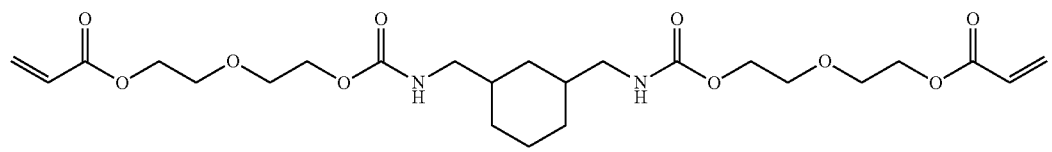
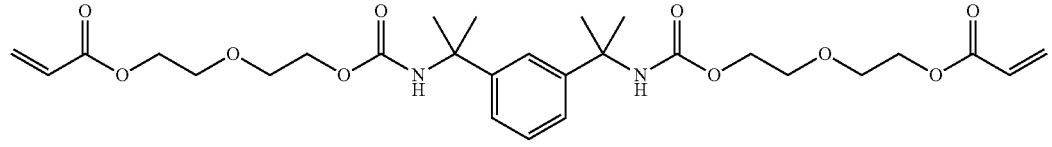
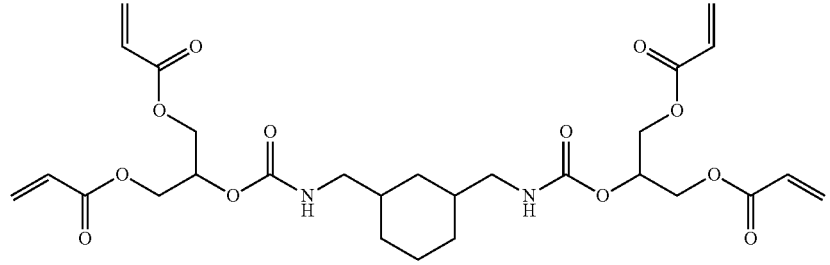
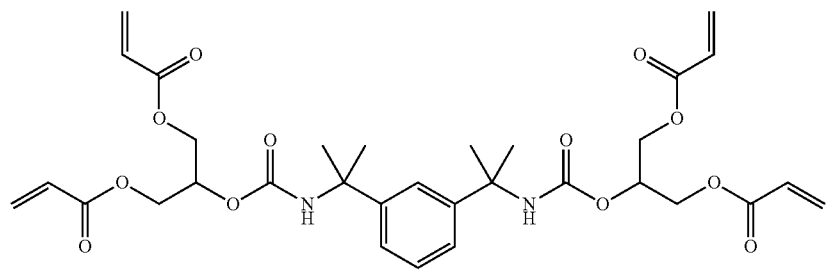

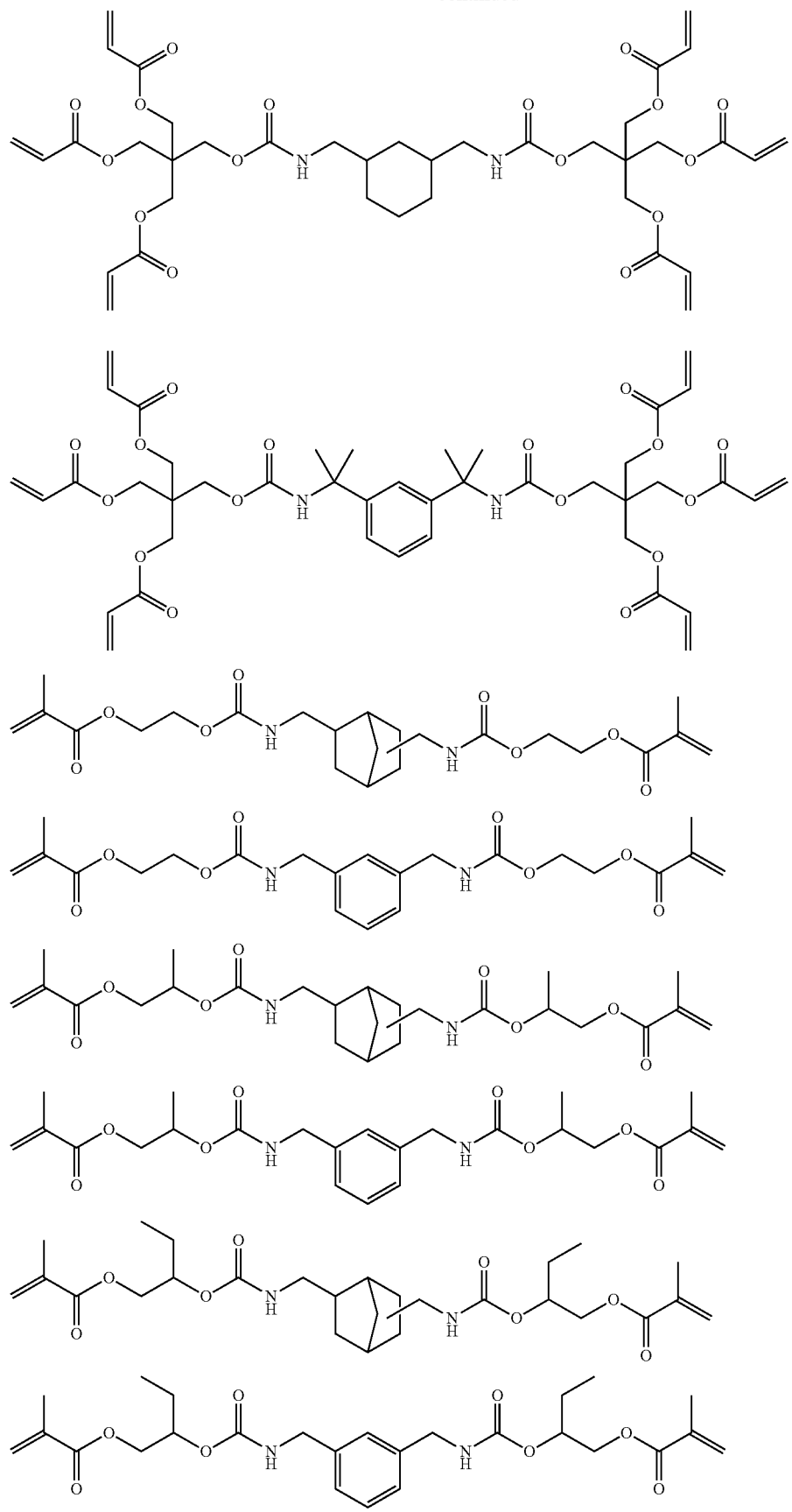

-continued
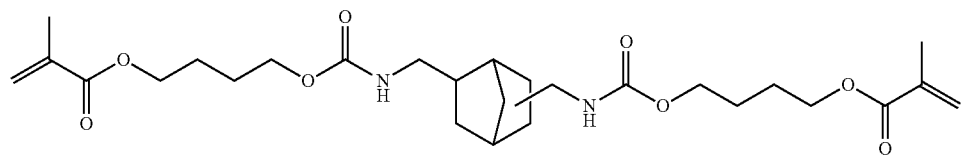
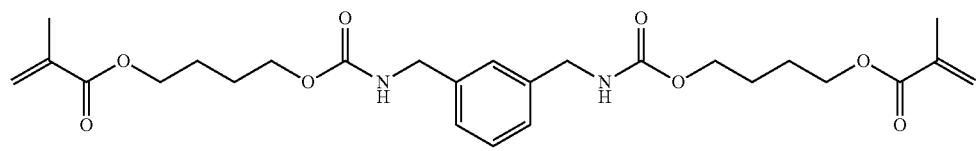
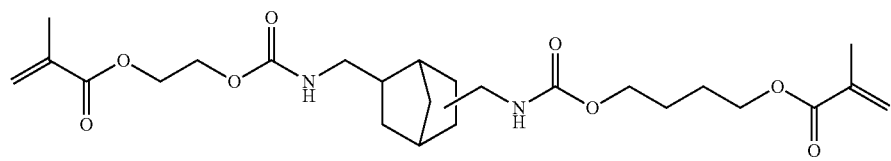
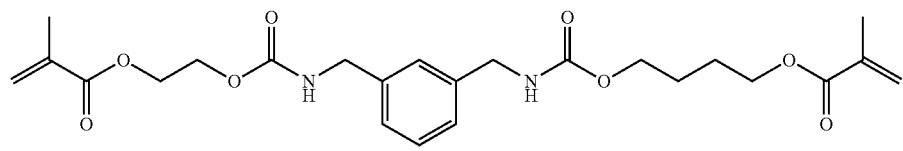
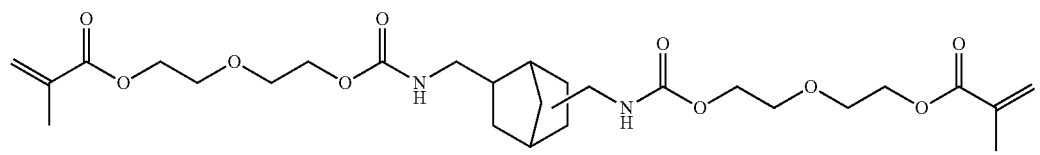
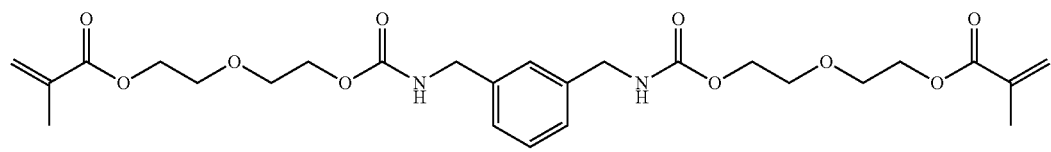
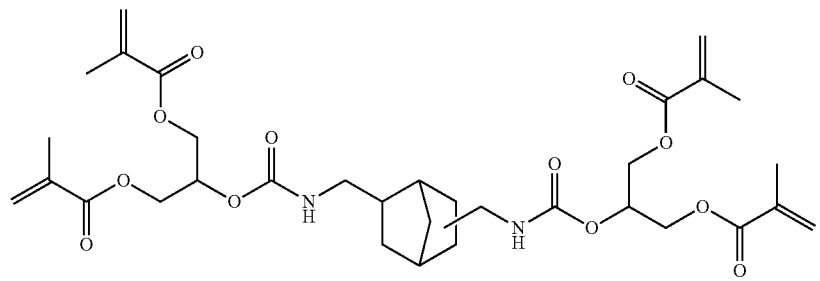
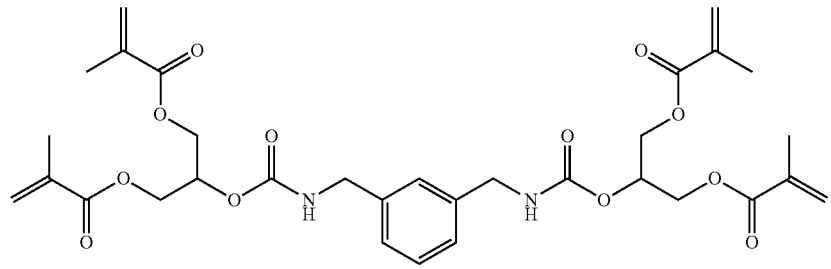

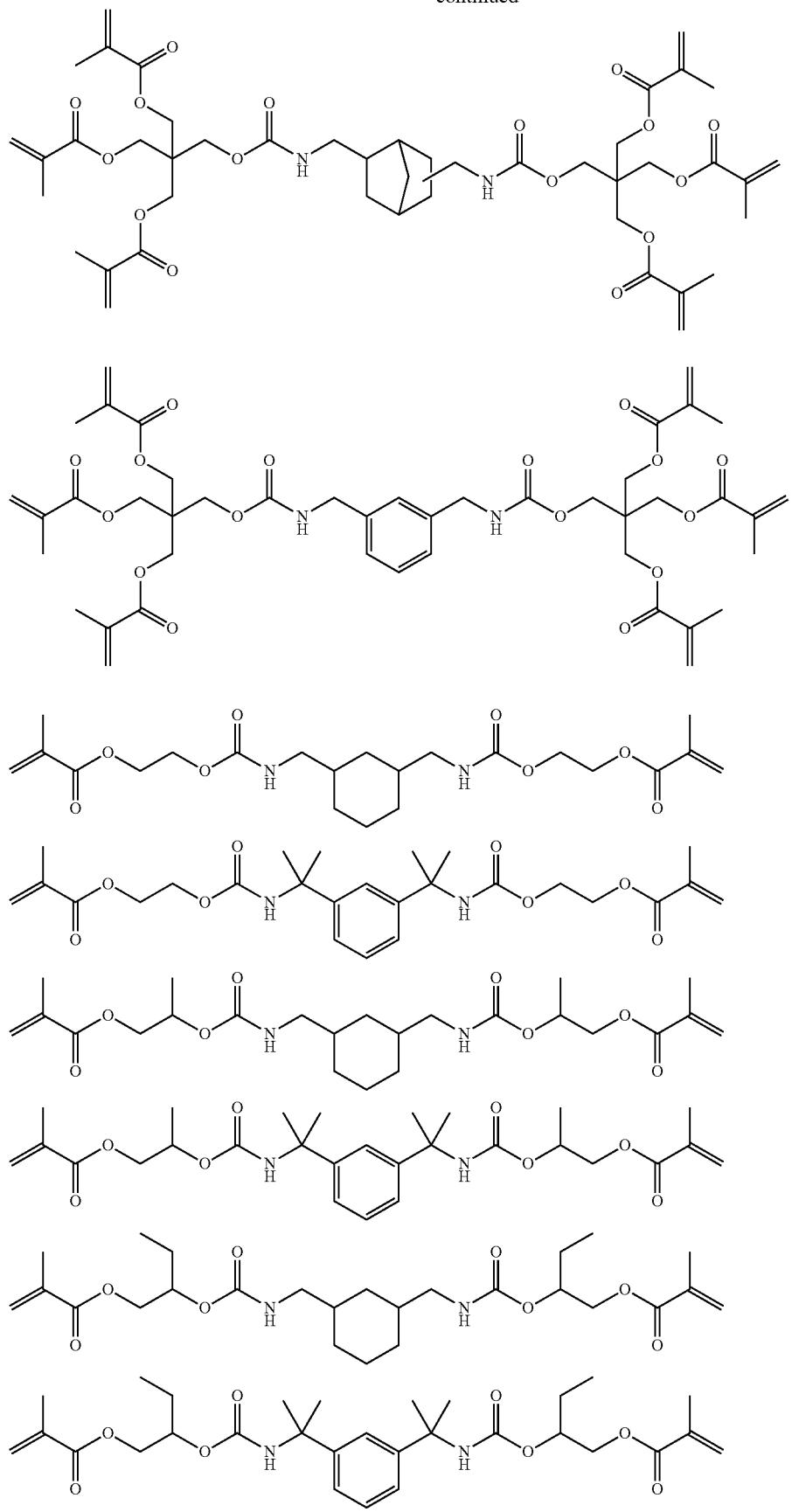

-continued
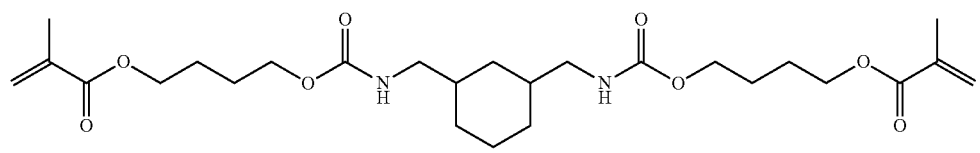
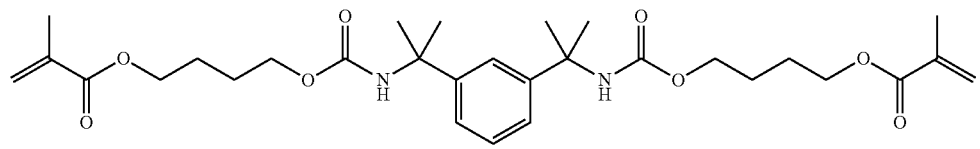
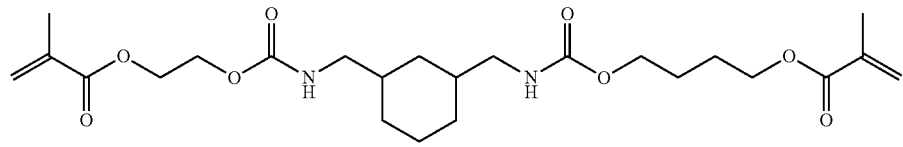
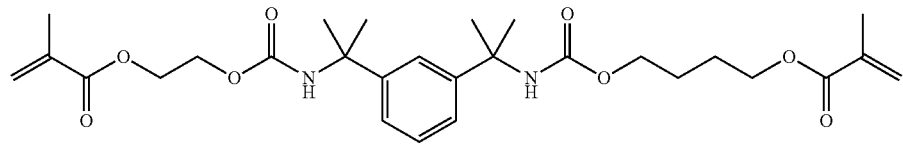
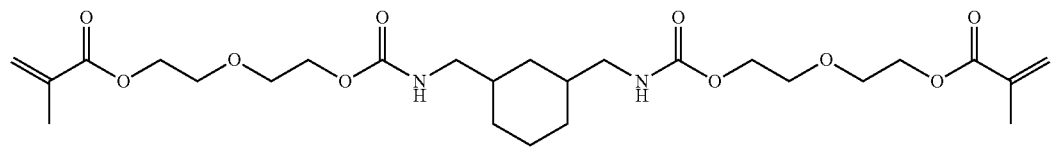
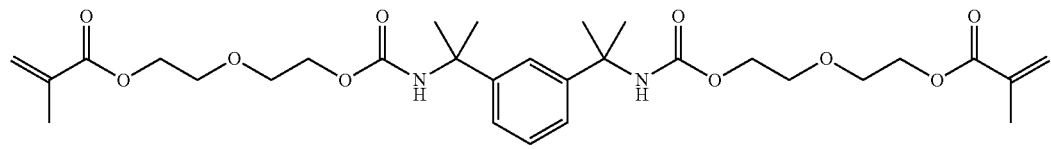
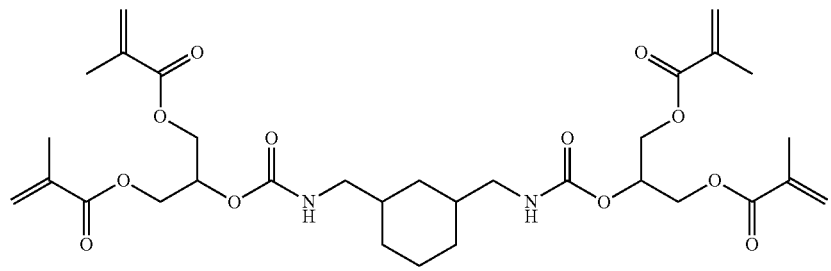
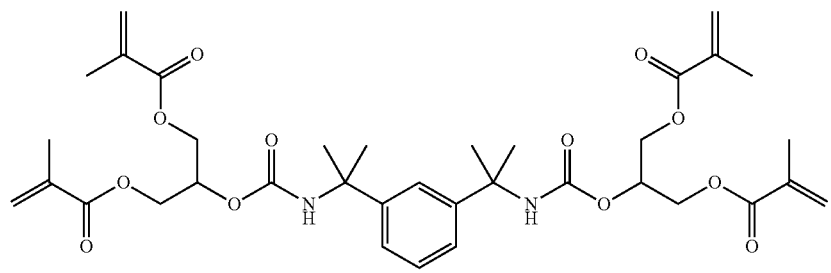

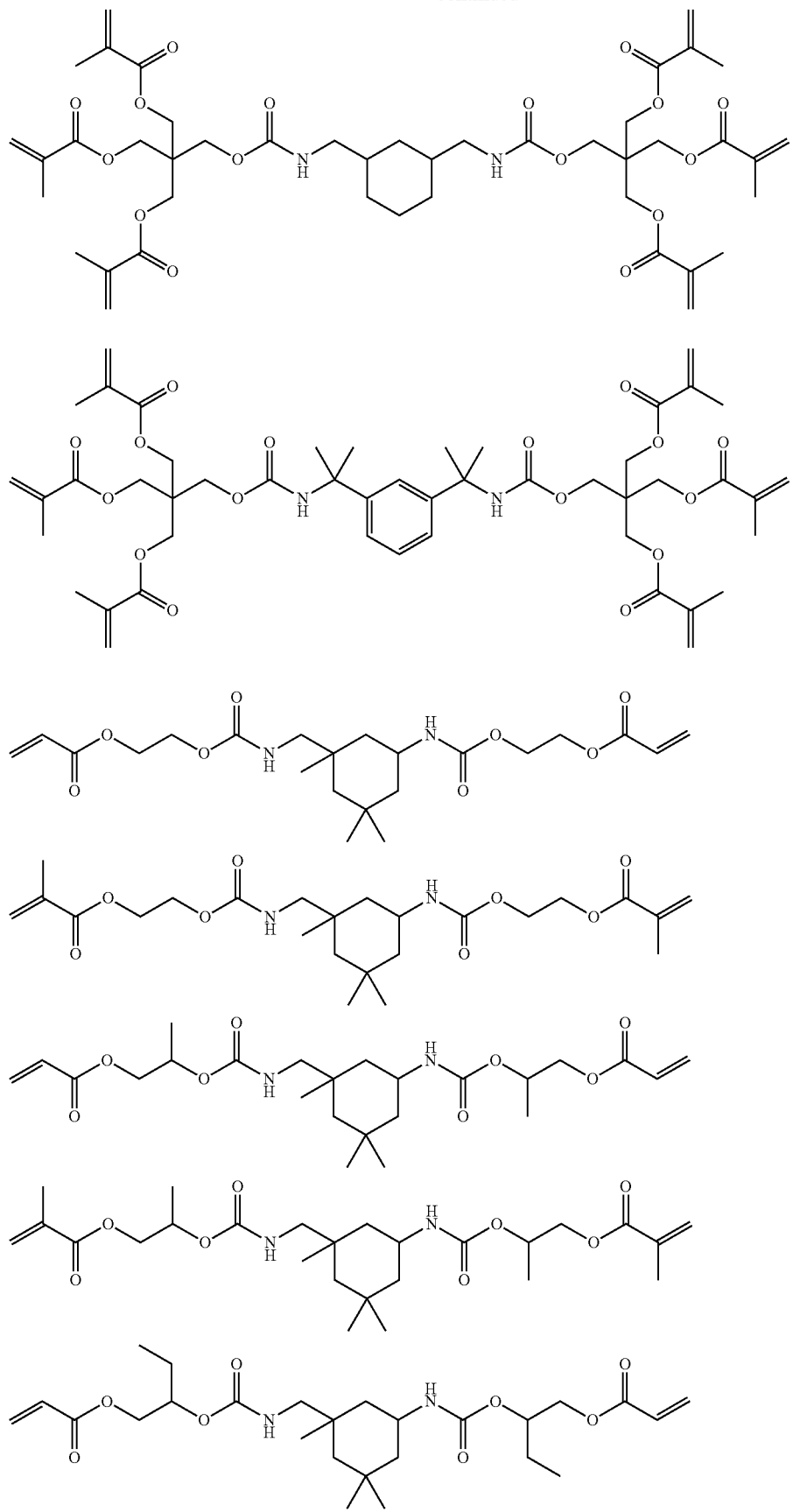

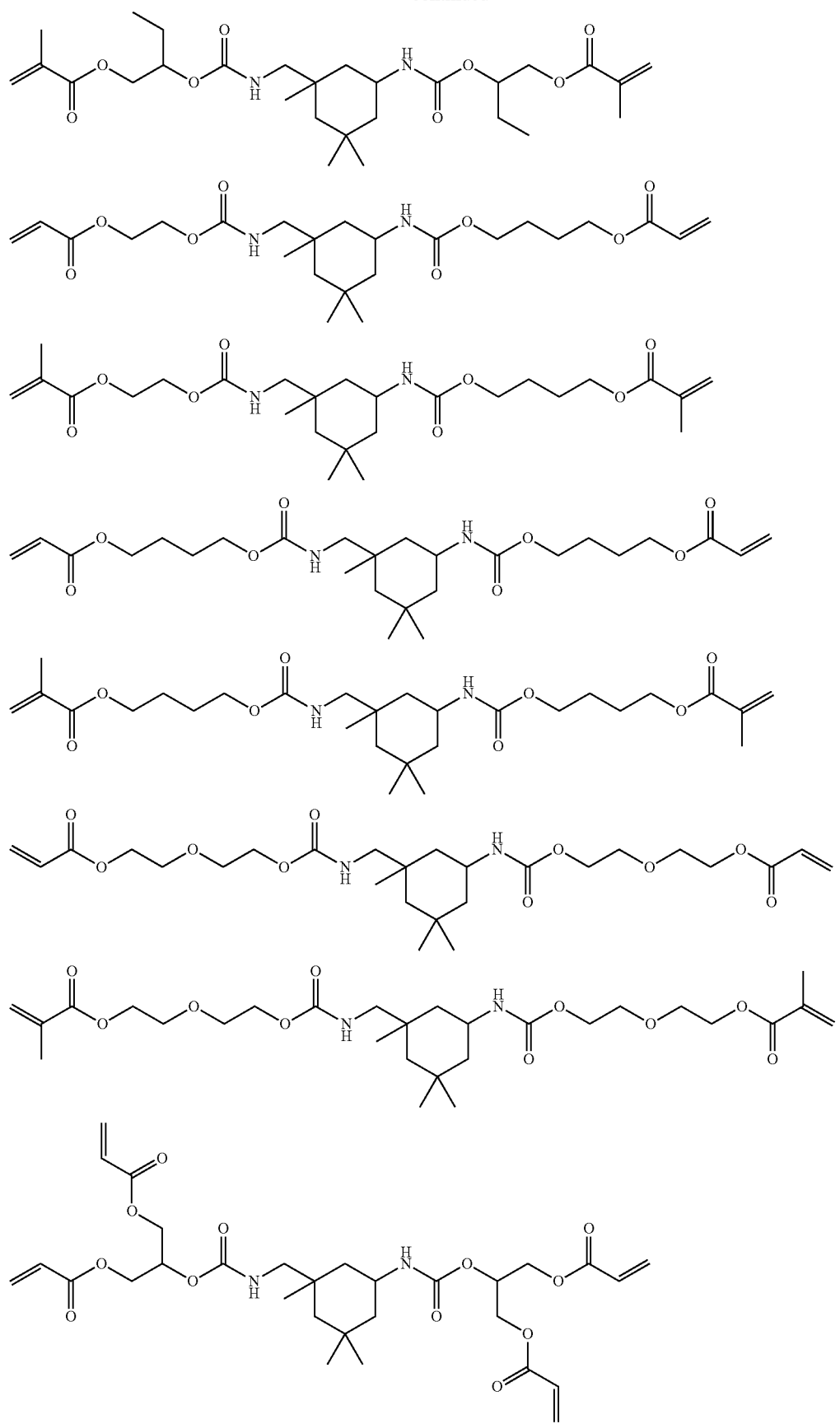

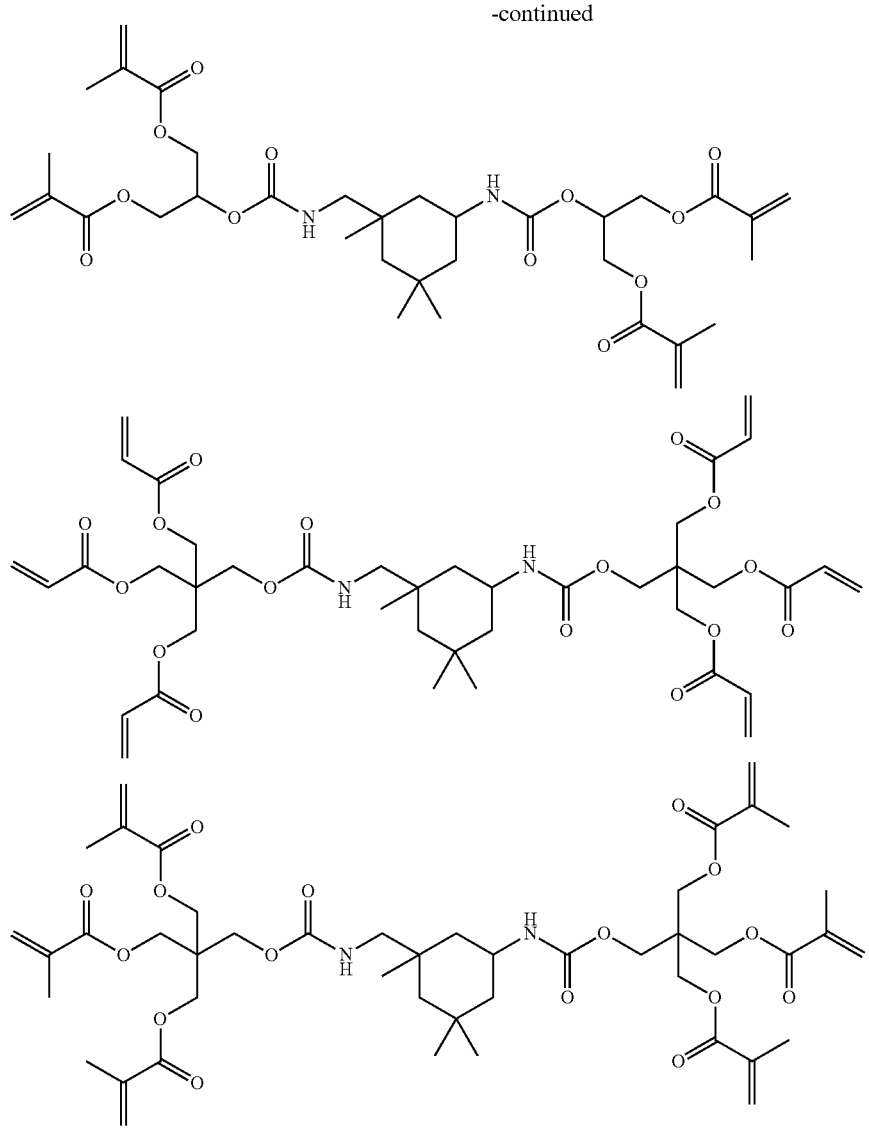

These compounds contain structures that exhibit appropriate hydrophobicity, appropriate rigidity and appropriate flexibility so as to make it possible to attain the advantageous effects of the second aspect. Here, the hydrophobicity of compounds may be evaluated based on the 1-octanol/water partition coefficient measured in accordance with JIS 7260-107 or JIS 7260-117. The larger the partition coefficient, the higher the hydrophobicity. The introduction of appropriate hydrophobicity to the polymerizable monomer (Ab) for dental adhesive compositions is preferable in order to attain the advantageous effects of the second aspect. Further, the hydrophobic tendency may be calculated by evaluating an index of expected equilibrium water content using a computational scientific technique. The lower the expected equilibrium water content, the higher the hydrophobicity.

The urethane (meth)acrylates may be used singly, or two or more may be appropriately used in combination.

The polymerizable monomer (Ab) for dental adhesive compositions may be obtained by, for example, reacting a diisocyanate (a1b) with appropriate hydrophobicity and appropriate rigidity represented by the general formula (11b) below with a hydroxy(meth)acrylate (a2b) with appropriate flexibility represented by the general formula (12b) below.

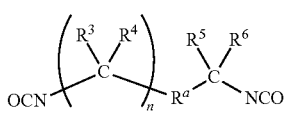

(11b)

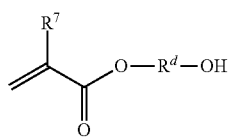

(12b)

In the general formula (11b), $R^a$ is defined the same as $R^a$ in the general formula (1'b), that is, $R^a$ is a divalent aromatic hydrocarbon group or a divalent optionally bridged cyclic hydrocarbon group. Details (for example, preferred embodiments) of $R^a$ are the same as the detailed description of $R^a$ in the general formula (1'b) or (1b). $R^3$, $R^4$, $R^5$ and $R^6$ in the general formula (11b) are each a hydrogen atom or a hydrocarbon group. Details (for example, preferred embodiments) of $R^3$, $R^4$, $R^5$ and $R^6$ are the same as the detailed description of $R^3$, $R^4$, $R^5$ and $R^6$ in the general formula (1'b) or (1b). Of the diisocyanates (a1b), at least one compound selected from those compounds represented by the general formulas (13b) to (17b) below is preferable in order to attain appropriate rigidity. In this preferred embodiment, those structures represented by the general formulas (13b) to (16b) are preferable, those structures represented by the general formulas (13b) to (15b) are more preferable, those structures represented by the general formulas (13b) and (14b) are still more preferable, and the structure represented by the general formula (13b) is particularly preferable. Of the diisocyanates (a1b), to attain appropriate hydrophobicity, at least one compound selected from those compounds represented by the general formulas (15b) to (17b) below is preferable. In this preferred embodiment, the structure represented by the general formula (15b) is preferable.

(13b)

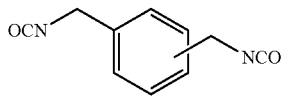
(14b)

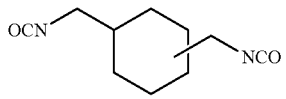
(15b)

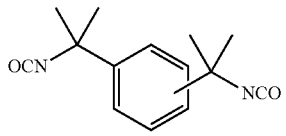
(16b)

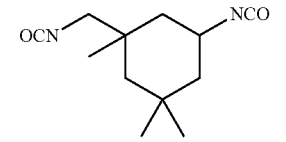
(17b)

The general formulas (14b) to (16b) represent mixtures of regioisomers. In particular, regioisomers represented by the following general formulas (18b) to (20b) are preferable.

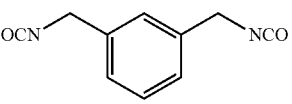
(18b)

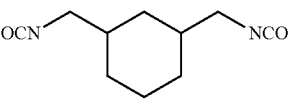
(19b)

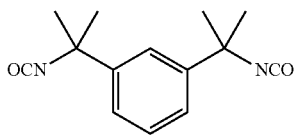
(20b)

The diisocyanates (a1b) may be used singly, or two or more may be used in combination.

$R^d$ in the general formula (12b) is a $C_{2-6}$ linear alkylene group or a $C_{2-6}$ linear oxyalkylene group which each independently is optionally substituted with a $C_{1-3}$ alkyl group or a (meth)acryloyloxymethylene group in place of a hydrogen atom. Details (for example, preferred embodiments) of $R^d$ in the general formula (12b) are the same as the detailed description of $R^b$ and $R^c$ in the general formula (1'b) or (1b). $R^7$ in the general formula (12b) is a hydrogen atom or a methyl group. $R^7$ is preferably a methyl group from the point of view of hydrophobicity, and is preferably a hydrogen atom from the point of view of polymerization reactivity.

The hydroxy(meth)acrylates (a2b) may be used singly, or two or more may be used in combination.

In the reaction, the diisocyanate (a1b) and the hydroxy (meth)acrylate (a2b) may be used in any quantitative ratio without limitation. Usually, they are used in such amounts that the proportion of the isocyanate groups in the diisocyanate (a1b) is equal to that of the hydroxyl groups in the hydroxy(meth)acrylate (a2b), namely, the ratio is 1:1. If the proportion of the isocyanate groups in the diisocyanate (a1b) is above this ratio, isocyanate groups will remain after the reaction. If the proportion of the hydroxyl groups in the hydroxymethacrylate (a2b) is above this ratio, hydroxyl groups will remain after the reaction. Depending on the purpose of use, the compounds are sometimes reacted in such a ratio that one of the raw materials will remain in a slight amount.

As described hereinabove, the polymerizable monomer (Ab) for dental adhesive compositions is obtained by reacting the diisocyanate (a1b) with the hydroxy(meth)acrylate (a2b). The reaction may be performed by a known method or a method that is deemed as known.

For example, the polymerizable monomer (Ab) may be obtained by mixing the diisocyanate (a1b) with the hydroxy (meth)acrylate (a2b). During this process, the isocyanate groups in the diisocyanate (a1b) react with the hydroxyl groups in the hydroxy(meth)acrylate (a2b) to form carbamoyl groups. This reaction is sometimes called the urethane-forming reaction.

The reaction may be performed in the presence or absence of a catalyst. To enhance the reaction rate, a catalyst is preferably added. Known catalysts capable of accelerating the urethane-forming reaction may be used as the catalysts.

Specific examples and preferred examples of the urethane-forming catalysts are the same as those of the urethane-forming catalysts used in the production of the dental polymerizable monomers (A) and (Aa).

Details (such as, for example, preferred quantitative ratio) of the diisocyanate (a1b) and the hydroxy(meth)acrylate (a2b) used in the reaction catalyzed by the urethane-forming catalyst are the same as the detailed description of the diisocyanate (a1a) and the hydroxymethacrylate (a2a) in the production of the dental polymerizable monomers (A) and (Aa). Details (such as, for example, preferred temperature) of the urethane-forming reaction are the same as the detailed description regarding the urethane-forming reaction for the production of the dental polymerizable monomers (A) and (Aa).

The polymerizable monomer (Ab) for dental adhesive compositions has polymerization activity. Therefore, undesired polymerization can take place during its production when the monomer is subjected to high temperatures. To prevent such undesired polymerization, a known polymerization inhibitor may be added before the start of the reaction or during the reaction. Details (for example, specific examples and preferred quantitative ratio) of such polymerization inhibitors are the same as the detailed description of the polymerization inhibitors used in the production of the dental polymerizable monomers (A) and (Aa).

Details of other conditions of the urethane-forming reaction are the same as the detailed description of the conditions in the urethane-forming reaction for the production of the dental polymerizable monomers (A) and (Aa).

Of the polymerizable monomers (Ab) for dental adhesive compositions, those in which $R^7$ and $R^8$ are methyl groups may be produced by the same method as those dental polymerizable monomers (A) and dental polymerizable monomers (Aa) representing a preferred embodiment of the monomers in which $R^7$ and $R^8$ are methyl groups.

[(Meth)Acrylate Monomers (Bb) Containing Acidic Group and (Meth)Acryloyl Group in Molecule]

A dental adhesive composition (b) representing an embodiment of the second aspect of the present invention preferably contains a (meth)acrylate monomer (Bb) containing an acidic group and a (meth)acryloyl group in the molecule. The structure of the (meth)acrylate monomer (Bb) is not limited as long as it has an acidic group and a (meth)acryloyl group in the molecule. By virtue of the incorporation of the (meth)acrylate monomer (Bb), the dental adhesive composition (b) can give a cured product exhibiting a higher bonding performance.

Details of other characteristics of the (meth)acrylate monomer (Bb) (such as specific examples and preferred number of the acidic groups, and specific examples of the monomers) are the same as the detailed description of the (meth)acrylate monomer (11a), optionally present in the aforementioned dental composition (a), containing an acidic group and a (meth)acryloyl group in the molecule.

[Low-Viscosity (Meth)Acrylate Monomers (Cb)]

The polymerizable monomer (Ab) for dental adhesive compositions, and the (meth)acrylate monomer (Bb) containing an acidic group and a (meth)acryloyl group in the molecule are sometimes highly viscous around room temperature, for example, at 25° C. The addition of such monomers often results in a highly viscous dental adhesive composition (b). Such a highly viscous dental adhesive composition has poor handleability and can cause problems in clinical use.

In order to reduce the viscosity of the dental adhesive composition (b), a low-viscosity (meth)acrylate monomer (Cb) may be added to the dental adhesive composition (b). The low-viscosity (meth)acrylate monomer (Cb) may be any of known (meth)acrylate monomers having low viscosity. The viscosity thereof at 25° C. is preferably 1 to 5,000 mPa·s, and more preferably 1 to 2,000 mPa·s. The low-viscosity (meth)acrylate monomers (Cb) do not belong to the polymerizable monomers (Ab) for dental adhesive compositions, or to the (meth)acrylate monomers (Bb) containing an acidic group and a (meth)acryloyl group in the molecule.

Details of other characteristics of the low-viscosity (meth)acrylate monomer (Cb) (such as specific examples of the monomers, preferred groups, and preferred number of groups) are the same as the detailed description of the (meth)acrylate monomer (Ca) optionally present in the aforementioned dental composition (a).

[Polymerization Initiators (Db)]

The dental adhesive composition (b) may contain a polymerization initiator (Db). The polymerization initiator (Db) may be any of general polymerization initiators used in the dental field, and is usually selected in consideration of the polymerizability of the polymerizable monomers and the polymerization conditions. By selecting the type of a polymerization initiator, room-temperature polymerizability, thermal polymerizability or photopolymerizability may be imparted to the dental adhesive composition (b). Details of other characteristics (such as, for example, specific examples) of the polymerization initiators (Db) are the same as the detailed description of the polymerization initiators (Da) optionally used in the dental composition (a).

The dental adhesive composition (b) may contain a reductant together with the polymerization initiator (Db). In this case, polymerization can take place efficiently. When the polymerization initiator (Db) is used together with a reductant, the polymerization initiator (Db) is preferably an oxidant, and more preferably an organic peroxide. By using the dental polymerizable monomer (Ab) in combination with a reductant (Dc) described later in the third aspect, the stability (storage stability) of the dental adhesive composition (b) may be enhanced, namely, the dental adhesive composition (b) is allowed to exhibit sufficient curability and to maintain such curability over a long period. Specifically, in one of preferred embodiments, the reductant is a mixture of an amine compound (Db1) or a salt thereof, and a sulfinic acid compound (Db2) or a salt thereof. Details of the amine compounds (Db1) or salts thereof (such as specific compounds, preferred content, and combinations with other compounds) are the same as the detailed description of amine compounds (Dc1) or salts thereof described later in the third aspect, and details of the sulfinic acid compounds (Db2) or salts thereof (such as specific compounds, preferred content, and combinations with other compounds) are the same as the detailed description of sulfinic acid compounds (Dc2) or salts thereof described later in the third aspect.

A more preferred embodiment of the dental adhesive composition (b) is constituted by a combination of a preferred embodiment of the dental polymerizable monomer (Ab) in the second aspect with a preferred embodiment of the reductant (Dc) described in the third aspect. This combination makes it possible to provide a dental adhesive composition (b) which exhibits a high bonding performance and enhanced storage stability.

The reductant may include, as the amine compound (Db1), an aromatic amine compound (bb) with a nonaromatic carbonyl group that is a secondary amine, and may include, as the sulfinic acid compound (Db2), an organic sulfinic acid compound (cb) with an electron withdrawing group. Using one or both of such compounds constitutes a more preferred embodiment from the points of view of the curability and storage stability of the dental adhesive composition (b). Details (such as preferred structures and specific compounds) of the aromatic amine compounds (bb) with a nonaromatic carbonyl group are the same as the detailed description of aromatic amine compounds (be) with a nonaromatic carbonyl group described later in the fifth aspect. Details (such as preferred Hammett substituent constant of electron withdrawing groups, specific compounds, and content) of the organic sulfinic acid compounds (cb) with an electron withdrawing group are the same as the detailed description of organic sulfinic acid compounds (ce) with an electron withdrawing group described later in the fifth aspect.

A more preferred embodiment of the dental adhesive composition (b) is constituted by a combination of a preferred embodiment of the dental polymerizable monomer (Ab) in the second aspect with a preferred embodiment of the reductant described in the fifth aspect. This combination makes it possible to provide a dental curable composition which exhibits a higher bonding performance with respect to tooth structure and has higher storage stability, and a dental cement including such a composition.

[Polymerization Inhibitors (Eb)]

The dental adhesive composition (b) may contain a polymerization inhibitor (Eb). The polymerization inhibitor (Eb) may be any of known compounds which can inhibit undesired polymerization of the (meth)acryloyl groups present in the polymerizable monomer (Ab) for dental adhesive compositions, the (meth)acrylate monomer (Bb) containing an acidic group and a (meth)acryloyl group in the molecule, and the low-viscosity (meth)acrylate monomer (Cb). Details of other characteristics (such as, for example, specific examples and manner of addition) of the polymerization inhibitors (Eb) are the same as the detailed description of the polymerization inhibitors (Ea) optionally present in the dental composition (a).

[Fillers (Fb)]

The dental adhesive composition (b) may contain a filler (Fb).

The filler may be any of general fillers used in the dental field. The fillers are usually broadly categorized into organic fillers and inorganic fillers. Specific examples of the organic fillers and the inorganic fillers usable as the fillers (Fb) are the same as those of the organic fillers and the inorganic fillers usable as the fillers (Fa) optionally added to the dental composition (a).

As the filler (Fb), an organic inorganic composite filler may be used which is obtained by adding a polymerizable monomer beforehand to an inorganic filler to give a paste, which is then cured by polymerization and crushed.

In a preferred embodiment of the dental adhesive composition (b), the composition contains a microfiller having a particle size of 0.1 µm or less. Such a composition is suited as a dental composite resin. Preferred examples of the materials of such microfillers include silica (for example, product name: AEROSIL), alumina, zirconia and titania.

These fillers are sometimes subjected to surface treatments with agents such as silane coupling agents in accordance with purposes. Details of the surface treatments for the fillers (Fb) (such as, for example, specific examples and concentrations of surface treating agents) are the same as the detailed description of the surface treatments for the fillers (Fa) optionally present in the dental composition (a).

The fillers may be used singly, or two or more may be appropriately used in combination.

As the filler (Fb) that is an organic filler, the dental adhesive composition (b) may contain a flexible filler (Fc). The incorporation of a flexible filler (Dd) according to the fourth aspect described later into the dental adhesive composition (b) makes it possible to enhance the strength, flexibility and toughness of cured products of the composition. Details of the flexible filler (Fc) (such as index of flexibility, embodiments of crosslinked polymers, combinations with other compounds, specific compounds, preferred amount of ethylenic double bonds, preferred particle size, and preferred content) are the same as the detailed description of the flexible filler (Dd) described in the fourth aspect.

A more preferred embodiment of the dental adhesive composition (b) is constituted by a combination of a preferred embodiment of the dental polymerizable monomer (Ab) in the second aspect with a preferred embodiment of the flexible filler (Dd) described in the fourth aspect. The dental adhesive composition (b) described hereinabove is useful as a mobile tooth fixing material. When, in particular, the dental polymerizable monomer (Ab) is an acrylate monomer, the composition is suited as a mobile tooth fixing material in that higher toughness is attained.

[Other Additives]

Where necessary, the dental adhesive composition (b) may contain, as additional additives, compounds which are known as dental materials.

Examples of such additional additives include (meth)acrylate monomers other than the polymerizable monomers (Ab) for dental adhesive compositions, the (meth)acrylate monomers (Bb) containing an acidic group and a (meth)acryloyl group in the molecule, and the low-viscosity (meth)acrylate monomers (Cb), and water and organic solvents. Specifically, examples of the (meth)acrylate monomers include 2,2-bis[4-(3-methacryloyloxy-2-hydroxypropoxy)phenyl]propane (Bis-GMA) and 2,2,4-trimethylhexamethylenebis(2-carbamoyloxyethyl) dimethacrylate (UDMA), and examples of the organic solvents include acetone.

Examples of the additional additives, other than those described above, include known pigments, dyes and fibers.

The additional additives may be selected appropriately in accordance with the purpose of use, and may be added in appropriate amounts as long as the advantageous effects of the second aspect of the present invention are not impaired.

[Dental Adhesive Compositions (b)]

The dental adhesive composition (b) representing an embodiment of the second aspect of the present invention contains the polymerizable monomer (Ab) described hereinabove. The dental adhesive composition (b) preferably contains 0.1 to 99 wt %, or more preferably 1 to 99 wt % of the polymerizable monomer (Ab) for dental adhesive compositions.

The dental adhesive composition (b) may contain, instead of the polymerizable monomer (Ab), the polymerizable monomer (A) described hereinabove. The dental adhesive composition (b) preferably contains 0.1 to 99 wt %, or more preferably 1 to 99 wt % of the polymerizable monomer (A) for dental adhesive compositions.

Of the polymerizable monomers (A) added to the dental adhesive composition (b), a polymerizable monomer which constitutes a preferred embodiment is one represented by the general formula (1) in which $R^a$ is a divalent aromatic hydrocarbon group or a divalent optionally bridged cyclic hydrocarbon group, and m and n are each independently 0 or 1 (hereinafter, this monomer will be also written as the dental polymerizable monomer (Ab')).

Details (such as preferred number of carbon atoms in the groups, and specific examples) of the divalent aromatic hydrocarbon groups and the divalent optionally bridged cyclic hydrocarbon groups present in the polymerizable monomer (A) or (Ab') are the same as the detailed description of the divalent aromatic hydrocarbon groups and the divalent optionally bridged cyclic hydrocarbon groups represented by $R^a$ in the polymerizable monomer (Ab) for dental adhesive compositions.

By virtue of the incorporation of the polymerizable monomer (Ab) or (A) for dental adhesive compositions into the dental adhesive composition (b), the dental adhesive composition exhibits a high bonding performance and excellent storage stability.

The detailed reasons why the dental adhesive composition attains such characteristics are not clear. It is, however, assumed that the exhibition of the above characteristics is attributed to the presence of the divalent aromatic hydrocarbon group or the divalent optionally bridged cyclic hydrocarbon group in the molecule of the polymerizable monomer (Ab) or (A) for dental adhesive compositions.

The divalent aromatic hydrocarbon group or the divalent optionally bridged cyclic hydrocarbon group in the molecule probably imparts appropriate rigidity to the molecule of the polymerizable monomer (Ab) or (A) for dental adhesive compositions, thus enhancing the strength and elastic modulus of cured products of the composition. Further, it is probable that the polymerizable monomer (Ab) or (A) for dental adhesive compositions which has the specific structure, when added to the adhesive composition, contributes to increasing the strength of adhesive components themselves and prevents a breakage or a so-called cohesive failure of the adhesive layer, and consequently the strength of the adhesive layer is enhanced.

Further, the divalent aromatic hydrocarbon group or the divalent optionally bridged cyclic hydrocarbon group present in the molecule of the polymerizable monomer (Ab) or (A) for dental adhesive compositions probably imparts appropriate hydrophobicity to the molecule of the polymerizable monomer (Ab) or (A) for dental adhesive compositions. For example, (i) a conventional polymerizable monomer for dental adhesive compositions such as Bis-GMA has a hydroxyl group which is a hydrophilic group in the molecule, whilst the polymerizable monomer (Ab) or (A) for dental adhesive compositions does not have hydroxyl groups in the molecule. Further, (ii) the divalent aromatic hydrocarbon group or the divalent optionally bridged cyclic hydrocarbon group in the molecule is a highly hydrophobic group. Appropriate hydrophobicity in the polymerizable monomer (Ab) or (A) for dental adhesive compositions contributes to lowering the water absorptivity of the polymerizable monomer for dental adhesive compositions itself, and thereby makes it possible to suppress the decomposition of the molecules of the polymerizable monomer for dental adhesive compositions. Further, appropriate hydrophobicity in the polymerizable monomer (Ab) or (A) for dental adhesive compositions probably has an influence on the enhancement of the permeability of the dental adhesive composition (b) into tooth structure. Furthermore, the enhanced permeability of the dental adhesive composition (b) into tooth structure will lead to an enhancement in bond strength. Here, the hydrophobicity of the polymerizable monomer (A) used in the dental adhesive composition (b) may be evaluated by the aforementioned method for evaluating the hydrophobicity of the polymerizable monomer (A).

The polymerizable monomer (Ab) or (A) for dental adhesive compositions contains linear alkylene groups or linear oxyalkylene groups in the molecule. The presence of such structures exhibiting appropriate flexibility is probably a reason for the enhancement in the elastic modulus of cured products.

As described above, the polymerizable monomer (Ab) or (A) for dental adhesive compositions has a structure exhibiting appropriate hydrophobicity, a structure exhibiting appropriate rigidity, and a structure exhibiting appropriate flexibility. This is probably a reason why the dental composition (b) containing the polymerizable monomer (Ab) or (A) exhibits a high bonding performance.

The storage stability of the dental adhesive composition (b) is possibly affected by the hygroscopicity of the composition. As already described, dental adhesive compositions often fail to maintain their performance due to the decomposition of monomers and catalysts by moisture absorption. The aforementioned high hydrophobicity of the polymerizable monomer (Ab) or (A) probably decreases the hygroscopicity of the dental adhesive composition (b) containing the monomer, and consequently leads to an enhancement in the storage stability of the composition. Thus, the use of the polymerizable monomer (Ab) or (A) for dental adhesive compositions which has the specific structure is important in order to enhance the performance of the dental adhesive composition (b) which represents an embodiment of the second aspect of the present invention.

The content of the polymerizable monomer (Ab) or (A) is preferably not less than 5 parts by weight, more preferably not less than 10 parts by weight, and still more preferably not less than 15 parts by weight per 100 parts by weight of the total weight of the dental adhesive composition (b) (when the composition is stored in the form of two or more separate compositions and the final composition that is used is a mixture of such compositions, the weight herein means the total weight after the final mixing; the same applies to the weight of the composition (b) hereinafter).

The content of the polymerizable monomer (Ab) or (A) is preferably not less than 0.1 part by weight, more preferably not less than 0.5 parts by weight, and still more preferably not less than 1 part by weight per 100 parts by weight of the total weight of the polymerizable monomer(s) present in the dental adhesive composition (b). If the content is below the lower limit of this range, the storage stability of the dental adhesive composition (b) at and above room temperature may not be ensured at times.

Of the polymerizable monomers (Ab) or (A) which are acrylates represented by the general formula (1), that is, which have hydrogen atoms as $R^1$ and $R^2$, a polymerizable monomer which constitutes a preferred embodiment is one in which:

$R^a$ is a divalent $C_{6-9}$ aromatic hydrocarbon group or a divalent $C_{6-9}$ bridged cyclic hydrocarbon group, and m and n are each independently 0 or 1, or $R^a$ is a divalent $C_{6-9}$ unbridged cyclic hydrocarbon group, and m and n are each 1.

The polymerizable monomer (Ab) or (A) has a structure exhibiting appropriate hydrophobicity, a structure exhibiting appropriate rigidity and a structure exhibiting appropriate flexibility. Probably by virtue of this structural characteristic of the polymerizable monomer (Ab) or (A), the dental composition (b) containing the polymerizable monomer (Ab) or (A) exhibits a high bonding performance. When the polymerizable monomer (A) is an acrylate monomer, the above structural characteristic will also provide an enhancement of the toughness of cured products of the composition and thus constitutes a preferred embodiment.

When the polymerizable monomer (Ab) or (A) is an acrylate (when $R^1$ and $R^2$ in the general formula (1) are each a hydrogen atom), the content of the polymerizable monomer (Ab) or (A) is preferably in the range of 1 to 99 wt %, and more preferably to 99 wt % relative to 100 wt % of the total of the dental adhesive composition (b). If the content is below the lower limit of the range, the strength, flexibility and toughness of cured products are sometimes decreased. If the content exceeds the upper limit, the adhesion is sometimes decreased.

In a preferred embodiment, the dental adhesive composition (b) contains a filler.

When, for example, the dental adhesive composition (b) is used as a mobile tooth fixing material, the content of the polymerizable monomer (Ab) or (A) is preferably in the range of 50 to 99 wt %, and more preferably 60 to 95 wt % relative to 100 wt % of the total of the dental adhesive composition (b).

When the dental adhesive composition (b) is used as an adhesive cement, the content of the polymerizable monomer (Ab) or (A) is preferably in the range of 1 to 50 wt %, and more preferably 2 to 40 wt % relative to 100 wt % of the total of the dental adhesive composition (b).

In a preferred embodiment, the dental adhesive composition (b) contains the (meth)acrylate monomer (Bb) described hereinabove which contains an acidic group and a (meth)acryloyl group in the molecule, in addition to the polymerizable monomer (Ab) or (A). By virtue of the incorporation of these two types of monomers, the dental adhesive composition (b) exhibits a higher bonding performance and higher storage stability. Further, the combination of these two types of monomers tends to result in enhancements in the strength and elastic modulus of cured products of the composition. Probably, the combination makes a greater contribution to increasing the strength of adhesive components themselves and prevents more effectively a breakage or a so-called cohesive failure of the adhesive layer, and consequently the strength of the adhesive layer tends to be further enhanced.

The content of the (meth)acrylate monomer (Bb) is not particularly limited as long as the advantageous effects of the second aspect of the present invention are not impaired. The content is generally 0.1 to 50 wt %, preferably 0.1 to 30 wt %, more preferably 0.5 to 20 wt %, still more preferably 1 to 20 wt %, and further preferably 1 to 10 wt % in the dental adhesive composition (b). If the content is below the lower limit of the range, the adhesion may not be ensured at times.

In the dental adhesive composition (b), the number of the polymerizable groups present in the (meth)acrylate monomer (Bb) is preferably not more than 50% relative to the number of all the polymerizable groups present in the dental adhesive composition (b). To attain the advantageous effects of the second aspect of the present invention, the number of the polymerizable groups present in the (meth)acrylate monomer (Bb) is more preferably less than 50% relative to the number of all the polymerizable groups present in the dental adhesive composition (b), and is still more preferably 0.1 to 20%, and particularly preferably 0.5 to 10%.

The dental adhesive composition (b) may contain the low-viscosity (meth)acrylate monomer (Cb) described hereinabove. The viscosity of the low-viscosity (meth)acrylate monomer (Cb) at 25° C. is preferably 1 to 5,000 mPa·s. The content thereof is not particularly limited as long as the advantageous effects of the second aspect of the present invention are not impaired, but is preferably 1 to 90 wt %, and more preferably 5 to 40 wt %.

The dental adhesive composition (b) may contain the polymerization initiator (Db) described hereinabove. The content thereof is not particularly limited as long as the advantageous effects of the second aspect of the present invention are not impaired, but is usually 0.01 to 5 wt %, and preferably 0.1 to 1 wt %. When the polymerization initiator (Db) is composed of a plurality of components, the weight of the polymerization initiator discussed here means the total weight of such components.

The dental adhesive composition (b) may contain the polymerization inhibitor (Eb) described hereinabove. The content thereof is not particularly limited as long as the advantageous effects of the second aspect of the present invention are not impaired, but is usually 0.01 to 5 wt %, and preferably 0.1 to 1 wt %. It is preferable to add the polymerization inhibitor at 0.001 to 0.5 wt %, more preferably at 0.002 to 0.3 wt %, and still more preferably at 0.005 to 0.1 wt %.

The dental adhesive composition (b) may contain the filler (Fb) described hereinabove. The content thereof is not particularly limited as long as the advantageous effects of the second aspect of the present invention are not impaired, but is usually 1 to 90 wt %, and preferably 5 to 80 wt %.

The dental adhesive composition (b) may be produced by mixing prescribed amounts of the polymerizable monomer (Ab) for dental adhesive compositions, and other optional components. The production method is not limited and may be conventional. For example, prescribed amounts of the components may be kneaded sufficiently with use of a known kneading apparatus, and the kneadate may be subjected to treatments such as deaeration under reduced pressure as required. The proportions of the components are not particularly limited, and the components may be added in effective amounts in accordance with the use application of the dental adhesive composition (b).

The viscosity of the dental adhesive composition (b) at 25° C. is preferably 1 to 100,000 mPa·s, and more preferably 10 to 10,000 mPa·s.

In the production of the dental adhesive composition (b), the polymerizable monomer (Ab) for dental adhesive compositions and optionally other components used in accordance with the purpose may be mixed together in prescribed amounts, and the resultant composition may be subjected to practical use as a one-part composition. Alternatively, in consideration of factors such as polymerization mode and storage stability, the components may form a kit including two or more separate compositions, and such compositions may be mixed together by a known method immediately before use to give a composition.

When the dental adhesive composition (b) is used, the target to which the composition will be applied is sometimes surface-treated by a known method. For example, the surface of a tooth may be etched or primer coated by a known method. Alternatively, for example, the surface of a prosthesis is sometimes surface-treated by a known method.

The dental adhesive composition (b) may be used in any applications without limitation. Typical examples include adhesive cements, bonding materials, mobile tooth fixing adhesives, and temporary implant cements.

A dental adhesive curable composition (c) according to the third aspect of the present invention will be described in detail below.

In the description of the third aspect below, the phrase "XX to YY" (XX and YY are values or the like) such as one used to indicate a preferred numerical range means "not less than XX and/or not more than YY".

The dental adhesive curable composition (c) is characterized in that it contains the dental polymerizable monomer (A) described hereinabove or a polymerizable monomer (Ac) with a specific structure described below, a polymerizable monomer (Bc) having an acidic group in the molecule, a polymerization initiator (Cc) and a reductant (Dc).

The polymerizable monomers used in the invention, unless otherwise mentioned, contain at least one group selected from the polymerizable groups described hereinabove in the molecule. Examples include polyfunctional monomers having a plurality of polymerizable groups, and monofunctional monomers having one polymerizable group (the polymerizable groups in the polymerizable monomers described hereinbelow should be understood similarly as described here).

The dental adhesive curable composition (c) contains the dental polymerizable monomer (A). In a preferred embodiment, the polymerizable monomer (A) used in the dental adhesive curable composition (c) is a polymerizable monomer (Ac) represented by the following general formula (1c) in which $R^7$ and $R^8$ are each a hydrogen atom.

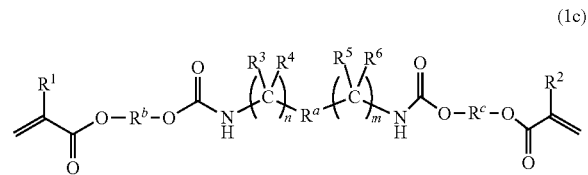

(1c)

The definitions of $R^a$, $R^1$, $R^2$, $R^3$, $R^4$, $R^5$, $R^6$, $R^b$ and $R^c$ in the general formula (1c) are the same as in the general formula (1). Hereinbelow, the polymerizable monomers (A) used as the dental adhesive composition (c), and the polymerizable monomers (Ac) representing a preferred embodiment of the monomers will be described collectively.

When used as the dental adhesive curable composition (c), the divalent aromatic hydrocarbon group and the divalent optionally bridged cyclic hydrocarbon group present in $R^a$ in the general formulas (1) and (1c) may have any number of carbon atoms without limitation. To attain appropriate rigidity, the number of carbon atoms is 6 to 9, and preferably 6 to 7.

In a preferred embodiment, the divalent group present in $R^a$ is an aromatic hydrocarbon group. Specific examples of such aromatic hydrocarbon groups include phenylene group. In the general formulas (1) and (1c), the aromatic ring present in the aromatic hydrocarbon group may be bonded to the two carbon atoms adjacent to $R^a$ at any positions of ortho positions, meta positions and para positions. To attain the advantageous effects of the present invention, it is preferable that such two bonds be present on the meta positions or the para positions, and it is more preferable that such two bonds be on the meta positions. Such regioisomers may be used singly, or two or more may be used in combination.

In a preferred embodiment, the divalent group present in $R^a$ is an optionally bridged cyclic hydrocarbon group. Specifically, the optionally bridged cyclic hydrocarbon group is a cyclic hydrocarbon group having a bridged structure, or a cyclic hydrocarbon group having no bridged structures. Specific examples of the bridged cyclic hydrocarbon groups include bicyclo[2.2.1]heptylene group (commonly known as "norbornene group"). Specific examples of the unbridged cyclic hydrocarbon groups include cyclohexylene group and 3,5,5-trimethylcyclohexylene group. In the general formulas (1) and (1c), the hydrocarbon ring present in the optionally bridged cyclic hydrocarbon group may be bonded to the two carbon atoms adjacent to $R^a$ at any positions without limitation. To attain the advantageous effects of the third aspect of the present invention, it is preferable that such two bonds be not present on the same carbon atom in the hydrocarbon ring, and it is more preferable that such two bonds be not on carbon atoms adjacent to each other. Such regioisomers may be used singly, or two or more may be used in combination.

To attain appropriate rigidity, the divalent group present in $R^a$ is preferably an aromatic hydrocarbon group or a bridged cyclic hydrocarbon group, and particularly preferably a bridged cyclic hydrocarbon group.

$R^3$, $R^4$, $R^5$ and $R^6$ in the general formulas (1) and (1c) are each a hydrogen atom or a hydrocarbon group. To attain appropriate rigidity, $R^3$, $R^4$, $R^5$ and $R^6$ are preferably each a hydrogen atom.

In the general formulas (1) and (1c), m and n are each independently 0 to 4, and m and n are preferably each 0 or 1. When m and n are 0, one of the carbon atoms in $R^a$ is bonded to nitrogen in the carbamoyl group. To attain appropriate rigidity, it is preferable that at least one of m and n be 1. In a preferred embodiment, m and n in the general formulas (1) and (1c) are each 1. In another preferred embodiment, one of m and n in the general formulas (1) and (1c) is 0 and the other is 1.

The moiety of the general formula (2c) below that is interposed between the two carbamoyl groups in the general formulas (1) and (1c) is, in a preferred embodiment, a structure represented by the following general formula (3c).

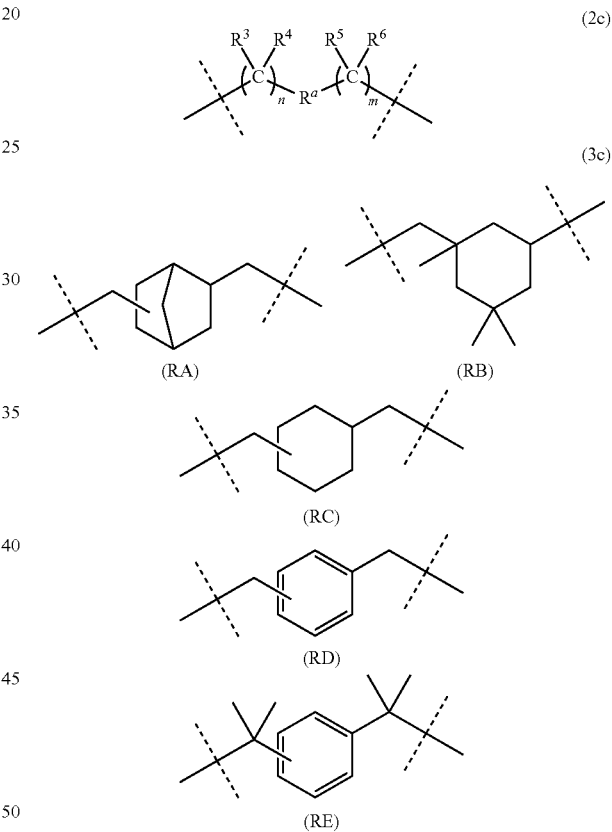

$R^b$ and $R^c$ in the general formulas (1) and (1c) are each independently a $C_{2-6}$ linear alkylene or $C_{2-6}$ linear oxyalkylene group optionally substituted with a $C_{1-3}$ alkyl group or a (meth)acryloyloxymethylene group in place of a hydrogen atom.

Preferably, $R^b$ and $R^c$ are each a $C_{2-6}$ linear alkylene or $C_{2-6}$ linear oxyalkylene group optionally substituted with a $C_{1-3}$ alkyl group or an acryloyloxymethylene group in place of a hydrogen atom.

Examples of the linear alkylene groups include —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—. Of these, preferred linear alkylene groups are, for example, —$CH_2CH_2$—, —$CH_2CH_2CH_2$— and —$CH_2CH_2CH_2CH_2$—. Examples of the linear oxyalkylene groups include —CH$_2$CH$_2$OCH$_2$CH$_2$— and —CH$_2$CH$_2$OCH$_2$CH$_2$OCH$_2$CH$_2$—. Of these, a preferred linear oxyalkylene group is, for example, —CH$_2$CH$_2$OCH$_2$CH$_2$—. To ensure that the dental adhesive curable composition (c) will exhibit appropriate flexibility, the linear alkylene groups or the linear oxyalkylene groups each usually have 2 to 6 carbon atoms, preferably 2 to 4 carbon atoms, and more preferably 2 carbon atoms.

Examples of the alkyl groups which may substitute for hydrogen atoms in the linear alkylene groups or the linear oxyalkylene groups include CH$_3$—, CH$_3$CH$_2$—, CH$_3$CH$_2$CH$_2$— and (CH$_3$)$_2$CH—. To ensure that the dental adhesive curable composition (c) will exhibit appropriate flexibility, the alkyl groups preferably have 1 to 3 carbon atoms, more preferably 1 to 2 carbon atoms, and still more preferably 1 carbon atom.

Examples of the (meth)acryloyloxymethylene groups which may substitute for hydrogen atoms in the linear alkylene groups or the linear oxyalkylene groups include methacryloyloxymethylene group and acryloyloxymethylene group.

In the general formulas (1) and (1c), $R^1$ and $R^2$ are each independently a hydrogen atom or a $C_{1-3}$ alkyl group. $R^1$ and $R^2$ are preferably each a $C_{1-3}$ alkyl group.

Specific examples of the alkyl groups include methyl group and ethyl group. From the point of view of hydrophobicity, methyl groups are more preferable than hydrogen atoms.

In the general formulas, $R^7$ and $R^8$ are each independently a hydrogen atom or a methyl group. It is preferable that $R^7$ and $R^8$ be each a hydrogen atom. When $R^7$ and $R^8$ are both hydrogen atoms, as mentioned earlier, the compound is represented by the general formula (1c).

The compounds with the specific structure represented by the general formula (1) or (1c) have the same structure as reaction products between, for example, a diisocyanate and a hydroxyalkyl methacrylate, and may be produced by a known production method. For example, the compound may be produced by the same method as the aforementioned dental polymerizable monomers (A) and (Aa). The compound with the specific structure represented by the general formula (1) or (1c) (for example, a compound in which the moiety interposed between the two carbamoyl groups is a structure represented by the formula (3c) described hereinabove) may be derived from a diisocyanate containing a cyclic hydrocarbon group or an aromatic hydrocarbon group. The polymerizable monomer (A) or (Ac) used in the dental adhesive curable composition (c) is preferably one which contains a cyclic hydrocarbon group or an aromatic hydrocarbon group.

The content of the polymerizable monomers is preferably not less than 5 parts by weight and not more than 99 parts by weight, more preferably not less than 10 parts by weight and not more than 95 parts by weight, and still more preferably not less than 15 parts by weight and not more than 90 parts by weight per 100 parts by weight of the total weight of the dental adhesive curable composition (c) (when the composition is stored in the form of two or more separate compositions and the final composition that is used is a mixture of such compositions, the weight herein means the total weight after the final mixing; the same applies to the weight of the composition (c) hereinafter).

The content of the polymerizable monomer (A) that is a compound with the specific structure represented by the general formula (1) is preferably not less than 0.1 part by weight and not more than 99 parts by weight, more preferably not less than 0.5 parts by weight and not more than 95 parts by weight, and still more preferably not less than 1 part by weight and not more than 90 parts by weight per 100 parts by weight of the total weight of the polymerizable monomers present in the dental adhesive curable composition (c). If the content is below the lower limit of this range, the storage stability of the dental adhesive curable composition (c) at and above room temperature may not be ensured at times.

The dental adhesive curable composition (c) includes a polymerizable monomer (Bc) containing an acidic group in the molecule. Examples of the acidic groups present in the polymerizable monomer (Bc) include phosphoric groups, carboxylic groups (including acid anhydride groups), thiophosphoric groups and sulfonic groups. Examples of the polymerizable groups present in the polymerizable monomer (Bc) include those groups having a radically polymerizable carbon-carbon unsaturated double bond, such as (meth)acryloyl groups, (meth)acrylamide groups, styryl groups, vinyl groups and allyl groups. Of the polymerizable groups, methacryloyl groups are preferable as the polymerizable groups in view of facts such as that the dental adhesive curable composition (c) is mainly used in the mouth and the monomer is resistant to decomposition in the mouth by hydrolysis or the like.

Examples of the polymerizable monomers having a phosphoric group include (meth)acryloyloxyalkyl dihydrogen phosphates such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate and 20-(meth)acryloyloxyicosyl dihydrogen phosphate, bis[(meth)acryloyloxyalkyl]hydrogen phosphates such as bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate and bis[10-(meth)acryloyloxydecyl]hydrogen phosphate, 1,3-di(meth)acryloyloxypropyl dihydrogen phosphate, 2-(meth)acryloyloxyethylphenylhydrogen phosphate, 2-(meth)acryloyloxyethyl-2-bromoethylhydrogen phosphate, bis[2-(meth)acryloyloxy-(1-hydroxymethyl)ethyl]hydrogen phosphate, and acid chlorides, alkali metal salts and ammonium salts of these compounds. The phosphoric groups in these compounds may be replaced by thiophosphoric groups. The polymerizable monomers having a phosphoric group may be used singly, or two or more may be used in combination. In the dental adhesive curable composition (c), 2-(meth)acryloyloxyethylphenyl acid phosphate and 10-(meth)acryloyloxydecyl acid phosphate are preferable among the above compounds.

Examples of the polymerizable monomers having a pyrophosphoric group include bis[2-(meth)acryloyloxyethyl]pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, bis[10-(meth)acryloyloxydecyl] pyrophosphate, and acid chlorides, alkali metal salts and ammonium salts of these compounds. The pyrophosphoric groups in these compounds may be replaced by thiopyrophosphoric groups. The polymerizable monomers having a pyrophosphoric group may be used singly, or two or more may be used in combination.

Examples of the polymerizable monomers having a phosphonic group include 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and acid chlorides, alkali metal salts and ammonium salts of these compounds. The phosphonic groups in these compounds may be replaced by thiophosphonic groups. The polymerizable monomers having a phosphonic group may be used singly, or two or more may be used in combination.

Examples of the polymerizable monomers having a sulfonic group include 2-sulfeethyl (meth)acrylate, 2-sulfo-1-propyl (meth)acrylate, 1-sulfo-2-propyl (meth)acrylate, 1-sulfo-2-butyl (meth)acrylate, 3-sulfo-2-butyl (meth)acrylate, 3-bromo-2-sulfo-2-propyl (meth)acrylate, 3-methoxy-1-sulfo-2-propyl (meth)acrylate, 1,1-dimethyl-2-sulfoethyl (meth)acrylamide, and acid chlorides, alkali metal salts and ammonium salts of these compounds. The polymerizable monomers having a sulfonic group may be used singly, or two or more may be used in combination.

Examples of the polymerizable monomers having a carboxylic group (or a carboxylic anhydride group) include monocarboxylic acids, dicarboxylic acids, tricarboxylic acids and tetracarboxylic acids, and derivatives thereof, such as (meth)acrylic acid, maleic acid, p-vinylbenzoic acid, 11-(meth)acryloyloxy-1,1-undecanedicarboxylic acid (in the case of methacrylate: "MAC10"), 1,4-di(meth)acryloyloxyethylpyromellitic acid, 6-(meth)acryloyloxyethylnaphthalene-1,2,6-tricarboxylic acid, 4-(meth)acryloyloxymethyltrimellitic acid and an anhydride thereof, 4-(meth)acryloyloxyethyltrimellitic acid (in the case of methacrylate: "4-MET") and an anhydride thereof (in the case of methacrylate: 4-META), 4-(meth)acryloyloxybutyltrimellitic acid and an anhydride thereof, 4-[2-hydroxy-3-(meth)acryloyloxy]butyltrimellitic acid and an anhydride thereof, 2,3-bis(3,4-dicarboxybenzoyloxy)propyl (meth)acrylate, N,O-di(meth)acryloyltyrosine, O-(meth)acryloyltyrosine, N-(meth)acryloyltyrosine, N-(meth)acryloylphenylalanine, N-(meth)acryloyl-p-aminobenzoic acid, N-(meth)acryloyl-O-aminobenzoic acid, N-(meth)acryloyl-5-aminosalicylic acid (in the case of methacrylate: "5-MASA"), N-(meth)acryloyl-4-aminosalicylic acid, 2 or 3 or 4-(meth)acryloyloxybenzoic acid, addition product of 2-hydroxyethyl (meth)acrylate with pyromellitic dianhydride (in the case of methacrylate: "PMDM"), addition product of 2-hydroxyethyl (meth)acrylate with maleic anhydride or 3,3',4,4'-benzophenonetetracarboxylic dianhydride (in the case of methacrylate: "BTDA") or 3,3',4,4'-biphenyltetracarboxylic dianhydride, 2-(3,4-dicarboxybenzoyloxy)-1,3-di(meth)acryloyloxypropane, adduct of N-phenylglycine or N-tolylglycine with glycidyl (meth)acrylate, 4-[(2-hydroxy-3-(meth)acryloyloxypropyl)amino]phthalic acid, 3 or 4-[N-methyl-N-(2-hydroxy-3-(meth)acryloyloxypropyl)amino]phthalic acid, and acid chlorides, alkali metal salts and ammonium salts of these compounds. The polymerizable monomers having a carboxylic group may be used singly, or two or more may be used in combination.

The polymerizable monomers (Bc) may be used singly, or two or more may be used in combination.

The content of the polymerizable monomer (Bc) containing an acidic group in the molecule is preferably 0.1 to 30 parts by weight, more preferably 0.5 to 20 parts by weight, and still more preferably 1 to 10 parts by weight per 100 parts by weight of the total weight of the polymerizable monomers present in the dental adhesive curable composition (c). If the content is below the lower limit of this range, the adhesion may not be ensured at times.

The dental adhesive curable composition (c) may contain an additional polymerizable monomer (Ec) (an acidic group-free polymerizable monomer) which is copolymerizable with the dental polymerizable monomer (A) and the polymerizable monomer (Bc) having an acidic group in the molecule and which does not belong to the polymerizable monomers (A) and (Bc). A preferred polymerizable monomer (Ec) is a radically polymerizable monomer having a polymerizable group. Examples of the polymerizable groups include those groups having a radically polymerizable carbon-carbon unsaturated double bond, such as (meth)acryloyl groups, (meth)acrylamide groups, styryl groups, vinyl groups and allyl groups. Of the polymerizable groups, methacryloyl groups are preferable as the polymerizable groups in view of facts such as that the dental adhesive curable composition (c) is mainly used in the mouth and the monomer is resistant to decomposition in the mouth by hydrolysis or the like.

The content of the additional polymerizable monomer (Ec) is preferably not less than 1 part by weight and not more than 95 parts by weight, more preferably not less than 5 parts by weight and not more than 90 parts by weight, and still more preferably not less than 10 parts by weight and not more than 85 parts by weight per 100 parts by weight of the total weight of the polymerizable monomers present in the dental adhesive curable composition (c).

The additional polymerizable monomers (Ec) which may be used in the dental adhesive curable composition (c) are largely classified into monofunctional polymerizable monomers (Ec1) and polyfunctional polymerizable monomers. The polyfunctional monomers are largely divided into difunctional polymerizable monomers (Ec2) such as aromatic compound-based difunctional polymerizable monomers (Ec2R) and aliphatic compound-based difunctional polymerizable monomers (Ec2L), and trifunctional and polyfunctional polymerizable monomers (Ec3).

Examples of the monofunctional monomers (Ec1) include hydroxyalkyl (meth)acrylates such as 2-hydroxyethyl (meth)acrylate, 3-hydroxypropyl (meth)acrylate, 4-hydroxybutyl (meth)acrylate, 6-hydroxyhexyl (meth)acrylate and 10-hydroxydecyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N,N-(dihydroxyethyl) (meth)acrylamide, methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth)acrylate, 2,3-dibromopropyl (meth)acrylate, 3-(meth)acryloyloxypropyltrimethoxysilane, 11-(meth)acryloyloxyundecyltrimethoxysilane, (meth)acrylamide, dimethylaminoethyl methacrylate, dimethylaminopropyl methacrylate, dimethylaminobutyl methacrylate, and acrylates of these compounds.

Examples of the aromatic compound-based difunctional polymerizable monomers (Ec2R) include 2,2-bis((meth)acryloyloxyphenyl)propane, 2,2-bis[4-(3-(meth)acryloyloxy-2-hydroxypropoxy)phenyl]propane (commonly known as "bis-GMA"), 2,2-bis(4-(meth)acryloyloxyphenyl)propane, 2,2-bis(4-(meth)acryloyloxypolyethoxyphenyl)propane, 2,2-bis(4-(meth)acryloyloxydiethoxyphenyl)propane), 2,2-bis(4-(meth)acryloyloxytetraethoxyphenyl)propane, 2,2-bis(4-(meth)acryloyloxypentaethoxyphenyl)

propane, 2,2-bis(4-(meth)acryloyloxydipropoxyphenyl) propane, 2-(4-(meth)acryloyloxyethoxyphenyl)-2-(4-(meth) acryloyloxy diethoxyphenyl)propane, 2-(4-(meth) acryloyloxydiethoxyphenyl)-2-(4-(meth)acryloyloxytriethoxyphenyl)propane, 2-(4-(meth)acryloyloxydipropoxyphenyl)-2-(4-(meth)acryloyl oxytriethoxyphenyl) propane, 2,2-bis(4-(meth)acryloyloxypropoxyphenyl)propane, 2,2-bis(4-(meth)acryloyloxyisopropoxyphenyl) propane and 1,4-bis(2-(meth)acryloyloxyethyl) pyromellitate. Of these, 2,2-bis[4-(3-(meth)acryloyloxy)-2-hydroxypropoxyphenyl]pro pane (commonly known as "bis-GMA") and 2,2-bis(4-(meth)acryloyloxypolyethoxyphenyl)propane are preferable. Of the 2,2-bis(4-(meth)acryloyloxypolyethoxyphenyl)propanes, the compound having an average number of moles of ethoxy groups added of 2.6 (commonly known as "D2.6E") is preferable.

Examples of the aliphatic compound-based difunctional polymerizable monomers (Ec2L) include glycerol di(meth) acrylate, alkylene glycol di(meth)acrylates such as ethylene glycol di(meth)acrylate, diethylene glycol di(meth)acrylate, triethylene glycol di(meth)acrylate, propylene glycol di(meth)acrylate, butylene glycol di(meth)acrylate and neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,12-dodecanediol di(meth)acrylate, 1,2-bis(3-methacryloyloxy-2-hydroxypropoxy)ethane, 2,2,4-trimethylhexamethylenebis(2-carbamoyloxyethyl) dimethacrylate (commonly known as "UDMA") and 1,2-bis(3-methacryloyloxy-2-hydroxypropoxy)ethane. Of these, 2,2,4-trimethylhexamethylenebis(2-carbamoyloxyethyl) dimethacrylate (commonly known as "UDMA") and triethylene glycol di(meth)acrylate (commonly known as "TEGDMA") are preferable.

Examples of the trifunctional or polyfunctional polymerizable monomers (Ec3) include trimethylolpropane tri(meth) acrylate, trimethylolethane tri(meth)acrylate, trimethylolimethane tri(meth)acrylate, pentaerythritol tri(meth)acrylate, pentaerythritol tetra(meth)acrylate, dipentaerythritol penta (meth)acrylate, N,N-(2,2,4-trimethylhexamethylene)bis[2-(aminocarboxy)propane-1,3-diol] tetramethacrylate and 1,7-diacryloyloxy-2,2,6,6-tetraacryloyloxymethyl-4-oxyheptane.

The content of the monofunctional polymerizable monomer (Ec1), when the effects of the monomer are desired, is preferably 0.1 to 95 parts by weight, more preferably 1 to 80 parts by weight, and still more preferably 5 to 50 parts by weight per 100 parts by weight of the total weight of the polymerizable monomers present in the dental adhesive curable composition (c). This content ensures that the obtainable composition exhibits higher affinity for various types of adherends and cured products of the dental adhesive curable composition (c) attain excellent bond strength with respect to the adherends.

The content of the difunctional polymerizable monomer (Ec2) is preferably 0.1 to 95 parts by weight, more preferably 1 to 80 parts by weight, and still more preferably 5 to 70 parts by weight per 100 parts by weight of the total weight of the polymerizable monomers present in the dental adhesive curable composition (c). The lower limit of this range ensures that the composition (c) before curing exhibits enhanced handleability, while the upper limit ensures that excellent strength is imparted to cured products obtained from the composition (c).

The content of the aromatic compound-based difunctional polymerizable monomer (Ec2R) is preferably 0.1 to 95 parts by weight, more preferably 1 to 80 parts by weight, and still more preferably 5 to 70 parts by weight per 100 parts by weight of the total weight of the polymerizable monomers present in the dental adhesive curable composition (c). This amount of the polymerizable monomer (Ec2R) added to the dental adhesive curable composition (c) ensures that cured products obtained from the composition (c) attain enhanced strength.

The content of the aliphatic compound-based difunctional polymerizable monomer (Ec2L) is preferably 0.1 to 95 parts by weight, more preferably 1 to 80 parts by weight, and still more preferably 5 to 70 parts by weight per 100 parts by weight of the total weight of the polymerizable monomers present in the dental adhesive curable composition (c). This amount of the polymerizable monomer (Ec2L) added to the dental adhesive curable composition (c) ensures that the composition (c) before curing exhibits enhanced handleability.

The content of the trifunctional or polyfunctional polymerizable monomer (Ec3), when the effects of the monomer are desired, is preferably 1 to 90 parts by weight per 100 parts by weight of the total weight of the polymerizable monomers present in the dental adhesive curable composition (c).

In the case where the dental adhesive curable composition (c) is in the form of a kit composed of a plurality of separate compositions including a first composition, a second composition and the like for purposes such as storage, the polymerizable monomers described above may be present in one or more of such compositions.

The dental adhesive curable composition (c) contains a polymerization initiator (Cc).

A peroxide (Cc1) is preferably used as the polymerization initiator (Cc). Examples of the peroxides (Cc1) include organic peroxides such as diacyl peroxides, peroxyesters, dialkyl peroxides, peroxyketals, ketone peroxides and hydroperoxides; inorganic peroxides such as ammonium persulfate, potassium persulfate, potassium chlorate, potassium bromate and potassium superphosphate; alkylboranes, partial oxides of alkylboranes, inorganic sulfur compounds and azo compounds. Of these peroxides (Cc1), diacyl peroxides (Cc11) are preferable because they provide high chemical polymerizability.

Examples of the diacyl peroxides (Cc11) include diacetyl peroxide, dipropyl peroxide, dibutyl peroxide, dicapryl peroxide, dilauryl peroxide, dilauryl peroxide, benzoyl peroxide (BPO), p,p'-dichlorobenzoyl peroxide, p,p'-dimethoxybenzoyl peroxide, p,p'-dimethylbenzoyl peroxide and p,p'-dinitrodibenzoyl peroxide. Of these diacyl peroxides (Cc11), BPO is preferable.

Organoboron compounds (Cc12) or compositions containing such compounds may be also suitably used as the peroxides (Cc1). Examples of the organoboron compounds (Cc12) include trialkylborons such as triethylboron, tripropylboron, triisopropylboron, tributylboron, tri-sec-butylboron, triisobutylboron, tripentylboron, trihexylboron, trioctylboron, tridecylboron, tridodecylboron, tricyclopentylboron and tricyclohexylboron; alkoxyalkylborons such as butoxydibutylboron; and dialkylboranes such as butyldicyclohexylborane, diisoamylborane and 9-borabicyclo[3,3,1]nonane. Examples further include partial oxides of the above organoboron compounds. The organoboron compounds (Cc12) may be used singly, or two or more may be used in combination. Of the organoboron compounds (Cc12), tributylboron and partially oxidized tributylboron are preferable. For example, the partially oxidized tributylboron is preferably one in which 0.3 to 0.9 moles of oxygen molecules are added per 1 mol of tributylboron. Further, the polymerization initiator (Cc) may be a composition which includes the organoboron compound (Cc12), and an aprotic solvent and/or an organic oligomer or polymer (which may be liquid or solid) that is inert to organoboron compounds.

The polymerization initiator (Cc) may be a combination of the peroxide (Cc1) with a photopolymerization initiator (Cc2). The photopolymerization initiator (Cc2) is usually a compound which is sensitized by UV lights or visible lights. Examples of the photopolymerization initiators (Cc2) include α-ketocarbonyl compounds (Cc21) and acylphosphine oxide compounds (Cc22).

Examples of the α-ketocarbonyl compounds (Cc21) suitably used include α-diketones such as diacetyl, 2,3-pentadione, 2,3-hexadione, benzil, 4,4'-dimethoxybenzil, 4,4'-diethoxybenzil, 4,4'-oxybenzil, 4,4'-dichlorobenzil, 4-nitrobenzil, α-naphthol, β-naphthol, camphorquinone (CQ), camphorquinonesulfonic acid, camphorquinonecarboxylic acid and 1,2-cyclohexanedione; α-ketoaldehydes such as methylglyoxal and phenylglyoxal: pyruvic acid, benzoylformic acid, phenylpyruvic acid, methyl pyruvate, ethyl benzoylformate, methyl phenylpyruvate and butyl phenylpyruvate. Of the α-ketocarbonyl compounds (Cc21), α-diketones are preferable from points of view such as stability, and diacetyl, benzil and camphorquinone (CQ) are more preferable.

Examples of the acylphosphine oxide compounds (Cc22) include benzoyldimethoxyphosphine oxide, benzoylethoxyphenylphosphine oxide, benzoyldiphenylphosphine oxide, 2-methylbenzoyldiphenylphosphine oxide and 2,4,6-trimethylbenzoyldiphenylphosphine oxide.

The photopolymerization initiators (Cc2) may be used singly, or two or more may be used in combination.

The polymerization initiators (Cc) may be used singly, or two or more may be used in combination.

The content of the polymerization initiator (Cc) is preferably 0.0001 to 20 parts by weight, more preferably 0.05 to 10 parts by weight, and still more preferably 0.1 to 5 parts by weight per 100 parts by weight of the total weight of the polymerizable monomers present in the dental adhesive curable composition (c). If the content is below the lower limit of this range, curability is not sufficiently obtained at times.

The content of the peroxide (Cc1) is preferably 0.01 to 20 parts by weight, more preferably 0.05 to 10 parts by weight, and still more preferably 0.1 to 5 parts by weight per 100 parts by weight of the total weight of the polymerizable monomers present in the dental adhesive curable composition (c). If the content is below the lower limit of this range, chemical polymerizability cannot be ensured at times. If the content exceeds the upper limit, the curing rate is increased more than necessary to cause a risk that a sufficient working time cannot be ensured, and also the composition may form a precipitate.

The content of the diacyl peroxide (Cc11) is preferably 0.01 to 20 parts by weight, more preferably 0.05 to 10 parts by weight, and still more preferably 0.1 to 5 parts by weight per 100 parts by weight of the total weight of the polymerizable monomers present in the dental adhesive curable composition (c). If the content is below the lower limit of this range, chemical polymerizability cannot be ensured at times. If the content exceeds the upper limit, the curing rate is increased more than necessary to cause a risk that a sufficient working time cannot be ensured, and also the composition may form a precipitate.

The content of the organoboron compound (Cc12) is preferably 0.001 to 20 parts by weight, more preferably 0.01 to 10 parts by weight, and still more preferably 0.1 to 5 parts by weight per 100 parts by weight of the total weight of the polymerizable monomers present in the dental adhesive curable composition (c). Contents outside this range are not preferable because if the content is below the lower limit, the compound may fail to provide advantageous effects on the polymerizability of the composition, and if the content exceeds the upper limit, the composition may form a precipitate and may suffer a curing failure.

The content of the photopolymerization initiator (Cc2) is preferably 0.0001 to 15 parts by weight, more preferably 0.0005 to 5 parts by weight, and still more preferably 0.001 to 5 parts by weight per 100 parts by weight of the total weight of the polymerizable monomers present in the dental adhesive curable composition (c). If the content is below the lower limit of this range, polymerization may not proceed to a sufficient extent. If the content exceeds the upper limit, the composition may form a precipitate and may suffer a curing failure.

The content of the α-ketocarbonyl compound (Cc21) or the acylphosphine oxide compound (Cc22) is preferably 0.0001 to parts by weight, more preferably 0.001 to 10 parts by weight, and still more preferably 0.005 to 5 parts by weight per 100 parts by weight of the total weight of the polymerizable monomers present in the dental adhesive curable composition (c). If the dental adhesive curable composition (c) contains a large amount of the α-ketocarbonyl compound (Cc21), chemical polymerization of the composition sometimes results in a cured product that is strongly yellowish. Thus, the content of the α-ketocarbonyl compound (Cc21) is preferably 0.001 to 0.5 parts by weight per 100 parts by weight of the total weight of the polymerizable monomers present in the dental adhesive curable composition (c).

The dental adhesive curable composition (c) contains a reductant (Dc). In a composition containing an acid-forming component, as is the case in the dental adhesive curable composition (c), chemical polymerization using a polymerization initiator (Cc) is allowed to take place efficiently when a reductant (Dc) is used in combination. Examples of the reductants include amine compounds (Dc1) or salts thereof, and sulfinic acid compounds (Dc2) or salts thereof. These compounds or salts may be any known such compounds without limitation as long as the compounds can be used as reductants. The above compounds or salts may be any of aliphatic compounds, alicyclic compounds, aromatic compounds or salts of these compounds. In a preferred embodiment of the dental adhesive curable composition (c), the reductant (Dc) is a mixture of an amine compound (Dc1) or a salt thereof, and a sulfinic acid compound (Dc2) or a salt thereof.

Preferred amine compounds (Dc1) are aromatic substituted glycine compounds (Dc11) or salts thereof, and aromatic tertiary amines (Dc12).

The aromatic substituted glycine compounds (Dc11) or salts thereof may be aromatic substituted glycines, and usual alkali metal salts, alkaline earth metal salts, amine salts and ammonium salts thereof. The salts of the aromatic substituted glycine compounds (Dc11) may be salts of glycine and aromatic amines. Of these, the use of aromatic substituted glycine salts is more preferable because storage stability is enhanced. Examples of the alkali metal salts include lithium salts, sodium salts and potassium salts. Examples of the alkaline earth metal salts include magnesium salts, calcium salts, strontium salts and barium salts. Examples of the amine salts include salts of primary amines such as methylamine, ethylamine, propylamine, butylamine, aniline, toluidine, phenylenediamine and xylylenediamine; salts of secondary amines such as dimethylamine, diethylamine, dipropylamine, dibutylamine, piperidine, N-methylaniline, N-ethylaniline, diphenylamine and N-methyltoluidine; and salts of tertiary amines such as trimethylamine, triethylamine, pyridine, N,N-dimethylaniline, N,N-di(β-hydroxyethyl)aniline, N,N-diethylamine, N,N-dimethyltoluidine, N,N-diethyltoluidine and N,N-(β-hydroxyethyl)toluidine. Examples of the salts of ammonium compounds include ammonium salts, tetramethylammonium salts, tetraethylammonium salts, tetrapropylammonium salts and trimethylbenzylammonium salts.

Examples of the aromatic substituted glycine compounds (Dc11) include N-phenylglycine (NPG), N-tolylglycine (NTG) and N,N-(3-methacryloyloxy-2-hydroxypropyl)phenylglycine (NPG-GMA). These aromatic substituted glycine compounds and the salts of these compounds, among others, may be used as the aromatic substituted glycine compounds or salts thereof (Dc11). Of the aromatic substituted glycine compounds or salts thereof (Dc11), NPG and salts thereof are preferable. The aromatic substituted glycine compounds (Dc11) or salts thereof may be used singly, or two or more may be used in combination.

Examples of the aromatic tertiary amines (Dc12) include N,N-dimethylaniline (DMA), N,N-dimethyl p-toluidine (DMPT), N,N-diethyl p-toluidine, N,N-diethanol p-toluidine (DEPT), N,N-dimethyl-m-toluidine, N,N-diethyl-p-toluidine, N,N-dimethyl p-ethylaniline, N,N-dimethyl p-isopropylaniline, N,N-dimethyl p-tert-butylaniline, N,N-dimethylanisidine, N,N-dimethylxylidine, N,N-dimethyl-3,5-di-t-butylaniline, N,N-dimethyl p-chloroaniline, N,N-dimethyl p-fluoroaniline, N-methyl-N-phenylaminoethyl (meth)acrylate, N-ethyl-N-phenylaminoethyl (meth)acrylate, N, N-dimethyl aminobenzoic acid and alkyl esters thereof; methyl N,N-dimethylaminobenzoate, ethyl N,N-dimethylaminobenzoate (DMABAE), butoxyethyl N,N-dimethylaminobenzoate (DMABABE), N,N-diethylaminobenzoic acid (DEABA) and alkyl esters thereof, N,N-dimethylaminobenzaldehyde (DMABAd) and N,N-dimethylaminobenzophenone. Of these aromatic tertiary amines (Dc12), DMPT, DEPT, DEABAE and DMABABE are preferable. The aromatic tertiary amines (Dc12) may be used singly, or two or more may be used in combination.

Barbituric acid compounds (Dc13) and thioureas (Del 4) are also usable as the amine compounds (Dc1).

Examples of the barbituric acid compounds (Dc13) include 1,3,5-trimethylbarbituric acid, 1,3,5-triethylbarbituric acid, 1,3-dimethyl-5-ethylbarbituric acid, 1,5-dimethylbarbituric acid, 1-methyl-5-ethylbarbituric acid, 1-methyl-5-propylbarbituric acid, 5-ethylbarbituric acid, 5-propylbarbituric acid, 5-butylbarbituric acid, 5-methyl-1-butylbarbituric acid, 1-benzyl-5-phenylbarbituric acid, l-cyclohexyl-5-ethylbarbituric acid, and alkali metal salts of these acids.

Examples of the thioureas (Dc14) include thiourea, methylthiourea, ethylthiourea, N,N'-dimethylthiourea, N,N'-diethylthiourea, N,N'-di-n-propylthiourea, dicyclohexylthiourea, trimethylthiourea, triethylthiourea, tri-n-propylthiourea, tricyclohexylthiourea, tetramethylthiourea, tetraethylthiourea, tetra-n-propylthiourea and tetracyclohexylthiourea.

Examples of the sulfinic acid compounds (Dc2) or salts thereof include sulfinic acids, and usual alkali metal salts, alkaline earth metal salts, amine salts and ammonium salts of sulfinic acids. To attain excellent hue of cured products and excellent storage stability, aromatic sulfinate salts are preferably used, and aromatic sulfinate salts having an electron withdrawing functional group are more preferably used. Examples of the alkali metal salts include lithium salts, sodium salts and potassium salts. Examples of the alkaline earth metal salts include magnesium salts, calcium salts, strontium salts and barium salts. Examples of the amine salts include salts of primary amines such as methylamine, ethylamine, propylamine, butylamine, aniline, toluidine, phenylenediamine and xylylenediamine; salts of secondary amines such as dimethylamine, diethylamine, dipropylamine, dibutylamine, piperidine, N-methylaniline, N-ethylaniline, diphenylamine and N-methyltoluidine; and salts of tertiary amines such as trimethylamine, triethylamine, pyridine, N,N-dimethylaniline, N,N-di(β-hydroxyethyl)aniline, N,N-diethylamine, N,N-dimethyltoluidine, N,N-diethyltoluidine and N,N-(β-hydroxyethyl)toluidine. Examples of the salts of ammonium compounds include ammonium salts, tetramethylammonium salts, tetraethylammonium salts, tetrapropylammonium salts and trimethylbenzylammonium salts.

Examples of the organic sulfinic acid compounds (Dc2) include alkanesulfinic acids such as methanesulfinic acid, ethanesulfinic acid, propanesulfinic acid, hexanesulfinic acid, octanesulfinic acid, decanesulfinic acid and dodecanesulfinic acid; alicyclic sulfinic acids such as cyclohexanesulfinic acid and cyclooctanesulfinic acid; and aromatic sulfinic acids such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid, fluorobenzenesulfinic acid and naphthalenesulfinic acid.

Examples of the salts of the organic sulfinic acid compounds (Dc2) include salts of the above-listed sulfinic acid compounds (Dc2), for example, lithium methanesulfinate, sodium methanesulfinate, potassium methanesulfinate, magnesium methanesulfinate, calcium methanesulfinate, strontium methanesulfinate, barium methanesulfinate, butylamine methanesulfinate salt, aniline methanesulfinate salt, toluidine methanesulfinate salt, phenylenediamine methanesulfinate salt, diethylamine methanesulfinate salt, diphenylamine methanesulfinate salt, triethylamine methanesulfinate salt, tributylamine methanesulfinate salt, ammonium methanesulfinate salt, tetramethylammonium methanesulfinate, trimethylbenzylammonium methanesulfinate, lithium benzenesulfinate, sodium benzenesulfinate, potassium benzenesulfinate, magnesium benzenesulfinate, calcium benzenesulfinate, strontium benzenesulfinate, barium benzenesulfinate, butylamine benzenesulfinate salt, aniline benzenesulfinate salt, toluidine benzenesulfinate salt, phenylenediamine benzenesulfinate salt, diethylamine benzenesulfinate salt, diphenylamine benzenesulfinate salt, triethylamine benzenesulfinate salt, tributylamine benzenesulfinate salt, ammonium benzenesulfinate salt, tetramethylammonium benzenesulfinate and trimethylbenzylammonium benzenesulfinate.

Examples of the salts of the organic sulfinic acid compounds (Dc2) further include lithium o-toluenesulfinate, sodium o-toluenesulfinate, potassium o-toluenesulfinate, calcium o-toluenesulfinate, cyclohexylamine o-toluenesulfinate salt, aniline o-toluenesulfinate salt, ammonium o-toluenesulfinate salt, tetraethylammonium o-toluenesulfinate, lithium p-toluenesulfinate, sodium p-toluenesulfinate, potassium p-toluenesulfinate, calcium p-toluenesulfinate, barium p-toluenesulfinate, ethylamine p-toluenesulfinate salt, butylamine p-toluenesulfinate salt, toluidine p-toluenesulfinate salt, N-methylaniline p-toluenesulfinate salt, pyridine p-toluenesulfinate salt, ammonium p-toluenesulfinate salt, tetramethylammonium p-toluenesulfinate, tetraethylammonium p-toluenesulfinate, tetrabutylammonium p-toluenesulfinate, sodium β-naphthalenesulfinate, strontium β-naphthalenesulfinate, triethylamine β-naphthalenesulfinate, N-methyltoluidine β-naphthalenesulfinate, ammonium β-naphthalenesulfinate, trimethylbenzylammonium β-naphthalenesulfinate, lithium p-chlorobenzenesulfinate, sodium p-chlorobenzenesulfinate, potassium p-chlorobenzenesulfinate, calcium p-chlorobenzenesulfinate, barium p-chlorobenzenesulfinate, ethylamine p-chlorobenzenesulfinate salt, butylamine p-chlorobenzenesulfinate salt, toluidine p-chlorobenzenesulfinate salt, N-methylaniline p-chlorobenzenesulfinate salt, pyridine p-chlorobenzenesulfinate salt, ammonium p-chlorobenzenesulfinate salt, tetramethylammonium p-chlorobenzenesulfinate, tetraethylammonium p-chlorobenzenesulfinate and tetrabutylammonium p-chlorobenzenesulfinate.

Examples of the reductants (Dc), other than those compounds mentioned above, include inorganic reducing compounds (Dc3) and reducing borate compounds (Dc4).

The inorganic reducing compounds (Dc3) may be reducing inorganic compounds containing sulfur, nitrogen and/or boron. Examples of the sulfur-containing inorganic reducing compounds (Dc3) include sulfurous acid, bisulfurous acid, metasulfurous acid, metabisulfurous acid, pyrosulfurous acid, thiosulfuric acid, dithionous acid, hyposulfurous acid, hydrosulfurous acid, and salts of these acids. Of these, sulfite salts are preferable. Some preferred sulfite salts are sodium sulfite, potassium sulfite, sodium hydrogen sulfite and potassium hydrogen sulfite. Examples of the nitrogen-containing inorganic reducing compounds (Dc3) include nitrite salts such as sodium nitrite, potassium nitrite, calcium nitrite and ammonium nitrite. Preferred reducing borate compounds (Dc4) are arylborate compounds. The arylborate compounds may be any known borate compounds without limitation which have 1 to 4 aryl groups in the molecule.

The reductants (Dc) may be used singly, or two or more may be used in combination.

The content of the reductant (Dc) is preferably 0.001 to parts by weight, more preferably 0.005 to 10 parts by weight, and still more preferably 0.01 to 5 parts by weight per 100 parts by weight of the total weight of the polymerizable monomers present in the dental adhesive curable composition (c). If the content is below the lower limit of this range, the composition (c) may exhibit insufficient curability.

The content of the amine compound (Dc1) or salt thereof is preferably 0.001 to 20 parts by weight, more preferably 0.005 to 10 parts by weight, and still more preferably 0.01 to 5 parts by weight per 100 parts by weight of the total weight of the polymerizable monomers present in the dental adhesive curable composition (c). If the content is below the lower limit of this range, the composition (c) may exhibit insufficient curability. If the content exceeds the upper limit, the esthetic properties of the composition (c) are sometimes decreased by the discoloration of the amine compound.

The content of the sulfinic acid compound (Dc2) or salt thereof is preferably 0.001 to 15 parts by weight, more preferably 0.01 to 10 parts by weight, and still more preferably 0.1 to 5 parts by weight per 100 parts by weight of the total weight of the polymerizable monomers present in the dental adhesive curable composition (c). If the content is below the lower limit of this range, the polymerizability of the composition may not be ensured at times and, when the compound is used in combination with an amine compound as a reductant or the like, the suppressive effect of the sulfinic acid compound or salt thereof against a discoloration by the amine compound is decreased and consequently the esthetic properties of the composition (c) are sometimes decreased. On the other hand, any addition in excess of the upper limit may induce a curing failure of the composition.

The content of the aromatic substituted glycine compound (Dc11) or salt thereof is preferably 0.001 to 10 parts by weight, more preferably 0.005 to 10 parts by weight, and still more preferably 0.01 to 5 parts by weight per 100 parts by weight of the total weight of the polymerizable monomers present in the dental adhesive curable composition (c). If the content is below the lower limit of this range, the polymerizability of the composition (c) may be decreased. If the content exceeds the upper limit, the esthetic properties of the curable composition are sometimes decreased by the discoloration of the aromatic substituted glycine compound.

The content of the aromatic tertiary amine (Dc12) is preferably 0.001 to 20 parts by weight, more preferably 0.005 to 10 parts by weight, and still more preferably 0.01 to 5 parts by weight per 100 parts by weight of the total weight of the polymerizable monomers present in the dental adhesive curable composition (c). If the content is below the lower limit of this range, the polymerizability of the composition may be decreased. If the content exceeds the upper limit, the esthetic properties of the composition (c) are sometimes decreased by the discoloration of the aromatic amine compound.

The content of the inorganic reducing compound (Dc3) is preferably 0.01 to 10 parts by weight per 100 parts by weight of the total weight of the polymerizable monomers present in the dental adhesive curable composition (c). If the content is below the lower limit of this range, the effects of the compound may not be obtained at times. Any addition in excess of the upper limit may induce a curing failure of the composition (c).

The content of the reducing borate compound (Dc4) is preferably 0.01 to 10 parts by weight per 100 parts by weight of the total weight of the polymerizable monomers present in the dental adhesive curable composition (c). If the content is below the lower limit of this range, the effects of the compound may not be obtained at times.

The content of the reductant (Dc) is preferably 0.01 to 1000 parts by weight, more preferably 0.05 to 750 parts by weight, and still more preferably 1 to 500 parts by weight per 100 parts by weight of the total weight of the polymerization initiator (s) (Cc) present in the dental adhesive curable composition (c).

The dental adhesive curable composition (c) may further contain a filler (Fc). Examples of the fillers (Fc) include inorganic glass fillers (Fc1), fine particulate silica fillers (Fc2), organic fillers (Fc3) and organic-inorganic composite fillers (Fc4).

Examples of the inorganic materials which form the inorganic glass fillers (Fc1) and the fine particulate silica fillers (Fc2) include minerals based on silica such as silica, silica alumina, alumina quartz, kaolin, clay, silicate minerals and mica; ceramics based on silica and containing inorganic oxides other than silica such as aluminum oxide, boron oxide, titanium oxide, zirconium oxide, barium oxide, lanthanum oxide, strontium oxide, zinc oxide, calcium oxide, lithium oxide, sodium oxide and bismuth oxide; glasses such as lanthanum glass, barium glass, strontium glass, soda glass, lithium borosilicate glass, zinc glass, fluoroaluminosilicate glass, borosilicate glass and bioglass; crystalline quartz, hydroxyapatite, yttrium oxide, zirconia, calcium carbonate, aluminum sulfate, barium sulfate, calcium sulfate, calcium phosphate calcium phosphate, aluminum hydroxide, sodium fluoride, potassium fluoride, sodium monofluorophosphate, lithium fluoride and ytterbium fluoride.

Examples of the organic fillers (Fc3) include crushed polymers, powdery polymers obtained by dispersion polymerization, and crushed powders of polymers obtained by polymerization of polymerizable monomers including cross-linking agents. The types of organic materials which form the organic fillers (Fc3) are not particularly limited. Some preferred organic materials are polymers such as homopolymers and copolymers of polymerizable monomers. Examples of the polymers include polymethyl methacrylate (PMMA), polyethyl methacrylate, polypropyl methacrylate, polybutyl methacrylate (PBMA), polyvinyl acetate (PVAc), polyethylene glycol (PEG), polypropylene glycol (PPG) and polyvinyl alcohol (PVA).

Examples of the inorganic-organic composite fillers (Fc4) include fillers obtained by coating the surface of the aforementioned inorganic fillers with a polymer including a polymerizable monomer, followed by crushing. Specific examples include fillers (TMPT•f) obtained by coating inorganic fillers such as fine powdery silica and zirconium oxide with a polymer including polymerizable monomers based on trimethylolpropane tri(meth)acrylate (TMPT), and crushing the resultant composite products.

When the inorganic glass filler (Ec1), the fine particulate silica filler (Fc2) or the inorganic-organic composite filler (Fc4) is used as the filler (Fc), it is preferable to treat the surface of the filler with an agent such as a coupling agent in order to enhance the affinity for the polymerizable monomers used in the dental adhesive curable composition (c) and to enhance the dispersibility. Examples of the coupling agents include silane coupling agents, titanate coupling agents, aluminate coupling agents and zirco-aluminate coupling agents. Of these coupling agents, silane coupling agents are preferable. Preferred examples of the silane coupling agents include methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy) silane, γ-methacryloyloxypropyltrimethoxysilane, γ-chloropropyltrimethoxysilane, γ-glycidoxypropyltrimethoxysilane and hexamethyldisilazane. The surface treatment with agents such as coupling agents may be performed by a known method. Further, the surface treatment of the filler may be performed by graft polymerizing a radically polymerizable monomer onto the surface of the filler.

The filler (Fc) is preferably the inorganic glass filler (Fc1) or the fine particulate silica filler (Fc2), and is more preferably the inorganic glass filler (Fc1) or the fine particulate silica filler (Fc2) of which each is surface-treated with an organic compound such as a coupling agent. The fillers (Fc) may be used singly, or two or more may be used in combination.

The content of the filler (Fc) is preferably not more than 95 parts by weight, more preferably not more than 90 parts by weight, and still more preferably not more than 85 parts by weight per 100 parts by weight of the total weight of the polymerizable monomers present in the dental adhesive curable composition (c). To impart excellent strength to cured products obtained from the dental adhesive curable composition (c), the content of the filler (Fc) is preferably not less than parts by weight, more preferably not less than 10 parts by weight, and still more preferably not less than 20 parts by weight per 100 parts by weight of the total weight of the polymerizable monomers present in the dental adhesive curable composition (c).

The content of the filler (Fc) is preferably 5 to 95 wt %, more preferably 10 to 90 wt %, and still more preferably 20 to 85 wt % in the dental adhesive curable composition (c).

The dental adhesive curable composition (c) may further contain an additional additive (Gc) other than the (Ac), (Bc), (Cc), (Dc), (Ec) and (Fc) described hereinabove while still ensuring that the effects of the composition are not impaired. Examples of the additional additives (Gc) include calcium-containing compounds such as calcium chloride, fluorine-containing compounds such as sodium fluoride, polymerization inhibitors, stabilizers, pigments, fluorescent agents, UV absorbers, fungicides, antimicrobial agents, treatment components for performing treatments such as remineralization, and bioactive components.

The content of the additional additive (Gc) is preferably 0.00001 to 10 parts by weight, more preferably 0.00005 to 5 parts by weight, and still more preferably 0.0001 to 1 part by weight per 100 parts by weight of the total weight of the polymerizable monomers present in the dental adhesive curable composition (c). If the content is below the lower limit of this range, the additive (Gc) may fail to exhibit its characteristics. If the content exceeds the upper limit, the effects of the dental adhesive curable composition (c) may be impaired at times.

The curing time of the dental adhesive curable composition (c) (before thermal loading) is preferably 1 to 10 minutes, more preferably 1.5 to 8 minutes, and still more preferably 2 to 5 minutes. If the curing time is below the lower limit of this range, the polymerizability is higher than necessary and the pot life is so short that workability is poor at times. If the curing time exceeds the upper limit, the composition does not have sufficient polymerizability and takes too long to cure, possibly causing poor workability.

The curing time may be evaluated by a DSC method. In the evaluation of the curing time by a DSC method, the components for the dental adhesive curable composition (c) are mixed together and the mixture is placed into an aluminum cell (pan), the polymerization heat generated by radical polymerization is measured by differential thermal analysis, and the time from the start of the mixing to when the maximum temperature is reached is evaluated as the curing time. The DSC measurement may be performed using a differential scanning calorimeter (for example, DSC-60 manufactured by Shimadzu Corporation) at a measurement temperature of $37\pm2°$ C.

The tensile bond strength of cured products of the dental adhesive curable composition (c) is preferably not less than 4 MPa, more preferably not less than 6 MPa, and still more preferably not less than 8 MPa.

The dental adhesive curable composition (c) may be stored in the form of a dental adhesive curable kit (αc) composed of a plurality of separate compositions including a first composition, a second composition and the like. The dental adhesive curable kit (αc) may include three or more compositions (for example, a third composition, a fourth composition and the like).

When stored as the dental adhesive curable kit (αc), it is preferable in light of storage stability that the acidic group-containing polymerizable monomer (Bc) and the polymerization initiator (Cc) be not stored in the same composition as the reductant (Dc). When the composition is stored as such a kit, the other components for the dental adhesive curable composition (c) (for example, the polymerizable monomer (A), the additional polymerizable monomer (Ec), the filler (Fc) and the additive (Gc)) may be present together with the acidic group-containing polymerizable monomer (Bc), the polymerization initiator (Cc) or the reductant (Dc) or may be separate therefrom. Components to be contained in the respective compositions of the dental adhesive curable kit (αc) may be determined in consideration of factors such as storage stability and handleability.

In a preferred example of the dental adhesive curable kits (αc), at least one of the first composition and the second composition includes the polymerizable monomer (A), the first composition includes the reductant (Dc), and the second composition includes the acidic group-containing polymerizable monomer (Bc) and the polymerization initiator (Cc) (this dental adhesive curable kit will be also written as the dental adhesive curable kit (αc1) hereinbelow).

In the dental adhesive curable kit (αc1), the first composition and the second composition may contain other components for the dental adhesive curable composition (c) (for example, the additional polymerizable monomer (Ec), the filler (Fc) and the additive (Gc)) or may be free from such components. Such other components may be contained in compositions other than the first composition and the second composition (for example, a third composition and a fourth composition).

In a preferred embodiment of the dental adhesive curable kit (αc1), at least one of the first composition and the second composition further includes the additional polymerizable monomer (Ec) other than the polymerizable monomers (A) and (Bc).

Preferably, the dental adhesive curable kit (αc) has storage stability. Specifically, when the dental adhesive curable kit (αc) is stored at 76° C. for 24 hours and thereafter the components in the kit are mixed together to give a dental adhesive curable composition (c), the change in curing time relative to without the above thermal loading is preferably not more than 3 minutes, more preferably not more than 2 minutes, and still more preferably not more than 1 minute. Alternatively, the ratio of curing times (curing time after thermal loading/curing time before thermal loading) is preferably not more than 2, more preferably not more than 1.5, and still more preferably not more than 1.

The dental adhesive curable composition (c) obtained as described above may be used, for example, as a dental adhesive resin cement.

The dental adhesive curable composition (c) has very high usefulness when applied to various dental adhesive materials such as dental cements, bonding materials, coating materials and orthodontic adhesives. Further, even when stored long at room temperature, the composition has a small retardation of curing time and exhibits excellent adhesion with respect to various coronal restoration materials.

A mobile tooth fixing material (βd) according to the fourth aspect of the present invention will be described in detail below. The mobile tooth fixing material (βd) includes a specific dental adhesive composition (d). The dental adhesive composition (d) will be described below.

The dental adhesive composition (d) includes a polymerizable monomer represented by the general formula (1) described hereinabove in which $R^a$ is a divalent $C_{6-9}$ aromatic hydrocarbon group or a divalent $C_{6-9}$ optionally bridged cyclic hydrocarbon group, $R^1$ and $R^2$ are each a hydrogen atom or a methyl group, and $R^7$ and $R^8$ are each a hydrogen atom (hereinbelow, the monomer will be also written as the polymerizable monomer (Ad)). That is, the polymerizable monomer (Ad) may be represented by the following general formula (1d).

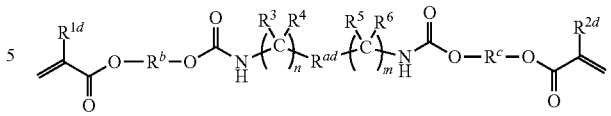

(1d)

In the general formula (1d), $R^{ad}$ is a divalent $C_{6-9}$ aromatic hydrocarbon group or a divalent $C_{6-9}$ optionally bridged cyclic hydrocarbon group, $R^{1d}$ and $R^{2d}$ are each a hydrogen atom or a methyl group, $R^3$, $R^4$, $R^5$ and $R^6$ are each a hydrogen atom or a hydrocarbon group, n and m are each independently an integer of 0 to 4, and $R^b$ and $R^c$ are each independently a $C_{2-6}$ linear alkylene or linear oxyalkylene group optionally substituted with a $C_{1-3}$ alkyl group or a (meth)acryloyloxymethylene group in place of a hydrogen atom.

When used as the dental adhesive composition (d), the divalent aromatic hydrocarbon group or the divalent optionally bridged cyclic hydrocarbon group present in $R^a$ or $R^{ad}$ has 6 to 9 carbon atoms to ensure appropriate rigidity, and preferably has 6 to 7 carbon atoms.

In a preferred embodiment, the divalent group present in $R^a$ or $R^{ad}$ is an aromatic hydrocarbon group. Specific examples of such aromatic hydrocarbon groups include phenylene group. The aromatic ring present in the aromatic hydrocarbon group may be bonded to the two carbon atoms adjacent to $R^a$ or $R^{ad}$ at any positions of ortho positions, meta positions and para positions. To attain the advantageous effects of the present invention, it is preferable that such two bonds be present on the meta positions or the para positions, and it is more preferable that such two bonds be on the meta positions. Such regioisomers may be used singly, or two or more may be used in combination.

In a preferred embodiment, the divalent group present in $R^a$ or $R^{ad}$ is an optionally bridged cyclic hydrocarbon group. Specifically, the optionally bridged cyclic hydrocarbon group is a cyclic hydrocarbon group having a bridged structure, or a cyclic hydrocarbon group having no bridged structures. Specific examples of the bridged cyclic hydrocarbon groups include bicyclo[2.2.1]heptylene group. Specific examples of the unbridged cyclic hydrocarbon groups include cyclohexylene group and 3,5,5-trimethylcyclohexylene group. The hydrocarbon ring present in the optionally bridged cyclic hydrocarbon group may be bonded to the two carbon atoms adjacent to $R^a$ or $R^{ad}$ at any positions without limitation. To attain the advantageous effects of the fourth aspect of the present invention, it is preferable that such two bonds be not present on the same carbon atom in the hydrocarbon ring, and it is more preferable that such two bonds be not on carbon atoms adjacent to each other. Such regioisomers may be used singly, or two or more may be used in combination.

To attain appropriate rigidity, the divalent group present in $R^a$ is preferably an aromatic hydrocarbon group or a bridged cyclic hydrocarbon group, and particularly preferably a bridged cyclic hydrocarbon group.

When used as the dental adhesive composition (d), $R^3$, $R^4$, $R^5$ and $R^6$ are each a hydrogen atom or a hydrocarbon group. To attain appropriate rigidity, $R^3$, $R^4$, $R^5$ and $R^6$ are preferably each a methyl group or a hydrogen atom, and more preferably each a hydrogen atom.

When used as the dental adhesive composition (d), n and m are each independently an integer of 0 to 4. To attain appropriate rigidity, it is preferable that at least one of n and m be 1.

When used as the dental adhesive composition (d), the moiety of the general formula (2'd) below (the general formula (2d) in the general formula (1d)) that is interposed between the two carbamoyl groups in the general formula (1) is, in a preferred embodiment, represented by any of the following general formulas (3d), (4d) and (8d) to (10d). Of these structures, those structures represented by the general formulas (3d), (4d) and (8d) are preferable, and the structure represented by the general formula (3d) is more preferable.

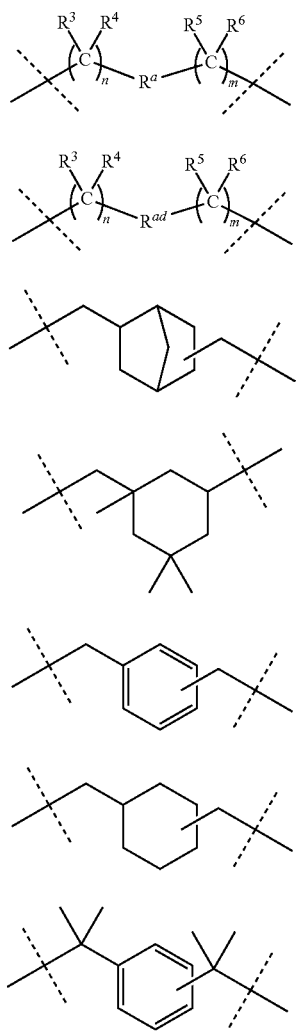

The general formulas (8d) to (10d) represent mixtures of regioisomers. In particular, isomers represented by the following general formulas (5d) to (7d) are preferable. While the general formula (3d) too represents a mixture of regioisomers, such isomers have similar effects and any one or a mixture of such isomers may be used.

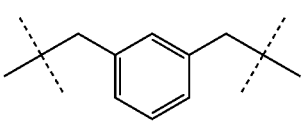

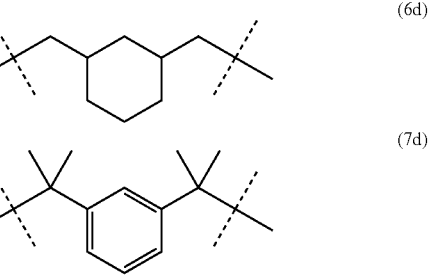

In a more preferred embodiment, the moiety of the general formula (2'd) in the general formula (1) (the general formula (2d) in the general formula (1d)) is a structure represented by any of the general formulas (3d) to (7d), desirably a structure represented by any of the general formulas (3d) to (5d), and more desirably a structure represented by the general formula (3d).

When used as the dental adhesive composition (d), $R^b$ and $R^c$ are each independently a $C_{2-6}$ linear alkylene or linear oxyalkylene group optionally substituted with a $C_{1-3}$ alkyl group or a (meth)acryloyloxymethylene group in place of a hydrogen atom.

When used as the dental adhesive composition (d), $R^b$ and $R^c$ are, in a preferred embodiment, each a $C_{2-4}$ linear alkylene or oxyalkylene group optionally substituted with a $C_{1-3}$ alkyl group in place of a hydrogen atom.

Examples of the linear alkylene groups include $-CH_2CH_2-$, $-CH_2CH_2CH_2-$, $-CH_2CH_2CH_2CH_2-$, $-CH_2CH_2CH_2CH_2CH_2-$ and $-CH_2CH_2CH_2CH_2CH_2CH_2-$. In a preferred embodiment, the linear alkylene group is, for example, $-CH_2CH_2-$, $-CH_2CH_2CH_2-$, $-CH_2CH_2CH_2CH_2-$ or the like. Examples of the linear oxyalkylene groups include $-CH_2CH_2OCH_2CH_2-$ and $-CH_2CH_2OCH_2CH_2OCH_2CH_2-$. In a preferred embodiment, the linear oxyalkylene group is, for example, $-CH_2CH_2OCH_2CH_2-$ or the like. To ensure that the polymerizable monomer (Ad) exhibits appropriate flexibility, the number of carbon atoms in the linear alkylene group or the linear oxyalkylene group is 2 to 6, preferably 2 to 4, and more preferably 2.

Examples of the alkyl groups which may substitute for hydrogen atoms in the linear alkylene groups or the linear oxyalkylene groups include $CH_3-$, $CH_3CH_2-$, $CH_3CH_2CH_2-$ and $(CH_3)_2CH-$. To ensure that the polymerizable monomer (Ad) will exhibit appropriate flexibility, the alkyl groups preferably have 1 to 3 carbon atoms, more preferably 1 to 2 carbon atoms, and still more preferably 1 carbon atom.

Examples of the (meth)acryloyloxymethylene groups which may substitute for hydrogen atoms in the linear alkylene group or the linear oxyalkylene group include methacryloyloxymethylene group and acryloyloxymethylene group.

Of the polymerizable monomers (Ad) that are urethane (meth)acrylates, those urethane (meth)acrylates represented by the following chemical formulas (11d) to (70d) are preferable.

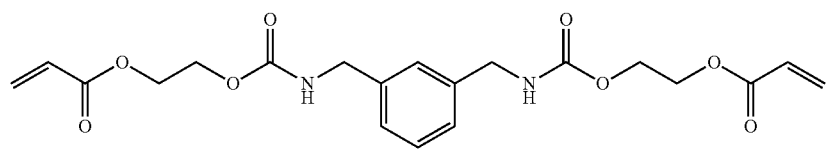
(11d)
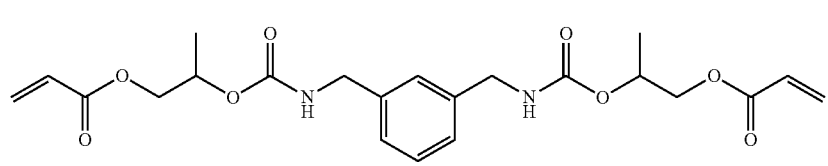
(12d)
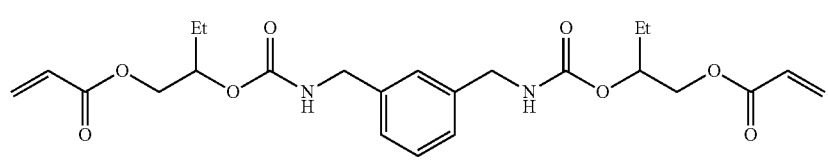
(13d)
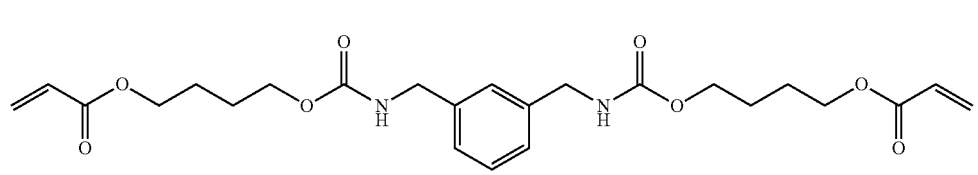
(14d)
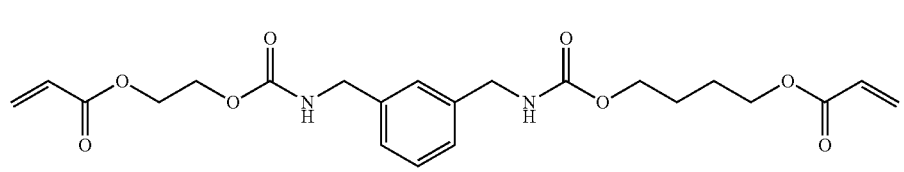
(15d)
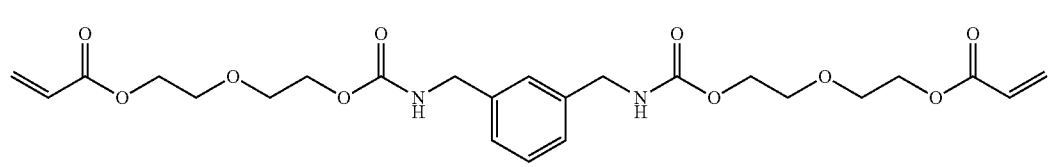
(16d)
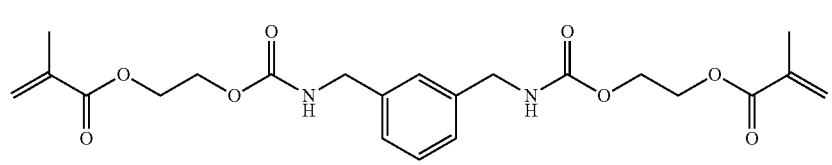
(17d)
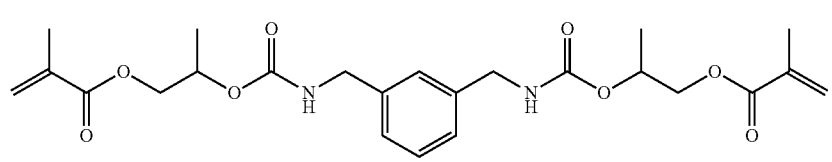
(18d)
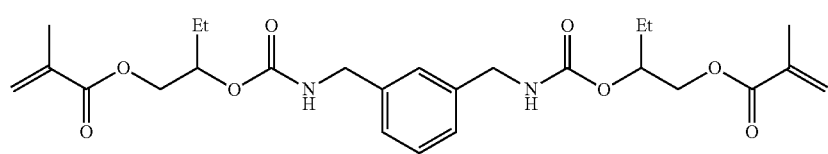
(19d)
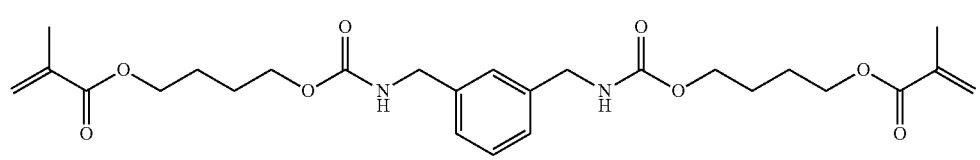
(20d)

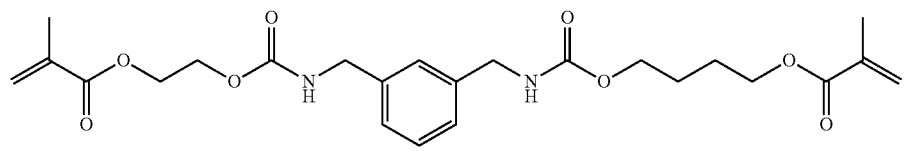
(21d)
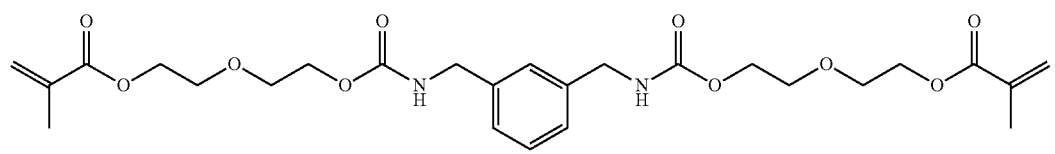
(22d)
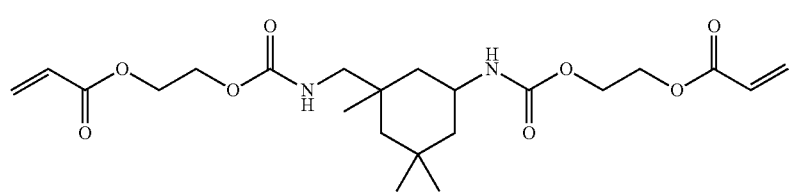
(23d)
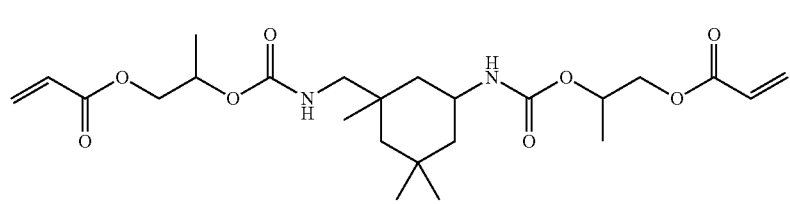
(24d)
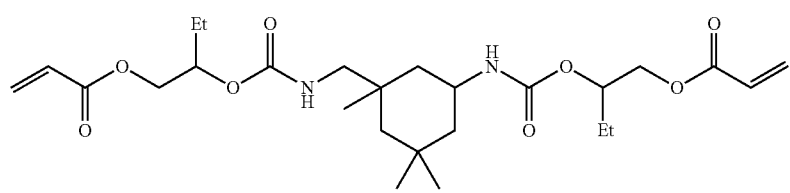
(25d)
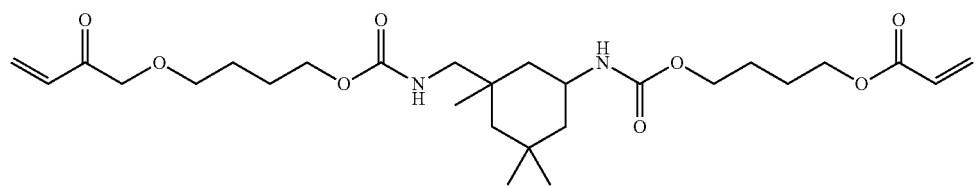
(26d)
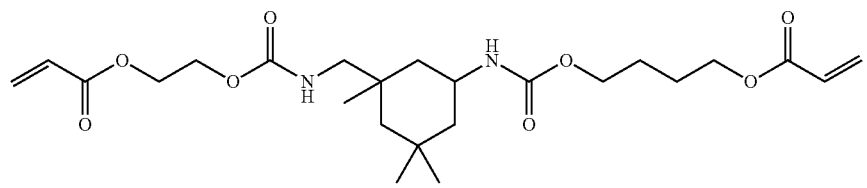
(27d)
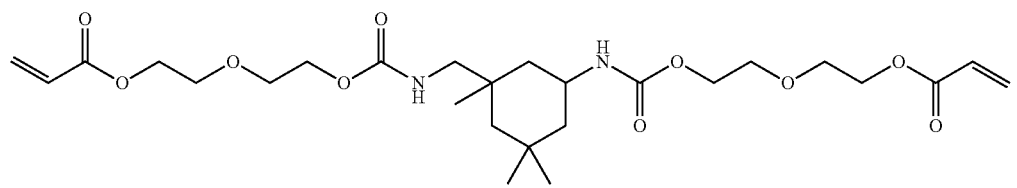
(28d)

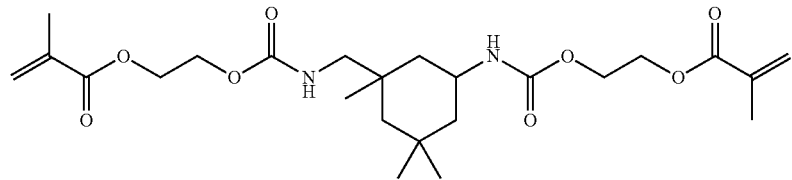
(29d)
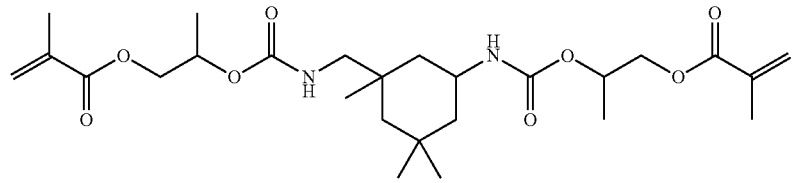
(30d)
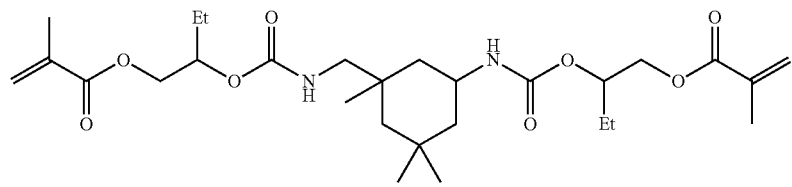
(31d)
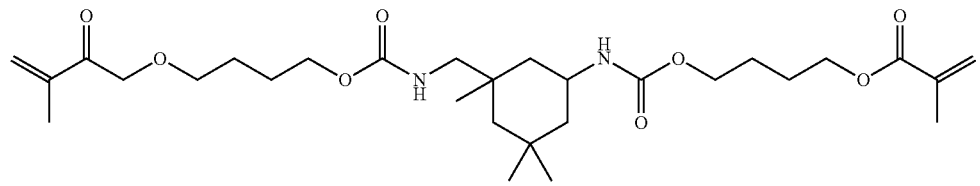
(32d)
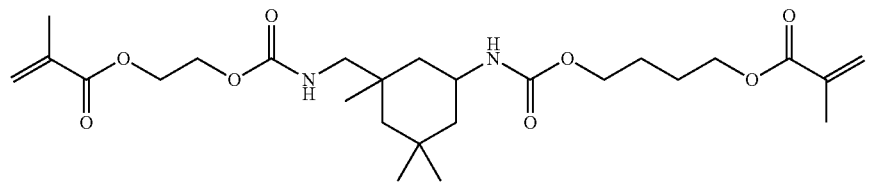
(33d)
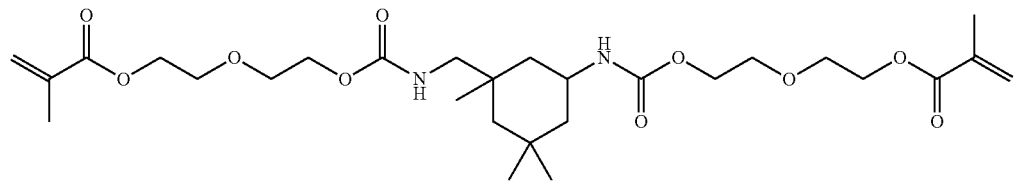
(34d)
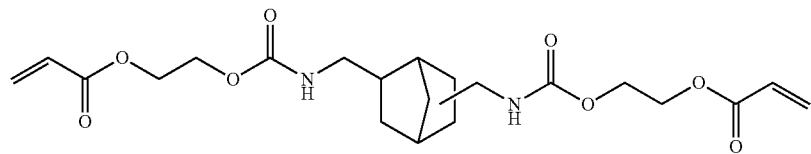
(35d)
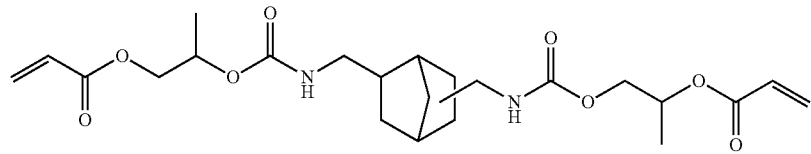
(36d)

-continued
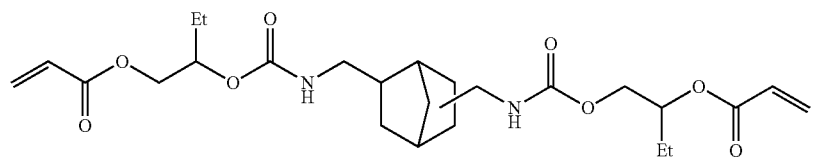
(37d)
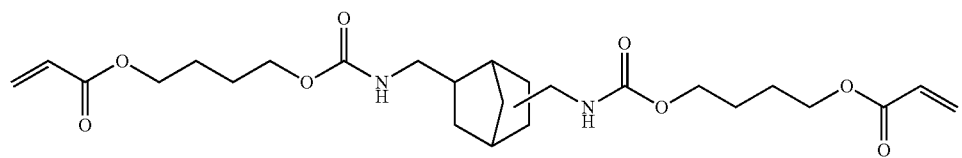
(38d)
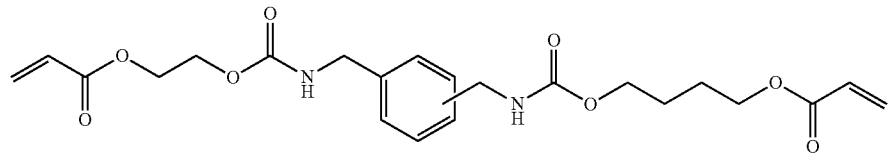
(39d)
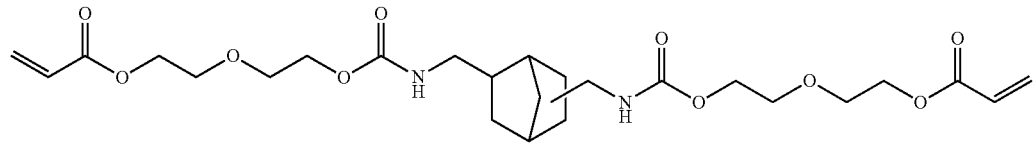
(40d)
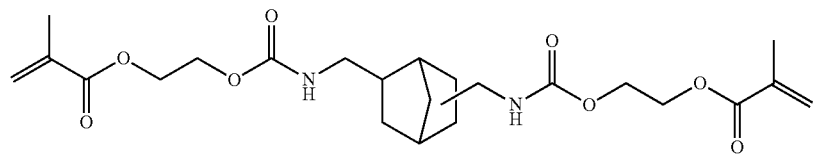
(41d)
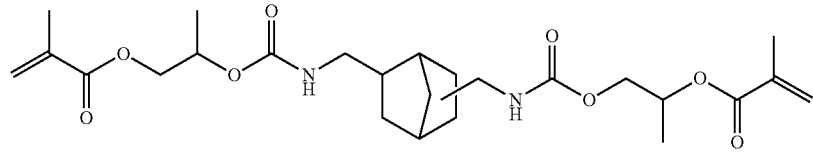
(42d)
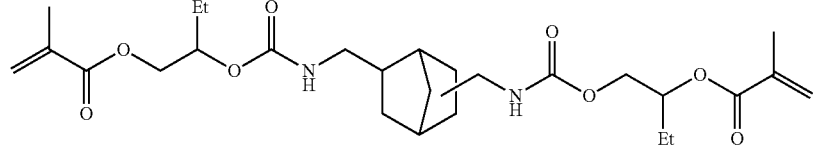
(43d)
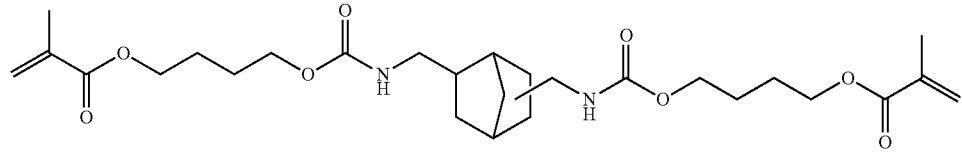
(44d)
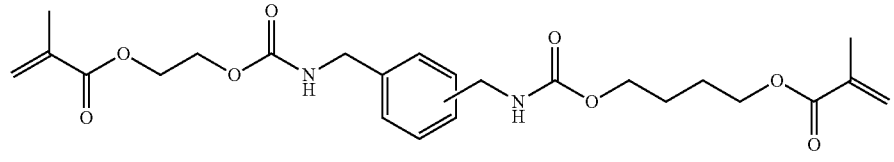
(45d)

-continued
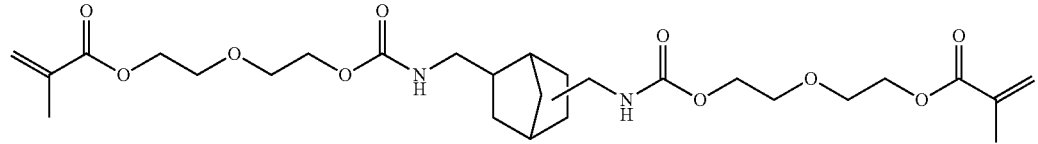
(46d)
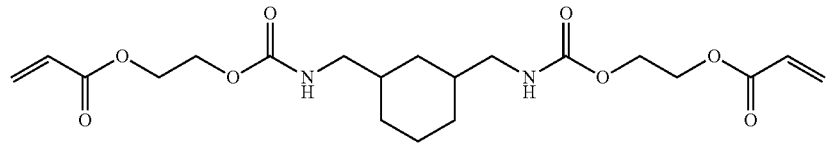
(47d)
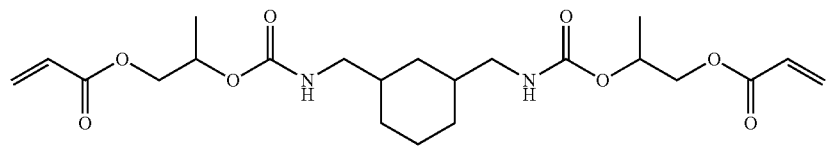
(48d)
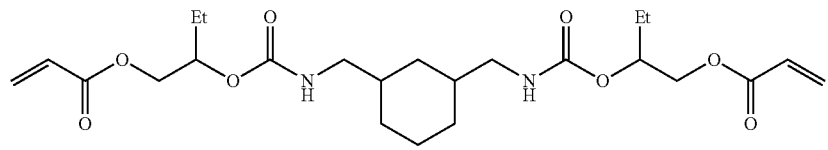
(49d)
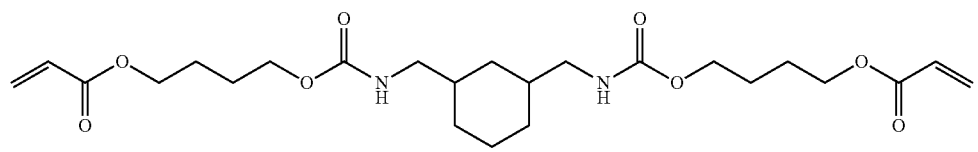
(50d)
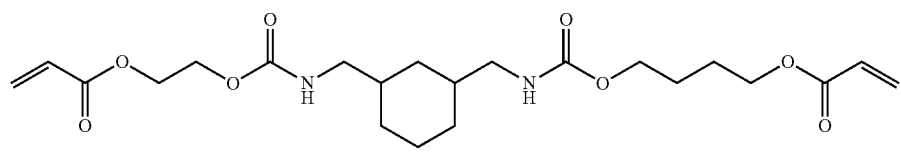
(51d)
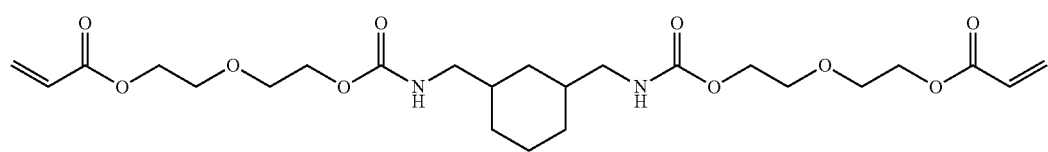
(52d)
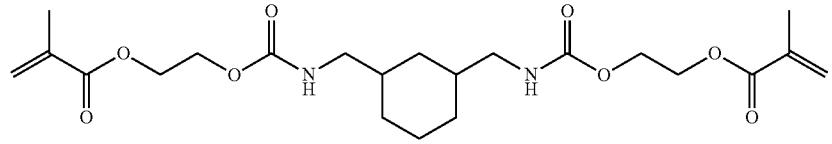
(53d)
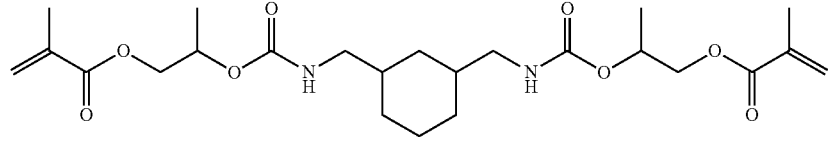
(54d)
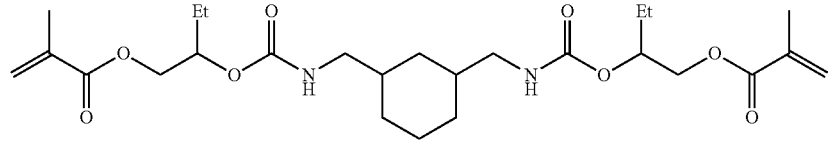
(55d)

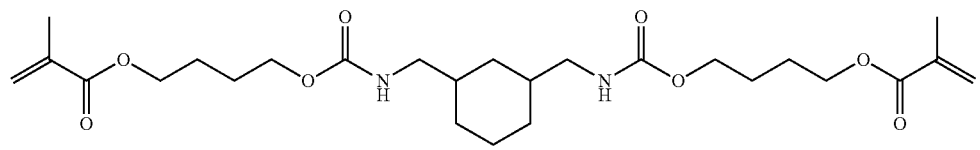 (56d)
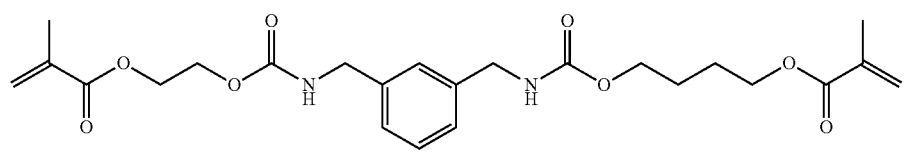 (57d)
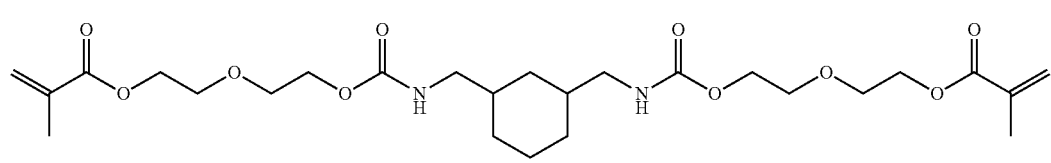 (58d)
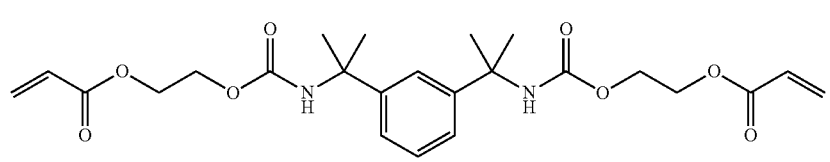 (59d)
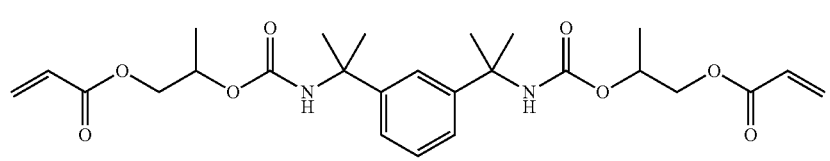 (60d)
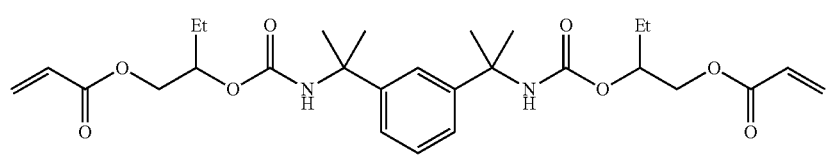 (61d)
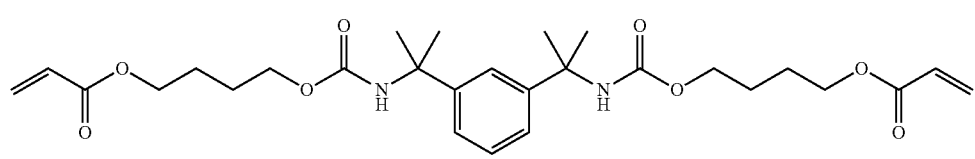 (62d)
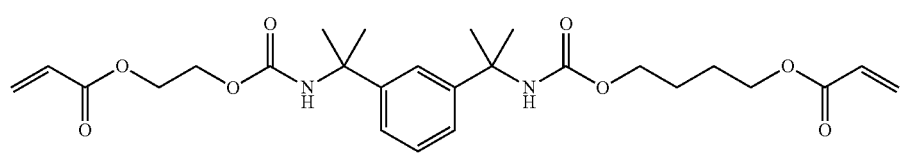 (63d)
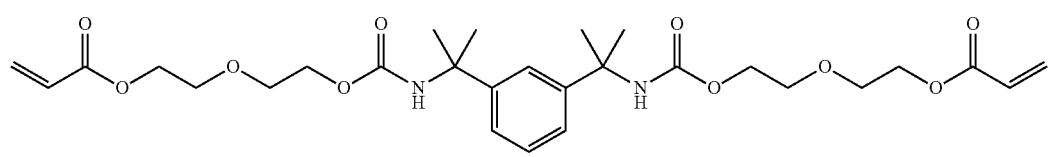 (64d)
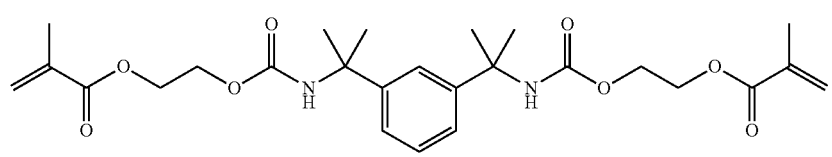 (65d)

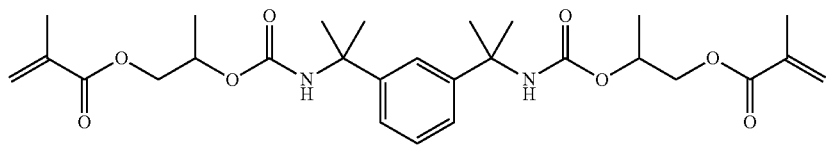

(66d)

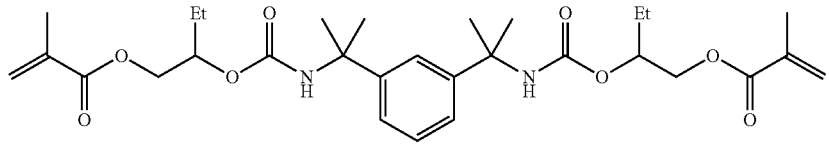

(67d)

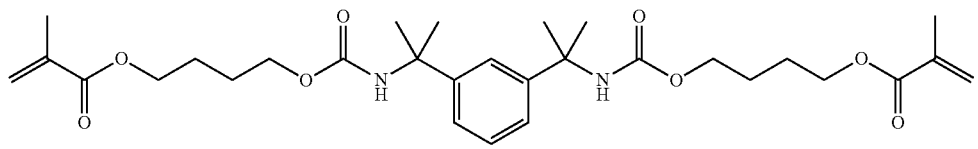

(68d)

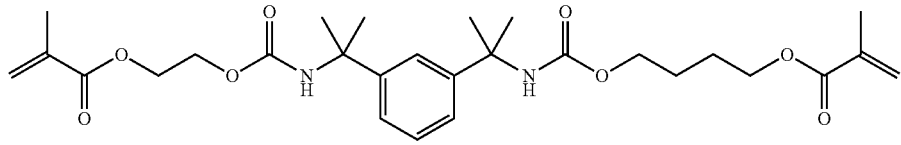

(69d)

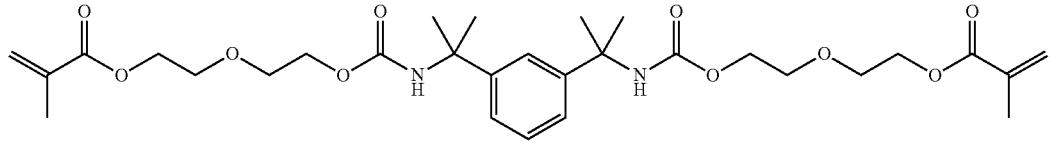

(70d)

In the above formulas, Et denotes an ethyl group.

The polymerizable monomer (Ad) that is used may be any of the formulas (11d) to (70d), preferably any of the formulas (11d) to (46d), and more preferably any of the formulas (35d) to (46d).

The polymerizable monomers (Ad) may be used singly, or two or more may be used in combination.

The content of the polymerizable monomer (Ad) is preferably 10 to 99 parts by weight, and more preferably 40 to 99 parts by weight per 100 parts by weight of the total of the polymerizable monomer (Ad), and a polymerizable monomer (Bd) having at least one acidic group in the molecule, and a photopolymerization initiator (Cd) that are described later.

The polymerizable monomer (Ad) is preferably used in the range of 1 to 99 wt %, and more preferably 30 to 99 wt % relative to the total of the dental adhesive composition (d) taken as 100 wt %. The content of the polymerizable monomer (Ad) is preferably 1 to 99 parts by weight, more preferably 10 to 98.5 parts by weight, and still more preferably 20 to 98 parts by weight per 100 parts by weight of the total of the polymerizable monomer (Ad), and a polymerizable monomer (Bd) having an acidic group in the molecule, a photopolymerization initiator (Cd), a flexible filler (Dd) and an additional polymerizable monomer (Ed) that are described later. If the content is below the lower limit of the range, the strength, flexibility and toughness of cured products are sometimes decreased. If the content exceeds the upper limit, the adhesion is sometimes decreased.

The dental adhesive composition (d) contains a polymerizable monomer (Bd) having at least one acidic group in the molecule, typically, a (meth)acrylate compound (B'd) having at least one acidic group in the molecule.

The polymerizable monomer (Bd) having at least one acidic group in the molecule, which is added to the dental adhesive composition (d), has a polymerizable group, preferably a radically polymerizable group, with examples including vinyl groups, vinyl cyanide groups, acryloyl groups, methacryloyl groups, acrylamide groups and methacrylamide groups. Examples of the acidic groups present in the polymerizable monomer (Bd) include carboxyl groups, phosphoric groups, thiophosphoric groups, sulfonic groups and sulfinic groups. The acidic groups comprehend those groups which can substantially function as acidic groups, for example, those groups which are readily decomposed into the aforementioned acidic groups under practical conditions, for example, acid anhydride groups of carboxyl groups. Of these, preferred acidic groups are carboxyl groups, phosphoric groups, sulfonic groups, and those groups which are readily decomposed into these acidic groups under practical conditions.

Examples of the polymerizable monomers having at least one carboxyl group in the molecule include α-unsaturated carboxylic acids such as (meth)acrylic acid and maleic acid; vinyl aromatic ring compounds such as 4-vinylbenzoic acid; carboxylic acid compounds having a linear hydrocarbon group between a (meth)acryloyloxy group and a carboxylic group, such as 11-(meth)acryloyloxy-1,1-undecanedicarboxylic acid; (meth)acryloyloxyalkylnaphthalene(poly)carboxylic acids such as 6-(meth)acryloyloxyethylnaphthalene-1,2,6-tricarboxylic acid; (meth)acryloyloxyalkyltrimellitic acids such as 4-(meth)acryloyloxymethyltrimellitic acid, 4-(meth)acryloyloxyethyltrimellitic acid and 4-(meth)acryloyloxybutyltrimellitic acid; compounds containing an acidic group and a hydroxyl group such as 4-[2-hydroxy-3-(meth)acryloyloxy]butyltrimellitic acid; compounds having a carboxybenzoyloxy such as 2,3-bis(3,4-dicarboxybenzoyloxy)propyl (meth)acrylate; N- and/or O-substituted mono or di(meth)acryloylamino acids such as N,O-di(meth)acryloyltyrosine, O-(meth)acryloyltyrosine, N-(meth)acryloyltyrosine, N-(meth)acryloylphenylalanine, O-(meth)acryloylphenylalanine and N,O-di(meth)acryloylphenylalanine; (meth)acryloyl compounds of benzoic acids having a functional substituent such as N-(meth)acryloyl-4-aminobenzoic acid, N-(meth)acryloyl-5-aminobenzoic acid, 2- or 3- or 4-(meth)acryloyloxybenzoic acid and 4- or 5-(meth)acryloylaminosalicylic acid; addition products of a hydroxyalkyl (meth)acrylate and an unsaturated polycarboxylic anhydride such as addition product of 2-hydroxyethyl (meth)acrylate with pyromellitic dianhydride, and addition product of 2-hydroxyethyl (meth)acrylate with maleic anhydride or 3,3',4,4'-benzophenonetetracarboxylic dianhydride or 3,3',4,4'-biphenyltetracarboxylic dianhydride; and compounds having a polycarboxybenzoyloxy and a (meth)acryloyloxy such as 2-(3,4-dicarboxybenzoyloxy)-1,3-di(meth)acryloyloxypropane, adduct of N-phenylglycine or N-tolylglycine with glycidyl (meth)acrylate, 4-[(2-hydroxy-3-(meth)acryloyloxypropyl)amino]phthalic acid and 3- or 4-[N-methyl-N-(2-hydroxy-3-(meth)acryloyloxypropyl)amino]phthalic acid. Of these, 11-(meth)acryloyloxy-1,1-undecanedicarboxylic acid and 4-(meth)acryloyloxyethyltrimellitic acid are preferable.

Some preferred groups in which at least one hydroxyl group is bonded to a phosphorus atom, and some preferred functional groups which may be readily converted into those groups in water are, for example, phosphate ester groups having one or two hydroxyl groups. Examples of the polymerizable monomers having such a group include (meth)acryloyloxyalkyl acid phosphates such as 2-(meth)acryloyloxyethyl acid phosphate, 2- and/or 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate and 12-(meth)acryloyloxydodecyl acid phosphate; acid phosphates having two or more (meth)acryloyloxyalkyl groups such as bis[2-(meth)acryloyloxyethyl] acid phosphate and bis[2- or 3-(meth)acryloyloxypropyl] acid phosphate; and acid phosphates having a (meth)acryloyloxyalkyl group via an aromatic ring such as a phenylene group or optionally further via a heteroatom such as an oxygen atom, such as 2-(meth)acryloyloxyethylphenyl acid phosphate and 2-(meth)acryloyloxyethyl-p-methoxyphenyl acid phosphate. Examples further include compounds corresponding to the above compounds except that the phosphoric group is replaced by a thiophosphoric group. Of these, 2-(meth)acryloyloxyethyl acid phosphate may be preferably used.

Examples of the polymerizable monomers having a sulfonic group or a functional group easily convertible into a sulfonic group in water include sulfoalkyl (meth)acrylates such as 2-sulfoethyl (meth)acrylate, 2- or 1-sulfo-1- or 2-propyl (meth)acrylate and 1- or 3-sulfo-2-butyl (meth)acrylate; compounds which have a group containing a heteroatom such as a halogen or oxygen in the alkyl moiety of the above sulfoalkyl (meth)acrylates, such as 3-bromo-2-sulfo-2-propyl (meth)acrylate and 3-methoxy-1-sulfo-2-propyl (meth)acrylate; acrylamides having a sulfonic group or a functional group easily convertible into a sulfonic group in water such as 1,1-dimethyl-2-sulfoethyl (meth)acrylamide and 2-methyl-2-(meth)acrylamidopropanesulfonic acid; and vinylarylsulfonic acids such as 4-styrenesulfonic acid and 4-(prop-1-en-2-yl)benzenesulfonic acid. Of these, 4-styrenesulfonic acid may be preferably used.

The polymerizable monomers (Bd) may be used singly, or two or more may be used in combination.

The content of the polymerizable monomer (Bd) having at least one acidic group in the molecule is preferably 0.5 to 80 parts by weight, and more preferably 0.5 to 50 parts by weight per 100 parts by weight of the total of the polymerizable monomer (Ad), the polymerizable monomer (Bd), and a photopolymerization initiator (Cd) that is described later.

The polymerizable monomer (Bd) having at least one acidic group in the molecule is preferably used in the range of 0.5 to 50 wt %, and more preferably 1 to 30 wt % relative to the total of the dental adhesive composition (d) taken as 100 wt %. The polymerizable monomer (Bd) is preferably used in the range of 0.5 to 50 parts by weight, more preferably 1.0 to 40 parts by weight, and still more preferably 1.5 to 30 parts by weight per 100 parts by weight of the total of the polymerizable monomer (Ad), the polymerizable monomer (Bd), and a photopolymerization initiator (Cd), a flexible filler (Dd) and an additional polymerizable monomer (Ed) that are described later. If the content is below the lower limit of the range, the adhesion may be decreased. If the content exceeds the upper limit, the strength, flexibility and toughness of cured products may be decreased and a discoloration tends to result at times.

The dental adhesive composition (d) contains a photopolymerization initiator (Cd). The photopolymerization initiator (Cd) is preferably one which can induce curing simply by being irradiated with light when desired. The photopolymerization initiator (Cd) may be a photosensitizer (Cd1) alone, or a combination of a photosensitizer (Cd1) and a photopolymerization accelerator (Cd2).

Examples of the photosensitizers (Cd1) include α-diketone compounds such as benzil and camphorquinone, α-naphthol, p,p'-dimethoxybenzil, pentadione, 1,4-phenanthrenequinone, naphthoquinone, acylphosphine oxides or derivatives thereof such as diphenyltrimethylbenzoylphosphine oxide, and other known compounds which induce polymerization by being excited with UV lights or visible lights. The photosensitizers (Cd1) may be used singly, or two or more may be used in combination. Of the above compounds, camphorquinone, and acylphosphine oxides or derivatives thereof such as diphenyltrimethylbenzoylphosphine oxide are particularly preferable.

When the photopolymerization initiator (Cd) is used, it is preferable to make use of a combination of the photosensitizer (Cd1) and a photopolymerization accelerator (Cd2). Examples of the photopolymerization accelerators (Cd2) include p-toluenesulfinic acid and alkali metal salts thereof; tertiary amines such as N,N-dimethylaniline, N,N-diethylaniline, N,N-dibenzylaniline, N,N-dimethyl-p-toluidine, p-N,N-dimethylaminobenzoic acid, p-N,N-diethylaminobenzoic acid, ethyl p-N,N-dimethylaminobenzoate, ethyl p-N,N-diethylaminobenzoate, methyl p-N,N-dimethylaminobenzoate, methyl p-N,N-diethylaminobenzoate, p-N,N-dimethylaminobenzaldehyde, 2-n-butoxyethyl p-N,N-dimethylaminobenzoate, 2-n-butoxyethyl p-N,N-diethylaminobenzoate, p-N,N-dimethylaminobenzonitrile, p-N,N-diethylaminobenzonitrile, p-N,N-dihydroxyethylaniline, p-dimethylaminophenethyl alcohol, N,N-dimethylaminoethyl methacrylate, triethylamine, tributylamine, tripropylamine and N-ethylethanolamine, secondary amines such as N-phenylglycine and alkali metal salts of N-phenylglycine; combinations of the above tertiary amines or secondary amines with citric acid, malic acid and 2-hydroxypropanoic acid; barbituric acids such as 5-butylaminobarbituric acid and 1-benzyl-5-phenylbarbituric acid; and organic peroxides such as benzoyl peroxide and di-tert-butyl peroxide. The photopolymerization accelerators (Cd2) may be used singly, or two or more may be used in combination. Of the above compounds, particularly preferred compounds are aromatic tertiary amines in which the nitrogen atom is bonded directly to the aromatic group such as ethyl p-N,N-dimethylaminobenzoate, 2-n-butoxyethyl p-N,N-dimethylaminobenzoate and N,N-dimethylaminoethyl methacrylate, aliphatic tertiary amines having a polymerizable group such as N,N-dimethylaminoethyl methacrylate, and secondary amines such as N-phenylglycine and alkali metal salts of N-phenylglycine.

The content of the photopolymerization initiator (Cd) is preferably 0.05 to 10 parts by weight per 100 parts by weight of the total of the polymerizable monomer (Ad), the polymerizable monomer (Bd) and the photopolymerization initiator (Cd).

The photopolymerization initiator (Cd) is preferably used in the range of 0.001 to 5 wt %, more preferably 0.05 to 2 wt %, and still more preferably 0.05 to 1 wt % relative to the total of the dental adhesive composition (d) taken as 100 wt %. The photopolymerization initiator (Cd) is preferably used in the range of 0.001 to 5 parts by weight, more preferably 0.05 to 2 parts by weight, and still more preferably 0.05 to 1 part by weight per 100 parts by weight of the total of the polymerizable monomer (Ad), the polymerizable monomer (Bd), the photopolymerization initiator (Cd), a flexible filler (Dd) and an additional polymerizable monomer (Ed). If the content is below the lower limit of the range, the curing rate is decreased at times. If the content exceeds the upper limit, the curing rate is so increased that handleability may be deteriorated. The amount of the photopolymerization accelerator (Cd2) is not limited as long as the photocuring performance is promoted, but is usually in the range of 5 to 1000 wt % relative to the photosensitizer (Cd1) taken as 100 wt %.

While the polymerization initiator used in the dental adhesive composition (d) is preferably the photopolymerization initiator (Cd), a thermal polymerization initiator or a room-temperature polymerization initiator may be used together therewith. Specific examples will be described below.

Some preferred thermal polymerization initiators are organic peroxides and diazo compounds. When the polymerization is to be performed quickly with good efficiency, compounds having a degradation half-life at 80° C. of not more than 10 hours are preferable. Examples of the organic peroxides include diacyl peroxides such as acetyl peroxide, isobutyl peroxide, decanoyl peroxide, benzoyl peroxide and succinic acid peroxide; peroxydicarbonates such as diisopropyl peroxydicarbonate, di-2-ethylhexyl peroxydicarbonate and diallyl peroxydicarbonate; peroxyesters such as tert-butyl peroxyisobutyrate, tert-butyl peroxyneodecanoate and cumene peroxyneodecanoate; and peroxysulfonates such as acetylcyclohexylsulfonyl peroxide.

Examples of the diazo compounds include 2,2'-azobisisobutyronitrile, 4,4'-azobis(4-cyanovaleric acid), 2,2'-azobis(4-methoxy-2,4-dimethoxyvaleronitrile) and 2,2'-azobis(2-cyclopropylpropionitrile). In particular, benzoyl peroxide and 2,2'-azobisisobutyronitrile are more preferable. Further, use may be made of a combination of an organic peroxide and a reductant such as a tertiary amine, or a redox initiator that initiates polymerization at around room temperature.

The dental adhesive composition (d) may contain a flexible filler (Dd). The flexible filler (Dd) is favorably flexible itself, and thus the material of the filler is preferably an organic material, typically, a polymer of an organic compound. An example index of flexibility is the reaction force per unit area exhibited by the filler being compressed in the longitudinal direction (measured as compressive strength). The reaction force per unit area obtained when the filler is compressed by 10% of the original length is preferably not more than 30 MPa, more preferably not more than 15 MPa, and still more preferably not more than 5 MPa. The reaction force per unit area obtained when the filler is compressed by 30% of the original length is preferably not more than 50 MPa, more preferably not more than 30 MPa, and still more preferably not more than 10 MPa. This value may be easily determined by micro compression test with respect to a single particle of the filler. Examples of such measurement devices include Micro Compression Tester MCT-510 manufactured by Shimadzu Corporation. With this tester, the compressive strength may be calculated with the application of the following equation described in JIS R 1639-5 (2007) that is used in the testing of compressive failure strength.

$$Cs = 2.48 \times (P/\pi \cdot d^2)$$

(In the above equation, Cs is the strength (MPa) or in this case the reaction force (MPa) per unit area, P the testing force (N), and d the particle size (mm)).

To ensure that the flexible filler (Dd) attains the above function, it is preferable that after the polymerization of the dental adhesive composition (d), the cured product resulting from the polymerization be a composite material, for example, an islands-sea structure which has independent phases based on the filler (Dd). Thus, it is preferable that the filler (Dd) be not dissolved into a solvent so that its domain will not disappear. To realize this, for example, it is preferable that the filler (Dd) be a polymer of an organic compound and the polymer be crosslinked.

When the filler (Dd) is a crosslinked polymer, the degree of crosslinking may be evaluated based on the gel fraction. That is, the proportion of residues which are insoluble due to crosslinks is measured. In the test, the crosslinked polymer is soaked into, for example, a solvent that is best to dissolve the uncrosslinked polymer or a component to which the crosslinked polymer will be actually exposed, at a prescribed temperature for a prescribed time, and the ratio of the undissolved residual solid (weight of residual solid after soaking and drying of solvent/weight before soaking) is measured to determine the gel fraction. When, for example, the filler (Dd) includes a polyurethane, the evaluation appropriately takes place in acetone, and the gel fraction is usually evaluated under soaking conditions of 20° C. and 24 hours. When the filler (Dd) is a crosslinked polymer, the gel fraction thereof is preferably not less than 30 wt %, more preferably not less than 60 wt %, and still more preferably not less than 90 wt %.

If the affinity is too low between the filler (Dd) and the polymerizable monomer components present in the dental adhesive composition (d) (for example, the polymerizable monomer (Ad), the polymerizable monomer (Bd) and a polymerizable monomer (Ed) described later) and/or the polymer components formed by the polymerization of the polymerizable monomer components, the composite material cannot maintain its integrity and consequently properties such as bond strength are disadvantageously decreased. It is therefore desirable that the affinity be high between the polymerizable monomer components that will form the matrix after the polymerization of the dental adhesive composition (d), and the filler (Dd). Examples of preferred embodiments include one in which the filler (Dd) is swollen by the polymerizable monomer components present in the dental adhesive composition (d) which will form the matrix after the polymerization, and one in which the filler (Dd) has a chemical or physical affinitive interaction such as covalent bonds, ionic bonds or intermolecular force with the matrix formed by the polymerization of the polymerizable monomer components present in the dental adhesive composition (d). More specific examples of such embodiments of the filler (Dd) include one in which the filler (Dd) has, on its surface, molecular chains having high compatibility with the matrix, one in which the filler (Dd) has, on its surface, ethylenic double bonds which are radically copolymerizable with the polymerizable monomer components present in the dental adhesive composition (d) that will form the matrix after the polymerization, and one in which the filler (Dd) has, on its surface, highly active groups such as hydroxyl groups, isocyanate groups, carboxylic groups, phosphoric groups, amino groups and amide groups which have affinity for and can interact (for example, can form bonds by reacting) with other highly reactive moieties present in the dental adhesive composition (d) that will form the matrix after the polymerization.

Examples of the organic materials which may constitute the fillers (Dd) include flexible polymers such as polyurethane, polybutyl acrylate, polyacrylate ester, polyamide, silicone, ethylene/vinyl acetate copolymer, ethylene/vinyl alcohol copolymer, ethylene/acrylic acid copolymer, polyethylene glycol, polypropylene glycol, polystyrene, nitrile rubber, polybutadiene, polyisoprene, and ethylene/αolefin copolymer. Crosslinked products and mixtures of these polymers may be similarly used as the fillers (Dd).

As already mentioned, it is preferable that cured products of the dental adhesive composition (d) satisfy strength, flexibility and toughness at the same time. In light of this, the materials of the fillers (Dd) are preferably polyurethane, polyacrylate ester and ethylene/acrylic acid copolymer, and more preferably crosslinked polyurethane. Commercial crosslinked polyurethane fillers may be used. Examples of the commercial crosslinked polyurethane fillers include Art Pearl "JB-800T", "P-800T", "C-800", "U-600T", "RZ-600T", "RY-600T", "RT-600T", "RX-600T" and "RW-600T" manufactured by Negami Chemical Industrial Co., Ltd. These fillers may be used singly, or two or more may be used in combination.

From the points of view of the strength, flexibility and toughness of cured products of the dental adhesive composition (d), in particular, a more preferred filler is a crosslinked polyurethane having ethylenic double bonds which are radically copolymerizable with the polymerizable monomer components present in the dental adhesive composition (d) that will form the matrix after the polymerization. Examples of such commercial products include "RZ-600T", "RY-600T", "RT-600T", "RX-600T" and "RW-600T".

The radically copolymerizable ethylenic double bonds which may be present in the filler (Dd) may be defined as the double bond equivalent weight (m-mol/kg) that indicates the number of millimoles of double bonds per 1 kg. When the filler (Dd) contains radically copolymerizable ethylenic double bonds, the double bond equivalent weight is preferably 200 to 6000 m-mol/kg, more preferably 500 to 3000 m-mol/kg, and still more preferably 1000 to 1800 m-mol/kg. If the equivalent weight is below the lower limit of this range, the effects on the enhancements of strength, flexibility and toughness of cured products may be insufficient due to the amount of the double bonds for chemical reaction with the polymerizable monomer components being small. If the equivalent weight exceeds the upper limit, problems such as coloration are sometimes caused.

The average particle size of the flexible filler (Dd) is preferably in the range of 1 to 1000 μm, more preferably in the range of 2 to 100 μm, and still more preferably in the range of 3 to 20 μm. If the average particle size is below the lower limit of this range, the powder is sometimes difficult to handle. If the average particle size exceeds the upper limit, the particles sometimes cause a surface roughening of the polymer.

The above average particle size is the cumulative volume 50% particle size measured with a laser diffraction grain size distribution analyzer (such as, for example, SALD-2100 manufactured by Shimadzu Corporation).

The flexible filler (Dd) is preferably used in the range of 0.5 to 70 parts by weight, more preferably 5 to 50 parts by weight, and still more preferably 10 to 40 parts by weight with respect to 100 parts by weight of the dental adhesive composition (d). If the amount is below the lower limit of this range, flexibility is not sufficiently exhibited at times. If the amount exceeds the upper limit, the composition lowers its fluidity and becomes extremely difficult to handle at times. By virtue of the use of the flexible filler (Dd) such as a crosslinked polyurethane powder in the above amount, the dental adhesive composition (d) can give cured products satisfying strength, flexibility and toughness at the same time.

The dental adhesive composition (d) may contain an additional polymerizable monomer (Ed) other than the polymerizable monomers (Ad) and (Bd). Examples of such additional polymerizable monomers (Ed) include esters of α-unsaturated carboxylic acids such as α-cyanoacrylic acid, (meth)acrylic acid, α-halogenated acrylic acid, crotonic acid, cinnamic acid, maleic acid and itaconic acid, (meth) acrylamides such as (meth)acrylamide and (meth)acrylamide derivatives, vinyl esters, vinyl ethers, mono-N-vinyl derivatives, styrene derivatives, and other known polymerizable monomers. Of these, (meth)acrylate esters and (meth) acrylamides are preferable because of their good polymerizability.

The additional polymerizable monomers (Ed) are largely classified into monofunctional monomers (Ed1) having one polymerizable group, difunctional monomers (Ed2) having two polymerizable groups, and trifunctional and polyfunctional monomers (Ed3) having three or more polymerizable groups. Examples of these polymerizable monomers will be described below.

Examples of the monofunctional monomers (Ed1) include methyl (meth)acrylate, iso-butyl (meth)acrylate, benzyl (meth)acrylate, lauryl (meth)acrylate, 2-(N,N-dimethylamino)ethyl (meth)acrylate, 2,3-dibromopropyl (meth)acrylate, 3-(meth)acryloyloxypropyltrimethoxysilane, 2-hydroxyethyl (meth)acrylate, 2-hydroxypropyl (meth)acrylate, 2-hydroxybutyl (meth)acrylate, 6-hydroxyhexyl (meth) acrylate, 10-hydroxydecyl (meth)acrylate, propylene glycol mono(meth)acrylate, glycerin mono(meth)acrylate, erythritol mono(meth)acrylate, N-methylol (meth)acrylamide, N-hydroxyethyl (meth)acrylamide, N,N-(dihydroxyethyl) (meth)acrylamide and (meth)acryloyloxydodecylpyridinium bromide.

Examples of the difunctional monomers (Ed2) include ethylene glycol di(meth)acrylate, triethylene glycol di(meth) acrylate, propylene glycol di(meth)acrylate, neopentyl glycol di(meth)acrylate, 1,6-hexanediol di(meth)acrylate, 1,10-decanediol di(meth)acrylate, bisphenol A diglycidyl (meth) acrylate, 2-hydroxy-3-(meth)acryloyloxypropyl (meth)

acrylate, 2,2-bis[4-(meth)acryloyloxypolyethoxyphenyl] propane, 1,2-bis[3-(meth)acryloyloxy-2-hydroxypropoxy] ethane, 1,2-bis[3-(meth)acryloyloxy-2-hydroxypropyloxy] triethylene glycol, 1,2-bis[3-(meth)acryloyloxy-2-hydroxypropyloxy]glycerin, pentaerythritol di(meth) acrylate and 2,2,4-trimethylhexamethylene bis(2-carbamoyloxyethyl) di(meth)acrylate.

Examples of the trifunctional and polyfunctional monomers (Ed3) include trimethylolpropane tri(meth)acrylate, trimethylolethane tri(meth)acrylate, tetramethylolmethane tri(meth)acrylate, tetramethylolmethane tetra(meth)acrylate, pentaerythritol tetra(meth)acrylate, 1,7-diacryloyloxy-2,2,6, 6-tetraacryloyloxymethyl-4-oxyheptane and dipentaerythritol hexa(meth)acrylate.

The monofunctional monomers (Ed1), the difunctional monomers (Ed2), and the trifunctional and polyfunctional monomers (Ed3) may be used singly, or two or more may be used in combination.

The difunctional monomers (Ed2) or the trifunctional and polyfunctional monomers (Ed3) include polyfunctional (meth)acrylates having a urethane bond (compounds having a urethane bond and two or more (meth)acryloyl groups) (this type of monomers does not include the polymerizable monomers (A)). Such polyfunctional (meth)acrylates having a urethane bond may be synthesized easily by, for example, addition reaction of an isocyanate group (—NCO)-containing compound described below and a hydroxyl group (—OH)-containing (meth)acrylate compound described below.

Examples of the isocyanate group-containing compounds include hexamethylene diisocyanate, tolylene diisocyanate, diphenylmethane diisocyanate and trimethylhexamethylene diisocyanate.

Examples of the hydroxyl group-containing (meth)acrylate compounds include hydroxy(meth)acrylates such as 2-hydroxyethyl (meth)acrylate, 2-hydroxypropyl (meth) acrylate, 2-hydroxybutyl (meth)acrylate, 6-hydroxyhexyl (meth)acrylate, 10-hydroxydecyl (meth)acrylate, 3-chloro-2-hydroxypropyl (meth)acrylate, 2-hydroxy-3-phenoxypropyl (meth)acrylate, glycerin mono(meth)acrylate, N-hydroxyethyl (meth)acrylamide, N,N-(dihydroxyethyl) (meth) acrylamide, bisphenol A diglycidyl (meth)acrylate, 2-hydroxy-3 acryloyloxypropyl (meth)acrylate, 2,2-bis[4-[3-(meth)acryloyloxy-2-hydroxypropoxy]phenyl]pro pane, 1,2-bis[3-(meth)acryloyloxy-2-hydroxypropoxy]ethane, pentaerythritol tri(meth)acrylate, and dipentaerythritol tri- or tetra(meth)(meth)acrylate.

The polymerizable monomers (Ed) may be used singly, or two or more may be used in combination.

The amount of the polymerizable monomer (Ed) may be determined appropriately in consideration of the handleability (viscosity and consistency) of the dental adhesive composition (d) and the mechanical properties of cured products thereof. The polymerizable monomer (Ed) is preferably used in the range of 0.5 to 50 parts by weight, and more preferably 1 to 30 parts by weight with respect to 100 parts by weight of the total of the dental adhesive composition (d).

The polymerizable monomer (Ed) is preferably used in the range of 0.5 to 50 parts by weight, more preferably 1 to 40 parts by weight, and still more preferably 1 to 30 parts by weight per 100 parts by weight of the total of the polymerizable monomer (Ad), the polymerizable monomer (Bd), the photopolymerization initiator (Cd), the flexible filler (Dd) and other polymerizable monomers. If the amount is below the lower limit of the range, the curing rate is decreased at times. If the amount exceeds the upper limit, the curing rate is so increased that handleability may be deteriorated.

Besides the flexible filler (Dd), the dental adhesive composition (d) may contain an additional filler (Fd) other than the filler (Dd) for purposes such as to control the viscosity of the composition (d) and to enhance the strength, flexibility and toughness of the obtainable cured products.

The additional filler (Fd) may be any of general fillers used in the dental field. The fillers (Fd) are usually broadly categorized into organic fillers (Fd1) and inorganic fillers (Fd2).

Examples of the organic fillers (Fd1) include fine powders of polymers such as polymethyl methacrylate, polyethyl methacrylate, methyl methacrylate-ethyl methacrylate copolymer, crosslinked polymethyl methacrylate and crosslinked polyethyl methacrylate.

Examples of the inorganic fillers (Fd2) include fine powders of inorganic substances such as various glasses (based on silicon dioxide and optionally containing oxides of, for example, heavy metals, boron and aluminum), various ceramics, diatomaceous earth, kaolin, clay minerals (such as montmorillonite), activated clay, synthetic zeolite, mica, calcium fluoride, ytterbium fluoride, calcium phosphate, barium sulfate, zirconium dioxide, titanium dioxide and hydroxyapatite. Specific examples of the inorganic fillers include barium borosilicate glasses (such as Kimble Raysorb T3000, Schott 8235, Schott GM27884 and Schott GM39923), strontium boroaluminosilicate glasses (such as Raysorb T4000, Schott G018-093 and Schott GM32087), lanthanum glasses (such as Schott GM31684), fluoroaluminosilicate glasses (such as Schott G018-091 and Schott G018-117), and boroaluminosilicate glasses containing zirconium and/or cesium (such as Schott G018-307, G018-308 and G018-310).

In an embodiment, as the filler (Ed), an organic inorganic composite filler (Fd3) may be used which is obtained by adding a polymerizable monomer beforehand to the inorganic filler (Fd2) to give a paste, which is then cured by polymerization and crushed.

In a preferred embodiment of the dental composition, the composition contains a microfiller having a particle diameter of 0.1 μm or less. Such a composition is suited as a dental composite resin. Preferred examples of the materials for such micron size fillers include silica (for example, product name: AEROSIL), alumina, zirconia and titania. These fillers may have been surface treated with agents such as silane coupling agents in accordance with purposes. Examples of such surface treating agents include known silane coupling agents, for example, organosilicon compounds such as γ-methacryloxyalkyltrimethoxysilanes (the number of carbon atoms between the methacryloxy group and the silicon atom: 3 to 12), γ-methacryloxyalkyltriethoxysilanes (the number of carbon atoms between the methacryloxy group and the silicon atom: 3 to 12), vinyltrimethoxysilane, vinylethoxysilane and vinyltriacetoxysilane. The surface treating agent is usually used with a concentration in the range of 0.1 to 20 wt %, and preferably 1 to 10 wt % with respect to 100 wt % of the filler.

The fillers (Ed) may be used singly, or two or more may be used in combination. The amount of the filler (Ed) may be determined appropriately in consideration of the handleability (viscosity and consistency) of the dental adhesive composition (d) and the mechanical properties of cured products thereof. The filler (Fd) is preferably used in the range of 10 to 2000 parts by weight, more preferably 50 to 1000 parts by weight, and still more preferably 100 to 600 parts by weight per 100 parts by weight of all the components used in the dental adhesive composition (d) other than the fillers (the filler (Dd) and the filler (Fd)).

Where necessary, the dental adhesive composition (d) may contain an additional additive (Gd). Examples of the additives (Gd) include UV absorbers such as 2-hydroxy-4-methylbenzophenone, polymerization inhibitors such as hydroquinone, hydroquinone monomethyl ether and 2,5-di-tertiary butyl-4-methylphenol, discoloration inhibitors, antimicrobial agents, and other known additives. The additives (Gd) may be used singly, or two or more may be used in combination.

Where necessary, the dental adhesive composition (d) may contain a dye and/or a pigment (Hd). Examples of the dyes and/or the pigments (Hd) include phloxine BK, acid red, fast acid magenta, phloxine B, fast green FGF, rhodamine B, basic fuchsine, acid fuchsine, eosine, erythrosine, safranin, rose bengal, Boehmer's hematoxylin, gentian violet, sodium copper chlorophyll, laccaic acid, fluorescein sodium, cochineal and shisonin, talc and titanium white. The dyes and/or the pigments (Hd) may be used singly, or two or more may be used in combination.

A cured product obtained by bonding the dental adhesive composition (d) to tooth structure followed by polymerization reaction desirably has excellent durability against external stress. For this purpose, it is desirable that the cured product have appropriate strength, flexibility and toughness.

The elastic modulus of cured products obtained from the dental adhesive composition (d), as measured by the testing method described below, is preferably 0.5 to 4 GPa, and more preferably 1 to 3 GPa. If the elastic modulus is higher than the upper limit of this range, flexibility and toughness are sometimes decreased. If the elastic modulus is below the lower limit, the cured products are sometimes too flexible or poorly strong.

To ensure strength, the maximum stress of the cured products is preferably not less than 65 MPa, more preferably not less than 80 MPa, and still more preferably not less than 100 MPa. Below this range, strength is sometimes poor.

To ensure flexibility and toughness, the breaking energy of the cured products is preferably not less than 65 mJ, more preferably not less than 80 mJ, and still more preferably not less than 100 m J. Below this range, flexibility and toughness are sometimes poor.

"Three-Point Bending Test"

The dental adhesive composition (d) was packed into a 2×2×25 mm mold and was brought into press contact with a polypropylene film and a glass plate. Nine points on each of the front and back sides were irradiated with light (PENCURE 2000, J. Morita MEG. Corp.) for 10 seconds, and the surface was polished with #320 waterproof abrasive paper. Thereafter, a cured product for three-point bending test was obtained, and was soaked in water at 37° C. overnight. After the overnight soaking, the cured product was subjected to a three-point bending test with a precision universal tester (AUTOGRAPH AG-IS manufactured by Shimadzu Corporation) at a crosshead speed of 1.0 mm/min (N=3).

In the fourth aspect of the present invention, the dental adhesive composition (d) is used as a mobile tooth fixing material (βd). For this use, it is desirable that the composition have effective bond strength with respect to tooth structure. Although not particularly limited thereto, a cured product obtained from the dental adhesive composition (d), after being soaked in water at 37° C. overnight, preferably has a tensile bond strength measured at a crosshead speed of 2 mm/min of not less than 3 MPa, more preferably not less than 5 MPa, and still more preferably not less than 7 MPa. The mobile tooth fixing material (βd) including the dental adhesive composition (d) is used as a fixing material in the fixation of teeth that have become loose for reasons such as periodontal disease to adjacent teeth (this procedure is called the mobile tooth fixation).

The dental adhesive composition (d) used as a mobile tooth fixing material (βd) has good viscosity and shaping properties before curing, thus exhibiting excellent handleability. Further, the composition shows good adhesion with respect to tooth structure. Furthermore, the cured products are excellent in strength, flexibility and toughness. Thus, the dental adhesive composition (d) is accommodated in, for example, a one-part syringe container and is used as a dental material, in particular, suitably used as a mobile tooth fixing material (βd). Cured products obtained from such a mobile tooth fixing material (βd) have appropriate strength, flexibility and toughness.

The dental adhesive composition (d) is preferably a one-part composition in which all the components have been mixed beforehand. From the point of view of handleability, the dental adhesive composition (d) is preferably used as a formulation loaded in a cylindrical syringe container. The shape of the cylindrical portion of the syringe container is preferably 10 cm in length and not more than 15 mm in inner diameter, and more preferably 7.5 cm in length and not more than 10 mm in inner diameter. To enhance handleability, a nozzle may be attached to the tip of the syringe. The shape of the nozzle is preferably 25 mm in length and not more than 2.5 mm in inner diameter of the opening, and more preferably 20 mm in length and not more than 2.0 mm in inner diameter of the opening.

The mobile tooth fixing material (βd) may be used in the mobile tooth fixation by a known method.

A dental curable kit (αe) according to the fifth aspect of the present invention will be described in detail below.

The dental curable kit (αe) includes at least a first composition and a second composition as components for forming a dental curable composition (e). The first composition and the second composition each include a polymerizable monomer (αe). The first composition includes an aromatic amine compound (be) having a nonaromatic carbonyl group and an organic sulfinic acid compound (ce) having an electron withdrawing group. The second composition includes a polymerization initiator (de). A mixture of the first composition and the second composition has a change in curing time of not more than 3 minutes before and after storage of the first composition at 75° C. for 24 hours.

Unless otherwise mentioned, the description in the fifth aspect below assumes that when any component is used in two or more compositions, the amount of such a component in parts by weight indicates the total amount of the component.

In the description of the fifth aspect below, the phrase "XX to YY" (XX and YY are values or the like) such as one used to indicate a preferred numerical range means "not less than XX and/or not more than YY".

In the dental curable kit (αe), the first composition and the second composition used as components for forming a dental curable composition (e) each include a polymerizable monomer (αe). The polymerizable monomer (αe) is preferably a radically polymerizable monomer having a polymerizable group. Because of easy radical polymerization, the polymerizable group is preferably a (meth)acrylic group or a (meth)acrylamide group. A dental composition prepared from the dental curable kit (αe) is used in the mouth. The environment in the mouth is wet, and there is a risk that the polymerizable groups may be detached by hydrolysis or the like. In consideration of the irritating properties of the detached polymerizable groups on the living body, a more preferred polymerizable group is a methacrylic group or a methacrylamide group.

The polymerizable monomers (αe) are broadly categorized into acidic group-free polymerizable monomers (αe-1) and acidic group-containing polymerizable monomers (αe-2).

Examples of the acidic group-free polymerizable monomers (αe-1) include polyfunctional monomers having a plurality of polymerizable groups described hereinabove, and monofunctional monomers (αe-11) having one polymerizable group.

Examples of the polyfunctional monomers include difunctional polymerizable monomers (αe-12) and trifunctional or polyfunctional polymerizable monomers (αe-13).

Examples of the difunctional polymerizable monomers (αe-12) include 2,2-bis((meth)acryloyloxyphenyl)propane, 2,2-bis[4-(3-(meth)acryloyloxy-2-hydroxypropoxy)phenyl] pro pane (commonly known as "bis-GMA"), 2,2-bis(4-(meth)acryloyloxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxyethoxyphenyl)-2-(4-(meth)acryloyloxy diethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyl oxytriethoxyphenyl)propane, 2,2-bis(4-(meth)acryloyloxypropoxyphenyl)propane, 2,2-bis(4-(meth)acryloyloxyisopropoxyphenyl)propane, 1,4-bis(2-(meth)acryloyloxyethyl)pyromellitate, glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentylglycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylenebis(2-carbamoyloxyethyl) dimethacrylate (commonly known as "UDMA"), 1,2-bis(3-methacryloyloxy-2-hydroxypropoxy) ethane, and urethane dimethacrylates represented by the following formulas (1e) to (4e). Of these, 2,2-bis[4-(3-(meth)acryloyloxy)-2-hydroxypropoxyphenyl]pro pane (commonly known as "bis-GMA"), 2,2-bis(4-(meth)acryloyloxypolyethoxyphenyl)propane, and urethane dimethacrylates represented by the following formulas (1e) to (4e) are preferable because cured products obtained from the dental curable kit (αe) have high mechanical strength. Of the 2,2-bis(4-(meth)acryloyloxypolyethoxyphenyl)propanes, the compound having an average number of moles of ethoxy groups added of 2.6 (commonly known as "D2.6E") is preferable. Because of excellent handleability of the obtainable dental curable composition (e), glycerol di(meth)acrylate, triethylene glycol di(meth)acrylate, neopentylglycol di(meth)acrylate, 2,2,4-trimethylhexamethylenebis(2-carbamoyloxyethyl) dimethacrylate and 1,2-bis(3-methacryloyloxy-2-hydroxypropoxy)ethane are preferable. Further, because the obtainable dental curable composition (e) also attains excellent thermal stability, urethane dimethacrylates represented by the following formulas (1e) to (4e) are particularly preferable.

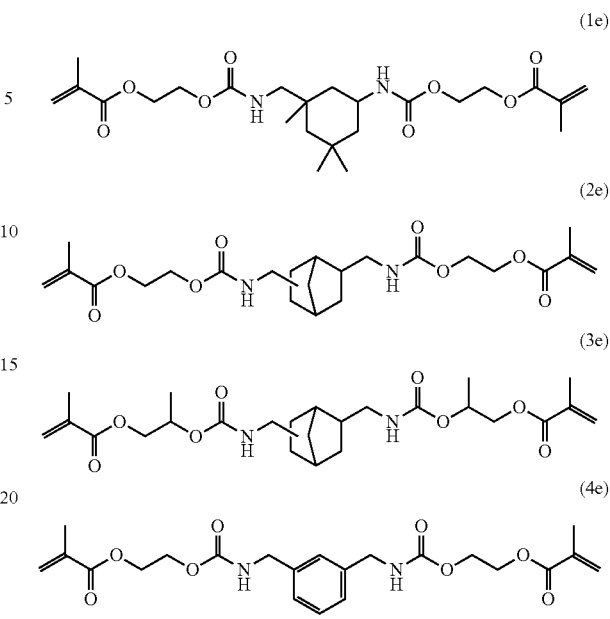

Examples of the trifunctional or polyfunctional polymerizable monomers (αe-13) include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol hexa(meth)acrylate, N,N-(2,2,4-trimethylhexamethylene)bis[2-(aminocarboxy)propane-1,3-diol] tetramethacrylate and 1,7-diacryloyloxy-2,2,6,6-tetraacryloyloxymethyl-4-oxyheptane.

Examples of the monofunctional monomers (αe-11) include hydroxyalkyl (meth)acrylates such as 2-hydroxyethyl (meth)acrylate, 3-hydroxypropyl (meth)acrylate, 4-hydroxybutyl (meth)acrylate, 6-hydroxyhexyl (meth)acrylate and 10-hydroxydecyl (meth)acrylate, hydroxyl group-containing (meth)acrylate or (meth)acrylamide monomers such as propylene glycol mono(meth)acrylate, glycerol mono (meth)acrylate, erythritol mono(meth)acrylate, N-methylol (meth)acrylamide, N-hydroxyethyl (meth)acrylamide and N,N-(dihydroxyethyl) (meth)acrylamide; hydrocarbon group-containing (meth)acrylates such as methyl (meth)acrylate, ethyl (meth)acrylate, propyl (meth)acrylate, isopropyl (meth)acrylate, butyl (meth)acrylate, isobutyl (meth)acrylate, benzyl (meth)acrylate and lauryl (meth)acrylate; halogen atom-containing (meth)acrylates such as 2,3-dibromopropyl (meth)acrylate, silicon atom-containing (meth)acrylates such as 3-(meth)acryloyloxypropyltrimethoxysilane and 11-(meth)acryloyloxyundecyltrimethoxysilane; and (meth)acrylamide monomers such as (meth)acrylamide. Of these, 2-hydroxyethyl (meth)acrylate, 3-hydroxypropyl (meth)acrylate, glycerol mono(meth)acrylate and erythritol mono(meth)acrylate are preferable because the dental curable composition (e) obtained from the dental curable kit (αe) exhibits high affinity for tooth structure and also because cured products obtained from the dental curable composition (e) have high bond strength.

The polymerizable monomer (αe-1) may be contained in any of the plurality of compositions present in the dental curable kit (αe), and is preferably contained in the first composition that is mixed to constitute a dental curable composition (e).

In the dental composition (e) obtained from the dental curable kit (αe), the acidic group-free polymerizable monomer (αe-1) is preferably present in an amount in the range of 50 to 99.99 wt %, more preferably 60 to 99.9 wt %, and still more preferably 70 to 99.5 wt % in the dental curable composition (e) excluding, if any present in the dental curable composition (e), a filling agent (fe) such as a filler described later, and a solvent such as water, acetone or alcohol. If the content is below the lower limit of this range, the dental curable composition (e) from the dental curable kit (αe) sometimes fails to give cured products or sometimes gives brittle cured products, and the time of curing of the dental curable composition (e) may be significantly short. If the content exceeds the upper limit, the dental curable composition (e) may fail to cure or may take a markedly long time to cure.

The acidic group-containing polymerizable monomer (αe-2) present in the dental curable kit (αe) may be any polymerizable monomer having an acidic group in the molecule. A single or a plurality of such polymerizable monomers may be used. The monomer may be also used in combination with the acidic group-free polymerizable monomer (αe-1).

For example, the acidic group-containing polymerizable monomer (αe-2) has an acidic group such as a carboxyl group, a phosphoric group, a thiophosphoric group, a sulfonic group or a sulfinic group. A single or a combination of these acidic groups may be introduced in the acidic group-containing polymerizable monomer (αe-2).

While acid anhydrides such as 4-(meth)acryloyloxyethyltrimellitic anhydride (4-META) described later are apparently free from acidic groups, their structures are hydrolyzed quickly and readily to form acidic groups in an environment to which the composition is applied (an environment at room temperature and rich in water) such as in the mouth, and therefore such acid anhydride groups are also regarded as the acidic groups.

The acidic group-containing polymerizable monomer (αe-2) may be a carboxyl group-containing polymerizable monomer (αe-21) having at least one carboxyl group in the molecule. Some polymerizable monomers (αe-21) are monocarboxylic acids, dicarboxylic acids, tricarboxylic acids and tetracarboxylic acids, and derivatives thereof. Examples of the polymerizable monomers (αe-21) include (meth)acrylic acid, maleic acid, p-vinylbenzoic acid, 11-(meth)acryloyloxy-1,1-undecanedicarboxylic acid (in the case of methacrylate: "MAC-10"), 1,4-di(meth)acryloyloxyethylpyromellitic acid, 6-(meth)acryloyloxyethylnaphthalene-1,2,6-tricarboxylic acid, 4-(meth)acryloyloxymethyltrimellitic acid and an anhydride thereof, 4-(meth)acryloyloxyethyltrimellitic acid (in the case of methacrylate: "4-MET") and an anhydride thereof (in the case of methacrylate: 4-META), 4-(meth)acryloyloxybutyltrimellitic acid and an anhydride thereof, 4-[2-hydroxy-3-(meth)acryloyloxy]butyltrimellitic acid and an anhydride thereof, 2,3-bis(3,4-dicarboxybenzoyloxy)propyl (meth)acrylate, N,O-di(meth)acryloyltyrosine, O-(meth)acryloyltyrosine, N-(meth)acryloyltyrosine, N-(meth)acryloylphenylalanine, N-(meth)acryloyl-p-aminobenzoic acid, N-(meth)acryloyl-O-aminobenzoic acid, N-(meth)acryloyl-5-aminosalicylic acid (in the case of methacrylate: "5-MASA"), N-(meth)acryloyl-4-aminosalicylic acid, 2 or 3 or 4-(meth)acryloyloxybenzoic acid, addition product of 2-hydroxyethyl (meth)acrylate with pyromellitic dianhydride (in the case of methacrylate: "PMDM"), addition product of 2-hydroxyethyl (meth)acrylate with maleic anhydride or 3,3',4,4'-benzophenonetetracarboxylic dianhydride (in the case of methacrylate: "BTDA") or 3,3',4,4'-biphenyltetracarboxylic dianhydride, 2-(3,4-dicarboxybenzoyloxy)-1,3-di(meth)acryloyloxypropane, adduct of N-phenylglycine or N-tolylglycine with glycidyl (meth)acrylate, 4-[(2-hydroxy-3-(meth)acryloyloxypropyl)amino]phthalic acid and 3 or 4-[N-methyl-N-(2-hydroxy-3-(meth)acryloyloxypropyl)amino]phthalic acid.

Of the carboxyl group-containing polymerizable monomers (αe-21), MAC-10, 4-MET, 4-META and 5-MASA are preferable. A single or a combination of the carboxyl group-containing polymerizable monomers (αe-21) may be used.

The acidic group-containing polymerizable monomer (αe-2) may be a phosphoric group-containing polymerizable monomer (αe-22) having at least one phosphoric group in the molecule. Examples of the polymerizable monomers (αe-22) include 2-(meth)acryloyloxyethyl acid phosphate, 2 and 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxydodecyl acid phosphate, bis{2-(meth)acryloyloxyethyl} acid phosphate, bis{2 or 3-(meth)acryloyloxypropyl} acid phosphate, 2-(meth)acryloyloxyethylphenyl acid phosphate and 2-(meth)acryloyloxyethyl-p-methoxyphenyl acid phosphate. Compounds corresponding to the above compounds except that the phosphoric group is replaced by a thiophosphoric group are also usable as the acidic group-containing polymerizable monomers (αe-2).

Of the phosphoric group-containing polymerizable monomers (αe-22), 2-(meth)acryloyloxyethylphenyl acid phosphate and 10-(meth)acryloyloxydecyl acid phosphate are preferable. A single or a combination of the phosphoric group-containing polymerizable monomers (αe-22) may be used.

Compounds corresponding to the above polymerizable monomers (αe-22) except that the phosphoric group is replaced by a thiophosphoric group are also usable as the acidic group-containing polymerizable monomers (αe-2).

The acidic group-containing polymerizable monomer (αe-2) may be a sulfonic group-containing polymerizable monomer (αe-23) having at least one sulfonic group in the molecule. Examples of the polymerizable monomers (αe-23) include 2-sulfoethyl (meth)acrylate, 2-sulfo-1-propyl (meth)acrylate, 1-sulfo-2-propyl (meth)acrylate, 1-sulfo-2-butyl (meth)acrylate, 3-sulfo-2-butyl (meth)acrylate, 3-bromo-2-sulfo-2-propyl (meth)acrylate, 3-methoxy-1-sulfo-2-propyl (meth)acrylate and 1,1-dimethyl-2-sulfoethyl (meth)acrylamide.

Of the sulfonic group-containing polymerizable monomers (αe-23), 2-methyl-2-(meth)acrylamidopropanesulfonic acid is preferable. A single or a combination of the sulfonic group-containing polymerizable monomers (αe-23) may be used.

Preferably, the acidic group-containing polymerizable monomer (αe-2) is contained in the second composition, of the dental curable kit (αe), that is a component for forming a dental curable composition (e). When the second composition contains the polymerizable monomer (αe-2), the acidic group-free polymerizable monomer (αe-1) may be present together with the polymerizable monomer (αe-2). When the polymerizable monomer (αe-2) is contained in the first composition, the amount thereof is preferably small, and it is more preferable that the monomer be not contained in the first composition. If the first composition contains a large amount of the polymerizable monomer (αe-2), the organic sulfinic acid compound (ce) having an electron withdrawing group may be decomposed into sulfinic acid, and the storage stability of the first composition may be adversely affected.

In the dental curable kit (αe), the first composition used as a component for forming a dental curable composition (e) includes an aromatic amine compound (be) having a nonaromatic carbonyl group. The aromatic amine compound (be) having a nonaromatic carbonyl group is a compound which has an amine group bonded to the aromatic ring and has a carbonyl group without a direct bond to the aromatic ring.

The amine group may be any of a primary amine, a secondary amine and a tertiary amine, and is preferably a secondary amine group. The carbonyl group in the compound (be) is preferably present in the form of a carboxylic acid or a carboxylate salt, and more preferably in the form of a carboxylate salt. The nitrogen atom in the amine group and the carbon atom in the carbonyl group are preferably bonded to each other via a carbon chain having 3 or less carbon atoms, and are more preferably bonded to each other via one carbon atom, namely, a methylene group (—CH$_2$—).

Of the compounds (be), those compounds represented by the following formula (5e) are more preferable.

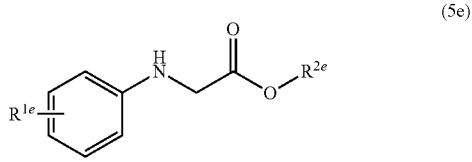

(5e)

In the formula (5e), $R^{1e}$ is a hydrogen atom or an alkyl group optionally having a functional group, and $R^{2e}$ is a hydrogen atom or a metal atom.

Examples of the compounds represented by the formula (5e) include N-phenylglycine (NPG) in which $R^{1e}$ is a hydrogen atom and $R^{2e}$ is a hydrogen atom, and salts thereof, and N-tolylglycine (NTG) and salts thereof. Of these, NPG and alkali metal salts thereof are preferable, and NPG and sodium salt thereof (NPG-Na) are more preferable.

A single or a combination of the aromatic amine compounds (be) having a nonaromatic carbonyl group may be used.

In the dental curable kit (αe), the first composition used as a component for forming a dental curable composition (e) includes an organic sulfinic acid compound (ce) having an electron withdrawing group. The organic sulfinic acid compound (ce) having an electron withdrawing group is a polymerization promoting component. From the point of view of the thermal stability of the first composition present in the dental curable kit (αe) and the thermal stability of a dental curable composition (e) obtained from the kit, the organic sulfinic acid compound (ce) has an electron withdrawing group. On the other hand, excessively high electron withdrawing properties of the electron withdrawing group present in the organic sulfinic acid compound (ce) make the progress of polymerization difficult. Thus, the Hammett substituent constant σp of the electron withdrawing group is preferably in the range of 0.01 to 2.00, more preferably in the range of 0.05 to 1.50, and still more preferably in the range of 0.10 to 1.00. From the points of view of stability and polymerization promoting effects, the organic sulfinic acid compound (ce) having an electron withdrawing group preferably has an aromatic ring such as a benzene ring, and more preferably has an aromatic ring directly bonded to the sulfinic group.

When the organic sulfinic acid compound (ce) has an aromatic ring, it is preferable that the electron withdrawing group be bonded to the aromatic ring.

Examples of the organic sulfinic acid compounds (ce) having an electron withdrawing group include lithium salts, sodium salts, potassium salts, rubidium salts, cesium salts, magnesium salts, calcium salts, strontium salts, iron salts, zinc salts, ammonium salts, tetramethylammonium salts and tetraethylammonium salts of fluorobenzenesulfinic acid, chlorobenzenesulfinic acid, bromobenzenesulfinic acid, iodobenzenesulfinic acid, alkyloxycarbonylbenzenesulfinic acid, trifluoromethylbenzenesulfinic acid, cyanobenzenesulfinic acid and nitrobenzenesulfinic acid. Of these, lithium salts, sodium salts, potassium salts, magnesium salts and calcium salts of chlorobenzenesulfinic acid are preferable from the points of view of the curability and storage stability of the first composition present in the dental curable kit (αe) and of a dental curable composition (e) obtained from the kit.

The content of the organic sulfinic acid compound (ce) having an electron withdrawing group is not particularly limited. To avoid a delay in the rate of curing of the obtainable dental curable composition (e) and to prevent a decrease in the bond strength of cured products from the composition (e), the content is preferably not less than 0.001 part by weight, more preferably not less than 0.01 part by weight, and still more preferably not less than 0.1 part by weight per 100 parts by weight of the total amount of the polymerizable monomers (αe), present in the dental curable kit (αe), that are used as the dental curable composition (e). To avoid a risk that the obtainable dental curable composition (e) will be cured so quickly that a sufficient working time cannot be ensured, the content of the organic sulfinic acid compound (ce) is preferably not more than 20 parts by weight, more preferably not more than 15 parts by weight, and still more preferably not more than 10 parts by weight per 100 parts by weight of the total amount of the polymerizable monomers (αe).

From the point of view of the hue stability of cured products obtained from the dental curable kit (αe), the weight ratio ((ce)/(be)) of the organic sulfinic acid compound (ce) having an electron withdrawing group to the aromatic amine compound (be) in the dental curable kit (αe) is preferably 1/10 to 100/1, more preferably 1/5 to 75/1, and still more preferably 1/1 to 50/1.

In the dental curable kit (αe), the second composition used as a component for a dental curable composition (e) includes a polymerization initiator (de). The polymerization initiator (de) is preferably a peroxide (de-1). The peroxides (de-1) include organic peroxides (de-11) and inorganic peroxides (de-12), and any of such peroxides may be used as the polymerization initiator in the dental curable kit (αe) as long as they can initiate polymerization.

Examples of the organic peroxides (de-11) include diacetyl peroxide, dipropyl peroxide, dibutyl peroxide, dicapryl peroxide, dilauryl peroxide, benzoyl peroxide (BPO), p,p'-dichlorobenzoyl peroxide, p,p'-dimethoxybenzoyl peroxide, p,p'-dimethylbenzoyl peroxide and p,p'-dinitrodibenzoyl peroxide.

Examples of the inorganic peroxides (de-12) include ammonium persulfate, potassium persulfate, potassium chlorate, potassium bromate and potassium superphosphate.

A single or a combination of the polymerization initiators (de) may be used.

The polymerization initiator (de) represented by a peroxide (de-1) is preferably used in an amount in the range of 0.1 to 10 wt %, more preferably 0.3 to 8 wt %, and still more preferably 0.5 to 7 wt % in 100 wt % of all the components possibly present in the second composition of the dental curable kit (αe) except a filling agent (fe) such as a filler described later. If the amount of the polymerization initiator (de) represented by a peroxide (de-1) exceeds the upper limit of this range, the dental curable composition (e) from the dental curable kit (αe) starts to polymerize in a significantly short time, and a sufficient pot life cannot be ensured at times.

The first composition of the dental curable kit (αe) may include an aromatic tertiary amine (ee) (this compound does not correspond to the aromatic amine compounds (be) having a nonaromatic carbonyl group). The aromatic tertiary amine (ee) may be any tertiary amine compound in which at least one of the organic groups bonded to the nitrogen atom is an aromatic group (preferably the nitrogen atom is bonded directly to an atom constituting the aromatic ring). Any such known compounds may be used without limitation. Of the aromatic tertiary amines (ee), those tertiary amine compounds are preferable in which one aromatic group and two aliphatic groups are bonded to the nitrogen atom because such compounds have higher polymerization activity, have excellent storage stability, are less volatile and thus less odorous, and are available easily. Typical examples of the aromatic tertiary amine compounds include those represented by the following general formula (6e).

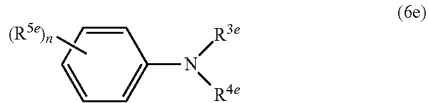

(6e)

In the formula (6e), $R^{3e}$ and $R^{4e}$ are each independently an optionally substituted alkyl group, $R^{5e}$ is an optionally substituted alkyl, aryl, alkenyl, alkoxy or alkyloxycarbonyl group, and n is an integer of 0 to 5. When n is 2 or greater, the plurality of $R^{5e}$s may be the same as or different from one another, and $R^{5e}$s may be bonded together to form a ring.

For example, the optionally substituted alkyl groups represented by $R^{3e}$, $R^{4e}$ and $R^{5e}$ are preferably groups having 1 to 6 carbon atoms. Examples of such optionally substituted alkyl groups include unsubstituted alkyl groups such as methyl group, ethyl group, n-propyl group, i-propyl group, n-butyl group and n-hexyl group, halogen-substituted alkyl groups such as chloromethyl group and 2-chloroethyl group; and hydroxyl-substituted alkyl groups such as 2-hydroxyethyl group.

Examples of the optionally substituted aryl groups represented by $R^{5e}$ include groups having 6 to 12 carbon atoms such as phenyl group, p-methoxyphenyl group, p-methylthiophenyl group, p-chlorophenyl group and 4-biphenylyl group. Examples of the optionally substituted alkenyl groups include groups having 2 to 12 carbon atoms such as vinyl group, allyl group and 2-phenylethenyl group. Examples of the optionally substituted alkoxy groups include groups having 1 to 10 carbon atoms such as methoxy group, ethoxy group and butoxy group. Examples of the optionally substituted alkyloxycarbonyl groups include groups in which the alkyloxy moiety in the alkyloxycarbonyl group has 1 to 10 carbon atoms such as methoxycarbonyl group, ethoxycarbonyl group, butoxycarbonyl group, amyloxycarbonyl group and isoamyloxycarbonyl group.

Of the above groups represented by $R^{3e}$ and $R^{4e}$, $C_{1-6}$ optionally substituted alkyl groups are preferable, and, in particular, $C_{1-3}$ unsubstituted alkyl groups (for example, methyl group, ethyl group and n-propyl group) and 2-hydroxyethyl group are more preferable.

In the formula (6e), when n=1, $R^{5e}$ is preferably bonded to the para position with respect to the group $NR^{3e}R^{4e}$. In this case, $R^{5e}$ is preferably an alkyloxycarbonyl group or an alkyl group.

In the formula (6e), when n=2 or 3 (when two or three groups $R^{5e}$ are bonded), $R^{5e}$s are preferably bonded to the ortho position (s) and/or the para position with respect to the group $NR^{3e}R^{4e}$.

In the aromatic tertiary amine compounds represented by the formula (6e), for example, $R^{5e}$ may be an alkyloxycarbonyl group bonded to the para position. Examples of such compounds in which $R^{5e}$ is an alkyloxycarbonyl group bonded to the para position with respect to the group $NR^{3e}R^{4e}$ include alkyl p-dialkylaminobenzoates such as methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate and propyl p-diethylaminobenzoate. Examples of the aromatic tertiary amine compounds represented by the formula (6e) further include N,N-dimethylaniline, N,N-dibenzylaniline, N,N-dimethyl-p-toluidine, N,N-diethyl-p-toluidine, N,N-di(β-hydroxyethyl)-p-toluidine, N,N,2,4,6-pentamethylaniline, N,N,2,4-tetramethylaniline and N,N-diethyl-2,4,6-trimethylaniline.

As necessary, the aromatic tertiary amine compounds (ee) may be used singly, or two or more kinds of the compounds may be used in combination.

When $R^{5e}$ is an electron donating group (having a Hammett substituent constant $\sigma_p$ of −1.00 to −0.01) or when n is 0, the content of the aromatic tertiary amine compound (ee) is preferably 0.001 to 3 parts by weight, more preferably 0.005 to 2 parts by weight, and still more preferably 0.01 to 1 part by weight per 100 parts by weight of the total of the polymerizable monomers (αe) present in the dental curable kit (αe) that are used as a dental curable composition (e). If the content is less than 0.001 part by weight, the composition sometimes fails to attain mechanical characteristics required as dental cements after polymerization curing. If the content exceeds 3 parts by weight, the polymerization rate is so increased that clinical handleability is sometimes deteriorated.

When $R^{5e}$ is an electron withdrawing group (having a Hammett substituent constant $\sigma_p$ of 0.01 to 2.00), the content of the aromatic tertiary amine compound (ee) is preferably 0.1 to 20 parts by weight, more preferably 0.3 to 10 parts by weight, and still more preferably 0.5 to 5 parts by weight per 100 parts by weight of the total of the polymerizable monomers (αe) present in the dental curable kit (αe) that are used as a dental curable composition (e). If the content is less than 0.1 part by weight, the composition after polymerization curing may show poor discoloration resistance. If the content exceeds 20 parts by weight, the composition becomes excessively sensitive to an optical stimulus and the clinical handleability is sometimes deteriorated.

Substituents having a Hammett substituent constant σp of above −0.01 and below 0.01 are usually only hydrogen atoms. Thus, substituents in this numerical range may be regarded as belonging to the electron donating groups.

In the dental curable kit (αe), at least one of the first composition and the second composition used as components for a dental curable composition (e) may further include a filling agent (fe) such as a filler. A single or a combination of filling agents (fe) such as fillers may be used. When the filling agents are present in both the first composition and the second composition, the types of the compositions in the first composition and the second composition may be the same as or different from each other. Examples of the filling agents (fe) such as fillers include inorganic fillers (fe1), organic fillers (fe2), and composite fillers (fe3) including inorganic fillers and organic fillers.

Examples of the inorganic materials which form the inorganic fillers (fe1) include minerals based on silica such as silica, kaolin, clay, silicate minerals and mica; and ceramics and glasses based on silica and containing $Al_2O_3$, $B_2O_3$, $TiO_2$, $ZrO_2$, BaO, $La_2O_3$, SrO, ZnO, CaO, $P_2O_5$, $Li_2O$, $Na_2O$ and the like. Some preferred glasses are, for example, lanthanum glass, barium glass, strontium glass, soda glass, lithium borosilicate glass, zinc glass, fluoroaluminosilicate glass, borosilicate glass and bioglass. Other preferred inorganic materials are, for example, crystalline quartz, hydroxyapatite, alumina, titanium oxide, yttrium oxide, zirconia, calcium phosphate, barium sulfate, aluminum hydroxide, sodium fluoride, potassium fluoride, sodium monofluorophosphate, lithium fluoride and ytterbium fluoride.

Example materials for the organic fillers (fe2) are polymers. Examples of such polymers include polymethyl methacrylate, polyethyl methacrylate, polymers of polyfunctional methacrylates, polyamide, polystyrene, polyvinyl chloride, chloroprene rubber, nitrile rubber, styrene-butadiene rubber, copolymers such as random copolymers, block copolymers and graft copolymers obtained by copolymerizing monomer components of the above polymers, uniform blends of these polymers, and nonuniform blends having a matrix-dispersed phase structure, a layered structure or a structure with an unclear boundary and a gradient mixing ratio.

Examples of the composite fillers (fe3) including inorganic fillers and organic fillers include dispersions of inorganic fillers in organic fillers, and inorganic/organic composite fillers obtained by coating inorganic fillers with various polymers.

When the filling agent (fe) such as a filler, for example, the inorganic filler (fe1) is used to enhance curability, mechanical strength and handleability, the filler may be used after being surface-treated beforehand with a known surface treating agent such as a silane coupling agent. Examples of the surface treating agents include vinyltrimethoxysilane, vinyltriethoxysilane, vinyltrichlorosilane, vinyltri(β-methoxyethoxy) silane, γ-methacryloyloxypropyltrimethoxysilane, γ-glycidoxypropyltrimethoxysilane, γ-mercaptopropyltrimethoxysilane and γ-aminopropyltriethoxysilane.

The amount of the filling agent (fe) such as a filler is preferably in the range of 10 to 80 wt %, more preferably in the range of 30 to 80 wt %, and still more preferably in the range of 50 to 75 wt % based on the total weight of the dental curable composition (e) obtained by mixing the compositions such as the first composition and the second composition present in the dental curable kit (αe).

The first composition contains the aromatic amine compound (be) having a nonaromatic carbonyl group, the organic sulfinic acid compound (ce) having an electron withdrawing group, and optionally the aromatic tertiary amine (ee). A system consisting solely of these compounds sometimes has a difficulty in forming a uniform liquid phase. It is therefore appropriate that the polymerizable monomer (αe) to be mixed therewith be one that is liquid at room temperature. A solvent such as acetone has excellent solvent properties with respect to the above compounds, is not significantly harmful to human bodies, is easily evaporated and hardly inhibits bonding. However, the use of such a solvent as an alternative to the above approach encounters various problems and is not realistic.

The first composition and the second composition may be each stored as sub-compositions which include any of the components including:
the acidic group-free polymerizable monomer (αe-1),
the acidic group-containing polymerizable monomer (αe-2),
the aromatic amine compound (be) having a nonaromatic carbonyl group,
the organic sulfinic acid compound (ce) having an electron withdrawing group,
the polymerization initiator (de), and
the aromatic tertiary amine (ee). Of these components, the aromatic amine compound (be), the organic sulfinic acid compound (ce) and the optional aromatic tertiary amine (ee) each exhibit insufficient storage stability when mixed together with the acidic group-containing polymerizable monomer (αe-2) or the polymerization initiator (de). Thus, combinations of the components may be selected appropriately except such undesired combinations (when expressed set-theoretically, ((be)∪(ee)∩n((ce)∪(αe-2)∪(de))).

When a dental curable composition (e) obtained by mixing the first composition, the second composition and the like of the dental curable kit (αe) is applied to the bonding of a tooth, in particular, dentin, it is desirable that the tooth be treated beforehand with a dental surface treating agent in order to obtain good adhesion. Thus, in a preferred embodiment, the dental curable kit (αe) includes a dental surface treating agent separately from the first composition, the second composition and the like for forming the dental composition (e). The chemical composition of such a dental surface treating agent is not particularly limited. An example is a dental surface treating agent which contains an acidic group-containing polymerizable monomer (αe-2) described hereinabove, a transition metal compound and water.

The acidic group-containing polymerizable monomer (αe-2) present in the dental surface treating agent may be the same as or different from the acidic group-containing polymerizable monomer (αe-2) present in the second composition used as the dental curable composition (e). To attain good adhesion to teeth and high stability of the dental surface treating agent, the acidic group-containing polymerizable monomer (αe-2) present in the dental surface treating agent is preferably 4-(meth)acryloyloxyethyltrimellitic acid (in the case of methacrylate: "4-MET"), a salt thereof or an anhydride thereof (in the case of methacrylate: 4-META).

The transition metal compound present in the dental surface treating agent may be a known compound. Examples of the transition metal compounds include salts of inorganic acids, specifically, bromides such as vanadium bromide, nickel bromide, copper bromide, iron bromide and cobalt bromide; chlorides such as nickel chloride, vanadium chloride, palladium chloride, nickel chloride, titanium chloride, iron chloride and cobalt chloride; fluorides such as vanadium fluoride, cobalt fluoride, copper fluoride, nickel fluoride and titanium potassium fluoride; sulfate salts such as palladium sulfate, nickel sulfate, titanium sulfate, copper sulfate, iron sulfate and cobalt sulfate; nitrate salts such as nickel nitrate, palladium nitrate, nickel nitrate, iron nitrate and cobalt nitrate; and phosphate salts such as iron diphosphate and cobalt phosphate;

salts of organic acids such as nickel acetate, copper acetate, cobalt acetate, cobalt benzoate, copper citrate, iron citrate, titanium potassium oxalate, iron oxalate, cobalt oxalate, iron lactate, iron fumarate, copper acrylate, copper methacrylate, nickel sulfamate, vanadium oxide stearate, cobalt stearate, vanadium naphthenate, cobalt naphthenate and cobalt gluconate;

hydroxides such as palladium hydroxide, nickel hydroxide, iron hydroxide, copper hydroxide and cobalt hydroxide;

pi-electron organic complexes such as titanocene dichloride, and organic complexes of EDTA and acetylacetones such as vanadium acetylacetonate, nickel acetylacetonate, copper acetylacetonate, iron acetylacetonate and cobalt acetylacetonate.

The transition metal compounds may be of any valence. Of the transition metal compounds, compounds of iron, cobalt and copper are preferable, and compounds of iron and copper are more preferable. A single or a combination of the transition metal compounds may be used.

Examples of the water used in the dental surface treating agent include purified water (Japanese Pharmacopoeia), distilled water, ion-exchanged water and physiological saline. Of these, distilled water and ion-exchanged water are preferable.

The second composition present in the dental curable kit (αe) that is mixed to constitute a dental curable composition (e), and/or the dental surface treating agent may further contain a photopolymerization initiator (ge) so that polymerization may be initiated by irradiation with light. Examples of the photopolymerization initiators (ge) include α-diketones (ge1), ketals (ge2), thioxanthones (ge3), acylphosphine oxides (ge4) and α-aminoacetophenones (ge5).

Examples of the α-diketones (ge1) include diacetyl, benzil, camphorquinone, 2,3-pentadione, 2,3-octadione, 9,10-phenanthrenequinone, 4,4'-oxybenzil and acenaphthenequinone. Of these, camphorquinone is preferable because excellent photocurability is obtained in the visible and near ultraviolet regions, and sufficient photocurability is obtained with any of a halogen lamp, a light emitting diode (LED) and a xenon lamp as the light source.

Examples of the ketals (ge2) include benzyl dimethyl ketal and benzyl diethyl ketal.

Examples of the thioxanthones (ge3) include 2-chlorothioxanthone and 2,4-diethylthioxanthone.

Examples of the acylphosphine oxides (ge4) include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl) phosphine oxide and 2,4,6-trimethylbenzoylethoxyphenylphosphine oxide.

Examples of the α-aminoacetophenones (ge5) include 2-benzyl-2-dimethylamino-1-(4-morpholinophenyl)-butanone-1,2-benzyl-2-diethylamino-1-(4-morpholinophenyl)-butanone-1, 2-benzyl-2-dimethylamino-1-(4-morpholinophenyl)-propanone-1,2-benzyl-2-diethylamino-1-(4-morpholinophenyl)-propanone 1,2-benzyl-2-dimethylamino-1-(4-morpholinophenyl)-pentanone-1 and 2-benzyl-2-diethylamino-1-(4-morpholinophenyl)-pentanone-1.

A single or a combination of the photopolymerization initiators (ge) may be used.

The amount of the photopolymerization initiator (ge) is not particularly limited. In the dental curable composition (e) prepared from the first composition, the second composition and the like of the dental curable kit (αe), from the point of view of photocurability, the amount thereof is preferably 0.01 to 10 parts by weight, and more preferably 0.10 to 3 parts by weight per 100 parts by weight of the total amount of the polymerizable monomers (αe) present in the dental curable composition (e). Similarly, in the dental surface treating agent, the amount is preferably 0.01 to 10 parts by weight, and more preferably 0.10 to 3 parts by weight per 100 parts by weight of the total amount of the polymerizable monomer(s) (αe) present in the dental surface treating agent.

The first composition or the second composition which is a component for constituting the dental curable composition (e), or the dental surface treating agent may further contain a sulfur-containing reducing inorganic compound as a redox polymerization accelerator. Examples of the sulfur-containing reducing inorganic compounds include sulfite salts, bisulfite salts, pyrosulfite salts, thiosulfate salts, thionate salts and dithionite salts. Of these, sulfite salts and bisulfite salts are preferable. Some preferred compounds are, for example, sodium sulfite, potassium sulfite, calcium sulfite, ammonium sulfite, sodium hydrogen sulfite and potassium hydrogen sulfite. A single or a combination of the sulfur-containing reducing inorganic compounds may be used.

The first composition or the second composition which is a component for constituting the dental curable composition (e), or the dental surface treating agent may contain a fluoride ion releasing substance in order to impart acid resistance to tooth structure. Examples of the fluoride ion releasing substances include fluoride ion releasing polymers such as copolymer of methyl methacrylate and methacrylic fluoride, fluoride ion releasing substances such as cetylamine hydrofluoride salt, fluoroaluminosilicate glass already mentioned as an inorganic filler, sodium fluoride, potassium fluoride, sodium monofluorophosphate, lithium fluoride and ytterbium fluoride.

The first composition or the second composition which is a component for constituting the dental curable composition (e), or the dental surface treating agent may contain additives such as stabilizers (polymerization inhibitors), colorants, fluorescent agents and UV absorbers. The first composition or the second composition which is a component for constituting the dental curable composition (e), or the dental surface treating agent may contain antimicrobial substances such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride and triclosan.

The first composition or the second composition which is a component for constituting the dental curable composition (e), or the dental surface treating agent may contain a known dye or pigment.

The dental curable kit (αe) includes at least the first composition and the second composition. The first composition and the second composition include (a) the polymerizable monomer (αe). The first composition includes the aromatic amine compound (be) having a nonaromatic carbonyl group, and (c) the organic sulfinic acid compound (ce) having an electron withdrawing group. The second composition includes the polymerization initiator (de). In the dental curable kit (αe), the components that will form a dental curable composition (e) are not necessarily limited to the first composition and the second composition alone, and may include other compositions such as a third composition. Examples of other compositions that may constitute a dental curable composition (e) include compositions containing a polymerization accelerator and the like.

In a preferred embodiment of the dental curable kit (αe), the components that will form a dental curable composition (e) are the first composition and the second composition (so-called two-paste kit). In the case of a two-paste kit, the first composition and the second composition are stored separately from each other, and the two compositions are mixed together immediately before use to cause the polymerization of a dental curable composition (e) to proceed. In this case, when the photopolymerization initiator (ge) is further present in addition to the polymerization initiator (de), it is preferable that the composition be cured by photopolymerization in addition to chemical polymerization.

The dental curable kit (αe) preferably has storage stability. When, specifically, the first composition including the polymerizable monomer (αe), the aromatic amine compound (be) having a nonaromatic carbonyl group, and the organic sulfinic acid compound (ce) having an electron withdrawing group is stored at 76° C. for 24 hours and thereafter the first composition and the second composition in the dental curable kit (αe) are mixed together, the change in curing time of the mixture relative to without the above thermal loading is preferably not more than 3.0 minutes, more preferably not more than 2.0 minutes, and still more preferably not more than 1.5 minutes.

Before and after the above thermal loading, the ratio of curing times (curing time after thermal loading/curing time before thermal loading) of the mixture of the first composition and the second composition in the dental curable kit (αe) is preferably not more than 1.5, more preferably not more than 1.4, and still more preferably not more than 1.3.

The tensile bond strength of cured products obtained from the dental curable composition (e) is preferably not less than 3.0 MPa, more preferably not less than 4.0 MPa, and still more preferably not less than 5.0 MPa.

The components in the dental curable kit (αe) such as the first composition and the second composition that will form a dental curable composition (e) are mixed together and used as a dental cement.

When the composition is used as a dental cement, it is preferable to use the dental surface treating agent described hereinabove. The dental surface treating agent may be applied to an unhealthy tooth and air may be blown thereto with use of a dental air syringe; thereafter, the first composition and the second composition for a dental curable composition may be mixed together and applied to the treated surface, and the composition may be let cure by chemical polymerization, thereby completing the treatment. Alternatively, the treatment may be completed by curing the composition with a device such as a dental visible light irradiator. Further, the polymerizable monomers may be semi-cured by temporary irradiation and the surface to be fixed may be conditioned.

The dental curable composition (e) prepared from the dental curable kit (αe) is applied in a slightly excess amount to the inner wall surface of a coronal restoration material, and the restoration material is brought into press contact with tooth structure. During this pressing operation, the excess of the composition (e) is allowed to squeeze out from the joint (margin) between the tooth structure and the coronal restoration material, and the excess cement that has squeezed out is semi-cured by temporary irradiation with use of a dental light irradiator. The excess cement in the cured state is then removed with use of a dental probe or the like.

The dental curable kit (αe) has excellent storage stability and is useful as a dental adhesive, a coating material, a filling or sealing material, and a tooth structure and coronal restoration material.

EXAMPLES

The present invention will be described in greater detail by presenting Examples hereinbelow. The scope of the invention is not limited to such Examples below.

Hereinbelow, Examples of the first aspect of the present invention will be described.

The following are the abbreviations of compounds used in Examples of the first aspect.

HEMA: 2-hydroxyethyl methacrylate (TOKYO CHEMICAL INDUSTRY CO., LTD.)
HPMA: 2-hydroxypropyl methacrylate (TOKYO CHEMICAL INDUSTRY CO., LTD.)
NBDI: norbornane diisocyanate (Mitsui Chemicals, Inc.)
DBTDL: dibutyltin dilaurate (TOKYO CHEMICAL INDUSTRY CO., LTD.)
BHT: dibutylhydroxytoluene (TOKYO CHEMICAL INDUSTRY CO., LTD.)
UDMA: 2,2,4-trimethylhexamethylenebis(2-carbamoyloxyethyl) dimethacrylate (Negami Chemical Industrial Co., Ltd.)
TEGDMA: triethylene glycol dimethacrylate (SHIN-NAKAMURA CHEMICAL CO., LTD.)
CQ: camphorquinone (Wako Pure Chemical Industries, Ltd.)
DMABA-BE: 2-butoxyethyl 4-(dimethylamino)benzoate (TOKYO CHEMICAL INDUSTRY CO., LTD.)

[Method of Viscosity Measurement]

In Examples and Comparative Examples of the first aspect, the viscosity was measured using a cone-plate viscometer (TVE-22H manufactured by TOKI SANGYO CO., LTD.). The temperature was controlled to a prescribed temperature using a circulation thermostatic water bath.

[Method for Measuring Polymerization Shrinkage Factor]

A photopolymerizable dental composition was obtained as described in Examples of the first aspect later. The photopolymerizable dental composition was packed into an aluminum mold 10 mm in diameter and 2 mm in depth, and the top and bottom of the mold were interposed between glass covers. With a dental visible light irradiator (twin polymerizer manufactured by SHOFU INC.), light was applied thereto for 3 minutes on each side, namely, a total of 6 minutes on both sides. A cured product was thus obtained. The density of the dental composition before curing, and that of the cured product were measured with a dry densimeter (ACCUPYC 1330 manufactured by Shimadzu Corporation). The polymerization shrinkage factor was determined using the following equation (1).

$$\text{Polymerization shrinkage factor (\%)} = ((\text{Density of cured product after polymerization}) - (\text{Density of dental composition before polymerization}))/(\text{Density of cured product after polymerization}) \times 100 \qquad \text{Equation (1)}:$$

[Bending Test]

The bending test in Examples and Comparative Examples of the first aspect was performed in the following manner.

(Fabrication of Test Pieces for Bending Test of Photopolymerizable Monomer Compositions for Dental Compositions)

A photopolymerizable dental composition was obtained as described in Examples of the first aspect later. The photopolymerizable dental composition was placed into a 2×2×25 mm stainless steel mold and was irradiated with light from a visible light irradiator (Solidilite V manufactured by SHOFU INC.) for 3 minutes on each side, namely, for a total of 6 minutes on both sides, thereby giving a cured product. The cured product as a test piece was soaked in distilled water in a closable sample bottle and was held at 37° C. for 24 hours. The test piece thus obtained was subjected to testing.

(Three-Point Bending Test)

The test piece fabricated in the above manner was subjected to a three-point bending test with a tester (AUTOGRAPH EZ-S manufactured by Shimadzu Corporation) under conditions in which the distance between the supports was 20 mm and the crosshead speed was 1 mm/min.

Synthesis of Monomers

Production Example 1a

A thoroughly dried container equipped with a stirring blade and a thermometer was loaded with 557.3 parts by weight of HEMA, 1.0 part by weight of DBTDL and 0.5 parts by weight of BHT. The mixture was heated to 60° C. and was stirred to uniformity. Subsequently, 441.6 parts by weight of NBDI was added dropwise while controlling the inside temperature to not more than 90° C. After the whole amount of NBDI had been added dropwise, the reaction was performed for 7 hours while keeping the reaction temperature at 85° C. Consequently, 1000.0 parts by weight of the target urethane methacrylate illustrated below was obtained. During this process, the progress of the reaction was tracked by HPLC analysis to determine the end point of the reaction. The number of moles of HEMA was twice the number of moles of NBDI, and the ratio of the hydroxyl groups in HEMA to the isocyanate groups in NBDI was 1:1. The viscosity of the urethane methacrylate at 65° C. was 750 mPa·s.

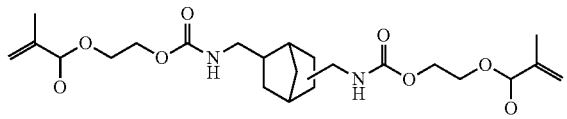

Production Examples 2a to 4a

Urethane (meth)acrylates were obtained by the same synthetic procedures as in Production Example 1a while using the hydroxy (meth)acrylates and the diisocyanates illustrated in Table 1a below. The number of moles of the hydroxy (meth)acrylate was twice the number of moles of the diisocyanate, and the ratio of the hydroxyl groups in the (meth)acrylate to the isocyanate groups in the diisocyanate was 1:1. The viscosities of the urethane methacrylates at 65° C. are described in Table 1a below.

TABLE 1a

| | Hydroxy (meth)acrylate | Diisocyanate | Product | Viscosity (mPa·s (65° C.)) |
|---|---|---|---|---|
| Prod. Ex. 1a | [structure] | [structure] | [structure] | 750 |
| Prod. Ex. 2a | [structure] | [structure] | [structure] | 1800 |
| Prod. Ex. 3a | [structure] | [structure] | [structure] | 2450 |
| Prod. Ex. 4a | [structure] | [structure] | [structure] | 770 |

Example 1a

A container was loaded with 700 parts by weight of the urethane methacrylate obtained in Production Example 1a and 300 parts by weight of TEGDMA (viscosity at 25° C. was 9 mPa·s). The mixture was stirred to uniformity at 50° C. to give a dental polymerizable monomer composition. The viscosity of the dental polymerizable monomer composition at 25° C. was measured to be 680 mPa·s.

Examples 2a to 9a

Dental polymerizable monomer compositions were obtained in the same manner as in Example 1a while using the urethane methacrylates and the (meth)acrylate monomers described in Table 2a below. The viscosities of the dental polymerizable monomer compositions at 25° C. are described in Table 2a.

TABLE 2a

| | Urethane methacrylate monomer | (Meth)acrylate monomer | Viscosity of polymerizable monomer composition (mPa · s (25° C.)) |
|---|---|---|---|
| Ex. 1a | Prod. Ex. 1/700 parts by weight | TEGDMA/300 parts by weight | 680 |
| Ex. 2a | Prod. Ex. 1/750 parts by weight | TEGDMA/250 parts by weight | 1600 |
| Ex. 3a | Prod. Ex. 1/800 parts by weight | TEGDMA/200 parts by weight | 3200 |
| Ex. 4a | Prod. Ex. 1/825 parts by weight | TEGDMA/175 parts by weight | 5000 |
| Ex. 5a | Prod. Ex. 2/700 parts by weight | TEGDMA/300 parts by weight | 1500 |
| Ex. 6a | Prod. Ex. 2/750 parts by weight | TEGDMA/250 parts by weight | 2500 |

TABLE 2a-continued

| | Urethane methacrylate monomer | (Meth)acrylate monomer | Viscosity of polymerizable monomer composition (mPa · s (25° C.)) |
|---|---|---|---|
| Ex. 7a | Prod. Ex. 2/800 parts by weight | TEGDMA/200 parts by weight | 6400 |
| Ex. 8a | Prod. Ex. 3/700 parts by weight | TEGDMA/300 parts by weight | 2300 |
| Ex. 9a | Prod. Ex. 4/700 parts by weight | TEGDMA/300 parts by weight | 710 |

Example 10a

To 1000 parts by weight of the dental polymerizable monomer composition obtained in Example 1a, 5 parts by weight of CQ and 5 parts by weight of DMABA-BE were further added. The mixture was stirred to uniformity at room temperature to give a photopolymerizable dental composition. The bending test of a cured product of the dental composition was performed by the aforementioned testing method. The elastic modulus was 2.5 GPa and the flexural strength was 106 MPa. The polymerization shrinkage factor was 7.6%.

Examples 11a to 13a

Dental compositions were obtained in the same manner as in Example 10a while using the dental polymerizable monomer compositions described in Table 3a below. The bending test of cured products of the dental compositions was performed by the aforementioned testing method. The results are described in Table 3a.

Comparative Example 1a

A dental polymerizable monomer composition was prepared in the same manner as in Example 1a, except that the urethane methacrylate obtained in Production Example 1a was replaced by UDMA, and thereafter the same procedures as in Example 10a were performed to produce a dental composition. The bending test of a cured product of the dental composition was performed by the aforementioned testing method. The results are described in Table 3a.

TABLE 3a

| | Dental polymerizable monomer composition | Polymerization initiator | Flexural elastic modulus (GPa) | Flexural breaking strength (MPa) | Polymerization shrinkage factor (%) |
|---|---|---|---|---|---|
| Ex. 10a | Ex. 1a/1000 parts by weight (Prod. Ex. 1a/700 parts by weight, TEGDMA/300 parts by weight) | CQ/5 parts by weight and DMAB2-BE/5 parts by weight | 2.5 | 106 | 7.6 |
| Ex. 11a | Ex. 5a/1000 parts by weight (Prod. Ex. 2a/700 parts by weight, TEGDMA/300 parts by weight) | CQ/5 parts by weight and DMAB2-BE/5 parts by weight | 2.6 | 108 | 7.4 |
| Ex. 12a | Ex. 8/1000 parts by weight (Prod. Ex. 3a/700 parts by weight, TEGDMA/300 parts by weight) | CQ/5 parts by weight and DMAB2-BE/5 parts by weight | 2.2 | 95 | 7.0 |
| Ex. 13a | Ex. 9/1000 parts by weight (Prod. Ex. 4a/700 parts by weight, TEGDMA/300 parts by weight) | CQ/5 parts by weight and DMAB2-BE/5 parts by weight | 2.2 | 95 | 7.8 |
| Comp. Ex. 1a | UDMA/700 parts by weight TEGDMA/300 parts by weight | CQ/5 parts by weight and DMAB2-BE/5 parts by weight | 2.0 | 87 | 9.5 |

As shown in Table 3a, the cured products of the dental compositions (a) according to an embodiment of the first aspect of the present invention attained higher elastic modulus and higher flexural strength and also had a lower polymerization shrinkage factor than the cured product of the dental composition which contained UDMA generally used in conventional dental compositions. These properties are advantageous in the use as dental compositions.

Hereinbelow, Examples of the second aspect of the present invention will be described.

The following are the abbreviations of compounds used in Examples of the second aspect.
HEA: 2-hydroxyethyl acrylate (TOKYO CHEMICAL INDUSTRY CO., LTD.)
NBDI: norbornane diisocyanate (Mitsui Chemicals, Inc.)
UDMA: 2,2,4-trimethylhexamethylenebis(2-carbamoyloxyethyl) dimethacrylate (Negami Chemical Industrial Co., Ltd.)
DBTDL: dibutyltin dilaurate (TOKYO CHEMICAL INDUSTRY CO., LTD.)
BHT: dibutylhydroxytoluene (TOKYO CHEMICAL INDUSTRY CO., LTD.)
UDMA: di-2-methacryloyloxyethyl-2,2,4-trimethylhexamethylene dicarbamate (Negami Chemical Industrial Co., Ltd.)
Bis-GMA: 2,2-bis[4-(3-methacryloyloxy-2-hydroxypropoxy)phenyl]propane (SHIN-NAKAMURA CHEMICAL CO., LTD.)

TEGDMA: triethylene glycol dimethacrylate (SHIN-NAKAMURA CHEMICAL CO., LTD.)
HEMA: 2-hydroxyethyl methacrylate (TOKYO CHEMICAL INDUSTRY CO., LTD.)
CDMA: glycerol dimethacrylate (TOKYO CHEMICAL INDUSTRY CO., LTD.)
4-MET: 4-(meth)acryloyloxyethyltrimellitic acid (Sun Medical Co., Ltd.)
RT-600T: crosslinked polyurethane powder (6 μm, refractive index: 1.49, ultra-soft grade, double bond equivalent weight 2900, at least 90% gel fraction, Negami Chemical Industrial Co., Ltd.)
RW-600T: crosslinked polyurethane powder (6 μm, refractive index: 1.53, soft grade, double bond equivalent weight 2900, 10% micro compressive strength 2.01 MPa, at least 90% gel fraction, Negami Chemical Industrial Co., Ltd.)
CQ: camphorquinone (Wako Pure Chemical Industries, Ltd.)
DTMPO: diphenyl(2,4,6-trimethylbenzoyl)phosphine oxide (Sigma Aldrich Japan)
DMABAE: ethyl 4-(dimethylamino)benzoate (TOKYO CHEMICAL INDUSTRY CO., LTD.)
DMABA-BE: 2-butoxyethyl 4-(dimethylamino)benzoate (TOKYO CHEMICAL INDUSTRY CO., LTD.)
MEHQ: 4-methoxyphenol (Wako Pure Chemical Industries, Ltd.)
MDP: 10-methacryloyloxydecyl dihydrogen phosphate (Sun Medical Co., Ltd.)
BPO: benzoyl peroxide (TOKYO CHEMICAL INDUSTRY CO., LTD.)
NPG-Na: sodium salt of N-phenylglycine (TOKYO CHEMICAL INDUSTRY CO., LTD.)
p-TS.Na: sodium p-toluenesulfinate (TOKYO CHEMICAL INDUSTRY CO., LTD.)
p-CBS.Na: sodium p-chlorobenzenesulfinate (TOKYO CHEMICAL INDUSTRY CO., LTD.)

Synthesis of Monomers

Production Example 1b

A thoroughly dried container equipped with a stirring blade and a thermometer was loaded with 530.3 parts of HEA, 1.0 part of DBTDL and 0.5 parts of BHT. The mixture was heated to 60° C. and was stirred to uniformity. Subsequently, 468.6 parts of NBDI was added dropwise while controlling the inside temperature to not more than 90° C. After the whole amount of NBDI had been added dropwise, the reaction was performed for 7 hours while keeping the reaction temperature at 85° C. Consequently, 1000.0 parts of the target urethane acrylate was obtained. During this process, the progress of the reaction was tracked by HPLC analysis to determine the end point of the reaction. The number of moles of HEA was twice the number of moles of NBDI, and the ratio of the hydroxyl groups in HEA to the isocyanate groups in NBDI was 1:1.

Production Examples 2b to 8b

Urethane (meth)acrylates were obtained by the same synthetic procedures as in Production Example 1b while using the hydroxy(meth)acrylates and the diisocyanates illustrated in Table 1b below. The number of moles of the hydroxy(meth)acrylate was twice the number of moles of the diisocyanate, and the ratio of the hydroxyl groups in the (meth)acrylate to the isocyanate groups in the diisocyanate was 1:1.

TABLE 1b

| | Hydroxy (meth)acrylate | Diisocyanate | Product |
|---|---|---|---|
| Prod. Ex. 1b | | | |
| Prod. Ex. 2b | | | |
| Prod. Ex. 3b | | | |
| Prod. Ex. 4b | | | |
| Prod. Ex. 5b | | | |

TABLE 1b-continued

| | Hydroxy (meth)acrylate | Diisocyanate | Product |
|---|---|---|---|
| Prod. Ex. 6b | (structure) | (structure) | (structure) |
| Prod. Ex. 7b | (structure) | (structure) | (structure) |
| Prod. Ex. 8b | (structure) | (structure) | (structure) |

Test Example Assuming Mobile Tooth Fixing Adhesives (Preparation of Compositions)

Table 2b describes the types and amounts of monomers and organic fillers used in Examples 1b to 8b and Comparative Examples 1b to 3b. Table 3b describes the types and amounts of polymerization initiators and stabilizers used in Examples 1b to 8b and Comparative Examples 1b to 3b.

(Three-Point Bending Test)

The compositions obtained in Examples and Comparative Examples were each packed into a 2×2×25 mm mold and was brought into press contact with a polypropylene film and a glass plate. Nine points on each of the front and back sides were irradiated with light (PENCURE 2000, J. Morita MEG. Corp.) for seconds, and the surface was polished with #320 waterproof abrasive paper. Thereafter, a cured product TABLE 2b

| | Monomer | Content | UDMA | Bis-GMA | TEGDMA | HEMA | GDMA | 4-MET | Organic filler | |
|---|---|---|---|---|---|---|---|---|---|---|
| | Type | (%) | (%) | (%) | (%) | (%) | (%) | (%) | Type | (%) |
| Ex. | | | | | | | | | | |
| 1b | Prod. Ex. 1b | 90.2 | | | 5 | | | 4 | — | 0 |
| 2b | Prod. Ex. 1b | 75.2 | | | 5 | | | 4 | RT-600T | 15 |
| 3b | Prod. Ex. 1b | 75.2 | | | | 5 | | 4 | RT-600T | 15 |
| 4b | Prod. Ex. 1b | 75.2 | | | | | 5 | 4 | RT-600T | 15 |
| 5b | Prod. Ex. 2b | 78.2 | | | 2 | | | 4 | RT-600T | 15 |
| 6b | Prod. Ex. 3b | 70.2 | | | 10 | | | 4 | RW-600T | 15 |
| 7b | Prod. Ex. 4b | 80.2 | | | 0 | | | 4 | RT-600T | 15 |
| 8b | Prod. Ex. 5b | 75.2 | | | 5 | | | 4 | RT-600T | 15 |
| Comp. Ex. | | | | | | | | | | |
| 1b | | | 5.2 | 49 | 21 | | | 4 | RT-600T | 20 |
| 2b | | | 10.2 | 60 | 10 | | | 4 | RT-600T | 15 |
| 3b | | | 5.2 | 65 | 10 | | | 4 | RT-600T | 15 |

TABLE 3b

| CQ (%) | DTMPO (%) | DMABAE (%) | DMABABE (%) | MEHQ (%) | BHT (%) |
|---|---|---|---|---|---|
| 0.2 | 0.1 | 0.1 | 0.1 | 0.2 | 0.1 |

(Methods for Measuring Properties)

In the test example assuming mobile tooth fixing adhesives, properties were measured by the following methods.

for three-point bending test was obtained, and was soaked in water at 37° C. overnight. After the overnight soaking, the cured product was subjected to a three-point bending test with a precision universal tester (AUTOGRAPH AG-IS manufactured by Shimadzu Corporation) at a crosshead speed of 1.0 mm/min (N=3).

The results of the three-point bending test of Examples 1b to 8b and Comparative Examples 1b to 3b are described in Table 4b.

(Tensile Adhesion Test)

A bovine front lower tooth was polished with #180 emery paper while pouring water thereto to expose a flat enamel face for bonding, and was washed with water and dried. To the tooth face, an etching material (High-Viscosity Red/ manufactured by Sun Medical Co., Ltd.) was applied. After 30 seconds, the tooth was washed with water and dried. The face was then masked with a self-adhesive tape so as to define a circular bonding area 4.8 mm in diameter. Subsequently, a paste including any of the compositions obtained in Examples and Comparative Examples was applied to the bonding area of the tooth, and was cured by being irradiated with LED light from PENCURE 2000 for 10 seconds. Thereafter, an acrylic rod was brought into press contact with the cured product using Super-Bond (manufactured by Sun Medical Co., Ltd.), thus being allowed to stand. The cured sample was soaked in water at 37° C. overnight, and the tensile bond strength was evaluated using AUTO-GRAPH AG-IS (Shimadzu Corporation) at a crosshead speed of 2 mm/min (N=10).

The tensile bond strengths of Examples 1b to 8b and Comparative Examples 1b to 3b are described in Table 4b.

TABLE 4b

Table 4b

| | Flexural strength (MPa) | Elastic modulus (GPa) | Breaking energy (mJ) | Bond strength (MPa) |
|---|---|---|---|---|
| Ex. | | | | |
| 1b | 104.9 ± 10.2 | 2.26 ± 0.28 | 105.2 ± 8.7 | 12.5 ± 3.9 |
| 2b | 112.1 ± 6.2 | 2.51 ± 0.12 | >128.0 ± 10.5 | 17.4 ± 6.4 |
| 3b | 101.5 ± 1.5 | 2.11 ± 0.07 | 83.4 ± 6.6 | 16.0 ± 5.7 |
| 4b | 132.3 ± 4.9 | 3.00 ± 0.05 | 120.4 ± 18.3 | 13.4 ± 2.5 |
| 5b | 72.8 ± 3.1 | 1.54 ± 0.05 | 85.2 ± 2.6 | 9.5 ± 2.8 |
| 6b | 94.8 ± 6.6 | 2.01 ± 0.27 | 68.5 ± 15.1 | 7.8 ± 3.3 |
| 7b | 75 ± 2.3 | 1.57 ± 0.05 | 101.5 ± 20.3 | 8.4 ± 2.2 |
| 8b | 101.5 ± 3.7 | 2.23 ± 0.08 | 78.1 ± 3.7 | 12.6 ± 4.5 |
| Comp. Ex. | | | | |
| 1b | 83.9 ± 0.6 | 1.29 ± 0.03 | 43.8 ± 59 | |
| 2b | 101.3 ± 3.8 | 2.32 ± 0.09 | 42.9 ± 5.9 | 8.2 ± 2.4 |
| 3b | 86.1 ± 0.6 | 2.08 ± 0.10 | 28.2 ± 1.6 | 7.6 ± 3.5 |

Table 4b shows that the dental adhesive compositions of Examples 1b to 8b have higher breaking energy than the dental adhesive compositions of Comparative Examples 1b to 3b while exhibiting flexural strength and adhesion which are comparable to or higher than those of the comparative compositions. The adhesive compositions having such properties are materials resistant to breakage while exhibiting at least certain levels of adhesion and strength and are useful as mobile tooth fixing adhesives. Thus, the dental adhesive compositions (b) of the second aspect of the present invention represented by Examples 1b to 8b may be suitably used as mobile tooth fixing adhesives and are also useful as adhesive materials.

Test Example Assuming Adhesive Cements (Preparation of First Compositions and Second Compositions for Compositions)

The first compositions and the second compositions, described in Table 5b, Table 7b and Table 8b, for forming compositions of Examples and Comparative Examples were uniform pastes obtained by sufficiently kneading the components in a mortar. They were added into syringes having a volume of not more than 10 ml and were stored in a refrigerator. Before carrying out the procedures in Examples and Comparative Examples, the syringes were allowed to stand at room temperature (about 23° C.) for at least 15 minutes.

(Methods for Measuring Properties)

In the test example assuming adhesive cements, measurements were carried out by the following methods.

(Curing Time Measurement Test)

The curing time was evaluated by a DSC method. In the evaluation of the curing time by a DSC method, the first compositions and the second compositions of Examples and Comparative Examples were each kneaded together to give a composition. The compositions were each placed into an aluminum cell (pan), and the polymerization heat generated by radical polymerization was measured by differential thermal analysis. The time from the start of the mixing to when the maximum temperature was reached was evaluated as the curing time. The measurement was performed using a differential scanning calorimeter (DSC-60 manufactured by Shimadzu Corporation) at a measurement temperature of 37±2° C. The curing time is preferably not more than 10 minutes, and more preferably not more than 5 minutes.

(Storage Stability Test)

The storage stability was evaluated by the following method. The first composition as a component for a composition was packed into a light-tight resin syringe (manufactured by MIXPACS) and was stored at 76° C. for 24 hours to undergo a thermal load. After the prescribed storage period, the first composition and the second composition were kneaded together to give a composition (paste), and its curing time was evaluated by a DSC method and was compared to the curing time before the storage, namely, without the storage. Equal amounts of the first composition and the second composition collected on dental kneading paper were mixed with each other at room temperature for 20 seconds using a dental kneading rod, and approximately 0.1 g of the resultant kneadate was packed into an aluminum pan. After 40 seconds from the start of the kneading, the kneadate was placed into a differential thermal analyzer kept at an intraoral temperature (37±2° C.). The time in which the polymerization heat by radical polymerization reached the peak top was determined as the curing time. The thermal load was applied only to the first compositions which included reductants (D) and which would have a significant variation depending on the types of polymerizable monomers added. The difference in curing time with and without the storage is preferably not more than 3 minutes, more preferably not more than 2 minutes, and still more preferably not more than 1 minute.

(Test of Bonding to Coronal Restoration Materials without Surface Treatment)

The compositions obtained in Examples and Comparative Examples were tested to evaluate the bond strength with respect to coronal restorations by the following methods.

(Test of Bonding to Dental Noble Metals (Gold Alloy))

A face of gold alloy (PRIMECAST: manufactured by ISHIFUKU Metal Industry Co., Ltd., 10×10×3 mm) was rendered flat by polishing with up to waterproof emery paper #600. The polished face was sandblasted with alumina for about 10 seconds under 5 kg/cm² conditions (apparatus: Sahara (manufactured by JELENKO); abrasive agent: 50 μm aluminum oxide), and the treated gold alloy was ultrasonically washed in water and was dried by air blowing. To the treated face, a double-sided tape was attached which had a circular hole 4.8 mm in diameter for defining the bonding area. Any of the compositions obtained in Examples and Comparative Examples was applied inside the circular hole, and a SUS rod was held vertical to the material, was brought into press contact therewith and was allowed to stand at room temperature for 30 minutes. Table 6b describes the results of bond strength calculated in such a manner that the test piece which had been allowed to stand as described above was stored in a thermostatic chamber at 37° C. for 16 hours and was subjected to a tensile test at a crosshead speed of 2 mm/min. Table 8b describes the results of bond strength calculated in such a manner that the test piece which had been allowed to stand as described above was stimulated by temperature variations at 5° C.-55° C. 5000 times and was subjected to a tensile test at a crosshead speed of 2 mm/min.

(Test of Bonding to Zirconia)

A face of zirconia (Zirconia: manufactured by SHINAGAWA FINE CERAMICS CO., LTD., 10×10×3 mm) was rendered flat by polishing with up to waterproof emery paper #600. The polished face was sandblasted with alumina for about 10 seconds under kg/cm² conditions, and the treated zirconia was ultrasonically washed in water and was dried by air blowing. To the treated face, a double-sided tape was attached which had a circular hole 4.8 mm in diameter for defining the bonding area. Any of the compositions obtained in Examples and Comparative Examples was applied inside the circular hole, and a SUS rod was held vertical to the material, was brought into press contact therewith and was allowed to stand at room temperature for 30 minutes. Table 6b describes the results of bond strength calculated in such a manner that the test piece which had been allowed to stand as described above was stored in a thermostatic chamber at 37° C. for 16 hours and was subjected to a tensile test at a crosshead speed of 2 mm/min. Table 8b describes the results of bond strength calculated in such a manner that the test piece which had been allowed to stand as described above was stimulated by temperature variations at 5° C.-55° C. 5000 times and was subjected to a tensile test at a crosshead speed of 2 mm/min.

in Examples was applied inside the circular hole, and a SUS rod was held vertical to the material, was brought into press contact therewith and was allowed to stand at room temperature for 30 minutes. Table 6b describes the results of bond strength calculated in such a manner that the test piece which had been allowed to stand as described above was stored in a thermostatic chamber at 37° C. for 16 hours and was subjected to a tensile test at a crosshead speed of 2 mm/min. Table 8b describes the results of bond strength calculated in such a manner that the test piece which had been allowed to stand as described above was stimulated by temperature variations at 5° C.-55° C. 5000 times and was subjected to a tensile test at a crosshead speed of 2 mm/min.

(Test of Bonding to Glass Ceramics)

A face of glass ceramic (Hera Ceram: manufactured by Kulzer Japan Co., Ltd., 10×10×3 mm) was rendered flat by polishing with waterproof emery paper #600. The treated glass ceramic was ultrasonically washed in water and was dried by air blowing. To the treated face, a double-sided tape was attached which had a circular hole 4.8 mm in diameter for defining the bonding area. Any of the compositions obtained in Examples and Comparative Examples was applied inside the circular hole, and a SUS rod was held vertical to the material, was brought into press contact therewith and was allowed to stand at room temperature for 30 minutes. Table 6b describes the results of bond strength calculated in such a manner that the test piece which had been allowed to stand as described above was stored in a thermostatic chamber at 37° C. for 16 hours and was subjected to a tensile test at a crosshead speed of 2 mm/min. Table 8b describes the results of bond strength calculated in such a manner that the test piece which had been allowed to stand as described above was stimulated by temperature variations at 5° C.-55° C. 5000 times and was subjected to a tensile test at a crosshead speed of 2 mm/min.

TABLE 5b

| Ex. 9b | Monomer of Prod. Ex. 5b | MDP | UDMA | TEGDMA | BPO | CQ | NPG·Na | DMPT | DMABAE | p-TS·Na |
|---|---|---|---|---|---|---|---|---|---|---|
| First comp. | 70.0 | | | 25.0 | | | 0.5 | 0.3 | 1.7 | 2.5 |
| Second comp. | | 20.0 | 65.0 | 13.0 | 1.95 | 0.05 | | | | |
| Ex. 10b | Monomer of Prod. Ex. 5b | 4-MET | UDMA | TEGDMA | BPO | CQ | NPG·Na | DMPT | DMABAE | p-TS·Na |
| First comp. | 70.0 | | | 25.0 | | | 0.5 | 0.3 | 1.7 | 2.5 |
| Second comp. | | 20.0 | 65.0 | 13.0 | 1.95 | 0.05 | | | | |

(Test of Bonding to Feldspathic Ceramics)

A face of dental porcelain (VITA VMK MASTER: manufactured by VITA, 15×15×10 mm) was rendered flat by polishing with up to waterproof emery paper #600. The polished face was sandblasted with alumina for about 10 seconds under 2 kg/cm² conditions, and the treated dental porcelain was ultrasonically washed in water and was dried by air blowing. To the treated face, a double-sided tape was attached which had a circular hole 4.8 mm in diameter for defining the bonding area. Any of the compositions obtained TABLE 6b

| | Adherend | Gold alloy | Zirconia | Porcelain | Glass ceramic |
|---|---|---|---|---|---|
| Ex. 9b | Tensile adhesion test (MPa) | 9.6 ± 2.3 | 24.5 ± 11.1 | 11.5 ± 2.1 | 8.8 ± 3.4 |
| Ex. 10b | | 14.7 ± 1.9 | 17.4 ± 1.6 | 11.7 ± 2.7 | 9.3 ± 3.2 |

TABLE 7b

| | | Ex. 11b | | Ex. 12b | | Ex. 13b | | Ex. 14b | | Comp. Ex. 4b | |
|---|---|---|---|---|---|---|---|---|---|---|---|
| | | First comp. | Second comp. | First comp. | Second comp. | First comp. | Second comp. | First comp. | Second comp. | First comp. | Second comp. |
| (A) Polymerizable monomers of chemical formula (1) | Monomer of Prod. Ex. 5b | 25.59 | | | | | | | | | |
| | Monomer of Prod. Ex. 6b | | | 25.59 | | | | | | | |
| | Monomer of Prod. Ex. 7b | | | | | 25.59 | | | | | |
| | Monomer of Prod. Ex. 8b | | | | | | | 25.59 | | | |
| (Cb) Polymerizable monomers | bis-GMA | | | | | | | | | 25.59 | |
| | UDMA | | 24.51 | | 24.51 | | 24.51 | | 24.51 | | 24.51 |
| | TEGDMA | 12.00 | 4.90 | 12.00 | 4.90 | 12.00 | 4.90 | 12.00 | 4.90 | 12.00 | 4.90 |
| (Bb) Acidic group-containing polymerizable monomer | MDP | | 7.88 | | 7.88 | | 7.88 | | 7.88 | | 7.88 |
| (Db) Polymerization initiators | BPO | | 1.05 | | 1.05 | | 1.05 | | 1.05 | | 1.05 |
| | CQ | | 0.02 | | 0.02 | | 0.02 | | 0.02 | | 0.02 |
| Reductants | NPG•Na | 0.10 | | 0.10 | | 0.10 | | 0.10 | | 0.10 | |
| | DMPT | 0.06 | | 0.06 | | 0.04 | | 0.04 | | 0.06 | |
| | DMABAE | 0.24 | | 0.24 | | 0.24 | | 0.24 | | 0.24 | |
| | p-TS•Na | 1.00 | | 1.00 | | | | | | 1.00 | |
| | p-CBS•Na | | | | | 1.00 | | 1.00 | | | |
| (Fb) Fillers | F1 | 57.60 | 57.00 | 57.60 | 57.00 | 57.60 | 57.00 | 57.60 | 57.00 | 57.60 | 57.00 |
| | R812 | 3.30 | 4.50 | 3.30 | 4.50 | 3.30 | 4.50 | 3.30 | 4.50 | 3.30 | 4.50 |
| (Eb) Polymerization inhibitors | BHT | 0.08 | 0.09 | 0.08 | 0.09 | 0.08 | 0.09 | 0.08 | 0.09 | 0.08 | 0.09 |
| | MEHQ | 0.04 | 0.04 | 0.04 | 0.04 | 0.04 | 0.04 | 0.04 | 0.04 | 0.04 | 0.04 |
| Initial curing time (a, min) | | 3.8 | | 3.5 | | 6.9 | | 9.8 | | 1.7 | |
| Curing time after thermal loading (b, min) | | 5.1 | | 4.0 | | 8.0 | | 9.7 | | >30 | |
| Change in curing time ((b) − (a), min) | | 1.3 | | 0.5 | | 1.1 | | 0.1 | | >30 | |

TABLE 8b

| | | Ex. 11b | | Ex. 12b | | Ex. 13b | | Ex. 14b | |
|---|---|---|---|---|---|---|---|---|---|
| | | First comp. | Second comp. | First comp. | Second comp. | First comp. | Second comp. | First comp. | Second comp. |
| (A) Polymerizable monomers of chemical formula (1) | Monomer of Prod. Ex. 5b | 25.59 | | | | | | | |
| | Monomer of Prod. Ex. 6b | | | 25.59 | | | | | |
| | Monomer of Prod. Ex. 7b | | | | | 25.59 | | | |
| | Monomer of Prod. Ex. 8b | | | | | | | 25.59 | |
| (Cb) Polymerizable monomers | bis-GMA | | | | | | | | |
| | D-2.6E | | | | | | | | |
| | UDMA | | 24.51 | | 24.51 | | 24.51 | | 24.51 |
| | TEGDMA | 12.00 | 4.90 | 12.00 | 4.90 | 12.00 | 4.90 | 12.00 | 4.90 |
| (Bb) Acidic group-containing polymerizable monomer | MDP | | 7.88 | | 7.88 | | 7.88 | | 7.88 |
| (Db) Polymerization initiators | BPO | | 1.05 | | 1.05 | | 1.05 | | 1.05 |
| | CQ | | 0.02 | | 0.02 | | 0.02 | | 0.02 |
| Reductants | NPG•Na | 0.10 | | 0.10 | | 0.10 | | 0.10 | |
| | DMPT | 0.06 | | 0.06 | | 0.04 | | 0.04 | |
| | DMABAE | 0.24 | | 0.24 | | 0.24 | | 0.24 | |
| | p-TS•Na | 1.00 | | 1.00 | | | | | |
| | p-CBS•Na | | | | | 1.00 | | 1.00 | |
| (Fb) Fillers | F1 | 57.60 | 57.00 | 57.60 | 57.00 | 57.60 | 57.00 | 57.60 | 57.00 |
| | R812 | 3.30 | 4.50 | 3.30 | 4.50 | 3.30 | 4.50 | 3.30 | 4.50 |
| (Eb) Polymerization inhibitors | BHT | 0.08 | 0.09 | 0.08 | 0.09 | 0.08 | 0.09 | 0.08 | 0.09 |
| | MEHQ | 0.04 | 0.04 | 0.04 | 0.04 | 0.04 | 0.04 | 0.04 | 0.04 |
| Initial curing time (a, min) | | 3.8 | | 3.5 | | 6.9 | | 9.8 | |
| Curing time after thermal loading (b, min) | | 5.1 | | 4.0 | | 8.0 | | 9.7 | |
| Change in curing time ((b) − (a), min) | | 1.3 | | 0.5 | | 1.1 | | 0.1 | |
| Tensile bond strength (MPa) to coronal restorations | Gold alloy | 12.7 ± 3.5 | | 8.1 ± 2.1 | | 9.6 ± 4.2 | | 5.1 ± 1.3 | |
| | Porcelain | 7.4 ± 1.4 | | 9.7 ± 1.4 | | 12.9 ± 5.0 | | 11.7 ± 4.0 | |
| | Zirconia | 43.5 ± 4.8 | | 34.7 ± 15.7 | | 30.1 ± 10.6 | | 28.5 ± 12.7 | |
| | Glass ceramic | 6.6 ± 1.1 | | 4.8 ± 1.6 | | 8.2 ± 3.5 | | 13.5 ± 6.7 | |

TABLE 8b-continued

|  |  | Ex. 15b | | Ex. 16b | | Ex. 17b | |
| --- | --- | --- | --- | --- | --- | --- | --- |
|  |  | First comp. | Second comp. | First comp. | Second comp. | First comp. | Second comp. |
| (A) Polymerizable monomers of chemical formula (1) | Monomer of Prod. Ex. 5b | 22.82 |  | 17.21 |  | 7.38 |  |
|  | Monomer of Prod. Ex. 6b |  |  |  |  |  |  |
|  | Monomer of Prod. Ex. 7b |  |  |  |  |  |  |
|  | Monomer of Prod. Ex. 8b |  |  |  |  |  |  |
| (Cb) Polymerizable monomers | bis-GMA |  |  | 3.69 |  | 8.61 |  |
|  | D-2.6E |  |  | 3.69 |  | 8.61 |  |
|  | UDMA |  | 24.51 |  | 24.51 |  | 24.51 |
|  | TEGDMA | 10.70 | 4.90 | 11.52 | 4.90 | 11.52 | 4.90 |
| (Bb) Acidic group-containing polymerizable monomer | MDP |  | 7.88 |  | 7.88 |  | 7.88 |
| (Db) Polymerization initiators | BPO |  | 1.05 |  | 1.05 |  | 1.05 |
|  | CQ |  | 0.02 |  | 0.02 |  | 0.02 |
| Reductants | NPG•Na | 1.00 |  | 0.10 |  | 0.10 |  |
|  | DMPT | 0.05 |  | 0.08 |  | 0.08 |  |
|  | DMABAE | 2.92 |  | 2.00 |  | 2.00 |  |
|  | p-TS•Na |  |  |  |  |  |  |
|  | p-CBS•Na | 1.50 |  | 1.50 |  | 1.50 |  |
| (Fb) Fillers | F1 | 57.60 | 57.00 | 57.60 | 57.00 | 57.60 | 57.00 |
|  | R812 | 3.30 | 4.50 | 2.50 | 4.50 | 2.50 | 4.50 |
| (Eb) Polymerization inhibitors | BHT | 0.07 | 0.09 | 0.08 | 0.09 | 0.08 | 0.09 |
|  | MEHQ | 0.04 | 0.04 | 0.04 | 0.04 | 0.04 | 0.04 |
| Initial curing time (a, min) |  | 2.1 | | 2.1 | | 1.7 | |
| Curing time after thermal loading (b, min) |  | 1.8 | | 2.8 | | 2.3 | |
| Change in curing time ((b) − (a), min) |  | 0.3 | | 0.7 | | 0.6 | |
| Tensile bond strength (MPa) to coronal restorations | Gold alloy | 12.5 ± 2.5 | | 11.8 ± 4.3 | | 6.6 ± 2.1 | |
|  | Porcelain | 13.9 ± 3.8 | | 8.5 ± 0.9 | | 11.5 ± 4.5 | |
|  | Zirconia | 35.5 ± 13.8 | | 36.3 ± 12.0 | | 17.8 ± 10.1 | |
|  | Glass ceramic | — | | — | | — | |

As shown in Table 6b, the dental adhesive compositions (b) exhibited good bonding performance with respect to the various coronal restoration materials.

As shown in Table 7b, the changes in curing time of the dental adhesive compositions (b) before and after the thermal loading were in the preferred range described hereinabove, and thus the compositions were demonstrated to have excellent storage stability. In Comparative Example 4b, in which bis-GMA that was a general polymerizable monomer was used in place of the polymerizable monomer (Ab) or (A) used in the second aspect, the composition that had been subjected to the thermal loading was not cured even in 30 minutes and longer. This result shows that the incorporation of the polymerizable monomer (Ab) or (A) provides a marked enhancement in the storage stability of the dental adhesive composition.

As shown in Table 8b, the dental adhesive compositions (b) containing the polymerizable monomer (Ab) or (A) had a change in curing time before and after the thermal loading in the preferred range described hereinabove, and were thus demonstrated to have excellent storage stability. At the same time, the dental adhesive compositions (b) containing the polymerizable monomer (Ab) or (A) exhibited good bonding performance with respect to the various coronal restoration materials.

That is, the dental adhesive compositions (b) containing the polymerizable monomer (Ab) or (A) that are represented by Examples 11b to 17b may be suitably used in applications where dental materials are required to have adhesion and storage stability.

While no particular pretreatments were performed on the surface of the coronal restorations used in the adhesion tests in Examples of the second aspect, noble metals such as gold alloy may be treated with, for example, a surface modifier including 6-(4-vinylbenzyl-n-propyl)amino-1,3,5-triazine-2,4-dithione (VTD), and zirconia, feldspathic ceramics and lithium disilicate ceramics may be treated with a silane treating agent or the like immediately before the dental adhesive composition (b) is applied thereto.

When the dental adhesive composition (b) is applied to bond an object to tooth structure, in particular, dentin, the surface of the tooth structure may be treated beforehand in accordance with the tooth conditions with various pretreatment agents such as etching agents (for example, aqueous solution of phosphoric acid, citric acid or EDTA optionally containing a metal salt), primers for tooth structure (for example, those containing polymerizable monomers, polymerization initiators and/or reductants), and bonding materials.

Hereinbelow, Examples of the third aspect of the present invention will be described.

The following are the abbreviations of compounds used in Examples of the third aspect.

[Polymerizable Monomers (A) that are Compounds with Specific Structure Represented by General Formula (1)]

NBUDMA-1: compound represented by the chemical formula (4c)

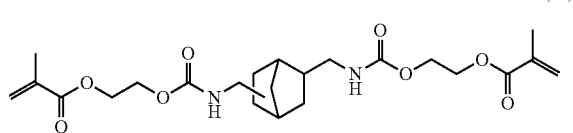

NBUDMA-2: compound represented by the chemical formula (5c)

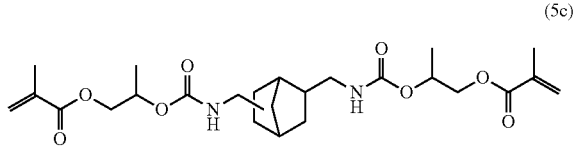

IPUDMA: compound represented by the chemical formula (6c)

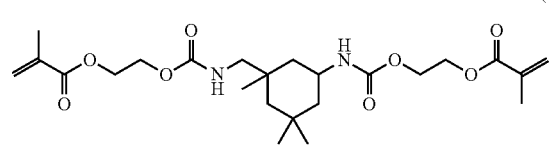

XUDMA: compound represented by the chemical formula (7c)

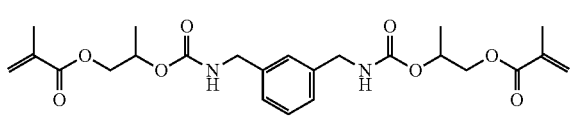 [SMILES: C=C(C)C(=O)OCC(C)OC(=O)NCc1cccc(CNC(=O)OC(C)COC(=O)C(=C)C)c1]

[Other Polymerizable Monomers (Ec)]
bis-GMA:
2,2-bis[(3-methacryloyloxy-2-hydroxypropyloxy)phenyl]propane (adduct of 1 mole of bisphenol A with 2 moles of glycidyl methacrylate)
D-2.6E: 2,2-bis(4-methacryloyloxypolyethoxyphenyl)propane
UDMA:
1,6-bis(methacryloxyethyloxycarbonylamino)-2,2,4-trimethyl hexane
TEGDMA: triethylene glycol dimethacrylate
[Acidic Group-Containing Polymerizable Monomers (Bc)]
MDP: 10-methacryloyloxydecyl dihydrogen phosphate
4-MET: 4-methacryloyloxyethyltrimellitic acid
[Polymerization Initiators (Cc)]
BPO: benzoyl peroxide
CQ: camphorquinone
[Reductants (Dc)]
NPG-Na: sodium salt of N-phenylglycine
DMPT: N,N-dimethyl-p-toluidine
DMABAE: ethyl N,N-dimethylaminobenzoate
p-TS.Na: sodium p-toluenesulfinate
p-CBS.Na: sodium p-chlorobenzenesulfinate

[Fillers (Fc)]
F1: silane-treated barium glass powder, silane-treated fluoroaluminosilicate powder, etc.
R812: fumed silica (trade name "AEROSIL R812" manufactured by NIPPON AEROSIL CO., LTD.)
[Others]
[Polymerization Inhibitors]
BHT: 2,6-di-t-butyl-4-methylphenol
MEHQ: 4-methoxyphenol
(Preparation of First Compositions and Second Compositions for Compositions)

The first compositions and the second compositions, described in Tables 1c and 3c, for forming compositions of Examples and Comparative Examples were uniform pastes obtained by sufficiently kneading the components in a mortar. They were added into syringes having a volume of not more than 10 ml and were stored in a refrigerator. Before carrying out the procedures in Examples and Comparative Examples, the syringes were allowed to stand at room temperature (about 23° C.) for at least 15 minutes.
(Methods for Measuring Properties)

In Examples of the third aspect, measurements were carried out by the following methods.
(Curing Time Measurement Test)

The initial curing time was evaluated by a DSC method. The evaluation of the curing time by a DSC method was made in the same manner as the curing time measurement test performed in the test example assuming adhesive cements in the second aspect described hereinabove. The curing time is preferably not more than 10 minutes, and more preferably not more than 5 minutes.
(Storage Stability Test)

The storage stability was evaluated in the same manner as the storage stability test performed in the test example assuming adhesive cements in the second aspect described hereinabove. The change in curing time before and after the storage is preferably not more than 3 minutes, more preferably not more than 2 minutes, and still more preferably not more than 1 minute.
(Test of Bonding to Coronal Restoration Materials without Surface Treatment)

The compositions obtained in Examples and Comparative Examples were tested to evaluate the bond strength with respect to coronal restorations by the following methods.
(Test of Bonding to Dental Noble Metals (Gold Alloy))

The bond strength to gold alloy (PRIMECAST: manufactured by ISHIFUKU Metal Industry Co., Ltd., 10×10×3 mm) was tested in the same manner as the test of bonding to gold alloy performed in the test example assuming adhesive cements in the second aspect described hereinabove. Table 4c describes the results of bond strength calculated in such a manner that the test piece which had been allowed to stand was stimulated by temperature variations at 5° C.-55° C. 5000 times and was subjected to a tensile test at a crosshead speed of 2 mm/min.
(Test of Bonding to Zirconia)

The bond strength to zirconia (Zirconia: manufactured by SHINAGAWA FINE CHEMIC CO., LTD., 10×10×3 mm) was tested in the same manner as the test of bonding to zirconia performed in the test example assuming adhesive cements in the second aspect described hereinabove.
(Test of Bonding to Feldspathic Ceramics)

The bond strength to dental porcelain (VITA VMK MASTER: manufactured by VITA, 15×15×10 mm) was tested in the same manner as the test of bonding to feldspathic ceramics performed in the test example assuming adhesive cements in the second aspect described hereinabove. Table 4c describes the results of bond strength calculated in such a manner that the test piece which had been allowed to stand was stimulated by temperature variations at 5° C.-55° C. 5000 times and was subjected to a tensile test at a crosshead speed of 2 mm/min.

(Test of Bonding to Glass Ceramics)

The bond strength to glass ceramic (Hera Ceram: manufactured by Kulzer Japan Co., Ltd., 10×10×3 mm) was tested in the same manner as the test of bonding to glass ceramics performed in the test example assuming adhesive cements in the second aspect described hereinabove. Table 4c describes the results of bond strength calculated in such a manner that the test piece which had been allowed to stand was stimulated by temperature variations at 5° C.-55° C. 5000 times and was subjected to a tensile test at a crosshead speed of 2 mm/min.

The formulation of Example 1c in Table 1c satisfied the conditions of the third aspect of the present invention. The composition exhibited a good bonding performance with respect to the various coronal restoration materials (Table 2c).

The formulations of Examples 3c to 9c in Table 3c satisfied the conditions of the third aspect of the present invention. The compositions had a change in curing time before and after the thermal loading in the preferred range described hereinabove. Thus, the dental adhesive curable kits (αc) including the first composition and the second composition for preparing a dental adhesive curable composition (c) were demonstrated to have excellent storage stability.

In Comparative Example 1, the dental adhesive curable kit contained no polymerizable monomers (A) in the first composition, and the first composition included bis-GMA that was a general polymerizable monomer. The composition obtained from this first composition and the second composition after the thermal loading was not cured even in 30 minutes and longer. This result shows that a dental adhesive curable kit having excellent storage stability can be obtained by using the polymerizable monomer (A), in particular, a polymerizable methacrylate monomer (A).

Table 3c describes the results of the storage stability test in Examples 3c to 9c and Comparative Example 1c, and Table 4c describes the results of the tests of bonding to coronal restoration materials in Examples 3c to 9c. From the results of the storage stability test, it is apparent that the dental adhesive curable kits (αc) obtained according to the third aspect of the present invention attain excellent storage stability.

Further, the results of the adhesion tests in Examples 3c to 9c show that the dental adhesive curable compositions (c) obtained in the third aspect of the invention exhibit an excellent bonding performance with respect to coronal restorations such as dental noble metals, dental porcelains and ceramic materials even without special pretreatments.

While no particular pretreatments were performed on the surface of the coronal restorations used in the adhesion tests in Examples of the third aspect, noble metals such as gold alloy may be treated with, for example, a surface modifier including 6-(4-vinylbenzyl-n-propyl)amino-1,3,5-triazine-2,4-dithione (VTD), and zirconia, feldspathic ceramics and lithium disilicate ceramics may be treated with a silane treating agent or the like immediately before the dental adhesive curable composition (c) is applied thereto.

When the dental adhesive curable composition (c) is applied to bond an object to tooth structure, in particular, dentin, the surface of the tooth structure may be treated beforehand in accordance with the tooth conditions with various pretreatment agents such as etching agents (for example, aqueous solution of phosphoric acid, citric acid or EDTA optionally containing a metal salt), primers for tooth structure (for example, those containing polymerizable monomers, polymerization initiators and/or reductants), and bonding materials.

TABLE 1c

| Ex. 1c | NBUDMA-1 | MDP | UDMA | TEGDMA | BPO | CQ | NPG · Na | DMPT | DMABAE | p-TS · Na |
|---|---|---|---|---|---|---|---|---|---|---|
| First comp. | 70.0 | | | 25.0 | | | 0.5 | 0.3 | 1.7 | 2.5 |
| Second comp. | | 20.0 | 65.0 | 13.0 | 1.95 | 0.05 | | | | |

| Ex. 2c | NBUDMA-1 | 4-MET | UDMA | TEGDMA | BPO | CQ | NPG · Na | DMPT | DMABAE | p-TS · Na |
|---|---|---|---|---|---|---|---|---|---|---|
| First comp. | 70.0 | | | 25.0 | | | 0.5 | 0.3 | 1.7 | 2.5 |
| Second comp. | | 20.0 | 65.0 | 13.0 | 1.95 | 0.05 | | | | |

TABLE 2c

| | Adherend | Gold alloy | Zirconia | Porcelain | Glass ceramic |
|---|---|---|---|---|---|
| Ex. 1c | Tensile adhesion test (MPa) | 9.6 ± 2.3 | 24.5 ± 11.1 | 11.5 ± 2.1 | 8.8 ± 3.4 |
| Ex. 2c | | 14.7 ± 1.9 | 17.4 ± 1.6 | 11.7 ± 2.7 | 9.3 ± 3.2 |

TABLE 3c

| | | Ex. 3c | | Ex. 4c | | Ex. 5c | | Ex. 6c | |
|---|---|---|---|---|---|---|---|---|---|
| | | First comp. | Second comp. | First comp. | Second comp. | First comp. | Second comp. | First comp. | Second comp. |
| (A) Polymerizable monomers of chemical formula (1) | NBUDMA-1 | 25.59 | | | | | | | |
| | NBUDMA-2 | | | 25.59 | | | | | |
| | IPUDMA | | | | | 25.59 | | | |

TABLE 3c-continued

| | | First comp. | Second comp. | First comp. | Second comp. | First comp. | Second comp. | First comp. | Second comp. |
|---|---|---|---|---|---|---|---|---|---|
| | XUDMA | | | | | | | | 25.59 |
| | NBUDA | | | | | | | | |
| Polymerizable monomers | bis-GMA | | | | | | | | |
| | UDMA | | 24.51 | | 24.51 | | 24.51 | | 24.51 |
| | TEGDMA | 12.00 | 4.90 | 12.00 | 4.90 | 12.00 | 4.90 | 12.00 | 4.90 |
| (Bc) Acidic group-containing polymerizable monomer | MDP | | 7.88 | | 7.88 | | 7.88 | | 7.88 |
| (Cc) Polymerization initiators | BPO | | 1.05 | | 1.05 | | 1.05 | | 1.05 |
| | CQ | | 0.02 | | 0.02 | | 0.02 | | 0.02 |
| (Dc) Reductants | NPG•Na | 0.10 | | 0.10 | | 0.10 | | 0.10 | |
| | DMPT | 0.06 | | 0.06 | | 0.04 | | 0.04 | |
| | DMABAE | 0.24 | | 0.24 | | 0.24 | | 0.24 | |
| | p-TS•Na | 1.00 | | 1.00 | | | | | |
| | p-CBS•Na | | | | | 1.00 | | 1.00 | |
| (Ec) Fillers | F1 | 57.60 | 57.00 | 57.60 | 57.00 | 57.60 | 57.00 | 57.60 | 57.00 |
| | R812 | 3.30 | 4.50 | 3.30 | 4.50 | 3.30 | 4.50 | 3.30 | 4.50 |
| Polymerization inhibitors | BHT | 0.08 | 0.09 | 0.08 | 0.09 | 0.08 | 0.09 | 0.08 | 0.09 |
| | MEHQ | 0.04 | 0.04 | 0.04 | 0.04 | 0.04 | 0.04 | 0.04 | 0.04 |
| Initial curing time (a, min) | | 3.8 | | 3.5 | | 6.9 | | 9.8 | |
| Curing time after thermal loading (b, min) | | 5.1 | | 4.0 | | 8.0 | | 9.7 | |
| Change in curing time ((b) − (a), min) | | 1.3 | | 0.5 | | 1.1 | | 0.1 | |

| | | Ex. 7c | | Ex. 8c | | Ex. 9c | | Comp. Ex. 1c | |
|---|---|---|---|---|---|---|---|---|---|
| | | First comp. | Second comp. | First comp. | Second comp. | First comp. | Second comp. | First comp. | Second comp. |
| (A) Polymerizable monomers of chemical formula (1) | NBUDMA-1 | 22.82 | | 17.21 | | 7.38 | | | |
| | NBUDMA-2 | | | | | | | | |
| | IPUDMA | | | | | | | | |
| | XUDMA | | | | | | | | |
| | NBUDA | | | 3.69 | | 8.61 | | | |
| Polymerizable monomers | bis-GMA | | | 3.69 | | 8.61 | | 25.59 | |
| | UDMA | | 24.51 | | 24.51 | | 24.51 | | 24.51 |
| | TEGDMA | 10.70 | 4.90 | 11.52 | 4.90 | 11.52 | 4.90 | 12.00 | 4.90 |
| (Bc) Acidic group-containing polymerizable monomer | MDP | | 7.88 | | 7.88 | | 7.88 | | 7.88 |
| (Cc) Polymerization initiators | BPO | | 1.05 | | 1.05 | | 1.05 | | 1.05 |
| | CQ | | 0.02 | | 0.02 | | 0.02 | | 0.02 |
| (Dc) Reductants | NPG•Na | 1.00 | | 0.10 | | 0.10 | | 0.10 | |
| | DMPT | 0.05 | | 0.08 | | 0.08 | | 0.06 | |
| | DMABAE | 2.92 | | 2.00 | | 2.00 | | 0.24 | |
| | p-TS•Na | | | | | | | 1.00 | |
| | p-CBS•Na | 1.50 | | 1.50 | | 1.50 | | | |
| (Ec) Fillers | F1 | 57.60 | 57.00 | 57.60 | 57.00 | 57.60 | 57.00 | 57.60 | 57.00 |
| | R812 | 3.30 | 4.50 | 2.50 | 4.50 | 2.50 | 4.50 | 3.30 | 4.50 |
| Polymerization inhibitors | BHT | 0.07 | 0.09 | 0.08 | 0.09 | 0.08 | 0.09 | 0.08 | 0.09 |
| | MEHQ | 0.04 | 0.04 | 0.04 | 0.04 | 0.04 | 0.04 | 0.04 | 0.04 |
| Initial curing time (a, min) | | 2.1 | | 2.1 | | 1.7 | | 1.7 | |
| Curing time after thermal loading (b, min) | | 1.8 | | 2.8 | | 2.3 | | >30 | |
| Change in curing time ((b) − (a), min) | | 0.3 | | 0.7 | | 0.6 | | >30 | |

TABLE 4c

| | | Ex. 3c | Ex. 4c | Ex. 5c | Ex. 6c | Ex. 7c | Ex. 8c | Ex. 9c |
|---|---|---|---|---|---|---|---|---|
| Tensile bond strength (MPa) to coronal restorations | Gold alloy | 12.7 ± 3.5 | 8.1 ± 2.1 | 9.6 ± 4.2 | 5.1 ± 1.3 | 12.5 ± 2.5 | 11.8 ± 4.3 | 6.6 ± 2.1 |
| | Porcelain | 7.4 ± 1.4 | 9.7 ± 1.4 | 12.9 ± 5.0 | 11.7 ± 4.0 | 13.9 ± 3.8 | 8.5 ± 0.9 | 11.5 ± 4.5 |
| | Zirconia | 43.5 ± 4.8 | 34.7 ± 15.7 | 30.1 ± 10.6 | 28.5 ± 12.7 | 35.5 ± 13.8 | 36.3 ± 12.0 | 17.8 ± 10.1 |
| | Glass ceramic | 6.6 ± 1.1 | 4.8 ± 1.6 | 8.2 ± 3.5 | 13.5 ± 6.7 | — | — | — |

Hereinbelow, Examples of the fourth aspect of the present invention will be described.

The abbreviations indicate the following compounds.

UDMA: di-2-methacryloyloxyethyl-2,2,4-trimethylhexamethylene dicarbamate (SHIN-NAKAMURA CHEMICAL CO., LTD.)

3G: triethylene glycol dimethacrylate (SHIN-NAKAMURA CHEMICAL CO., LTD.)

DGMA: 2,2-bis[4-(3-methacryloyloxy-2-hydroxypropoxy)phenyl]propane (SHIN-NAKAMURA CHEMICAL CO., LTD.)

HEMA: 2-hydroxyethyl methacrylate (TOKYO CHEMICAL INDUSTRY CO., LTD.)

CDMA: glycerol dimethacrylate (TOKYO CHEMICAL INDUSTRY CO., LTD.)
Bis-GMA: 2,2-bis[4-(3-methacryloyloxy-2-hydroxypropoxy)phenyl]propane (SHIN-NAKAMURA CHEMICAL CO., LTD.)
RT-600T: crosslinked polyurethane powder (6 μm, refractive index: 1.49, ultra-soft grade, double bond equivalent weight 2900, at least 90% gel fraction, Negami Chemical Industrial Co., Ltd.)
RW-600T: crosslinked polyurethane powder (6 Jim, refractive index: 1.53, soft grade, double bond equivalent weight 2900, 10% micro compressive strength 2.01 MPa, at least 90% gel fraction, Negami Chemical Industrial Co., Ltd.)
4-MET: 4-(meth)acryloyloxyethyltrimellitic acid (Sun Medical Co., Ltd.)
CQ: camphorquinone (Wako Pure Chemical Industries, Ltd.)
DTMPO: diphenyl(2,4,6-trimethylbenzoyl)phosphine oxide (Sigma Aldrich Japan)
DMABA-BE: 2-butoxyethyl 4-(dimethylamino)benzoate (TOKYO CHEMICAL INDUSTRY CO., LTD.)
DMABAE: ethyl 4-(dimethylamino)benzoate (TOKYO CHEMICAL INDUSTRY CO., LTD.)
MEHQ: 4-methoxyphenol (Wako Pure Chemical Industries, Ltd.)
BHT: dibutylhydroxytoluene (TOKYO CHEMICAL INDUSTRY CO., LTD.)
DBTDL: dibutyltin dilaurate (TOKYO CHEMICAL INDUSTRY CO., LTD.)

Production Example 1d

A thoroughly dried container equipped with a stirring blade and a thermometer was loaded with 530.3 parts of 2-hydroxyethyl acrylate (TOKYO CHEMICAL INDUSTRY CO., LTD.), 1.0 part of DBTDL and 0.5 parts of BHT. The mixture was heated to 60° C. and was stirred to uniformity. Subsequently, 468.6 parts of Compound 1d was added dropwise while controlling the inside temperature to not more than 90° C. After the whole amount of Compound 1d had been added dropwise, the reaction was performed for 7 hours while keeping the reaction temperature at 85° C., thus obtaining 1000.0 parts (Compound 6d). During this process, the progress of the reaction was tracked by HPLC analysis to determine the end point of the reaction. The number of moles of 2-hydroxyethyl acrylate was twice the number of moles of Compound 1d, and the ratio of the hydroxyl groups in 2-hydroxyethyl acrylate to the isocyanate groups in Compound 1d was 1:1.

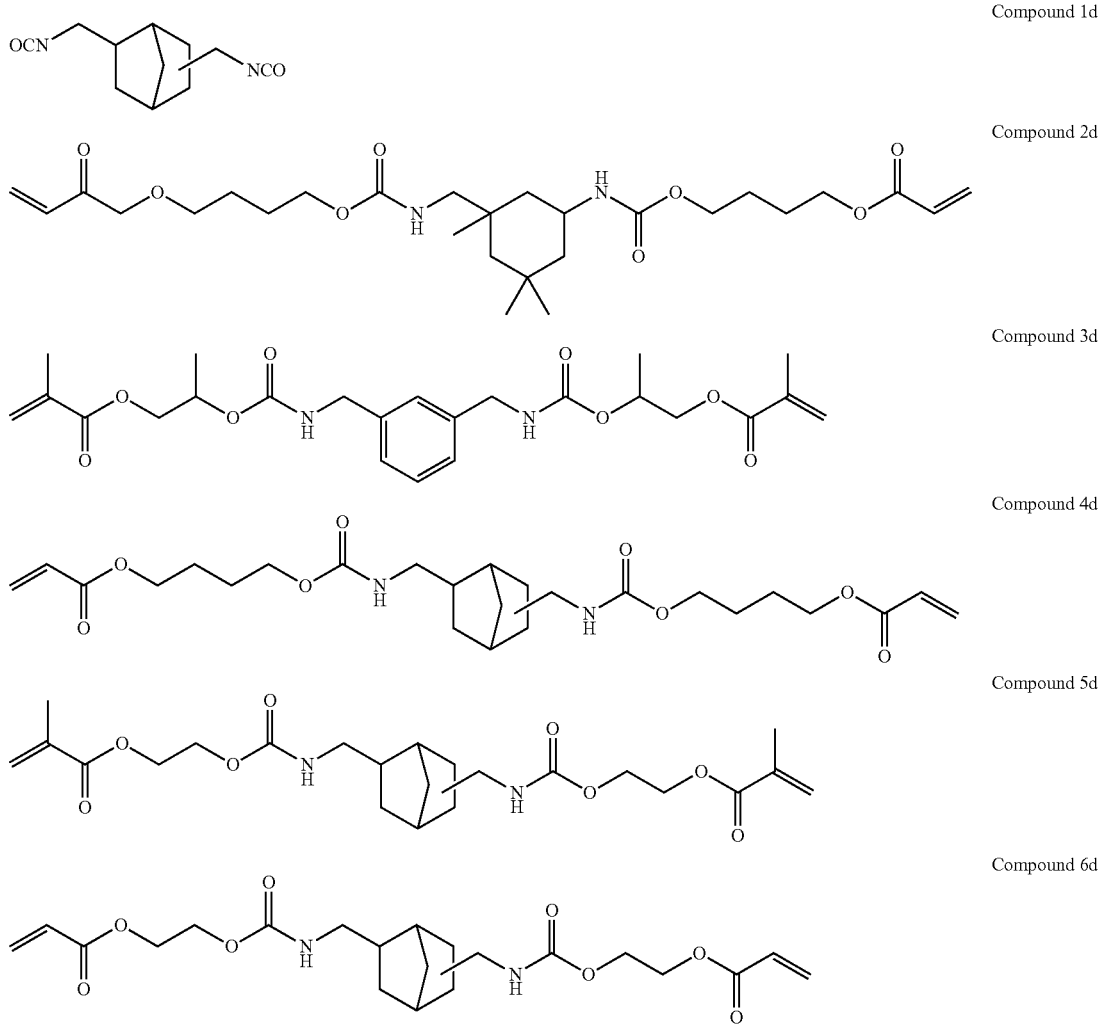

Compound 1d

Compound 2d

Compound 3d

Compound 4d

Compound 5d

Compound 6d

Production Examples 2d to 5d

Urethane (meth)acrylate compounds 2d to 5d were obtained by the same synthetic procedures as in Production Example 1d while using the hydroxy acrylates and the diisocyanates illustrated in Table 1d below.

TABLE 1d

| | Alcohol | Isocyanate |
|---|---|---|
| Compound 2d | CH2=CH-C(=O)-O-(CH2)4-OH | OCN-CH2-(isophorone diisocyanate structure)-NCO |
| Compound 3d | CH2=C(CH3)-C(=O)-O-CH2-CH(OH)-CH3 | OCN-CH2-(m-xylylene)-CH2-NCO |
| Compound 4d | CH2=CH-C(=O)-O-(CH2)4-OH | OCN-CH2-(norbornane)-CH2-NCO |
| Compound 5d | CH2=C(CH3)-C(=O)-O-(CH2)2-OH | OCN-CH2-(norbornane)-CH2-NCO |
| Compound 6d | CH2=CH-C(=O)-O-(CH2)2-OH | OCN-CH2-(norbornane)-CH2-NCO |

Table 2d describes the formulations of the dental adhesive compositions used in Examples 1d to 8d and Comparative Examples 1d to 3d. Table 3d describes the types and amounts of polymerization initiators and stabilizers used in Examples 1d to 8d and Comparative Examples 1d to 3d. In Comparative Examples 4d and 5d, a commercial mobile tooth fixing material (G-FIX (manufactured by GC Corporation)) and Super-Bond (manufactured by Sun Medical Co., Ltd.) were used, respectively, in accordance with the instructions of the products.

TABLE 2d

| | Monomer Type | Content (%) | UDMA (%) | DGMA (%) | 3G (%) | HEMA (%) | GDMA (%) | 4-MET (%) | Organic filler Type | (%) |
|---|---|---|---|---|---|---|---|---|---|---|
| Examples | | | | | | | | | | |
| 1d | Compound 2d | 78.2 | | | 2 | | | 4 | RT-600T | 15 |
| 2d | Compound 3d | 70.2 | | | 10 | | | 4 | RW-600T | 15 |
| 3d | Compound 4d | 80.2 | | | 0 | | | 4 | RT-600T | 15 |
| 4d | Compound 5d | 75.2 | | | 5 | | | 4 | RT-600T | 15 |
| 5d | Compound 6d | 90.2 | | | 5 | | | 4 | — | 0 |
| 6d | Compound 6d | 75.2 | | | 5 | | | 4 | RT-600T | 15 |
| 7d | Compound 6d | 75.2 | | | | 5 | | 4 | RT-600T | 15 |
| 8d | Compound 6d | 75.2 | | | | | 5 | 4 | RT-600T | 15 |
| Comparative Examples | | | | | | | | | | |
| 1d | | | 5.2 | 49 | 21 | | | 4 | RT-600T | 20 |
| 2d | | | 10.2 | 60 | 10 | | | 4 | RT-600T | 15 |
| 3d | | | 5.2 | 65 | 10 | | | 4 | RT-600T | 15 |

TABLE 3d

| CQ (%) | DTMPO (%) | DMABAE (%) | DMABABE (%) | MEHQ (%) | BHT (%) |
|---|---|---|---|---|---|
| 0.2 | 0.1 | 0.1 | 0.1 | 0.2 | 0.1 |

(Three-Point Bending Test)

The compositions obtained in Examples and Comparative Examples were each packed into a 2×2×25 mm mold and was brought into press contact with a polypropylene film and a glass plate. Nine points on each of the front and back sides were irradiated with light (PENCURE 2000, J. Morita MEG. Corp.) for seconds, and the surface was polished with #320 waterproof abrasive paper. Thereafter, a cured product for three-point bending test was obtained, and was soaked in water at 37° C. overnight. After the overnight soaking, the cured product was subjected to a three-point bending test with a precision universal tester (AUTOGRAPH AG-IS manufactured by Shimadzu Corporation) at a crosshead speed of 1.0 mm/min (N=3).

In the dental adhesive compositions (d) of the fourth aspect of the present invention, it is desirable that cured products obtained by polymerization reaction in adhesive contact with tooth structure have appropriate strength, flexibility and toughness so that the cured products exhibit excellent durability against external stress. The cured products were evaluated as acceptable when their elastic modulus measured by the aforementioned testing method was 1 to 3 GPa, maximum stress was 65 MPa or above and breaking energy was 65 mJ or above.

The results of the three-point bending test of Examples 1d to 8d and Comparative Examples 1d to 5d are described in Table 4d.

(Tensile Adhesion Test)

A bovine front lower tooth was polished with #180 emery paper while pouring water thereto to expose a flat enamel face for bonding, and was washed with water and dried. To the tooth face, an etching material (High-Viscosity Red/ manufactured by Sun Medical Co., Ltd.) was applied. After 30 seconds, the tooth was washed with water and dried. The face was then masked with a self-adhesive tape so as to define a circular bonding area 4.8 mm in diameter. Subsequently, the composition (paste) obtained in any of Examples and Comparative Examples was applied to the bonding area of the tooth, and was cured by being irradiated with LED light from PENCURE 2000 for 10 seconds. Thereafter, an acrylic rod was brought into press contact with the tooth using Super-Bond (manufactured by Sun Medical Co., Ltd.), thus being allowed to stand. In Comparative Example 4d and Comparative Example 5d, the compositions were used in accordance with the instructions of the products. The cured sample was soaked in water at 37° C. overnight, and the tensile bond strength was evaluated using AUTOGRAPH AG-IS (Shimadzu Corporation) at a crosshead speed of 2 mm/min (N=10).

The tensile bond strengths of Examples 1d to 8d and Comparative Examples 1d to 5d are described in Table 4d.

TABLE 4d

Table 4d

| | Flexural strength (MPa) | Elastic modulus (GPa) | Breaking energy (mJ) | Bond strength (MPa) |
|---|---|---|---|---|
| Examples | | | | |
| 1d | 72.8 ± 3.1 | 1.54 ± 0.05 | 85.2 ± 2.6 | 9.5 ± 2.8 |
| 2d | 94.8 ± 6.6 | 2.01 ± 0.27 | 68.5 ± 15.1 | 7.8 ± 3.3 |
| 3d | 75 ± 2.3 | 1.57 ± 0.05 | 101.5 ± 20.3 | 8.4 ± 2.2 |
| 4d | 101.5 ± 3.7 | 2.23 ± 0.08 | 78.1 ± 3.7 | 12.6 ± 4.5 |
| 5d | 104.9 ± 10.2 | 2.26 ± 0.28 | 105.2 ± 8.7 | 12.5 ± 3.9 |
| 6d | 112.1 ± 6.2 | 2.51 ± 0.12 | >128.0 ± 10.5 | 17.4 ± 6.4 |
| 7d | 101.5 ± 1.5 | 2.11 ± 0.07 | 83.4 ± 6.6 | 16.0 ± 5.7 |
| 8d | 132.3 ± 4.9 | 3 ± 0.05 | 120.4 ± 18.3 | 13.4 ± 2.5 |
| Comparative Examples | | | | |
| 1d | 83.9 ± 0.6 | 1.29 ± 0.03 | 43.8 ± 59 | |
| 2d | 101.3 ± 3.8 | 2.32 ± 0.09 | 42.9 ± 5.9 | 8.2 ± 2.4 |
| 3d | 86.1 ± 0.6 | 2.08 ± 1.10 | 28.2 ± 1.6 | 7.6 ± 3.5 |
| 4d | 91.3 ± 10.2 | 2.82 ± 0.11 | 44 ± 21.8 | 12.3 ± 6.1 |
| 5d | 69.3 ± 3.8 | 1.84 ± 0.11 | >73.3 ± 1.8 | 15.0 ± 2.5 |

[Results]

Table 4d shows that Comparative Examples 1d to 4d failed to satisfy the ranges that had been set, whilst the ranges were met in Examples 1d to 8d and Comparative Example 5d. However, Super-Bond (manufactured by Sun Medical Co., Ltd.) used in Comparative Example 5d is a chemically polymerizable product composed of three components: liquid, powder and catalyst V, and thus the use thereof involves complicated handling and a waiting time for curing. In light of this fact, the dental adhesive compositions (d) according to the fourth aspect of the present invention have been shown to give cured products having appropriate flexibility, strength and toughness and to satisfy both durability and handleability that currently available commercial mobile tooth fixing materials have not succeeded. Further, it has been shown that the urethane (meth) acrylate with a rigid skeleton which is present in the dental adhesive composition (d) has great impacts on the strength, flexibility and toughness of cured products resulting from polymerization reaction.

After polymerization reaction, the dental adhesive compositions (d) according to the fourth aspect of the present invention give cured products which have appropriate flexibility, strength and toughness so as to exhibit excellent durability against external stress. Thus, facilitated treatment of mobile teeth can be expected.

Hereinbelow, Examples of the fifth aspect of the present invention will be described.

The following are the abbreviations of compounds used in Examples of the fifth aspect.

[Polymerizable Monomers (αe)]
[Acidic Group-Free Polymerizable Monomers (αe-1)]
bis-GMA: 2,2-bis[4-(3-(meth)acryloyloxy-2-hydroxypropoxy)phenyl] pro pane
D-2.6E: 2,2-bis(4-methacryloyloxypolyethoxyphenyl)propane (having an average number of moles of ethoxy groups added of 2.6)
TEGDMA: triethylene glycol dimethacrylate
UDMA: 2,2,4-trimethylhexamethylene diisocyanate
IPUDMA: 1,5,5-trimethyl-1-[(2-methacryloyloxyethyl)carbamoylmethyl]-3-(2-methacryloyloxyethyl)carbamoylcyclohexane, urethane dimethacrylate represented by the following formula (7e)

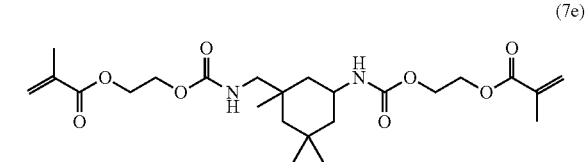 [SMILES: C=C(C)C(=O)OCCOC(=O)NCC1(C)CC(NC(=O)OCCOC(=O)C(=C)C)CC(C)(C)C1]

(7e)

[Acidic Group-Containing Polymerizable Monomers (Ae-2)]
MDP: 10-methacryloyloxydecyl dihydrogen phosphate
4-MET: 4-methacryloyloxyethyltrimellitic acid
[(b) Aromatic Amine Compounds Having Nonaromatic Carbonyl Group]
NPG-Na: sodium salt of N-phenylglycine
NPG.K: potassium salt of N-phenylglycine
[Organic Sulfinic Acid Compound (Ce) Having Electron Withdrawing Group]
p-CBSS: sodium 4-chlorobenzenesulfinate
[Organic Sulfinic Acid Compound Having No Electron Withdrawing Groups]
p-TsNa: sodium p-toluenesulfinate
[Peroxide (de-1)]
BPO: benzoyl peroxide
[Aromatic Tertiary Amines (ee)]
DMABAE: ethyl N,N-dimethylaminobenzoate
DMPT: N,N-dimethyl-p-toluidine
DEPT: N,N-diethanol-p-toluidine
[Filling Materials (fe) Such as Fillers]
F-R812: fumed silica (trade name "AEROSIL R 812" manufactured by NIPPON AEROSIL CO., LTD.)
F-8235: silane-treated barium glass powder (trade name "Schott 8235 Dental Glass" manufactured by SCHOTT AG)
[Photopolymerization Initiator]
CQ: camphorquinone
[Polymerization Inhibitor]
BHT: 2,6-di-t-butyl-4-methylphenol Examples 1e to 3e and Comparative Examples 1e and 2e (Preparation of First Compositions and Second Compositions for Resin Cements)

The raw materials described in Table 1e were kneaded together sufficiently in mortars at room temperature (25° C.) to give a first composition and a second composition as uniform pastes. The compositions were each packed into a light-tight resin syringe (manufactured by MIXPACS). Dental curable kits were thus obtained. The dental curable kits were stored in a refrigerator (6° C.). Before carrying out the tests, the first compositions and the second compositions were brought to room temperature by allowing the syringes to stand at room temperature for at least 15 minutes before the tests.

(Evaluation of Bonding Performance)

Unless otherwise specified, the bonding performance was evaluated in the following manner.

As an example method of the adhesion test, bovine dentin is manually polished with up to #180 waterproof emery paper while pouring water thereto to expose a flat face, and the water is removed with an air gun. A dental tooth surface treating agent having the chemical composition described below is applied to the polished face, allowed to stand for 20 seconds, and dried with an air gun for 3 seconds.

Dental tooth surface treating agent (100 parts by weight in total): 4-MET 12.5 parts by weight, HEMA 36.0 parts by weight, UDMA 8.5 parts by weight, water 27.8 parts by weight, acetone 15.0 parts by weight, iron (II) chloride tetrahydrate 0.2 parts by weight On the treated surface of the tooth, a bonding area 4.8 mm in diameter is defined, and a kneadate of the first composition and the second composition of the dental curable kit of the fifth aspect of the invention is arranged thereon. A SUS cylinder (hereinbelow, written as SUS rod or SUS) is manually held in press contact with the kneadate for 5 seconds. After 1 hour, the test piece is soaked in 37° C. water for 16 hours and is subjected to a tensile adhesion test (crosshead speed of 2 mm/min).

(Evaluation of Thermal Stability Performance)

Unless otherwise specified, the thermal stability performance was evaluated in the following manner.

The thermal stability was tested by a method which compared the curing times before and after a thermal load was applied to the first composition. To apply a thermal load to the first composition, the first composition was packed into a light-tight resin syringe (manufactured by MIXPACS) and was stored at 76° C. for 24 hours. The curing time was measured by a DSC method as follows. Equal amounts of the first composition and the second composition collected on dental kneading paper were mixed with each other at room temperature for 20 seconds using a dental kneading rod, and approximately 0.1 g of the resultant kneadate was packed into an aluminum pan. After 40 seconds from the start of the kneading, the kneadate was placed into a differential thermal analyzer kept at an intraoral temperature (37.0° C.). The time in which the polymerization heat by radical polymerization reached the peak top was determined as the curing time.

Table 1e describes the results of the bonding performance evaluation and the evaluation of the thermal stability of the first composition in Examples 1e to 3e and Comparative Examples 1e and 2e.

TABLE 1e

|  |  |  | Ex. 1e | | Ex. 2e | | Ex. 3e | | Comp. Ex. 1e | | Comp. Ex. 2e | |
| --- | --- | --- | --- | --- | --- | --- | --- | --- | --- | --- | --- | --- |
|  |  |  | First comp. | Second comp. | First comp. | Second comp. | First comp. | Second comp. | First comp. | Second comp. | First comp. | Second comp. |
| Raw materials | (ae-1) | bis-GMA | 26.0 | | 26.0 | | 9.0 | | 26.0 | | | |
|  |  | D-2.6E | | | | | 9.0 | | | | 26.0 | |
|  |  | IPUDMA | | | | | 9.0 | | | | | |
|  |  | TEGDMA | 12.0 | 5.0 | 12.0 | 5.0 | 11.0 | 5.0 | 12.0 | 5.0 | 12.0 | 5.0 |
|  |  | UDMA | | 25.0 | | 25.0 | | 25.0 | | 25.0 | | 25.0 |
|  | (ae-2) | MDP | | 7.0 | | 7.0 | | 7.0 | | 7.0 | | 7.0 |
|  | (be) | NPG·Na | 0.1 | | | | 0.1 | | 0.1 | | | |
|  |  | NPG·K | | | 0.1 | | | | | | | |
|  | (ce) | p-CBSS | 1.0 | | 1.0 | | 1.0 | | | | 1.0 | |
|  | Other organic sulfinic acid compound | p-tsNA | | | | | | | 1.0 | | | |
|  | (de) | BPO | | 1.0 | | 1.0 | | 1.0 | | 1.0 | | 1.0 |
|  | (ee) | DMABAE | 0.2 | | 0.2 | | 0.2 | | | | 0.2 | |
|  |  | DMPT | 0.1 | | 0.1 | | 0.1 | | 0.1 | | 0.1 | |
|  | (fe) | F-R812 | 3.3 | 4.0 | 3.3 | 4.0 | 3.3 | 4.0 | 3.3 | 4.0 | 3.3 | 4.0 |
|  |  | F-8235 | 57.2 | 57.9 | 57.2 | 57.9 | 57.2 | 57.9 | 57.4 | 57.9 | 57.3 | 57.9 |
|  | Photopolymerization initiator | CQ | | 0.02 | | 0.02 | | 0.02 | | 0.02 | | 0.02 |
|  | Polymerization inhibitor | BHT | 0.1 | 0.1 | 0.1 | 0.1 | 0.1 | 0.1 | 0.1 | 0.1 | 0.1 | 0.1 |
|  | (ce)/(ae) *100 | | | 1.33 | | 1.33 | | 1.33 | | 0.00 | | 1.33 |
|  | (ce)/(be) | | | 10.00 | | 10.00 | | 10.00 | | 0.00 | | — |
| Characteristics | Bond strength to tooth structure [MPa] | | 5.4 | | 6.4 | | 7.1 | | 7.2 | | 0.6 | |
|  | Curing time (control) [min] | | 3.5 | | 3.6 | | 2.6 | | 4.3 | | 7.3 | |
|  | Curing time (after thermal loading) [min] | | 4.5 | | 4.7 | | 2.7 | | 7.8 | | 7.7 | |
|  | Difference in curing time [min] | | 1.0 | | 1.1 | | 0.1 | | 3.5 | | 0.4 | |
|  | Ratio of curing times [—] | | 1.3 | | 1.3 | | 1.0 | | 1.8 | | 1.1 | |

The results described in Table 1e show that the resin cements in Examples of the fifth aspect have a small change in curing time before and after the thermal loading to the first composition and attain excellent thermal stability as compared to the resin cement of Comparative Example 1e which did not contain any organic sulfinic acid compounds (ce) having an electron withdrawing group.

The dental curable kits and the dental curable compositions according to the fifth aspect of the present invention have very high usefulness in the dental treatment field in the bonding of teeth and coronal restorations.

The invention claimed is:

1. A dental adhesive curable kit (αc) for preparing a dental adhesive curable composition (c), the dental adhesive curable composition (c) comprising a polymerizable monomer (III) comprising a polymerizable monomer (A) represented by the following general formula (1') and an acidic group-containing polymerizable monomer (Bc), a polymerization initiator (Cc) comprising a peroxide (Cc1) and a photopolymerization initiator (Cc2), and a reductant (Dc) comprising a sulfinic acid compound (Dc2) and/or a salt thereof, and a filler (Fc), wherein the content of the polymerizable monomer (A) is not less than 0.1 part by weight and not more than 99 parts by weight, and the content of the acidic group-containing polymerizable monomer (Bc) is 0.5 to 30 parts by weight based on the total weight of the polymerizable monomer (III);

the content of the peroxide (Cc1) is 0.01 to 20 parts by weight, the content of the photopolymerization initiator (Cc2) is 0.0001 to 15 parts by weight, and the content of the sulfinic acid compound (Dc2) or salt thereof is 0.001 to 15 parts by weight based on the polymerizable monomer (III); and the content of the filler (Fc) is 5 to 95 wt % in the dental adhesive curable composition (c):

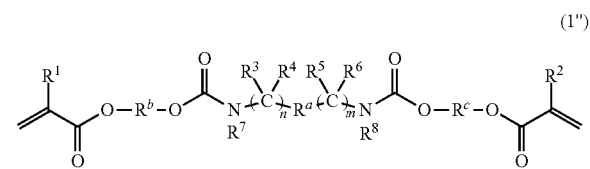
(1')

wherein $R^1$ and $R^2$ are each a hydrogen atom or a $C_{1-3}$ alkyl group, $R^7$ and $R^8$ are each a hydrogen atom or a methyl group, $R^b$ and $R^c$ are each independently a $C_{2-6}$ linear alkylene or $C_{2-6}$ linear oxyalkylene group optionally substituted with a $C_{1-3}$ alkyl group or a (meth)acryloyloxymethylene group in place of a hydrogen atom, and a moiety of the general formula (2c) below that is interposed between the two carbamoyl groups in the general formula (1') is a structure represented by any of the general formulas (RA) and (RD) below:

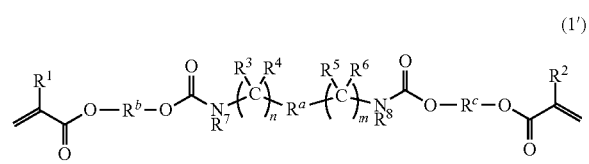
(2 c)

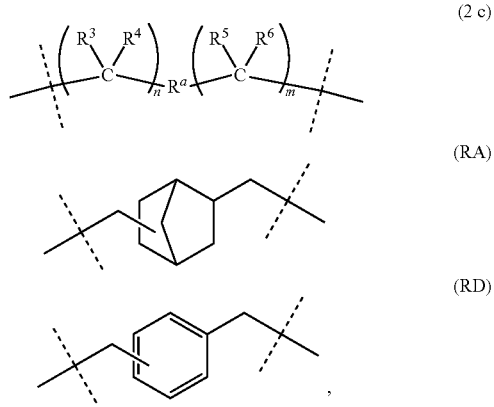
(RA)

(RD)

, the dental adhesive curable kit (αc) comprising at least a first composition and a second composition, at least one of the first composition and the second composition including the polymerizable monomer (A), the first composition including the reductant (Dc), the second composition including the acidic group-containing polymerizable monomer (Bc) and the polymerization initiator (Cc).

2. A mobile tooth fixing material (βd) comprising a dental adhesive composition (d), the dental adhesive composition (d) including a polymerizable monomer (A) represented by the following general formula (1"), a polymerizable monomer (Bd) having at least one acidic group in the molecule, and a photopolymerization initiator (Cd):

(1")

wherein $R^a$ is a divalent $C_{6-9}$ bridged cyclic hydrocarbon group, $R^1$ and $R^2$ are each a hydrogen atom or a methyl group, $R^3$, $R^4$, $R^5$ and $R^6$ are each a hydrogen atom or a hydrocarbon group, $R^7$ and $R^8$ are each a hydrogen atom, m and n are each independently 0 to 4, and $R^b$ and $R^c$ are each independently a $C_{2-6}$ linear alkylene or $C_{2-6}$ linear oxyalkylene group optionally substituted with a $C_{1-3}$ alkyl group or a (meth)acryloyloxymethylene group in place of a hydrogen atom.

3. A mobile tooth fixing material (βd) according to claim 2, wherein a cured product that is obtained by the following method and that is subjected to a three-point bending test exhibits a breaking energy of not less than 65 mJ, the cured product being obtained by packing the dental adhesive composition (d) into a 2×2×25 mm mold, which is brought into press contact with a polypropylene film and a glass plate, irradiating nine points on each of front and back sides with light for 10 seconds, and polishing a surface of the cured product with #320 waterproof abrasive paper, the three-point bending test being performed such that the obtained cured product is soaked in water at 37° C. overnight, and thereafter is subjected to the test at a crosshead speed of 1.0 mm/min; and wherein a test piece that is obtained by the following method and that is subjected to a tensile adhesion test exhibits a tensile bond strength of not less than 3 MPa, the test piece being obtained by applying the dental adhesive composition (d) on a bonding tooth face and curing the dental adhesive composition (d) by irradiation with light for 10 seconds, the bonding tooth face being obtained from a bovine front lower tooth having its flat enamel face exposed that is washed with water and dried and having a defined circular bonding area 4.8 mm in diameter, the tensile adhesion test being performed such that the obtained test piece is soaked in water at 37° C. overnight, and thereafter is subjected to the test at a crosshead speed of 2 mm/min.

4. The dental adhesive curable kit (αc) according to claim 1, wherein the content of the acidic group-containing polymerizable monomer (Bc) is 1 to 10 parts by weight based on the total weight of the polymerizable monomer (III).

* * * * *